(12) United States Patent
Tanaka et al.

(10) Patent No.: US 6,800,630 B2
(45) Date of Patent: Oct. 5, 2004

(54) PYRIMIDINE DERIVATIVES HAVING ANTITUMOR EFFECT

(75) Inventors: Hidekazu Tanaka, Osaka (JP); Kazuo Ueda, Shiga (JP); Shinji Suzuki, Shiga (JP); Hideyuki Takenaka, Shiga (JP)

(73) Assignee: Shionogi & Co., Ltd., Osaka (JP)

( * ) Notice: Subject to any disclaimer, the term of this patent is extended or adjusted under 35 U.S.C. 154(b) by 89 days.

(21) Appl. No.: 10/169,993

(22) PCT Filed: Jan. 9, 2001

(86) PCT No.: PCT/JP01/00036

§ 371 (c)(1),
(2), (4) Date: Jul. 12, 2002

(87) PCT Pub. No.: WO01/51488

PCT Pub. Date: Jul. 19, 2001

(65) Prior Publication Data

US 2003/0203894 A1 Oct. 30, 2003

(30) Foreign Application Priority Data

Jan. 14, 2000 (JP) .......................................... 2000-5553

(51) Int. Cl.[7] .................... C07D 239/42; C07D 413/12; A61K 31/505; A61P 35/00
(52) U.S. Cl. ...................... 514/256; 544/327; 544/328
(58) Field of Search ................................ 544/327, 328; 514/256

(56) References Cited

U.S. PATENT DOCUMENTS 5,608,067 A    3/1997   Afonso et al. ................. 546/82

FOREIGN PATENT DOCUMENTS

| WO | 95/09853 A1 | 4/1995 |
| WO | WO 95/25092 A1 | 9/1995 |
| WO | 00/04014 A1 | 1/2000 |

OTHER PUBLICATIONS

Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, pp. 451 and 596.*
West, Anthony R., Solid State Chemistry and its Applications, Wiley, New York, 1988, pp. 358 & 365.*
Thomas J. Murphy, "Chem 121, Organic Chemistry I", Fall 1999, [retrieved on Dec. 1, 2003]. Retreived from the Internet <http://condor.depaul.edu/~envirsci/TJM121SPOB99.html>.*
Draetta, G. and Pagano, M. in "Annual Reports in Medicinal Chemistry, vol. 31", 1996, Academic Press, San Diego, p 241–246.*

* cited by examiner

Primary Examiner—Thomas McKenzie
(74) Attorney, Agent, or Firm—Birch, Stewart, Kolasch & Birch, LLP

(57) ABSTRACT

A compound represented by the formula (I)

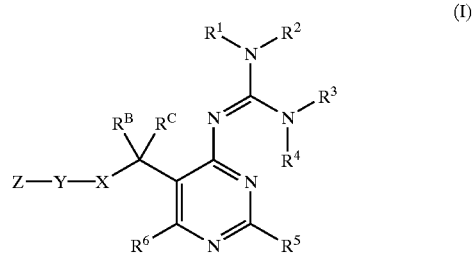

wherein, for example, $R^1$, $R^2$, $R^3$, and $R^4$ are each independently hydrogen atom, alkyl, and the like, $R^5$ and $R^6$ are each independently hydrogen atom, alkyl, and the like, $R^B$ and $R^C$ are each independently hydrogen atom, alkyl, and the like, X is —O—, —S—, and the like, Y is 5-membered heteroaryl-diyl and the like, Z is optionally substituted aryl and the like, their pharmaceutically acceptable salts, or their solvates.

13 Claims, No Drawings

PYRIMIDINE DERIVATIVES HAVING ANTITUMOR EFFECT

This application is the national phase under 35 U.S.C. § 371 of PCT International Application No. PCT/JP01/00036 which has an International filing date of Jan. 9, 2001.

TECHNICAL FIELD

The present invention relates to a novel pyrimidine derivative having an antitumor activity, a cytostatic activity, and an inhibitory activity against a signal derived from Ras oncogene products.

BACKGROUND ART

The oncogene "ras" such as H-ras, K-ras, and N-ras is mutated and activated in many of neoplasms. The "Ras", the products of ras oncogene, strongly concerns tumorigenesis caused by acceleration of cell cycle and induction of expression of many of genes associated with a malignant conversion such as a vascular endothelial growth factor and type-IV collagenase. Especially, it is found that there is highly frequent ras mutation in solid tumor such as pancreatic cancer (>80%), colon cancer (>40%), and lung cancer (>20%) which are difficult to be cured by using existing chemotherapeutics. Therefore, it is considered that Ras is one of the most important target molecules in the development of the chemotherapeutics against them.

A farnesyl-protein-transferase (FPT) inhibitor (FPTI) is known as chemotherapeutics of which target are Ras (WO95/13059, WO95/25086, WO95/25092, WO95/34535, U.S. Pat. No. 5,608,067, and JP-A-7-112930).

In the cells expressing activated Ras, the excess signals reach cell nucleus through some signaling pathways and some signal transmitter molecules such as MAPK (Mitogen Activated Protein Kinase) and PI3K (Phosphatidylinositol-3-Kinase). The signals activate the transcription factors such as AP1 (Activator Protein-1) and ETS (E26 transformation specific) in the cell nucleus and then they induce the expression of many genes related to malignant features through transcription activation element such as Ras Responsive Element (RRE). Therefore, it is possible to repress the malignant conversion of the cancer cells, when the signal transmission (a signal derived from ras oncogene products) is inhibited. Inhibitors of a signal derived from Ras oncogene products, of which basic structure is similar to that of the compounds of the present invention, are described in WO00/04014.

DISCLOSURE OF INVENTION

In the above situation, the inventors of the present invention have studied on the antitumor agent having an inhibitory activity against a signal derived from Ras oncogene products.

The activation of gene expression through RRE is in proportion to a signal derived from Ras and the signal can be measured by the amount of its expression. The inventors of the present invention artificially made cells having activated Ras wherein expression of firefly luciferase gene, reporter gene, is regulated by RRE and carried out a screening of the inhibitors taking luciferase activity shown by the cells as an index of signals through Ras. As a result, the inventors of the present invention found that a series of pyrimidine derivatives have a strong inhibitory activity against a signal derived from Ras oncogene products.

The present invention relates to I) a compound represented by the formula (I):

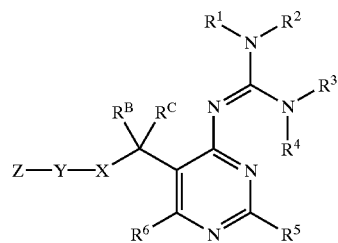

wherein $R^1$, $R^2$, $R^3$, and $R^4$ are each independently hydrogen atom, optionally substituted alkyl, optionally substituted alkenyl, optionally substituted alkynyl, optionally substituted aryl, optionally substituted heteroaryl, optionally substituted aralkyl, an optionally substituted non-aromatic heterocyclic group, acyl, optionally substituted amino, alkyloxy, hydroxy, cyano, or nitro; or $R^1$ and $R^2$, $R^3$ and $R^4$, and $R^2$ and $R^3$ each taken together with the adjacent nitrogen atom form the same or different 3- to 7-membered ring optionally containing O, N, or S, provided that $R^1$ and $R^2$, and $R^3$ and $R^4$ do not form a ring when $R^2$ and $R^3$ taken together form a ring;

$R^5$ and $R^6$ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen, hydroxy, mercapto, optionally substituted amino, carboxy, cyano, or nitro;

$R^B$ and $R^C$ are each independently hydrogen atom, alkyl, or alkyloxy; provided that in the case of both of $R^B$ and $R^C$ are hydrogen atom, $R^1$ is hydrogen atom or alkyl, $R^2$ is optionally substituted amino, alkyloxy, hydroxy, cyano, or nitro; and $R^3$ and $R^4$ are each independently hydrogen atom, optionally substituted alkyl, optionally substituted alkenyl, optionally substituted alkynyl, optionally substituted aryl, optionally substituted heteroaryl, optionally substituted aralkyl, optionally substituted non-aromatic heterocyclic group, acyl, optionally substituted amino, alkyloxy, hydroxy, cyano, or nitro; or $R^3$ and $R^4$ each taken together with the adjacent nitrogen atom form the same or different 3- to 7-membered ring optionally containing O, N, or S;

X is $-N(R^7)-$, $-NH-NH-$, $-O-$, or $-S-$ wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl or optionally substituted heteroaryl; its optical active compound, its prodrug thereof, or their pharmaceutically acceptable salt, or their solvate.

In more detail, the present invention relates to II)–XVI):

II) a compound described in I), represented by the formula (II):

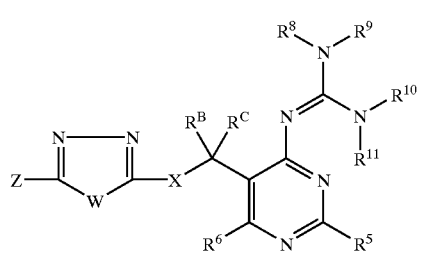

wherein $R^8$, $R^9$, $R^{10}$, and $R^{11}$ are each independently hydrogen atom, optionally substituted alkyl, alkenyl, alkynyl, optionally substituted aryl, optionally substituted heteroaryl, optionally substituted aralkyl, a non-aromatic heterocyclic group, acyl, optionally substituted amino, alkyloxy, hydroxy, cyano, or nitro;

$R^B$ and $R^C$ are each independently hydrogen atom, alkyl, or alkyloxy; provided that in the case of both of $R^B$ and $R^C$ are hydrogen atom, $R^8$ is hydrogen atom or alkyl, $R^9$ is substituted amino, alkyloxy, hydroxy, cyano, or nitro; and $R^{10}$ and $R^{11}$ are each independently hydrogen atom, optionally substituted alkyl, alkenyl, alkynyl, optionally substituted aryl, optionally substituted heteroaryl, optionally substituted aralkyl, non-aromatic heterocyclic group, acyl, optionally substituted amino, alkyloxy, hydroxy, cyano, or nitro;

W is —O—, —S—, or —N($R^A$)— wherein $R^A$ is hydrogen atom or optionally substituted alkyl;

$R^5$, $R^6$, X, and Z are as defined above mentioned I); its optical active compound, its prodrug thereof, or their pharmaceutically acceptable salt, or their solvate.

III) a compound described in I), represented by the formula (III):

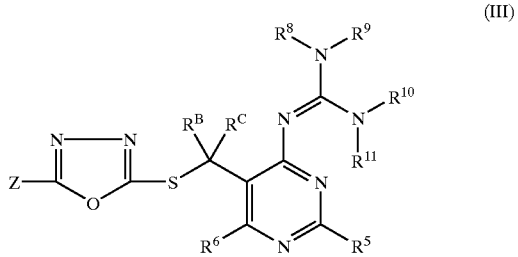

(III)

wherein $R^5$, $R^6$, and Z are as defined above mentioned I); $R^8$, $R^9$, $R^{10}$, $R^{11}$, $R^B$ and $R^C$ are as defined above mentioned II); its optical active compound, its prodrug thereof, or their pharmaceutically acceptable salt, or their solvate.

IV) a compound described in I), represented by the formula (IV):

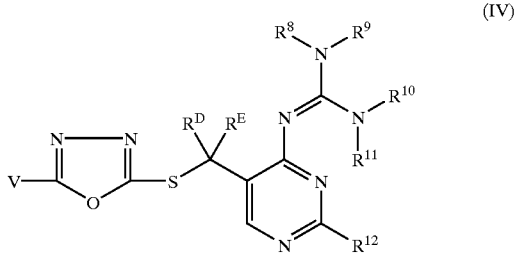

(IV)

wherein $R^8$, $R^9$, $R^{10}$ and $R^{11}$ are as defined above mentioned II);

$R^{12}$ is hydrogen atom or alkyl;

$R^D$ and $R^E$ are each independently hydrogen atom or alkyl; provided that in the case of both of $R^D$ and $R^E$ are hydrogen atom, $R^8$ is hydrogen atom or alkyl, $R^9$ is optionally substituted amino, alkyloxy, hydroxy, cyano, or nitro; and $R^{10}$ and $R^{11}$ are each independently hydrogen atom, optionally substituted alkyl, alkenyl, alkynyl, optionally substituted aryl, optionally substituted heteroaryl, optionally substituted aralkyl, non-aromatic heterocyclic group, acyl, optionally substituted amino, alkyloxy, hydroxy, cyano, or nitro;

V is optionally substituted aryl; its optical active compound, its prodrug thereof, or their pharmaceutically acceptable salt, or their solvate.

V) a compound represented by the formula (V):

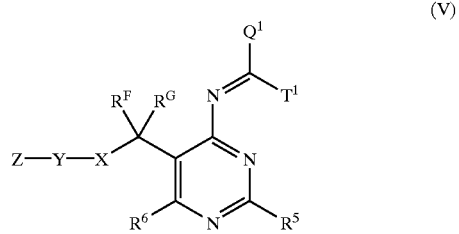

(V)

wherein $R^5$ and $R^6$ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen atoms, hydroxy, mercapto, optionally substituted amino, carboxy, cyano, or nitro;

$R^F$ and $R^G$ are each independently hydrogen atom, alkyl, or alkyloxy;

X is —N($R^7$)—, —NH—NH—, —O—, or —S— wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl or optionally substituted heteroaryl;

$Q^1$ is —$NR^1R^2$, —$OR^1$, or —$SR^1$, $T^1$ is —$OR^3$ or —$SR^3$ wherein $R^1$, $R^2$ and $R^3$ are each independently hydrogen atom, optionally substituted alkyl, optionally substituted alkenyl, optionally substituted alkynyl, optionally substituted aryl, optionally substituted heteroaryl, optionally substituted aralkyl, optionally substituted non-aromatic heterocyclic group, acyl, optionally substituted amino, alkyloxy, hydroxy, cyano, or nitro; or $R^1$ and $R^3$, and $R^2$ and $R^3$ each taken together with the adjacent heteroatom form 5- to 7-membered ring; its regioisomer, its optical active compound, its prodrug thereof, or their pharmaceutically acceptable salt, or their solvate.

VI) a compound described in V), represented by the formula (VI):

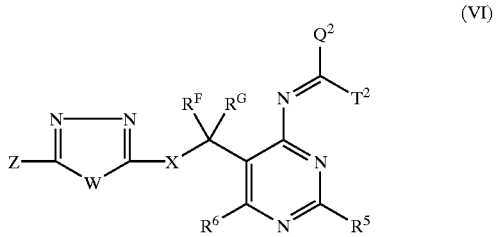

(VI)

wherein $Q^2$ is —$NR^8R^9$, —$OR^8$, or —$SR^8$, $T^2$ is —$OR^{10}$ or —$SR^{10}$ wherein $R^8$, $R^9$ and $R^{10}$ are each independently hydrogen atom, optionally substituted alkyl, alkenyl, alkynyl, optionally substituted aryl, optionally substituted heteroaryl, optionally substituted aralkyl, optionally substituted non-aromatic heterocyclic group, acyl, optionally substituted amino, alkyloxy, hydroxy, cyano, or nitro;

W is —O—, —S—, or —N($R^A$)— wherein $R^A$ is hydrogen atom or optionally substituted alkyl;

$R^5$, $R^6$, $R^F$, $R^G$, X, and Z are as defined above mentioned V); its regioisomer, its optical active compound, its prodrug thereof, or their pharmaceutically acceptable salt, or their solvate.

In the case of $R^8$ and $R^{10}$ are bonded directly with O or S, $R^8$ and $R^{10}$ peferably are each independently hydrogen atom, optionally substituted alkyl, alkenyl, alkynyl, optionally substituted aryl, optionally substituted heteroaryl, optionally substituted aralkyl, non-aromatic heterocyclic group, or acyl;

VII) a compound described in V), represented by the formula (VII):

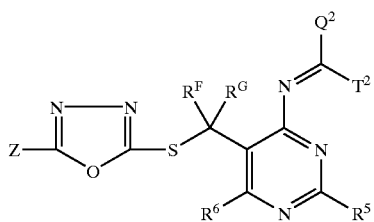

(VII)

wherein $R^5$, $R^6$, $R^F$, $R^G$, and Z are as defined above mentioned V);

$Q^2$ and $T^2$ are as defined above mentioned VI) its regioisomer, its optical active compound, its prodrug thereof, or their pharmaceutically acceptable salt, or their solvate.

VIII) a compound described in V), represented by the formula (VIII):

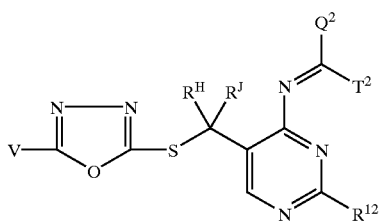

(VIII)

wherein $R^{12}$ is hydrogen or alkyl;

$R^H$ and $R^J$ are each independently hydrogen atom or alkyl;

V is optically substituted aryl;

the other symbols are as defined above mentioned VI); its regioisomer, its optical active compound, its prodrug thereof, or their pharmaceutically acceptable salt, or their solvate.

IX) a compound, its regioisomer, its optical active compound, its prodrug thereof, or their pharmaceutically acceptable salt, or their solvate as described in any one of the above I) to V), wherein $R^1$, $R^2$, $R^3$, and $R^4$ are each independently hydrogen atom, optionally substituted alkyl, alkenyl, alkynyl, or acyl;

X) a compound, its regioisomer, its optical active compound, its prodrug thereof, or their pharmaceutically acceptable salt, or their solvate as described in any one of the above VI) to VIII), wherein $R^8$, $R^9$, $R^{10}$, and $R^{11}$ are each independently hydrogen atom, optionally substituted alkyl, alkenyl, alkynyl, or acyl, XI) a pharmaceutical composition which contains as active ingredient a compound as described in any one of I) to X), XII) a pharmaceutical composition for use as an antitumor agent which contains as active ingredient a compound as described in any one of I) to X), XIII) a pharmaceutical composition for use as a cytostatic agent which contains as described in any one of I) to X), XIV) a pharmaceutical composition for use as an inhibitor against a signal derived from Ras oncogene products which contains as active ingredient a compound as described in any one of I) to X), XV) use of a compound of any one of I) to X) for the preparation of a pharmaceutical composition for treating cancer, and XVI) a method of treating a mammal, including a human, to alleviate a pathological effect of cancer, which comprises administration to the mammal of a compound as described in any one of I) to X).

The term "alkyl" employed alone or in combination with other terms in the present specification includes a straight or branched chain monovalent hydrocarbon group having 1 to 8 carbon atoms. Examples of the alkyl include methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl and the like. Preferably, C1 to C6 alkyl is exemplified. More preferably, C1 to C3 alkyl is exemplified.

The term "alkenyl" employed alone or in combination with other terms in the present specification includes a straight or branched chain monovalent hydrocarbon group having 2 to 8 carbon atoms and one or more double bonds. An example of the alkenyl includes vinyl, allyl, propenyl, crotonyl, prenyl, a variety of butenyl isomers and the like. Preferably, C2 to C6 alkenyl is exemplified. More preferably, C2 to C3 alkenyl is exemplified.

The term "alkynyl" employed alone or in combination with other terms in the present specification includes a straight or branched chain monovalent hydrocarbon group having 2 to 8 carbon atoms and one or more triple bonds. The alkynyl may contain (a) double bond(s). An example of the alkenyl includes ethynyl, propynyl, 6-heptynyl, 7-octynyl, and the like. Preferably, C2 to C6 alkynyl is exemplified. More preferably, C2 to C3 alkynyl is exemplified.

The term "aryl" employed alone or in combination with other terms in the present specification includes a monocyclic or condensed cyclic aromatic hydrocarbon. An example of the aryl includes phenyl, 1-naphthyl, 2-naphthyl, anthryl and the like. Preferably, phenyl, 1-naphthyl, and 2-naphthyl are exemplified. More preferably, phenyl is exemplified.

The term "aralkyl" in the present specification includes a group wherein the above-mentioned "alkyl" is substituted with the above-mentioned "aryl". An example of aralkyl includes benzyl, phenethyl (e.g., 2-phenylethyl), phenylpropyl (e.g., 3-phenylpropyl), naphthylmethyl (e.g., 1-naphthylmethyl and 2-naphthylmethyl), anthrylmethyl (e.g., 9-anthrylmethyl) and the like. Preferably, benzyl and phenylethyl are exemplified.

The term "heteroaryl" employed alone or in combination with other terms in the present specification includes a 5- to 6-membered aromatic cyclic group which contains one or more hetero atoms selected from the group consisting of oxygen, sulfur, and nitrogen atoms in the ring and may be fused with the above mentioned "aryl", the later mentioned "carbocyclic group", and "non-aromatic heterocyclic group", or "heteroaryl". Heteroaryl is bonded at any possible position when the heteroaryl is a condensed ring. Examples of the heteroaryl are pyrrolyl (e.g., 1-pyrrolyl), indolyl (e.g., 3-indolyl), carbazolyl (e.g., 3-carbazolyl), imidazolyl (e.g., 4-imidazolyl), pyrazolyl (e.g., 3-pyrazolyl and 5-pyrazolyl), benzimidazolyl (e.g., 2-benzimidazolyl), indazolyl (e.g., 3-indazolyl), indolizinyl (e.g., 6-indolizinyl), pyridyl (e.g., 3-pyridyl and 4-pyridyl), quinolyl (e.g., 5-quinolyl), isoquinolyl (e.g., 3-isoquinolyl), acridinyl (e.g., 1-acridinyl), phenanthridinyl (e.g., 2-phenanthridinyl), pyridazinyl (e.g., 3-pyridazinyl), pyrimidinyl (e.g., 4-pyrimidinyl), pyrazinyl (e.g., 2-pyrazinyl), cinnolinyl (e.g., 3-cinnolinyl), phthalazinyl (e.g., 2-phthalazinyl), quinazolinyl (e.g., 2-quinazolinyl), isoxazolyl (e.g., 3-isoxazolyl), benzisoxazolyl (e.g., 3-benzisoxazolyl), oxazolyl (e.g., 2-oxazolyl), benzoxazolyl (e.g., 2-benzoxazolyl), benzoxadiazolyl (e.g., 4-benzoxadiazolyl), isothiazolyl (e.g., 3-isothiazolyl), benzisothiazolyl (e.g., 2-benzisothiazolyl), thiazolyl (e.g., 4-thiazolyl), benzothiazolyl (e.g., 2-benzothiazolyl), furyl (e.g., 2-furyl and 3-furyl), benzofuryl (e.g., 3-benzofuryl), thienyl (e.g., 2-thienyl and 3-thienyl), benzothienyl (e.g., 2-benzothienyl), tetrazolyl, oxadiazolyl (e.g., 1,3,4-oxadiazolyl and 1,2,4-oxadiazolyl), oxazolyl, thiadiazolyl (e.g., 1,3,4-thiadiazolyl and 1,2,4-thiadiazolyl), 4H-1,2,4-triazolyl, quinoxalinyl, 2-pyridon-3-yl, and the like. Preferably, pyridyl, pyrazinyl, furyl, thienyl and the like are exemplified.

The term "5-membered heteroaryl-diyl" herein used includes a 5-membered divalent group derived from above-mentioned "heteroaryl". Examples of the 5-membered heteroaryl-diyl are furan-2,5-diyl, thiophene-2,5-diyl, pyrrole-2,5-diyl, pyrazole-3,5-diyl, 1,3,4-oxadiazole-2,5-diyl, 1,2,4-oxadiazole3,5-diyl, oxazole-3,5-diyl, isoxazole-3,5-diyl, 1,3,4-thiadiazole-3,5-diyl, 1,2,4-thiadiazole-3,5-diyl, 4H-1,2,4-triazole-3,5-diyl, and the like.

The term "non-aromatic heterocyclic group" employed alone or in combination with other terms in the present specification includes a 5- to 7-membered non-aromatic heterocyclic group which contains one or more hetero atoms selected from the group consisting of oxygen, sulfur, and nitrogen atoms in the ring and a cyclic group wherein two or more of the above-mentioned heterocyclic groups arc fused. Examples of the heterocyclic group are pyrrolidinyl (e.g., 1-pyrrolidinyl), pyrazolidinyl (e.g., 1-pyrazolidinyl), piperidinyl (e.g., piperidino and 2-piperidinyl), piperazinyl (e.g., 1-piperazinyl), morpholinyl (e.g., morpholino and 3-morpholinyl), and the like.

The term "5-membered non-aromatic heterocycle-diyl" herein used includes a 5-membered divalent group derived from the above-mentioned "non-aromatic heterocyclic group". Examples of the 5-membered non-aromatic heterocycle-diyl are pyrrolidindiyl (e.g., pyrrolidine-2,5-diyl) and the like.

The term "carbocyclic group" herein used includes a 3- to 7-membered non-aromatic carbocyclic group. Examples of the carbocyclic group are cycloalkyl (e.g., cyclopropyl, cyclobutyl, cyclopentyl, cyclohexyl, and cycloheptyl), cycloalkenyl (e.g., cyclopentenyl and cyclohexenyl), and the like.

In this specification, examples of the ring represented by "$R^1$ and $R^2$, and $R^3$ and $R^4$ each taken together with the adjacent nitrogen atom form the same or different 3- to 7-membered non-aromatic heterocyclic ring optionally containing O, N, or S" are aziridine, pyrrolidine, piperidine, piperazine, morpholine, imidazolidine, pyrazolidine, pyrrole, pyrimidine, triazine, azepine, perhydroazepine, and the like.

In this specification, examples of the ring represented by "$R^2$ and $R^3$ each taken together with the adjacent nitrogen atom form the same or different 3- to 7-membered non-aromatic heterocyclic ring optionally containing O, N, or S" are imidazolidine, hexahydropyridine, and perhydro-1,3-diazepine the like.

In this specification, examples of the ring represented by "$R^1$ and $R^3$, or $R^2$ and $R^3$ each taken together with heteroatom form 5- to 7-membered non-aromatic heterocyclic ring optionally containing O, N, or S" are thiazolidine, perhydro-1,3-thiadine, oxazolidine, perhydro-1,3-oxadine, 1,3-dithiolane, 1,3-dithiane, 1,3-oxathiolane, 1,3-oxathiane, perhydro-1,3-oxazepine, perhydro-1,3-thiazepine, and the like.

The term "acyl" employed alone or in combination with other terms in the present specification includes alkylcarbonyl of which alkyl part is the above-mentioned "alkyl" and arylcarbonyl of which aryl part is the above-mentioned "aryl". Examples of the acyl are acetyl, propanoyl, benzoyl, and the like.

The term "halogen" herein used means fluoro, chloro, bromo, and iodo.

Examples of "alkyloxy" herein used are methyloxy, ethyloxy, n-propyloxy, isopropyloxy, n-butyloxy, isobutyloxy, sec-butyloxy, tert-butyloxy, and the like. Preferably, methyloxy, ethyloxy, n-propyloxy, and isopropyloxy are exemplified.

Examples of "alkylthio" herein used are methylthio, ethylthio, n-propylthio, isopropylthio, n-butylthio, isobutylthio, sec-butylthio, tert-butylthio, and the like. Preferably, methylthio, ethylthio, n-propylthio, and isopropylthio are exemplified.

Examples of "alkyloxycarbonyl" herein used are methyloxycarbonyl, ethyloxycarbonyl, n-propyloxycarbonyl, and the like.

The term "optionally substituted amino" herein used means amino substituted with one or two of the above-mentioned "alkyl", the above-mentioned "aralkyl", the above-mentioned "acyl", optionally substituted arylsulfonyl (e.g., alkyloxyphenylsulfonyl), arylalkylene (e.g., benzylidene), alkylsulfonyl, carbamoyl and the like or non-substituted amino. Examples of the optionally substituted amino are amino, methylamino, ethylamino, dimethylamino, ethylmethylamino, diethylamino, benzylamino, benzoylamino, acetylamino, propionylamino, tert-butyloxycarbonylamino, benzylidenamino, methylsulfonylamino, 4-methoxyphenylsulfonylamino, and the like. Preferably, amino, methylamino, dimethylamino, diethylamino, acetylamino are exemplified.

Substituents on the aromatic ring of "optionally substituted aralkyl" are, for example, hydroxy, alkyloxy (e.g., methyloxy and ethyloxy), mercapto, alkylthio (e.g., methylthio), cycloalkyl (e.g., cyclopropyl, cyclobutyl, and cyclopentyl), halogen (e.g., fluoro, chloro, bromo, and iodo), carboxy, alkyloxycarbonyl (e.g., methyloxycarbonyl and ethyloxycarbonyl), nitro, cyano, haloalkyl (e.g., trifluoromethyl), aryloxy (e.g., phenyloxy), optionally substituted amino (e.g., amino, methylamino, dimethylamino, diethylamino, and benzylidenamino), alkyl (e.g., methyl, ethyl, n-propyl, isopropyl, n-butyl, isobutyl, sec-butyl, tert-butyl, n-pentyl, isopentyl, and neopentyl), alkenyl (e.g., vinyl and propenyl), alkynyl (e.g., ethynyl and phenylethynyl), formyl, lower alkanoyl (e.g., acetyl and propionyl), acyloxy (e.g., acetyloxy), acylamino, alkylsulfonyl (e.g., methylsulfonyl), and the like. These substituents may be substituted at one or more possible position(s).

Substituents of "optionally substituted alkyl", "optionally substituted alkyloxy", and "optionally substituted alkyloxycarbonyl" are, for example, hydroxy, alkyloxy (e.g., methyloxy and ethyloxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkyloxycarbonyl (e.g., methyloxycarbonyl and ethyloxycarbonyl), nitro, cyano, haloalkyl (e.g., trifluoromethyl), optionally substituted amino (e.g., amino, methylamino, dimethylamino, carbamoylamino, and tert-butyloxycarbonylamino), acyloxy (e.g., acetyloxy), optionally substituted aralkyloxy (e.g., benzyloxy and 4-methyloxybenzyloxy), and the like. These substituents may be substituted at one or more possible position(s).

Substituents of "optionally substituted alkenyl" and "optionally substituted alkynyl" are, for example, hydroxy, alkyloxy (e.g., methyloxy and ethyloxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkyloxycarbonyl (e.g., methyloxycarbonyl and ethyloxycarbonyl), nitro, cyano, haloalkyl (e.g., trifluoromethyl), optionally substituted amino (e.g., amino, methylamino, dimethylamino, carbamoylamino, and tert-butyloxycarbonylamino), acyloxy (e.g., acetyloxy), optionally substituted aralkyloxy (e.g., benzyloxy and 4-methyloxybenzyloxy), optionally substituted aryl (e.g., phenyl), and the like. These substituents may be substituted at one or more possible position(s).

The preferable examples of "optionally substituted alkyl" are methyl, ethyl, n-propyl, isopropyl, n-butyl, trifluoromethyl, 2,2,2-trifluoroethyl, hydroxymethyl, cyclohexylmethyl, carboxyethyl, acetyloxyethyl, and benzyloxymethyl. More preferably, methyl, ethyl, n-propyl, isopropyl, n-butyl, trifluoromethyl, 2,2,2-trifluoroethyl are exemplified Substituents of "optionally substituted aryl", "optionally substituted heteroaryl", "optionally substituted 5-membered heteroaryl-diyl", "optionally substituted 5-membered non-aromatic heterocycle-diyl", and "an optionally substituted non-aromatic heterocyclic group" are, for example, hydroxy, optionally substituted alkyloxy (e.g., methyloxy, ethyloxy, n-propyloxy, isopropyloxy, ethyloxycarbonylmethyloxy, carboxymethyloxy and 4-methoxybenzyloxy), mercapto, alkylthio (e.g., methylthio), cycloalkyl (e.g., cyclopropyl, cyclobutyl, cyclopentyl), halogen (e.g., fluoro, chloro, bromo, and iodo), carboxy, alkyloxycarbonyl (e.g., methyloxycarbonyl, ethyloxycarbonyl, and tert-butyloxycarbonyl), nitro, cyano, haloalkyl (e.g., trifluoromethyl), aryloxy (e.g., phenyloxy), optionally substituted amino (e.g., amino, methylamino, dimethylamino, ethylamino, diethylamino, acetylmethylamino, benzylidenamino, 4-methoxyphenylsulfonylamino, methylsulfonylamino, benzoylamino, acetylamino, propionylamino, and tert-butyloxycarbonylamino), optionally substituted sulfamoyl (e.g., sulfamoyl), optionally substituted alkyl (e.g., methyl, ethyl, n-propyl, isopropyl, n-butyl, isobutyl, sec-butyl, tert-butyl, n-pentyl, isopentyl, neopentyl, t-butyloxycarbonylaminomethyl, and aminomethyl), alkenyl (e.g., vinyl, propenyl, and prenyl), optionally substituted alkynyl (e.g., ethynyl and phenylethynyl), alkenyloxy (e.g., propenyloxy and prenyloxy), formyl, acyl (e.g., acetyl, propionyl, and benzoyl), acyloxy (e.g., acetyloxy), optionally substituted carbamoyl (e.g., carbamoyl and N,N-dimethylcarbamoyl), alkylsulfonyl (e.g., methylsulfonyl), aryl (e.g., phenyl), aralkyl (e.g., benzyl), carbothioamide, optionally substituted heterocyclic group (e.g., dioxolanyl, 2-methyl-1,3-dioxolan-2-yl, pyrrolidinyl, and piperidino), optionally substituted heteroaryl (e.g., 2-pyridyl, 3-pyridyl, 4-pyridyl, pyridine N-oxide-4-yl, 1-methyl-2-pyridon-4-yl, 1-pyrrolyl, 2-pyrrolyl, and 3-pyrrolyl), and the like. These substituents may be substituted at one or more possible position(s). Preferably, optionally substituted amino, halogen, nitro, alkyl, and alkyloxy are exemplified.

Examples of "optionally substituted aryl" are phenyl, 2-aminophenyl, 3-aminophenyl, 4-aminophenyl, 2-acetylaminophenyl, 4-acetylaminophenyl, 2-benzoylaminophenyl, 4-benzoylaminophenyl, 2-methylsulfonylaminophenyl, 2-propionylaminophenyl, 2-methylaminophenyl, 4-methylaminophenyl, 2-dimethylaminophenyl, 4-dimethylaminophenyl, 2-ethylaminophenyl, 4-ethylaminophenyl, 4-diethylaminophenyl, 2-(4-methoxyphenylsulfonylamino) phenyl, 2-hydroxyphenyl, 4-hydroxyphenyl, 2-ethyloxycarbonylmethyloxyphenyl, 2-carboxymethyloxyphenyl, 2-chlorophenyl, 4-chlorophenyl, 4-bromophenyl, 4-iodophenyl, 4-trifluoromethylphenyl, 2-methylphenyl, 4-methylphenyl, 4-methyloxyphenyl, 4-ethyloxyphenyl, 4-n-propyloxyphenyl, 4-isopropyloxyphenyl, 4-tert-butyloxycarbonylphenyl, 4-prenyloxyphenyl, 2-nitrophenyl, 4-nitrophenyl, 4-(4-methoxybenzyloxy)phenyl, 4-methyloxycarbonylphenyl, 4-sulfamoylphenyl, 4-(N,N-dimethylcarbamoyl)phenyl, 4-carboxyphenyl, 4-biphenylyl, 4-benzoylphenyl, 4-pyrrolidinophenyl, 4-piperidinophenyl, 3-aminonaphthalen-2-yl, 2-amino-5-chlorophenyl, 2-amino-3-chlorophenyl, 2-amino-4-chlorophenyl, 2-amino-6-chlorophenyl, 4-amino-2-chlorophenyl, 2-amino-4-fluorophenyl, 2-amino-5-fluorophenyl, 2-amino-6-fluorophenyl, 4-amino-2-fluorophenyl, 2-amino-4,5-difluorophenyl, 2-amino-3-methylphenyl, 2-amino-4-methylphenyl, 2-amino-5-methylphenyl, 2-amino-6-methylphenyl, 4-amino-3-methylphenyl, 4-amino-3-methyloxyphenyl, 2-amino-4-nitrophenyl, 4-amino-3-hydroxyphenyl, 2-amino-4-carboxyphenyl, 2-amino-4-methyloxycarbonylphenyl, 4-amino-2-hydroxyphenyl, 4-amino-3-(4-methoxybenzyloxy)phenyl, 2,4-diaminophenyl, 3,4-diaminophenyl, 2-acetylmethylaminophenyl, 2-acetylamino-4-fluorophenyl, 2-acetylamino-4-chlorophenyl, 2,3-dichlorophenyl, 2,4-dichlorophenyl, 4-amino-2-methylphenyl, 2-fluoro-4-nitrophenyl, 4-amino-2-methyloxyphenyl, 2-methyloxy-4-nitrophenyl, 4-fluoro-2-nitrophenyl, 4-amino-2-trifluoromethylphenyl, 4-amino-2-ethyloxyphenyl, 4-amino-2-trifluoromethyloxyphenyl, 2-chloro-4-nitrophenyl, 2-methyl-4-nitrophenyl, 4-nitro-2-trifluoromethyloxyphenyl, 4-nitro-2-trifluoromethylphenyl, 2-ethyloxy-4-nitrophenyl, and the like.

Examples of "optionally substituted heteroaryl" are pyridin-3-yl, 2-aminopyridin-3-yl, 2-aminopyridin-5-yl, 3-aminopyrazin-2-yl, 3-aminopyrazol4-yl, 4-amino-2-methylpyrimidin-5-yl, 2-aminothiophen-3-yl, 3-methyl thiophen-2-yl, 5-methylthiophen-2-nyl, furan-2-yl, furan-3-yl, 2-methylfuran-3-yl, 2,5-dimethylfuran-3-yl, 5-bromofuran-2-yl, 2-nitrofuran4-yl, 1-methyl-4-nitropyrazol-3-yl, 1-methyl-4-nitropyrazol-5-yl, 5-nitropyrazol-3-yl, 4-nitropyrazol-3-yl, 2-(3-pyridyl)thiazol-4-yl, 2-(4-pyridyl)thiazol-4-yl, 6-(1-pyrrolyl) pyridin-3-yl, N-methyl-2-pyridon-3-yl, and the like.

Examples of "optionally substituted 5-membered heteroaryl-diyl" are furan-2,5-diyl, thiophene-2,5-diyl, pyrrole-2,5-diyl, pyrazole-3,5-diyl, 1,3,4-oxadiazole-2,5-diyl, 1,2,4-oxadiazole-3,5-diyl, oxazole-2,5-diyl, isooxazole-3,5-diyl, 1,3,4-thiadiazole-2,5-diyl, 1,2,4-thiadiazole-3,5-diyl, 4H-1,2,4-triazole-3,5-diyl, 1-methylpyrazole-3,5-diyl, and the like.

Preferable examples of $R^1$ to $R^6$, $R^B$, $R^C$, X, Y, and Z of the compound represented by the formula (I) are shown below as groups (a) to (t).

$R^1$ and $R^2$ are (a) one is hydrogen atom, the other is optionally substituted amino, alkyloxy, hydroxy, cyano, or nitro.

$R^3$ and $R^4$ are (b) each independently hydrogen atom, optionally substituted alkyl, alkenyl, alkynyl, optionally substituted amino, alkyloxy, hydroxy, cyano, or nitro; (c) each independently hydrogen atom, alkyl optionally substituted with halogen atom, alkenyl, or alkynyl, optionally substituted amino, alkyloxy, hydroxy, cyano, or nitro; and (d) one is hydrogen atom and the other is alkyl optionally substituted with halogen, alkenyl, or alkynyl, optionally substituted amino, alkyloxy, hydroxy, cyano, or nitro.

$R^5$ is (e) hydrogen atom, alkyloxy, alkylthio, or optionally substituted alkyl; (f) hydrogen atom or alkyl; and (g) hydrogen atom or C1 to C2 alkyl.

$R^6$ is (h) hydrogen atom or alkyl; and (i) hydrogen atom.

X is (j) —O— or —S—; and (k) —S—.

Y is (1) 5-membered heteroaryl-diyl; (m) 1,3,4-oxadiazole-2,5-diyl, 1,2,4-oxadiazole-3,5-diyl, 1,3,4-thiadiazole-2,5-diyl, or 1,2,4-thiadiazole-3,5-diyl; and (n) 1,3,4-oxadiazole-2,5-diyl.

Z is (o) optionally substituted aryl or optionally substituted heteroaryl; (p) optionally substituted phenyl or optionally substituted monocyclic heteroaryl; and (q) phenyl, pyridyl, thienyl, or furyl, which are substituted with 1 to 3 substituents selected from the group consisting of optionally substituted amino, halogen, alkyl, alkyloxy, acyl, phenyl, alkyloxycarbonyl, hydroxy, nitro, or haloalkyl.

A preferable example of $R^B$ and $R^C$ is (r) ($R^B$, $R^C$) is (alkyl, hydrogen atom) or (hydrogen atom, hydrogen atom); and (s) $R^B$, $R^C$) is (hydrogen atom, hydrogen atom).

A preferred group of compounds represented by the formula (I) is shown below. [($R^1$, $R^2$), ($R^3$, $R^4$), $R^5$, $R^6$, X, Y, ($R^B$, $R^C$)]=[a, b, e, h, j, l, r], [a, b, e, h, j, l, s], [a, b, e, h, j, m, r], [a, b, e, h, j, m, s], [a, b, e, h, j, n, r], [a, b, e, h, j, n, s], [a, b, e, h, k, l, r], [a, b, e, h, k, l, s], [a, b, e, h, k, m, r], [a, b, e, h, k, m, s], [a, b, e, h, k, n, r], [a, b, e, h, k, n, s], [a, b, e, i, j, l, r], [a, b, e, i, j, l, s], [a, b, e, i, j, m, r], [a, b, e, i, j, m, s], [a, b, e, i, j, n, r], [a, b, s, i, j, n, s], [a, b, e, i, k, l, r], [a, b, e, i, k, l, s], [a, b, e, i, k, m, r], [a, b, e, i, k, m, s], [a, b, j, k, n, r], [a, b, e, i, k, n, s], [a, b, f, h, j, l, r], [a, b, f, h, j, l, s], [a, b, f, h, j, m, r], [a, b, f, h, j, m, s], [a, b, f, h, j, n, r], [a, b, f, h, j, n, s], [a, b, f, h, k, l, r], [a, b, f, h, k, l, s], [a, b, f, h, k, m, r], [a, b, f, h, k, m, s], [a, b, f, h, k, n, r], [a, b, f, h, k, n, s], [a, b, f, i, j, l, r], [a, b, f, i, j, l, s], [a, b, f, i, j, m, r], [a, b, f, i, j, m, s], [a, b, f, i, j, n, r], [a, b, f, i, j, n, s], [a, b, f, i, k, l, r], [a, b, f, i, k, l, s], [a, b, f, i, k, m, r], [a, b, f, i, k, m, s], [a, b, f, i, k, n, r], [a, b, f, i, k, n, s], [a, b, g, h, j, l, r], [a, b, g, h, j, l, s], [a, b, g, h, j, m, r], [a, b, g, h, j, m, s], [a, b, g, h, j, n, r], [a, b, g, h, j, n, s], [a, b, g, h, k, l, r], [a, b, g, h, k, l, s], [a, b, g, h, k, m, r], [a, b, g, h, k, m, s], [a, b, g, h, k, n, r], [a, b, g, h, k, n, s], [a, b, g, i, j, l, r], [a, b, g, i, j, l, s], [a, b, g, i, j, m, r], [a, b, g, i, j, m, s], [a, b, g, i, j, n, r], [a, b, g, i, j, n, s], [a, b, g, i, k, l, r], [a, b, g, i, k, l, s], [a, b, g, i, k, m, r], [a, b, g, i, k, m, s], [a, b, g, i, k, n, r], [a, b, g, i, k, n, s], [a, c, e, h, j, l, r], [a, c, e, h, j, l, s], [a, c, e, h, j, m, r], [a, c, e, h, j, m, s], [a, c, e, h, j, n, r], [a, c, e, h, k, l, r], [a, c, e, h, k, l, s], [a, c, e, h, k, m, r], [a, c, e, h, k, m, s], [a, c, e, h, k, n, r], [a, c, e, h, k, n, s], [a, c, e, i, j, l, r], [a, c, e, i, j, l, s], [a, c, e, i, j, m, r], [a, c, e, i, j, m, s], [a, c, e, i, j, n, r], [a, c, e, i, j, n, s], [a, c, e, i, k, l, r], [a, c, e, i, k, l, s], [a, c, e, i, k, m, r], [a, c, e, i, k, m, s], [a, c, e, i, k, n, r], [a, c, e, i, k, n, s], [a, c, f, h, j, l, r], [a, c, f, h, j, l, s], [a, c, f, h, j, m, r], [a, c, f, h, j, m, s], [a, c, f, h, j, n, r], [a, c, f, h, j, n, s], [a, c, f, h, k, l, r], [a, c, f, h, k, l, s], [a, c, f, h, k, m, r], [a, c, f, h, k, m, s], [a, c, f, h, k, n, r], [a, c, f, h, k, n, s], [a, c, f, i, j, l, r], [a, c, f, i, j, l, s], [a, c, f, i, j, m, r], [a, c, f, i, j, m, s], [a, c, f, i, j, n, r], [a, c, f, i, j, n, s], [a, c, f, i, k, l, r], [a, c, f, i, k, l, s], [a, c, f, i, k, m, r], [a, c, f, i, k, m, s], [a, c, f, i, k, n, r], [a, c, f, i, k, n, s], [a, c, g, h, j, l, r], [a, c, g, h, j, l, s], [a, c, g, h, j, m, r], [a, e, g, h, j, m, s], [a, c, g, h, j, n, r], [a, c, g, h, j, n, s], [a, c, g, h, k, l, r], [a, c, g, h, k, l, s], [a, c, g, h, k, m, r], [a, c, g, h, k, m, s], [a, c, g, h, k, n, r], [a, c, g, h, k, n, s], [a, c, g, i, j, l, r], [a, c, g, i, j, l, s], [a, c, g, i, j, m, r], [a, c, g, i, j, m, s], [a, c, g, i, j, n, r], [a, c, g, i, j, n, s], [a, c, g, i, k, l, r], [a, c, g, i, k, l, s], [a, c, g, i, k, m, r], [a, c, g, i, k, m, s], [a, c, g, i, k, n, r], [a, c, g, i, k, n, s], [a, d, e, h, j, l, r], [a, d, e, h, j, l, s], [a, d, e, h, j, m, r], [a, d, e, h, j, m, s], [a, d, e, h, j, n, r], [a, d, e, h, j, n, s], [a, d, e, h, k, l, r], [a, d, e, h, k, l, s], [a, d, e, h, k, m, r], [a, d, e, h, k, m, s], [a, d, e, h, k, n, r], [a, d, e, h, k, n, s], [a, d, e, i, j, l, r], [a, d, e, i, j, l, s], [a, d, e, i, j, m, r], [a, d, e, i, j, m, s], [a, d, e, i, j, n, r], [a, d, e, i, j, n, s], [a, d, e, i, k, l, r], [a, d, e, i, k, l, s], [a, d, e, i, k, m, r], [a, d, e, i, k, m, s], [a, d, e, i, k, n, r], [a, d, e, i, k, n, s], [a, d, f, h, j, l, r], [a, d, f, h, j, l, s], [a, d, f, h, j, m, r], [a, d, f, h, j, m, s], [a, d, f, h, j, n, r], [a, d, f, h, j, n, s], [a, d, f, h, k, l, r], [a, d, f, h, k, l, s], [a, d, f, h, k, m, r], [a, d, f, h, k, m, s], [a, d, f, h, k, n, r], [a, d, f, h, k, n, s], [a, d, f, i, j, l, r], [a, d, f, i, j, l, s], [a, d, f, i, j, m, r], [a, d, f, i, j, m, s], [a, d, f, i, j, n, r], [a, d, f, i, j, n, s], [a, d, f, i, k, l, r], [a, d, f, i, k, l, s], [a, d, f, i, k, m, r], [a, d, f, i, k, m, s], [a, d, f, i, k, n, r], [a, d, f, i, k, n, s], [a, d, g, h, j, l, r], [a, d, g, h, j, l, s], [a, d, g, h, j, m, r], [a, d, g, h, j, m, s], [a, d, g, h, j, n, r], [a, d, g, h, j, n, s], [a, d, g, h, k, l, r], [a, d, g, h, k, l, s], [a, d, g, h, k, m, r], [a, d, g, h, k, m, s], [a, d, g, h, k, n, r], [a, d, g, h, k, n, s], [a, d, g, i, j, l, r], [a, d, g, i, j, l, s], [a, d, g, i, j, m, r], [a, d, g, i, j, m, s], [a, d, g, i, j, n, r], [a, d, g, i, j, n, s], [a, d, g, i, k, l, r], [a, d, g, i, k, l, s], [a, d, g, i, k, m, r], [a, d, g, i, k, m, s], [a, d, g, i, k, n, r], [a, d, g, i, k, n, s]

Preferred embodiments of this invention are compounds wherein Z is any one of (o) to (q) and [($R^1$, $R^2$), ($R^3$, $R^4$), $R^5$, $R^6$, X, Y, ($R^B$, $R^C$)] is any one of the above combinations.

Preferable examples of $R^5$, $R^6$, $R^F$, $R^G$, $Q^1$, $T^1$, X, Y, and Z of the compound represented by the formula (V) are shown below as groups (a) to (r).

$R^5$ is (a) hydrogen atom, alkyloxy, alkylthio, or optionally substituted alkyl; (b) hydrogen atom or alkyl; and (c) hydrogen atom or C1 to C2 alkyl.

$R^3$ is (d) hydrogen atom or alkyl; and (e) hydrogen atom.

A preferable example of $R^F$ and $R^G$ is (f) ($R^B$, $R^C$) is (hydrogen atom, hydrogen atom), (hydrogen atom, alkyl), (alkyl, alkyl), or (hydrogen atom, alkyloxy); and (g) is (hydrogen atom, hydrogen atom), (hydrogen atom, alkyl), or (alkyl, alkyl).

$Q^1$ and $T^1$ are (h) $Q^1$ is —$NR^1R^2$ or —$SR^1$ wherein $R^1$ and $R^2$ are each independently hydrogen atom, optionally substituted alkyl, alkenyl, or alkynyl, $T^1$ is —$SR^3$ wherein $R^3$ is hydrogen atom, optionally substituted alkyl, alkenyl, or alkynyl; (i) $Q^1$ is —$NR^1R^2$ or —$SR^1$ wherein $R^1$ and $R^2$ are each independently hydrogen atom, alkyl optionally substituted with halogen, alkenyl, or alkynyl, $T^1$ is —$SR^3$ wherein $R^3$ is hydrogen atom, alkyl optionally substituted with halogen, alkenyl, or alkynyl; (j) $Q^1$ is —$NR^1R^2$ or —$SR^1$ wherein $R^1$ and $R^2$ are one is hydrogen atom and the other is C1 to C3 alkyl optionally substituted with halogen, $T^1$ is —$SR^3$ wherein $R^3$ is hydrogen atom or alkyl optionally substituted with halogen.

X is (k) —O— or —S—; and (l) —S—.

Y is (m) 5-membered heteroaryl-diyl; (n) 1,3,4-oxadiazole-2,5-diyl, 1,2,4-oxadiazole-3,5-diyl, 1,3,4-thiadiazole-2,5-diyl, or 1,2,4-thiadiazole-3,5-diyl; and (o) 1,3,4-oxadiazole-2,5-diyl.

Z is (p) optionally substituted aryl or optionally substituted heteroaryl; (q) optionally substituted phenyl or optionally substituted monocyclic heteroaryl; and (r) phenyl, pyridyl, thienyl, or furyl, which are substituted with 1 to 3 substituents selected from the group consisting of optionally substituted amino, halogen, alkyl, alkyloxy, acyl, phenyl, alkyloxycarbonyl, hydroxy, nitro, or haloalkyl.

A preferred group of compounds represented by the formula (V) is shown below. [$R^5$, $R^6$, ($R^F$, $R^G$), ($Q^1$, $T^1$), X, Y]=[a, d, f, h, k, m], [a, d, f, h, k, n], [a, d, f, h, k, o], [a, d, f, h, l, m], [a, d, f, h, l, n], [a, d, f, h, l, o], [a, d, f, i, k, m],

[a, d, f, i, k, n], [a, d, f, i, k, o], [a, d, f, i, l, m], [a, d, f, i, l, n], [a, d, f, i, l, o], [a, d, f, j, k, m], [a, d, f, j, k, n], [a, d, f, j, k, o], [a, d, f, j, l, m], [a, d, f, j, l, n], [a, d, f, j, l, o], [a, d, g, h, k, m], [a, d, g, h, k, n], [a, d, g, h, k, o], [a, d, g, h, l, m], [a, d, g, h, l, n], [a, d, g, h, l, o], [a, d, g, i, k, m], [a, d, g, i, k, n], [a, d, g, i, k, o], [a, d, g, i, l, m], [a, d, g, i, l, n], [a, d, g, i, l, o], [a, d, g, j, k, m], [a, d, g, j, k, n], [a, d, g, j, k, o], [a, d, g, j, l, m], [a, d, g, j, l, n], [a, d, g, j, l, o], [a, e, f, h, k, m], [a, e, f, h, k, n], [a, e, f, h, k, o], [a, e, f, h, l, m], [a, e, f, h, l, n], [a, e, f, h, l, o], [a, e, f, i, k, m], [a, e, f, i, k, n], [a, e, f, i, k, o], [a, e, f, i, l, m], [a, e, f, i, l, n], [a, e, f, i, l, o], [a, e, f, j, k, m], [a, e, f, j, k, n], [a, e, f, j, k, o], [a, e, f, j, l, m], [a, e, f, j, l, n], [a, e, f, j, l, o], [a, e, g, h, k, m], [a, e, g, h, k, n], [a, e, g, h, k, o], [a, e, g, h, l, m], [a, e, g h, l, n], [a, e, g, h, l, o], [a, e, g, i, k, m], [a, e, g, i, k, n], [a, e, g, i, k, o], [a, e, g, i, l, m], [a, e, g, i, l, n], [a, e, g, i, l, o], [a, e, g, j, k, m], [a, e, g, j, k, n], [a, e, g, j, k, o], [a, e, g, j, l, m], [a, e, g, j, l, n], [a, e, g, j, l, o], [b, d, f, h, k, m], [b, d, f, h, k, n], [b, d, f, h, k, o], [b, d, f, h, l, m], [b, d, f, h, l, n], [b, d, f, h, l, o], [b, d, f, i, k, m], [b, d, f, i, k, n], [b, d, f, i, k, o], [b, d, f, i, l, m], [b, d, f, i, l, n], [b, d, f, i, l, o], [b, d, f, j, k, m], [b, d, f, j, k, n], [b, d, f, j, k, o], [b, d, f, j, l, m], [b, d, f j, l, n], [b, d, f, j, l, o], [b, d, g, h, k, m], [b, d, g, h, k, n], [b, d, g, h, k, o], [b, d, g, h, l, m], [b, d, g, h, l, n], [b, d, g, h, l, o], [b, d, g, i, k, m], [b, d, g, i, k, n], [b, d, g, i, k, o], [b, d, g, i, l, m], [b, d, g, i, l, n], [b, d, g, i, l, o], [b, d, g, j, k, m], [b, d, g, j, k, n], [b, d, g, j, k, o], [b, d, g, j, l, m], [b, d, g, j, l, n], [b, d, g, j, l, o], [b, e, f, h, k, m], [b, e, f, h, k, n], [b, e, f, h, k, o], [b, e, f, h, l, m], [b, e, f, h, l, n], [b, e, f, h, l, o], [b, e, f, i, k, m], [b, e, f, i, k, n], [b, e f, i, k, o], [b, e, f, i, l, m], [b, e, f, i, l, n], [b, e, f, i, l, o], [b, e, f, j, k, m], [b, e, f, j, k, n], [b, e, f, j, k, o], [b, e, f, j, l, m], [b, e, f, j, l, n], [b, e, f, j, l, o], [b, e, g, h, k, m], [b, e, g, h, k, n], [b, e, g, h, k, o], [b, e, g, h, l, m], [b, e, g, h, l, n], [b, e, g, h, l, o], [b, e, g, i, k, m], [b, e, g, i, k, n], [b, e, g, i, k, o], [b, e, g, i, l, m], [b, e, g, i, l, n], [b, e, g, i, l, o], [b, e, g, j, k, m], [b, e, g, j, k, n], [b, e, g, j, k, o], [b, e, g, j, l, m], [b, e, j, l, n], [b, g, j, l, o], [c, d, f, h, k, m], [c, d, f, h, k, n], [c, d, f, h, k, o], [c, d, f, h, l, m], [c, d, f, h, l, n], [c, d, f, h, l, o], [c, d, f, i, k, m], [c, d, f, i, k, n], [c, d, f, i, k, o], [c, d, f, i, l, m], [c, d, f, i, l, n], [c, d, f, i, l, o], [c, d, f, j, k, m], [c, d, f, j, k, n], [c, d, f, j, k, o], [c, d, f, j, l, m], [c, d, f, j, l, n], [c, d, f, j, l, o], [c, d, g, h, k, m], [c, d, g, h, k, n], [c, d, g, h, k, o], [c, d, g, h, l, m], [c, d, g, h, l, n], [c, d, g, h, l, o], [c, d, g, i, k, m], [c, d, g, i, k, n], [c, d, g, i, k, o], [c, d, g, i, l, m], [c, d, g, i, l, n], [c, d, g, i, l, o], [c, d, g, j k, m], [c, d, g, j, k, n], [c, d, g, j, k, o], [c, d, g, j, l, m], [c, d, g, j, l, n], [c, d, g, j, l, o], [c, e, f, h, k, m], [c, e, f, h, k, n], [c, e, f, h, k, o], [c, e, f, h, l, m], [c, e, f, h, l, n], [c, e, f, h, l, o], [c, e, f, i, k, m], [c, e, f, i, k, n], [c, e, f, i, k, o], [c, e, f, i, l, m], [c, e f, i, l, n], [c, e, f, i, l, o], [c, e, f, j, k, m], [c, e, f, j, k, n], [c, e, f, j, k, o], [c, e, f, j, l, m], [c, e, j, l, n], [c, e, f, j, l, o], [c, e, g, h, k, m], [c, e, g, h, k, n], [c, e, g, h, k, o], [c, e, g, h, l, m], [c, e, g, h, l, n], [c, c, g, h, l, o], [c, e, g, i, k, m], [c, e, g i, k, n], [c, e, g, i, k, o], [c, e, g, i, l, m], [c, e, g, i, l, n], [c, e, g, i, l, o], [c, e, g, j, k, m], [c, e, g, j, k, n], [c, e, g, j, k, o], [c, e, g, j, l, m], [c, e, g, j, l, n], [c, e, g, j, l, o]

Preferred embodiments of this invention are compounds wherein Z is any one of (p) to (r) and [$R^5$, $R^6$, ($R^F$, $R^G$), ($Q^1$, $T^1$), X, Y] is any one of the above combinations.

In this specification, the compounds represented by the formula (I) may be represented by the below formula.

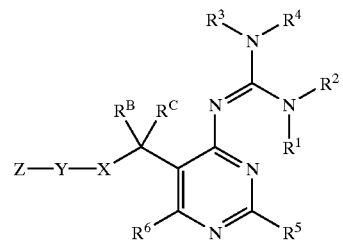

The compounds represented by the formula (II), (III), and (IV) are as well as the above.

In this specification, a compound of formula (I) wherein $R^1$ is hydrogen atom may be represented as an isomer of the formula (IX).

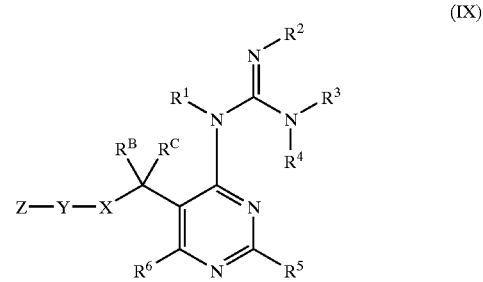

(IX)

wherein $R^2$, $R^3$, $R^4$, $R^5$, $R^6$, $R^B$, $R^C$, X, Y, and Z are as defined above; $R^1$ is hydrogen atom.

The compounds represented by the formula (II), (III), and (IV) are as well as the above.

In this specification, a compound of formula (V) wherein $T^1$ is —$SR^3$ wherein $R^3$ is hydrogen atom may be represented as an isomer of the formula (X). The compounds wherein $T^1$ is —$OR^3$ wherein $R^3$ is hydrogen atom are as well as the above.

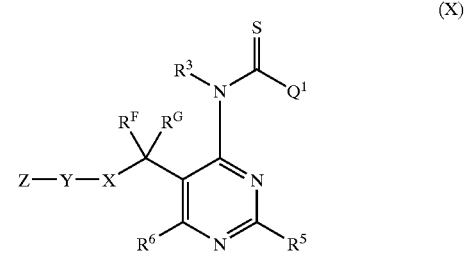

(X)

wherein $R^5$, $R^6$, $R^F$, $R^G$, $Q^1$, X, Y, and Z are as defined above; $R^3$ is hydrogen atom.

The compounds represented by the formulae (VI), (VII), and (VIII) are as well as the above.

In this specification, according to alkylation conditions for synthesis of the compounds (V) wherein $T^1$ is —$SR^3$ wherein $R^3$ is alkyl, the compounds represented by the formula (X) may be obtained. The compounds wherein $T^1$ is —$OR^3$ wherein $R^3$ is alkyl are as well as the above.

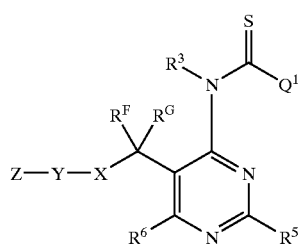

(X)

wherein $R^5$, $R^6$, $R^F$, $R^G$, $Q^1$, X, Y, and Z are as defined above; $R^3$ is alkyl.

The compounds represented by the formulae (VI), (VII), and (VIII) are as well as the above.

In this specification, the compounds of formula (I) wherein $R^B$ and $R^C$ are different, are represented as an optical active compound by the formulae (I') and (I").

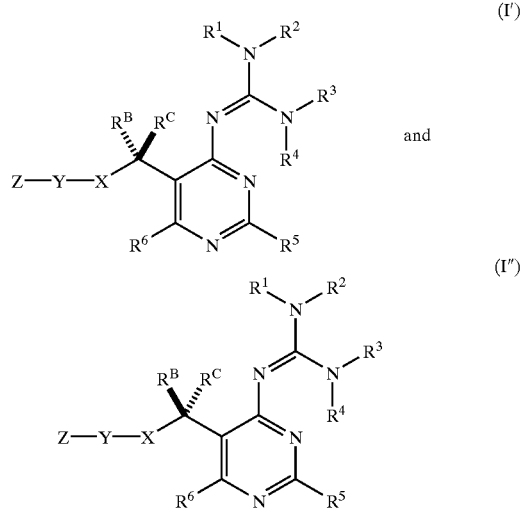

(I')

and (I")

wherein $R^1$, $R^2$, $R^3$, $R^4$, $R^5$, $R^6$, $R^B$, $R^C$, X, Y, and Z are as defined above.

The compounds represented by the formulae (II), (III), (IV), (V), (VI), (VII), and (VIII) are as well as the above.

BEST MODE FOR CARRYING OUT THE INVENTION

The compounds of the present invention represented by the formulae (I), (V), or (XIII) can be synthesized by the well-known methods described in a literature of chemistry. A summary of the useful methods for synthesis of the compounds of the present invention is shown below.
(Synthetic Method)

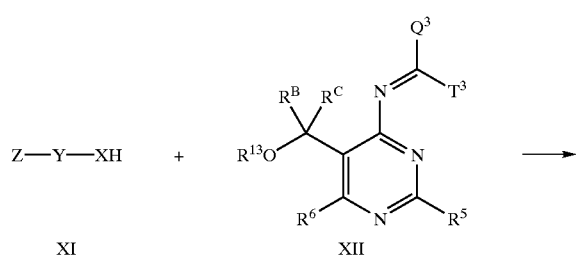

XI      XII

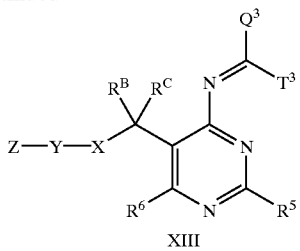

XIII wherein $R^5$, $R^6$, $R^B$, $R^C$, X, Y, and Z are as defined above; $R^{13}$ is a protective group of a hydroxy group such as methyl, ethyl, trimethylsilyl, and tert-butyldimethylsilyl or hydrogen atom; $Q^3$ is —$NR^1R^2$, —$OR^1$, or —$SR^1$; $T^3$ is —$NR^3R^4$, —$OR^1$, or —$SR^1$ wherein $R^1$, $R^2$, $R^3$, and $R^4$ are as defined above.

The compound represented by the formula (XIII) can be synthesized by reacting Z—Y—XH (XI) with the pyrimidine derivatives (XII) mentioned later such as (XII-1) to (XII-4). The pyrimidine derivatives (XII) in a solvent such as water, acetic acid, and pyridine are treated with a hydrohalogenic acid such as hydrochloric acid and hydrobromic acid to give hydrogen halide salts of 5-halogenomethylpyrimidine. When $R^{13}$ is hydrogen atom, a halogenation agent such as thionyl halide and phosphorous halide can be used. The obtained salts and Z—Y—XH (XI) in a solvent such as water, methanol, ethanol, N,N-dimethylformamide, dimethylsulfoxide, and tetrahydrofuran are reacted with an appropriate base, for example an inorganic base such as sodium hydroxide, potassium butoxide, sodium hydride, potassium hydride, and potassium carbonate or an organic base such as triethylamine, pyridine, and diisopropylethylamine at −20° C. to 100° C., preferably 0° C. to 30° C. for 1 min to 24 h, preferably 10 min to 12 h to give the aimed compound (XIII).

Compound (XI) and compound (XII) can be synthesized by the methods A to I and the methods J to N as shown below.

In the methods A to I, Z represents optionally substituted aryl or optionally substituted heteroaryl. The starting material of each method is commercially available or can be synthesized by well-know method from the compound which is commercially available.

Method A: Synthetic method of the compound wherein Y is an oxadiazole ring and X is —S—.

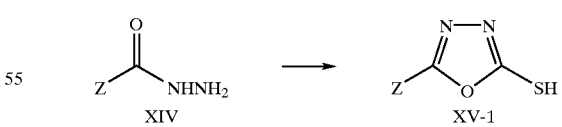

XIV      XV-1 wherein Z is above defined.

Compound (XIV) in a solvent such as ethanol and benzene is reacted with carbon disulfide and a base such as triethylamine, sodium hydroxide, and potassium carbonate at 0° C. to 100° C., preferably 60° C. to 100° C. for 10 min to 24 h, preferably 2 h to 12 h to give compound (XV-1).

Method B: Synthetic method of the compound wherein Y is an oxadiazole ring and X is —O—.

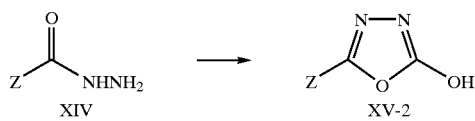

wherein Z is above defined.

To a solution of compound (XIV) in a solvent such as tetrahydrofuran and toluene, is added carbonyldiimidazole, and the mixture is reacted at 0° C. to 120° C., preferably 60° C. to 120° C. for 10 min to 24 h, preferably 2 h to 12 h to give compound (XV-2).

Method C: Synthetic method of the compound wherein Y is an oxadiazole ring and X is —N(R$^7$)—.

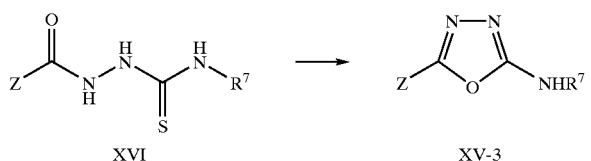

wherein Z is as defined above and R$^7$ is as defined above.

To a solution of compound (XVI) in a solvent such as ethanol and tetrahydrofuran, is added mercury oxide, and the mixture is reacted at 0° C. to 120° C., preferably 30° C. to 80° C. for 0.5 h to 24 h, preferably 1 h to 24 h to give compound (XV-3).

Method D: Synthetic method of the compound wherein Y is a thiadiazole ring and X is —S—.

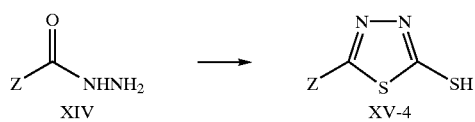

wherein Z is as defined above.

To a solution of compound (XIV) in a solvent such as ethanol and tetrahydrofuran are added carbon disulfide and a base such as triethylamine and sodium hydroxide and the mixture is reacted at 0° C. to 100° C., preferably 20° C. to 60° C. for 0.5 h to 24 h, 1 h to 12 h. After the solvent is removed, the residue is reacted with conc. sulfuric acid at −20° C. to 40° C., preferably 0° C. to 20° C. for 1 min to 12 h, preferably 10 min to 1 h to give compound (XV-4).

Method E: Synthetic method of the compound wherein Y is a furan ring and X is —S—.

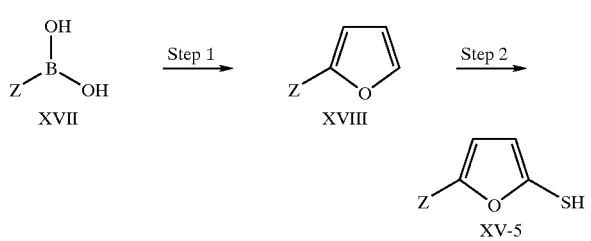

wherein Z is as defined above.
(Step 1)

Halogenated furan such as 2-bromofuran is reacted with compound (XVII) in a solvent such as N,N-dimethylformamide, toluene, xylene, benzene, tetrahydrofuran, and ethanol in the presence of palladium catalyst such as Pd(Ph$_3$P)$_4$ and a base such as potassium carbonate, calcium carbonate, triethylamine, and sodium methoxide to give the aimed compound (XVIII) (Suzuki reaction). The reaction temperature is room temperature to 100° C., preferably room temperature to 80° C. and the reaction time is 5 to 50 h, preferably 15 to 30 h.
(Step 2)

To a solution of compound (XVIII) in a solvent such as tetrahydrofuran, diethyl ether, and toluene is added a base such as n-butyllithium and sec-butyllithium, and the mixture is stirred at −100° C. to 50° C., preferably −80° C. to 0° C. for 1 min to 24 h preferably 10 min to 60 min. To the mixture is added sulfur, and the resulting mixture is reacted at −100° C. to 50° C., preferably −80° C. to 0° C. for 1 h to 24 h, preferably 1 h to 12 h to give the aimed compound (XV-5).

Method F: Synthetic method of the compound wherein Y is a thiophene ring and X is —S—.

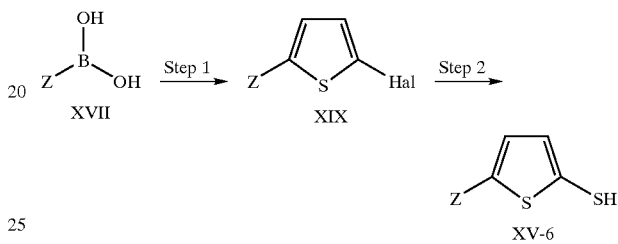

wherein Z is as defined above and Hal is halogen.

The steps 1 and 2 can be carried out in a manner similar to those described in step 1 and 2 of Method E.

Method G: Synthetic method of the compound wherein Y is an oxazole ring and X is —S—.

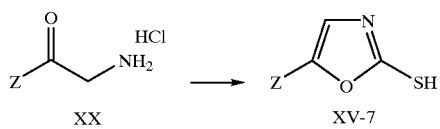

wherein Z is as defined above.

To a solution of compound (XX) in a solvent such as dichloromethane, toluene, and diethyl ether is added thiophosgene in the presence of a base such as triethylamine and sodium hydroxide and the mixture is reacted at −20° C. to 100° C., preferably 0° C. to 40° C. for 1 h to 48 h, preferably 1 h to 24 h to give compound (XV-7).

Method H: Synthetic method of the compound wherein Y is an oxazole ring and X is —O— or —S—.

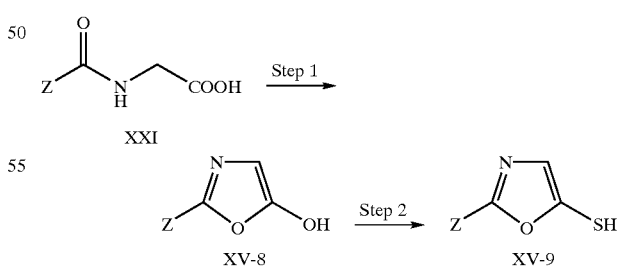

wherein Z is as defined above.
(Step 1)

Compound (XXI) in a solvent such as dichloromethane and acetonitrile is reacted with a coupling reagent such as dicyclohexylcarbodiimide at −20° C. to 50° C., preferably 0° C. to 20° C. for 5 min to 24 h, preferably 10 min to 2 h to give compound (XV-8).

(Step 2)

To a solution of compound (XV-8) in a solvent such as toluene and dioxane is added Lawesson's reagent, and the mixture is reacted at 60° C. to 150° C., preferably 80° C. to 120° C. for 1 h to 24 h, preferably 2 to 12 h to give compound (XV-9).

Method I: Synthetic method of the compound wherein Y is an isooxazole ring and X is —O— or —S—.

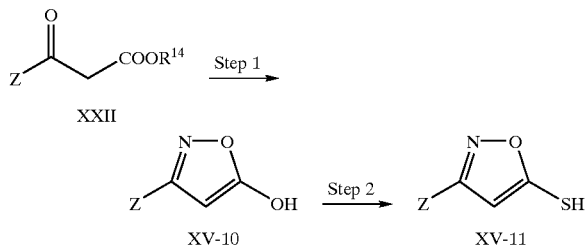

wherein Z is as defined above and $R^{14}$ is C1 to C3 alkyl.

(Step 1)

Compound (XXII) in a solvent such as methanol and tetrahydrofuran is reacted with hydroxylamine at 20° C. to 100° C., preferably 50° C. to 80° C. for 1 h to 24 h, preferably 2 h to 12 h to give compound (XV-10).

(Step 2)

Compound (XV-11) can be obtained in a manner similar to that described in step 2 of Method H.

The compounds which are not concretely shown in the above methods can be synthesized by a combination of the above methods A to I and well-know methods.

In the methods J to N, $R^5$, $R^6$, $R^{13}$, $Q^3$, and $T^3$ (wherein $R^1$, $R^2$, $R^3$, and $R^4$ are as defined above) are as defined above. The starting material of each method is commercially available or can be synthesized by well-know methods from the compound which is commercially available.

Methods J and K are processes for construction of a pyrimidine ring, and can be carried out in accordance with well-known methods (see Journal of Chemical Society, 1937, p-364, ibid., 1943, p-388 and J. Pharm. Soc. Japan 1954, p-742).

Methods L to N are processes for introduction a guanidino group to the pyrimidine derivative obtained in the Method J and Method K, and can be carried out in accordance with well-known methods (see Journal of Chemical Society, 1948, p-581, ibid., 1946, p-1063 and Synthesis, 1988, p-460).

Method J-1: Synthesis of a pyrimidine ring wherein both $R^X$ and $R^Y$ are hydrogen atom.

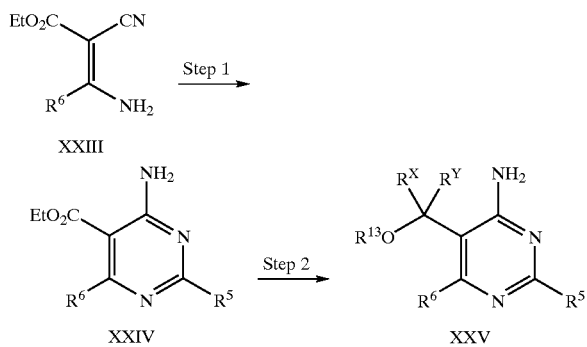

wherein $R^5$, $R^6$ and $R^{13}$ are as defined above; and $R^X$ and $R^Y$ are hydrogen atom.

(Step 1)

Compound (XXIII) in a solvent such as ethanol, tetrahydrofuran, and N,N-dimethylformamide is reacted with $R^5$—C(=S)—$NH_2$ in the presence of a base such as sodium ethylate and sodium hydroxide at 0° C. to 150° C., preferably 60° C. to 100° C. for 0.5 h to 48 h, preferably 1 h to 12 h to give compound (XXIV).

(Step 2)

Compound (XXIV) in a solvent such as ether and tetrahydrofuran or in a mixed solvent such as ether-tetrahydrofuran is reacted with a reducing agent such as lithium aluminum hydride and lithium borohydride at −80° C. to 100° C., preferably −20° C. to 40° C. for 0.5 h to 24 h, preferably 1 h to 12 h to give an alcohol derivative. The obtained alcohol derivative is protected by the method described in Protective Groups in Organic Synthesis, Theodora W Green (John Wiley & Sons) and the like, to give compound (XXV).

Method J-2: Synthesis of a pyrimidine ring wherein one of $R^X$ and $R^Y$ is hydrogen atom.

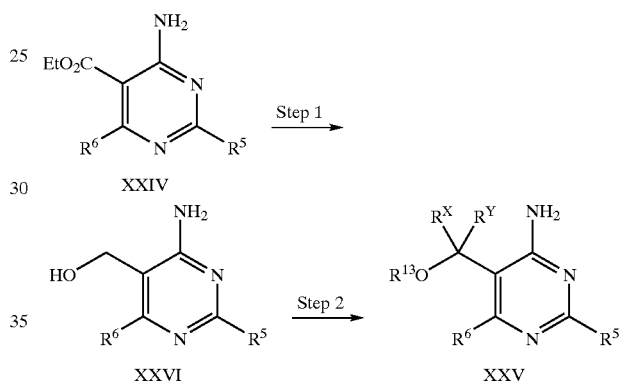

wherein $R^5$, $R^6$ and $R^{13}$ are as defined above; $R^X$ is alkyl; and $R^Y$ are hydrogen atom or alkyl.

(Step 1)

Compound (XXIV) in a solvent such as ether and tetrahydrofuran or in a mixed solvent such as ether-tetrahydrofuran is reacted with a reducing agent such as lithium aluminum hydride and lithium borohydride at −80° C. to 100° C., preferably −20° C. to 40° C. for 0.5 h to 24 h, preferably 1 h to 12 h to give compound (XXVI).

(Step 2)

Compound (XXVI) in a solvent such as dichloromethane and chloroform is reacted with a oxidizing agent such as manganese dioxide, pyridinium dichromate, and pyridinium chlorochromate at −20° C. to 100° C., preferably 0° C. to 40° C. for 0.5 h to 14 days, preferably 1 h to 7 days to give an aldehyde derivative. The obtained aldehyde derivative in a solvent such as ether and tetrahydrofuran or in a mixed solvent such as ether-tetrahydrofuran is reacted with Grignard reagent such as $R^X$MgBr or organometallic reagent such as $R^X$Li at −80° C. to 100° C., preferably −20° C. to 40° C. for 0.5 h to 24 h, preferably 1 h to 12 h to give an alcohol derivative. The obtained alcohol derivative is protected by the method described in Protective Groups in Organic Synthesis, Theodora W Green (John Wiley & Sons) and the like, to give compound (XXV).

Method J-3: Synthesis of a pyrimidine ring wherein both of $R^X$ and $R^Y$ are not hydrogen atom.

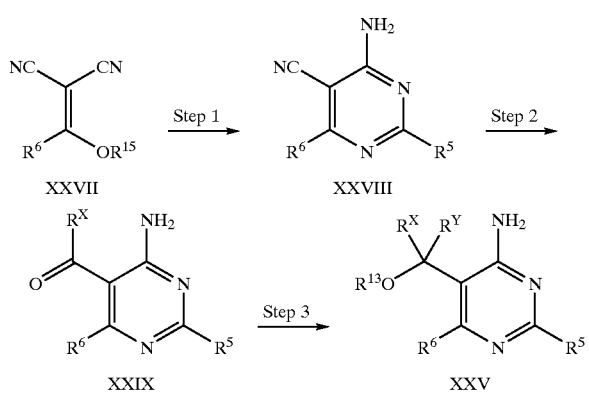

wherein $R^5$, $R^6$ and $R^{13}$ are as defined above; $R^X$ and $R^Y$ are each independently alkyl or alkyloxy; $R^{15}$ is alkyl such as methyl and ethyl.

(Step 1)

Compound (XXVII) in a solvent such as ethanol, tetrahydrofuran, and N,N-dimethylformamide is reacted with $R^5$—C(=N)—NH$_2$ in the presence of a base such as sodium ethylate and sodium hydroxide, at 0° C. to 150° C., preferably 60° C. to 100° C. for 0.5 h to 48 h, preferably 1 h to 12 h to give compound (XXVIII).

(Step 2)

Compound (XXVIII) in a solvent such as ether and tetrahydrofuran or in a mixed solvent such as ether-tetrahydrofuran is reacted with Grignard reagent such as $R^X$MgBr or organometallic reagent such as $R^X$Li at −80° C. to 100° C., preferably −20° C. to 40° C. for 0.5 h to 24 h, preferably 1 h to 12 h. To the mixture an acid aqueous solution such as hydrochloric acid and sulfuric acid is added, and then the resulting mixture is stirred at −20° C. to 100° C., preferably 0° C. to 40° C. for 0.5 h to 24 h, preferably 1 h to 12 h to give compound (XXIX).

(Step 3)

Compound (XXIX) in a solvent such as ether and tetrahydrofuran or in a mixed solvent such as ether-tetrahydrofuran is reacted with Grignard reagent such as $R^X$MgBr or organometallic reagent such as $R^X$Li at −80° C. to 100° C., preferably −20° C. to 40° C. for 0.5 h to 24 h, preferably 1 h to 12 h to give an alcohol derivative. The obtained alcohol derivative is protected by the method described in Protective Groups in Organic Synthesis, Theodora W Green (John Wiley & Sons) and the like, to give compound (XXX).

Method J-4: Synthesis of a pyrimidine ring wherein $R^X$ and $R^Y$ are same.

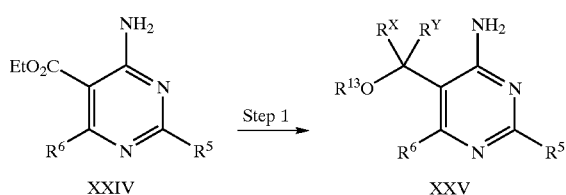

wherein $R^5$, $R^6$ and $R^{13}$ are as defined above; $R^X$ and $R^Y$ are same as alkyl or alkyloxy.

(Step 1)

Compound (XXIV) in a solvent such as ether and tetrahydrofuran or in a mixed solvent such as ether-tetrahydrofuran is reacted with Grignard reagent such as $R^X$MgBr or organometallic reagent such as $R^X$Li at −80° C. to 100° C., preferably −20° C. to 40° C. for 0.5 h to 24 h, preferably 1 h to 12 h to give an alcohol derivative. The obtained alcohol derivative is protected by the method described in Protective Groups in Organic Synthesis, Theodora W Green (John Wiley & Sons) and the like to give compound (XXV).

Method J-5: Synthesis of a pyrimidine ring wherein one of $R^X$ and $R^Y$ is hydrogen atom.

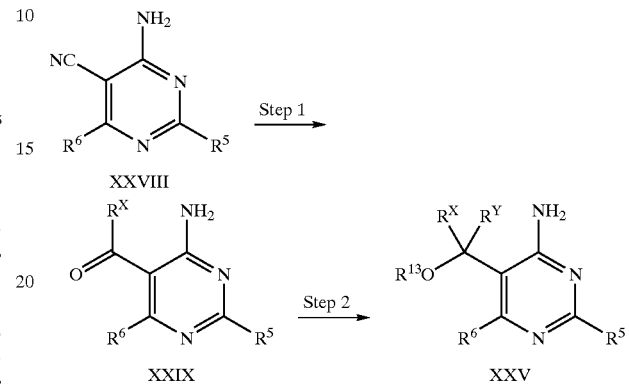

wherein $R^5$, $R^6$ and $R^{13}$ are as defined above; one of $R^X$ and $R^Y$ is hydrogen atom and the other is hydrogen atom, alkyl or alkyloxy.

(Step 1)

Compound (XXVIII) in a solvent such as ether and tetrahydrofuran or a mixed in solvent such as ether-tetrahydrofuran is reacted with Grignard reagent such as $R^X$MgBr or organometallic reagent such as $R^X$Li at −80° C. to 100° C., preferably −20° C. to 40° C. for 0.5 h to 24 h, preferably 1 h to 12 h. To the mixture an acid aqueous solution such as hydrochloric acid and sulfuric acid is added, and then the resulting mixture is stirred at −20° C. to 100° C., preferably 0° C. to 40° C. for 0.5 h to 24 h, preferably 1 h to 12 h to give compound (XXIX).

(Step 2)

Compound (XXIX) in a solvent such as ether, tetrahydrofuran, methanol, and ethanol or their mixed solvent is reacted with a reducing agent such as sodium borohydride, lithium borohydride, and lithium aluminum hydride at −80° C. to 100° C., preferably −20° C. to 40° C. for 0.5 h to 24 h, preferably 1 h to 12 h to give an alcohol derivative. The obtained alcohol derivative is protected by the method described in Protective Groups in Organic Synthesis, Theodora W Green (John Wiley & Sons) and the like to give compound (XXV).

Method K: Synthesis of a pyrimidine ring.

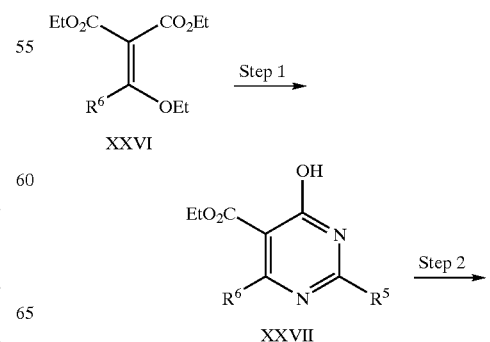

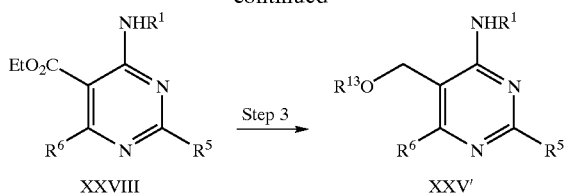

wherein $R^1$, $R^5$, $R^6$ and $R^{13}$ are as defined above.

(Step 1)

Compound (XXVI) in a solvent such as ethanol, tetrahydrofuran, and N,N-dimethylformamide is reacted with $R^5$—C(=NH)—$NH_2$ or its salt in the presence of a base such as sodium ethylate and sodium hydroxide at 0° C. to 150° C., preferably 60° C. to 100° C. for 0.5 h to 48 h, preferably 1 h to 12 h to give compound (XXVII) or its salt.

(Step 2)

Compound (XXVII) or its salt in a solvent such as toluene and dichloroethane or without solvent is reacted with a halogenating reagent such as thionyl chloride and phosphorus oxychloride at 0° C. to 150° C., preferably 60° C. to 120° C. for 0.5 h to 12 h, preferably 1 h to 5 h to give a halogenated compound. The obtained halogenated compound in a solvent such as ethanol and tetrahydrofuran is reacted with $R^1NH_2$ at −80° C. to 100° C., preferably −20° C. to 30° C. for 0.5 h to 48 h, preferably 1 h to 12 h to give compound (XXVIII).

(Step 3)

This step can be carried out in a manner similar to that described in step 2 of Method J-1.

Method L: Introduction of a guanidino group

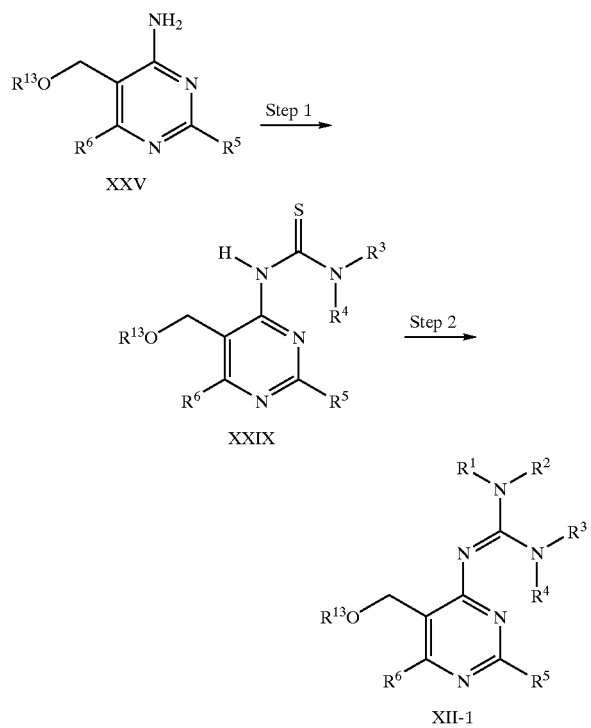

wherein $R^1$, $R^2$, $R^3$, $R^4$, $R^5$, $R^6$ and $R^{13}$ are as defined above.

(Step 1)

Compound (XXV) in a solvent such as N,N-dimethylformamide, pyridine, and tetrahydrofuran is reacted with $R^3$—NCS or $R^3R^4$NCS-Hal wherein Hal is halogen, in the presence or absence of a base such as sodium hydride at −20° C. to 120° C., preferably 0° C. to 120° C. for 0.5 h to 48 h, preferably 1 h to 24 h to give compound (XXIX).

(Step 2)

To a solution of compound (XXIX) in a solvent such as methanol and tetrahydrofuran are added a heavy metal salt or heavy metal oxide such as HgO and $R^1R^2$NH, and the mixture is reacted at −20° C. to 100° C., preferably 0° C. to 50° C. for 0.5 h to 48 h, preferably 1 h to 12 h to give compound (XII-1).

Method M: Introduction of a guanidino group

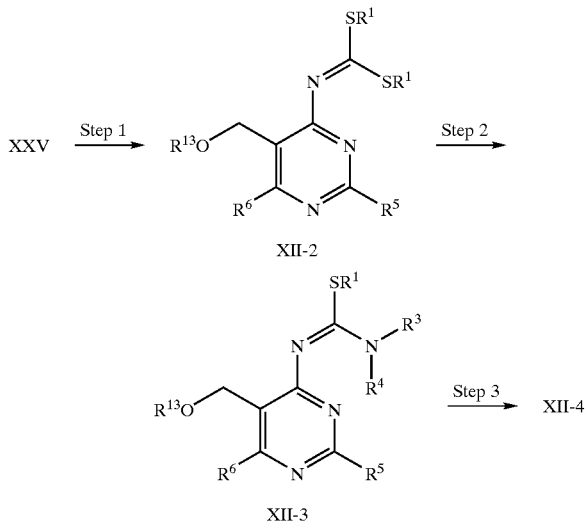

wherein $R^1$, $R^3$, $R^4$, $R^5$, $R^6$ and $R^{13}$ are as defined above.

(Step 1)

To a solution of compound (XXV) in a solvent such as N,N-dimethylformamide and tetrahydrofuran in the presence of a base such as sodium hydride and potassium butoxide added carbon disulfide and then alkylating reagent such as $R^1$I and $R^1_2SO_4$, and the mixture is reacted at 0° C. to 100° C., preferably 20° C. to 60° C. for 0.5 h to 48 h, preferably 1 h to 12 h to give compound (XII-2).

(Step 2)

Compound (XII-2) in a solvent such as methanol and N,N-dimethylformamide is reacted with $R^3R^4$NH at 0° C. to 150° C., preferably 0° C. to 100° C. for 0.5 h to 48 h, preferably 1 h to 12 h to give compound (XII-3).

(Step 3)

Compound (XII-3) in a solvent such as methanol and N,N-dimethylformamide is reacted with $R^1R^2$NH at 20° C. to 150° C., preferably 40° C. to 80° C. for 0.5 h to 48 h, preferably 4 h to 24 h to give compound (XII-4).

Method N: Introduction of a guanidino group wherein $R^1$ is not hydrogen atom.

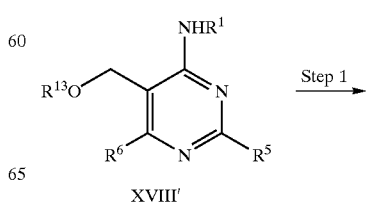

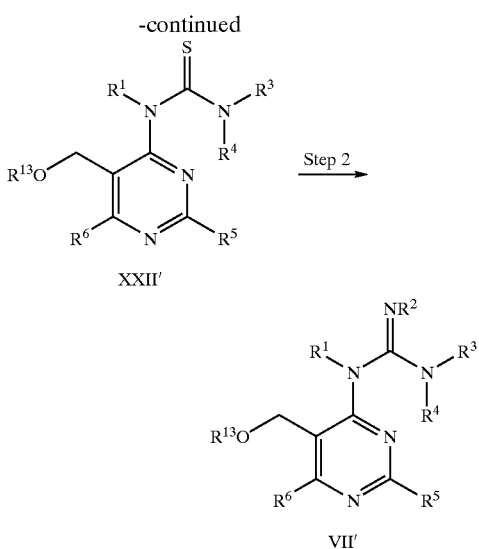

XXII'

VII' wherein $R^1$, $R^2$, $R^3$, $R^4$, $R^5$, $R^6$ and $R^{13}$ are as defined above.

(Step 1)

This step can be carried out in a manner similar to that described in step 1 of Method L.

(Step 2)

This step can be carried out in a manner similar to that described in step 2 of Method L.

When a compound contains a functional group(s) possibly interfering the reaction such as hydroxy, mercapto, and amino group in the each step of Method A to Method N, it can previously be protected and deprotected at an appropriate stage by the method described Protective Groups in Organic Synthesis, Theodora W. Green (John Wiley & Sons).

The term "the compounds of the present invention" herein used includes pharmaceutically acceptable salts and hydrates of the compounds. For example, salts with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g., acetic acid, citric acid, maleic acid, fumaric acid, benzenesulfonic acid, and p-toluenesulfonic acid) are exemplified. These salts can be formed by usual methods. The hydrates may coordinate with an arbitrary number of water molecule.

The compounds of the present invention is not restricted to any particular isomers but includes all possible isomers and racemate.

The compounds of the present invention have an inhibitory activity against a signal derived from Ras oncogene products as shown in the experimental examples below.

Consequently, the compounds of the present invention can be used as a therapeutic agent for cancer, preferably solid tumor such as pancreatic cancer, colon cancer, and lung cancer.

When the compounds of this invention is administered to a patient for the treatment of the above diseases, they can be administered by oral administration such as powder, granules, tablets, capsules, pilulae, liquid medicine, or the like, or by parenteral administration such as injections, suppository, percutaneous formulations, insufflation, or the like. An effective amount of the compound of this invention is formulated by being mixed with appropriate medicinal admixture such as excipient, binder, penetrant, disintegrators, lubricant, and the like, if necessary. When parenteral injection is prepared, the compound of this invention and an appropriate carrier are sterilized to formulate.

An appropriate dosage varies with the conditions of the patients, an administration route, their age, and their body weight. In the case of oral administration to an adult, the dosage can generally be between 0.01–100 mg/kg/day, preferably 0.1–20 mg/kg/day.

The following examples are provided to further illustrate the present invention and are not to be construed as limiting the scope thereof.

In the examples, the following abbreviations are used.

Me: methyl
Et: ethyl
Pr: n-propyl
i-Pr: isopropyl
Bu: n-butyl
DMF: dimethylformamide
THF: tetrahydrofuran
DMSO: dimethylsulfoxide
TBS: tert-butyldimethylsilyl
TBDPS; tert-butyldiphenylsilyl In $^1$H-NMR, the value of δ is represented by ppm, s is singlet, d is doublet, t is triplet, q is quartet, quit is quintet, sext is sextet, and br is broad. The value of J is represented by Hz.

EXAMPLE

Example 1

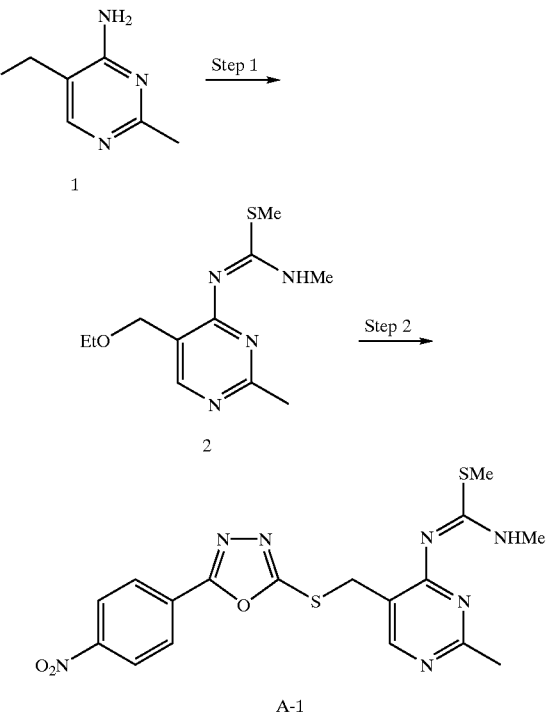

Step 1

To a solution of potassium t-butoxide (8.05 g) in 60 ml of DMF was added dropwise a solution of compound 1 (10.0 g) which was obtained by well-known method (M. Tomita, S. Uyeo, A. Takamizawa and R. Maeda, Yakugakuzasshi, 74, 742 (1954)), in 29 ml of DMF with stirring at ice-cooling. The reaction mixture was allowed to room temperature and stirred for 1 h. To the resulting mixture was added a solution of methylisothiocyanate (5.25 g) in 7.5 ml of DMF at ice-cooling and stirred for 2 h at room temperature. After confirming the disappearance of compound 1, a solution of methyl iodide (12.7 g) in 1.5 ml of DMF was added to the mixture at ice-cooling. The mixture was stirred for 1 h at room temperature and DMF was removed under reduced pressure, and then water was added to the residue. The mixture was extracted with diethyl ether, washed with brine, dried over anhydrous magnesium sulfate, and concentrated under reduced pressure. The residue was subjected to silica gel column chromatography to give 8.15 g of compound 2.

$^1$H-NMR(CDCl$_3$): 1.26(3H, t, J=6.9 Hz), 2.52(3H, s), 2.56(3H, s), 3.07(3H, d, J=5.3 Hz), 3.60(2H, q, J=6.9 Hz), 4.61(2H, s), 8.41(1H, s).

Step 2

A solution of compound 2 (2.50 g) in 25 ml of 25% hydrobromic acid/acetic acid was reacted for 7 h at 70° C. The solvent was removed under reduced pressure, and the residue was dissolved in 10 ml of DMF. The resulting mixture was added to a suspension of 2-(4-nitrophenyl)-5-mercapto-1,3,4-oxadiazole (2.41 g) which was obtained in similar to described (R. W. Young and K. H. Wood. J. Am. Chem. Soc., 77, 400 (1955)) and potassium carbonate (5.43 g) in 25 ml of DMF. The reaction mixture was stirred for 1 h at room temperature and added water. The appeared crystal was filtered to give 2.56 g of compound A-1. The physical data was shown in Table 1.

Example 2 to 17

Compounds A-2 to A-17 were synthesized in a manner similar to described in Example 1. The physical data were shown in Tables 1 to 2.

Example 18

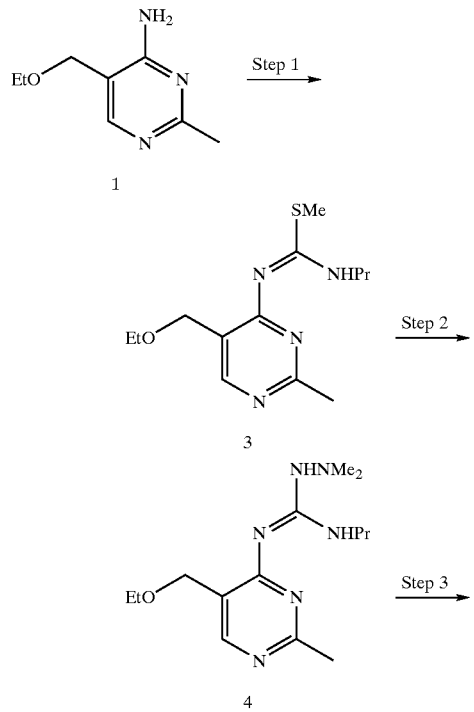

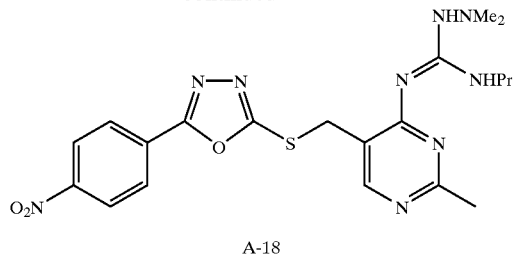

A-18

Step 1

To a solution of potassium t-butoxide (3.43 g) in 30 ml of DMF was added dropwise a solution of compound 1 (4.64 g) in 12 ml of DMF with stirring at ice-cooling. The reaction mixture was allowed to room temperature and stirred for 30 min. To the resulting mixture was added dropwise a solution of propylisothiocyanate (3.09 g) in 3 ml of DMF at ice-cooling and stirred for 1.5 h at room temperature. After confirming the disappearance of compound 1, a solution of methyl iodide (5.91 g) in 3 ml of DMF was added to the mixture at ice-cooling. The mixture was stirred for 1 h at room temperature. DMF was removed under reduced pressure and added water. The resulting mixture was extracted with diethyl ether, washed with brine, dried over anhydrous magnesium sulfate, and concentrated under reduced pressure. To the residue was added hexane, the appeared crystal was filtered to give 2.25 g of compound 3.

$^1$H-NMR(CDCl$_3$): 1.06(3H, t, J=7.3 Hz), 1.27(3H, t, J=7.3 Hz), 1.71(2H, sext, J=7.3 Hz); 2.51(3H, s), 2.55(3H, s), 3.35(2H, q, J=7.3 Hz), 3.60(2H, q, J=7.3 Hz), 4.61 (2H, s), 8.41(1H, s), 11.31(1H, br).

Step 2

A solution of compound 3 (0.10 g) and dimethylhydrazine (0.43 g) in 2 ml of ethanol was stirred for 3 days at 65° C. The reaction mixture was concentrated under reduced pressure, and the residue was subjected to silica gel column chromatography to give 0.03 g of compound 4.

$^1$H-NMR(CDCl$_3$): 0.96(3H, t, J=7.3 Hz), 1.26(3H, t, J=7.3 Hz), 1.62(2H, sext, J=7.3 Hz), 2.50(3H, s), 2.61(6H, s), 3.37(2H, q, J=7.3 Hz), 3.60(2H, q, J=7.3 Hz), 4.53(2H, s), 6.25(1H, br), 8.21(1H, s), 10.94(1H, br).

Step 3

A solution of compound 4 (0.03 g) in 0.3 ml of 25% hydrobromic acid in acetic acid was reacted for 7 h at 70° C. The solvent was removed under reduced pressure, and the residue was dissolved in 1 ml of DMF. The resulting mixture was added to a suspension of 2-(4-nitrophenyl)-5-mercapto-1,3,4-oxadiazole (0.03 g) and potassium carbonate (0.06 g) in 2 ml of DMF. The reaction mixture was stirred for 1 h at ice-cooling and added water. The appeared crystal was filtered and recrystalized from ethyl acetate/hexane to give 0.02 g of compound A-18. The physical data were shown in Table 2.

Example 19

Compounds A-19 was synthesized in a manner similar to described in Example 18. The physical data were shown in Table 3.

Example 20

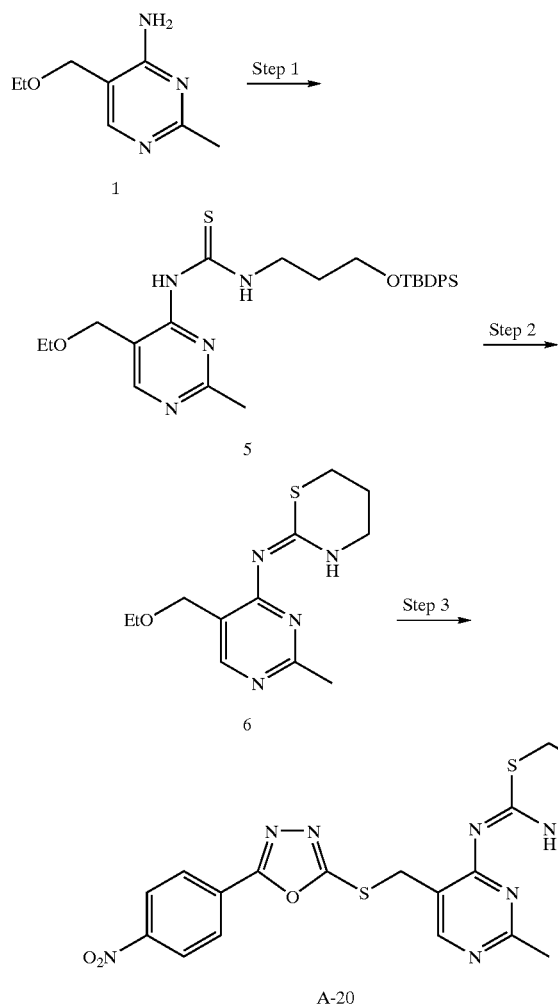

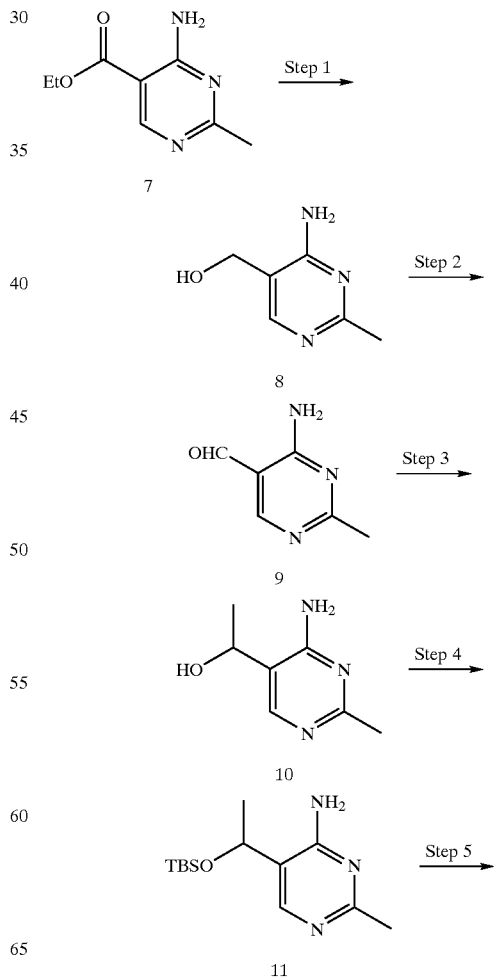

Step 1

To a solution of potassium t-butoxide (0.73 g) in 15 ml of DMF was added dropwise a solution of compound 1 (1.00 g) in 5 ml of DMF with stirring at ice-cooling. To the resulting mixture was added dropwise 3-t-butyldiphenylsilyloxypropylisothiocyanate (2.33 g) which was obtained easily from 3-amino-1-propanol by usual method and stirred for 17 h. To the reaction mixture was added water, and the mixture was extracted with diethyl ether, washed with brine, dried over anhydrous magnesium sulfate, and concentrated under reduced pressure. The residue was subjected to silica gel column chromatography to give 1.10 g of compound 5.

$^1$H-NMR(CDCl$_3$): 1.05(9H, s), 1.36(3H, t, J=6.9 Hz), 1.98(2H, quint, J=6.6 Hz), 2.42(3H, s), 3.63(2H, q, J=6.9 Hz), 3.81(2H, t, J=6.6 Hz), 3.89(2H, q, J=6.6 Hz), 4.51(2H, s), 7.31–7.41(6H, m), 7.64–7.68(4H, m), 8.22(1H, s), 9.40 (1H, br), 11.48(1H, br).

Step 2

A solution of compound 5 (1.00 g) and p-toluenesulfonic acid monohydrate (0.76 g) in 5 ml of toluene was heated with stirring for 2 h under reflux. To the resulting mixture were added water and saturated sodium hygrogencarbonate aqueous solution. The mixture was extracted with ethyl acetate, washed with brine, dried over anhydrous magnesium sulfate, and concentrated under reduced pressure. The residue was subjected to silica gel column chromatography to give 0.25 g of compound 6.

$^1$H-NMR(CDCl$_3$): 1.26(3H, t, J=6.9 Hz), 2.13–2.21(2H, m), 2.54(3H, s), 3.07–3.12(2H, m), 3.55–3.62(2H, m), 3.61 (2H, q, J=6.9 Hz), 4.57(2H, s), 8.38(1H, s), 11.81(1H, br).

Step 3

A solution of compound 6 (0.10 g) in 0.8 ml of 25% hydrobromic acid/acetic acid was reacted for 14 h at 70° C. The solvent was removed under reduced pressure, and the residue was dissolved in 1 ml of DMF. The resulting mixture was added to a suspension of 2-(4-nitrophenyl)-5-mercapto-1,3,4-oxadiazole (0.09 g) and potassium carbonate (0.21 g) in 2 ml of DMF at ice cooling. The reaction mixture was stirred for 1 h at ice-cooling and added water. The appeared crystal was filtered and recrystalized from dichloromethane/diethyl ether/hexane to give 0.07 g of compound A-20. The physical data were shown in Table 3.

Example 21

Compounds A-21 was synthesized in a manner similar to described in Example 20. The physical data were shown in Table 3.

Example 22

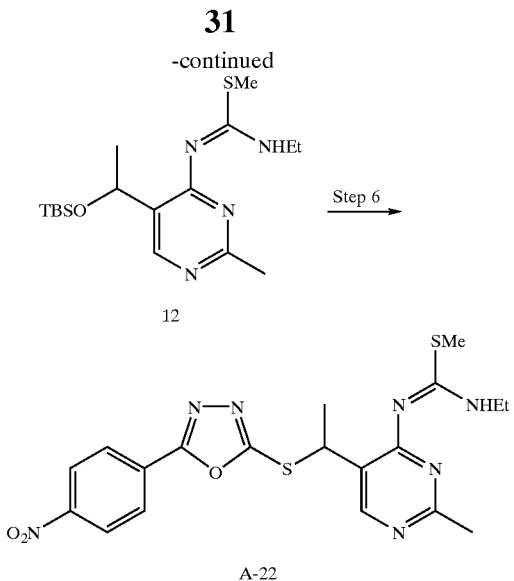

Step 1

To a suspension of lithium aluminum hydride (4.4 g) in 220 l of THF was added dropwise a solution of 4-amino-5-ethoxycarbonyl-2-methylpyrimidine 7 (22.0 g) which was obtained by the method described in literature (G. W. Kenner, B. Lythgoe, A. R. Todd and A. Topham. J. Chem. Soc., 388 (1943)) in 220 ml of THF with stirring at ice-cooling. The reaction mixture was allowed to room temperature and stirred for 2 h. To the mixture was added excess of ice and the stirring was continued for additional 2 h. To the reaction mixture was added anhydrous sodium sulfate, and the stirring was continued. The THF-insoluble material was filterd off and washed with methanol. The combined filtrate was concentrated completely under reduced pressure and added ethanol. The ethanol solution was heated and the insoluble material was filtered off. The ethanol-soluble filtrate was cooled and the appeared insoluble material was filtered off again. The filtrate was diluted with diethyl ether and the appeared crystals were filterd to give 14.5 g of compound 8.

Melting Point: 191~192° C.,
$^1$H-NMR(DMSO-d$_6$) 2.28(3H, s), 4.30(2H, s), 7.90(1H, s).

Step 2

To a solution of compound 8 (500 mg) in a combined solvent of 10 ml of dichloromethane and 5 ml of methanol was added active manganese dioxide (2.5 g), and stirred for 6 days at room temperature. The dichloromethane-insoluble material was filtered off and the solvent was removed under reduced pressure. The residue was subjected to silica gel column chromatography and crystalized from diethyl ether to give 284 mg of compound 9.
$^1$H-NMR(CDCl$_3$): 2.58(3H, s), 5.84(1H, br), 8.13(1H, br), 8.57(1H, s), 9.86(1H, s).

Step 3

A solution of compound 9 (280 mg) in 14 ml of THF was heated to dissolve and the mixture was allowed to ice-cooling. To the mixture was added dropwise 0.93 M solution of methylmagnesium bromide in THF (8.8 ml) with stirring at ice-cooling. The reaction mixture was stirred for 20 min at room temperature. Ice-water was added to the mixture, and the mixture was extracted with ethyl acetate. And the aqueous layer was rextracted with methyl ethyl ketone. The combined organic layer was concentrated under reduced pressure, and 10% solution of metanol in dichloromethane was added to the residue, then the insolble material was filtered off. The filtrate was subjected to silica gel column chromatography and then crystalized from diethyl ether/hexane to give 188 mg of compound 10.

$^1$H-NMR(CDCl$_3$): 1.57(3H, d, J=6.6 Hz), 2.13(1H, br), 2.48(3H, s), 4.86(1H, q, J=6.6 Hz), 5.55(2H, br), 7.94(11H, s).

Step 4

A solution of compound 10 (188 mg) and imidazole (100 mg) in 10 ml of DMF was added a solution of t-butyldimethylchlorosilane (200 mg) in 2 ml of DMF with stirring at ice-cooling. The mixture was stirred at room temperatuer for 2 h, and then imidazole (50 mg) and t-butyldimethylchlorosilane (100 mg) were added again to the mixture. The reaction mixture was stirred overnight, and added ethyl acetate. The resulting mixture was washed with brine, dried over anhydrous sodium sulfate, and concentrated under reduced pressure. The residue was subjected to silica gel column chromatography to give 285 mg of compound 11.

$^1$H-NMR(CDCl$_3$): 0.01(3H, s), 0.10(3H, s), 0.88(9H, s), 1.46(3H, d, J=6.6 Hz), 2.48(3H, s), 4.79(1H, q, J=6.6 Hz), 5.56(2H, br), 7.87(1H, s).

Step 5

Potassium t-butoxide (140 mg) was added to a solution of compound 11 (285 mg) in 5.0 ml of DMF with stirring at ice-cooling. After stirring for 5 min, ethylisothiocyanate (0.11 ml) was added dropwise. The resulting mixture was stirred for 10 min at ice-cooling and methyl iodide (0.08 ml) was added, and stirred for additional 1 h. To the reaction mixture was added water, extracted with ethyl acetate, washed with brine, dried over anhydrous sodium sulfate, and concentrated under reduced pressure. The residue was subjected to silica gel column chromatography to give 176 mg of compound 12.

$^1$H-NMR(CDCl$_3$): −0.01(3H, s), 0.05(3H, s), 0.90(9H, s), 1.33(3H, t, J=7.3 Hz), 1.40(3H, d, J=6.3 Hz), 2.48(3H, s), 2.55(3H, s), 3.42(2H, dq, J=5.6 Hz, 7.3 Hz), 5.36(1H, q, J=6.3 Hz), 8.54(1H, s), 11.18(1H, br).

Step 6

A solution of compound 12 (50 m g) in 1.0 ml of 25% hydrobromic acid/acetic acid was reacted for 15 h at 40° C. The solvent was removed under reduced pressure, and the residue was dissolved in 1 ml of DMF. The resulting mixture was added to a suspension of 2-(4-nitrophenyl)-5-mercapto-1,3,4-oxadiazole (50 mg) and potassium carbonate (105 mg) in 2 ml of DMF at ice-cooling. The reaction mixture was stirried for 1 h at ice-cooling and added water. The reaction mixture was extracted with dichloromethane, dried over anhydrous sodium sulfate, and concentrated under reduced pressure. The residue was subjected to silica gel column chromatography and crystalized from diethyl ether to give 16.8 mg of compound A-22. The physical data were shown in Table 3.

Example 23

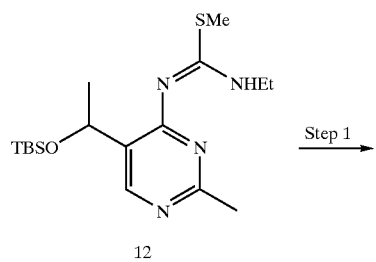

12

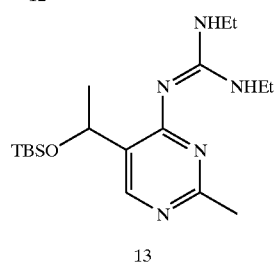

13

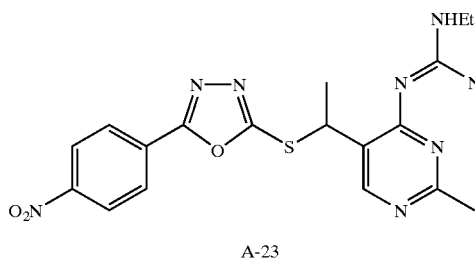

A-23

Step 1

To a solution of compound 12 (120 mg) in 3.0 ml of ethanol was added 70% ethylamine aqueous solution (0.27 ml), and the mixture was stirred for 5 h at 60° C. An additional 70% ethylamine aqueous solution (0.54 ml) was added to the reaction mixture, stirred overnight at 80° C. After cooling, the solvent was removed under reduced pressure to give 114 mg of compound 13.

$^1$H-NMR(CDCl$_3$): −0.00(3H, s), 0.04(3H, s), 0.91(9H, s), 1.28(6H, t, J=7.2 Hz), 1.39(3H, d, J=6.2 Hz), 2.48(3H, s), 3.33(4H, br), 5.27(1H, q, J=6.2 Hz), 8.35(1H, s).

Step 2

A solution of compound 13 (50 mg) in 1.0 ml of 25% hydrobromic acid/acetic acid was reacted for 15 h at 40° C. The solvent was removed under reduced pressure, and the residue was dissolved in 1 ml of DMF. The resulting mixture was added to a suspension of 2-(4-nitrophenyl)-5-mercapto-1,3,4-oxadiazole (50 mg) and potassium carbonate (105 mg) in 2 ml of DMF at ice-cooling. The reaction mixture was stirred for 3 h at ice-cooling and added water. The mixture was extracted with dichloromethane and successively with 20% 2-propanol/dichlorometane, and the combined organic layer was dried over anhydrous sodium sulfate, and concentrated under reduced pressure. The residue was subjected to silica gel column chromatography and crystalized from methanol to give 24.9 mg of compound A-23. The physical data were shown in Table 3.

Example 24

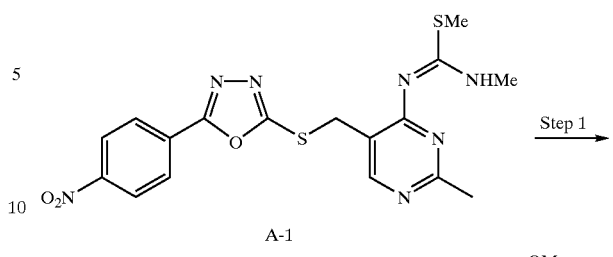

A-1

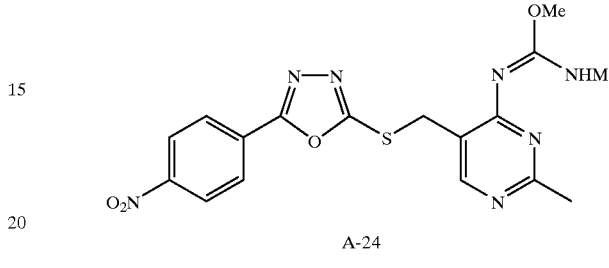

A-24

Step 1

To a solution of compound A-1 (100 mg) in a mxed solvent of dichoromethane (5.0 ml) and methanol(5.0 ml) was added silver(I) oxide (70 mg), and the reaction mixture was stirred for 4 h at room temperature. The dicholomethane-insoluble material was filtered off and the filtrate was concentrated under reduced pressure. The residue was subjected to silica gel column chromatography and recrystalized from diethyl ether to give 82.9 mg of compound A-24. The physical data were shown in Table 3.

Example 25 to 27

Compounds A-25 to A-27 were synthesized in a manner similar to described in Example 24.

The physical data were shown in Table 3.

Example 28

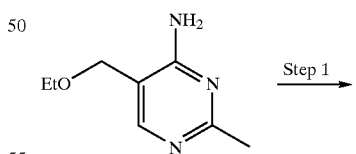

1

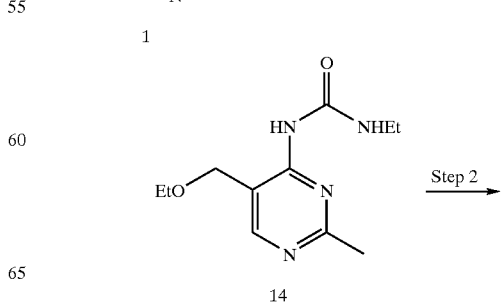

14

-continued

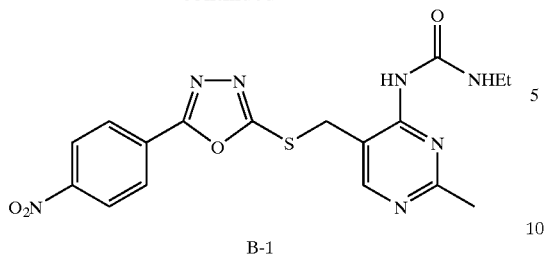

B-1

-continued

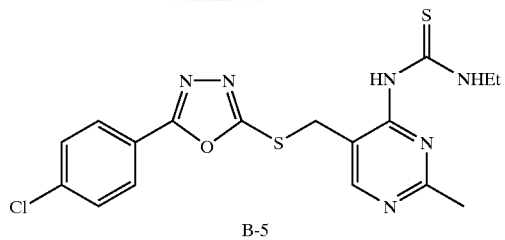

B-5

Step 1

To a solution of potassium t-butoxide (3.69 g) in 20 ml of DMF was added dropwise a solution of compound 1 (5.00 g) in 32 ml of DMF with stirring at ice-cooling. The reaction mixture was allowed at room temperature and stirred for 30 min. A solution of ethylisocyanate (2.34 g) in 6 ml of DMF was added dropwise to the mixture at ice-cooling, and the mixture was stirred for 1.5 h at room temperature. After removal of DMF under reduced pressure, water was added to the residure. The mixture was extracted with diethyl ether, washed with brine, dried over anhydrous magnesium sulfate, and concentrated under reduced pressure. The residue was subjected to silica gel column chromatography to give 6.27 g of compound 14.

$^1$H-NMR(CDCl$_3$): 1.26(3H, t, J=7.3 Hz), 1.27(3H, t, J=7.3 Hz), 2.60(3H, s), 3.43(2H, dq, J=5.6 Hz, 7.3 Hz), 3.55(2H, q, J=7.3 Hz), 4.46(2H, s), 7.99(1H, br), 8.17(1H, s), 9.36(1H, br).

Step 2

A solution of compound 14 (100 m g) in 2.5 ml of 25% hydrobromic acid in acetic acid was reacted for 5 h at 70° C. The solvent was removed under reduced pressure, and the residue was dissolved in 2 ml of DMF. The resulting mixture was added to a suspension of 2-(4-nitrophenyl)-5-mercapto-1,3,4-oxadiazole (120 mg) and potassium carbonate (230 mg) in 3 ml of DMF at ice-cooling. The reaction mixture was stirred for 1 h at ice-cooling, then water was added to the reaction mixture. The insolble precipitate was filtered, dried, and subjected to silica gel column chromatography and cryslalized from methanol to give 126 mg of compound B1. The physical data were shown in Table 5.

Example 29 to 31

Compounds B-2 to B-4 were synthesized in a manner similar to described in Example 28.

The physical data were shown in Table 5.

Example 32

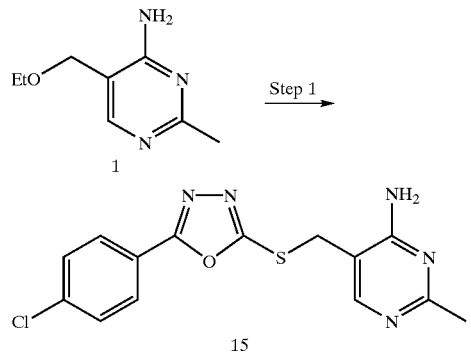

Step 1

A solution of compound 1 (2.24 g) in 30 ml of 25% hydrobromic acid/acetic acid was reacted for 15.5 h at 70° C. The solvent was removed under reduced pressure, and the residue was dissolved in 10 ml of DMF. The resulting mixture was added to a suspension of 2-(4-nitrophenyl)-5-mercapto-1,3,4-oxadiazole (3.13 g) and potassium carbonate (7.14 g) in 35 ml of DMF at ice-cooling. The reaction mixture was stirred for 1 h at ice-cooling and added water. The appeared crystal was filtered to give 3.99 g of compound 15.

$^1$H-NMR(DMSO-d$_6$): 2.28(3H, s), 4.37(2H, s), 7.09(2H, br), 7.67(2H, d, J=8.6 Hz), 7.98(2H, d, J=8.6 Hz), 8.06(1H, s).

Step 2

To a solution of compound 15 (200 mg) in 10 ml of DMF was added potassium t-butoxide (70 mg) with stirring at coiling with dryice/acetonitrile bath. The reaction mixture was stirred for 5 min and ethylisothiocyanate (0.06 ml) was added to the resulting mixture. The reaction mixture was stirred for 3 min and added acetic acid (0.05 ml). To the reaction mixture was added water at room temperature, extracted with dichloromethane, washed with brine, dried over anhydrous magnesium sulfate, and concentrated under reduced pressure. The residue was subjected to silica gel column chromatography and crystalized from diethyl ether to give 16.3 mg of compound B-5. The physical data were shown in Table 5.

Example 33

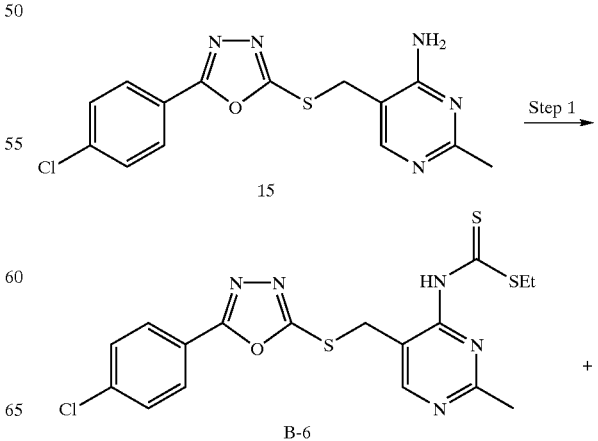

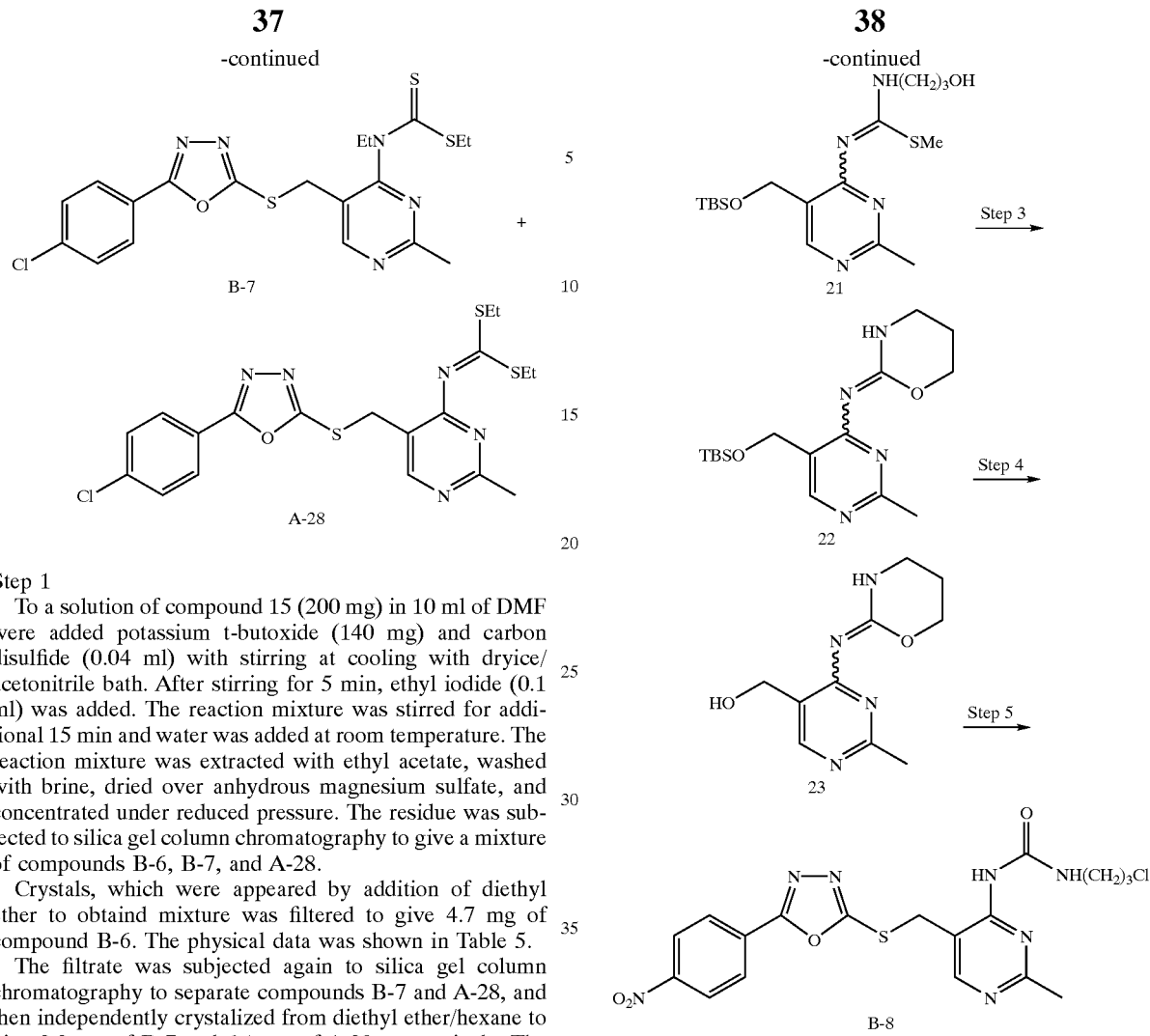

Step 1

To a solution of compound 15 (200 mg) in 10 ml of DMF were added potassium t-butoxide (140 mg) and carbon disulfide (0.04 ml) with stirring at cooling with dryice/acetonitrile bath. After stirring for 5 min, ethyl iodide (0.1 ml) was added. The reaction mixture was stirred for additional 15 min and water was added at room temperature. The reaction mixture was extracted with ethyl acetate, washed with brine, dried over anhydrous magnesium sulfate, and concentrated under reduced pressure. The residue was subjected to silica gel column chromatography to give a mixture of compounds B-6, B-7, and A-28.

Crystals, which were appeared by addition of diethyl ether to obtaind mixture was filtered to give 4.7 mg of compound B-6. The physical data was shown in Table 5.

The filtrate was subjected again to silica gel column chromatography to separate compounds B-7 and A-28, and then independently crystalized from diethyl ether/hexane to give 2.2 mg of B-7 and 6.1 mg of A.28, respectively. The physical data of compound B-7 and A-26 were shown in Table 5 and Table 3, respectively.

Example 34 to 40

Compounds A-29 to A-35 were synthesized in a manner similar to described above. The physical data were shown in Table 4.

Example 41

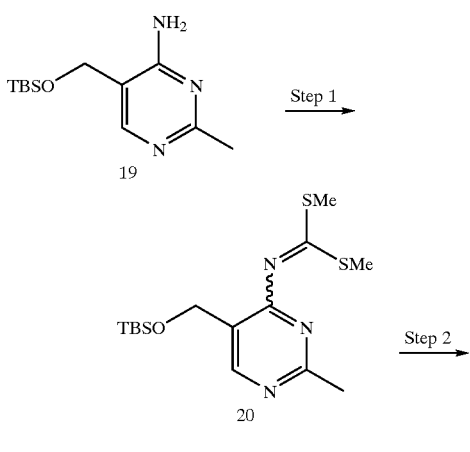

Step 1

To a suspension of sodium hydride (2.28 g) in 50 ml of DMF was added dropwise a solution of compound 19 (5.56 g) which was obtained by the method described in WO00/04014, and carbon disulfide (3.59 g) in 60 ml of DMF with stirring at ice-cooling. The reaction mixture was allowed to room temperature and stirred for 20 min, and a solution of methyl iodide (9.34 g) in 10 ml of DMF was added dropwise to the mixture at ice-cooling. The resulting mixture was stirred for 1.5 h at room temperature, and DMF was removed under reduced pressure. After addition of water the mixture was extracted with ethyl acetate, washed with brine, dried over anhydrous magnesium sulfate, and concentrated under reduced pressure. The residue was subjected to silica gel column chromatography to give 4.45 g of compound 20.

$^1$H-NMR(CDCl$_3$): 0.10(6H, s), 0.94(9H, s), 2.54(6H, s), 2.67(3H, s), 4.64(2H, s), 8.63(1H, s).

Step 2

A solution of compound 20 (0.06 g) and 3-amino-1-propanol (0.02 g) in 1 ml of methanol was stirred for 16 h at 30° C. The reaction mixture was concentrated under reduced pressure and the residue was subjected to silica gel column chromatography to give 0.06 g of compound 21.

$^1$H-NMR(CDC$_3$): 0.10(6H, s), 0.95(9H, s), 1.94(2H, quint, J=6.6 Hz), 2.48(3H, s), 2.55(3H, s), 3.54(2H, q, J=6.6 Hz), 3.83(2H, t, J=6.6 Hz), 4.83(2H, s), 8.48(1H, s), 11.22 (1H, br).

Step 3

To a solution of compound 21 (0.06 g) in 0.5 ml of THF was added potassium t-butoxide (0.02 g) with stirring at room temperature, and the reaction mixture was stirred for 4 h. The reaction mixture was concentrated under reduced pressure and the residue was subjected to silica gel column chromatography to give 0.05 g of compound 22.

$^1$H-NMR(CDCl$_3$): 0.10(6H, s), 0.94(9H, s), 2.11(2H, quint, J=5.3 Hz), 2.55(3H, s), 3.58(2H, t, J=5.3 Hz), 4.40 (2H, t, J=5.3 Hz), 4.79(2H, s), 8.45(1H, s), 11.38(1H, br).

Step 4

A solution of compound 22 (0.04 g) and tetrabutylammonium fluoride trihydrate (0.04 g) in 1 ml of THF was stirred for 18 h at room temperature. The reaction mixture was concentrated under reduced pressure and the residue was subjected to silica gel column chromatography to give 0.02 g of crude compound 23. This crude compound 23 was used for Step 5 without purification.

Step 5

To a solution of the crude compound 22 (0.02 g) which was obtained at Step 4 in 1 ml of 1,2-dichloroethane were added thionyl chloride (0.01 g) and catalytic amount of DMF with stirring at room temperature. The mixture was stirred for 1 h at room temperature and for 10 min at 80° C. The solvent was removed under reduced pressure and the residue was dissolved in 1 ml of DMF. The resulting mixture was added to a suspension of 2-(4-nitrophenyl)-5-mercapto-1,3,4-oxadiazole (0.02 g) which was obtained by similar method described in a literature (R. W. Young and K. H. Wood. J. Am. Chem. Soc., 77, 400 (1955)) and potassium carbonate (0.06 g) in 1 ml of DMF. The reaction mixture was stirred for 1 h at room temperature and added water. The resulting mixture was extracted with ethyl acetate, washed with brine, dried over anhydrous magnesium sulfate, and concentrated under reduced pressure. The residue was subjected to silica gel column chromatography and crystalized from methanol/diethyl ether/hexane to give 0.02 g of compound B-8. The physical data were shown in Table 5.

Example 42

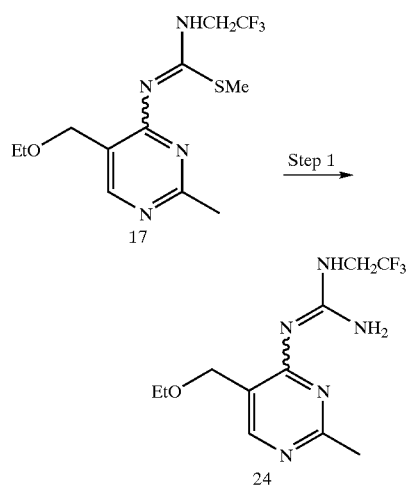

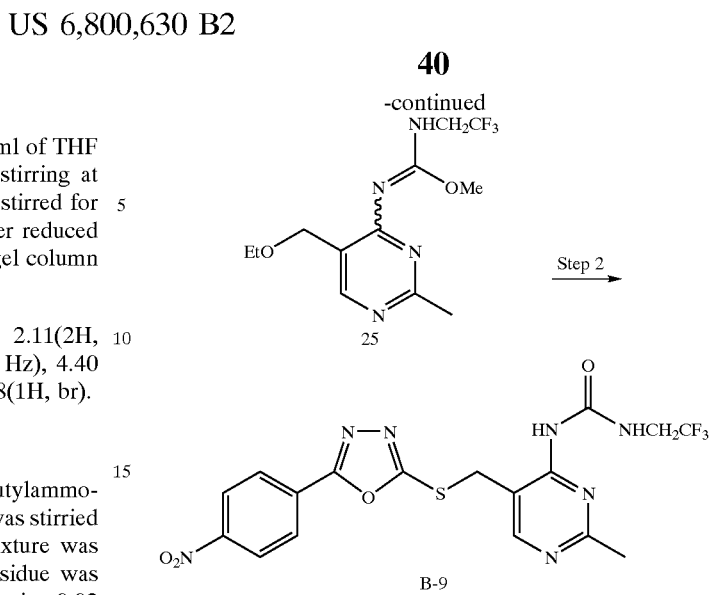

Step 1

A solution of compound 17 (0.95 g), which was obtained by similar method described in reference example 1, in 13 ml of 7N ammonia in methanol was reacted for 4 days at 80° C. in sealed lube. The solvent was removed under reduced pressure and added dichloromethane. The insoluble material was filtered to give 0.21 g of compound 24. The filtrate was cocentrated under reduced pressure and the residue was subjected to silica gel column chromatography to give 0.39 g of compound 25.

Compound 24

$^1$H-NMR(CDCl$_3$): 1.27(3H, t, J=7.3), 2.54(3H, s), 3.60 (2H, q, J=7.3 Hz), 4.09(2H, q-like, J=8.9 Hz), 4.54(2H, s), 8.34(1H, s).

Compound 25

$^1$H-NMR(CDCl$_3$): 1.27(3H, t, J=7.3), 2.58(3H, s), 3.61 (2H, q, J=7.3 Hz), 3.94(3H, s), 3.91–3.98(2H, m), 4.59(2H, s), 8.44(1H, s), 10.73(1H, br).

Step 2

A solution of compound 25 (0.10 g) in 1.0 ml of 25% hydrobromic acid/acetic acid was reacted for 7 h at 70° C. The solvent was removed under reduced pressure, and the residue was dissolved in 1.5 ml of DMF. The resulting mixture was added to a suspension of 2-(4-nitrophenyl)-5-mercapto-1,3,4-oxadiazole (0.08 g) and potassium carbonate (0.18 g) in 1 ml of DMF at ice-cooling. The reaction mixture was stirred for 1 h at ice-cooling and added water. The appeared crystal was filtered and crystalized from methanol/dichloromethane/diethyl ether to give 0.06 g of compound B-9. The physical data were shown in Table 5.

REFERENCE

Reference 1

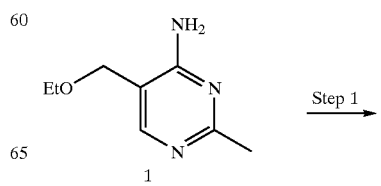

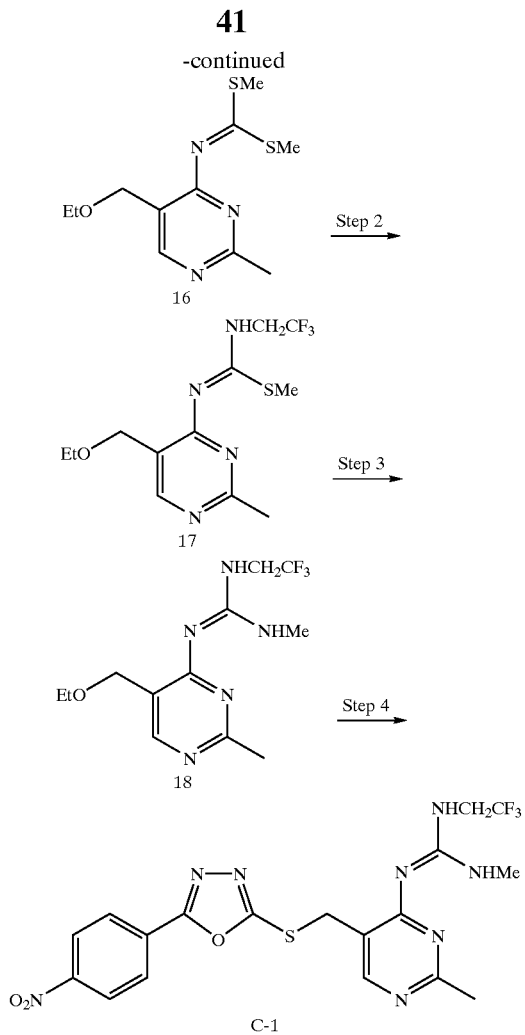

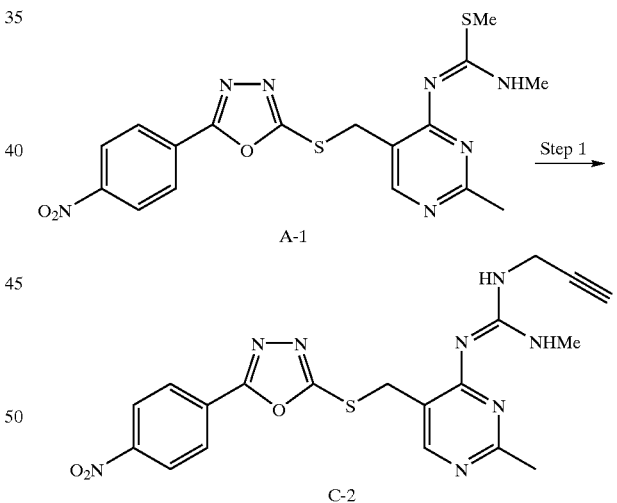

Step 1

To a solution of compound 1 (6.00 g) in 40 ml of DMF was added carbon disulfide (6.00 g) and the mixture was added dropwise to a solution of potassium t-butoxide (10.5 g) in 50 ml of DMF at ice-cooling. The reaction mixture was allowed to room temperature and stirred for 1.5 h, and then a solution of methyl iodide (15.3 g) in 10 ml of DMF was added at ice-cooling. The mixture was stirred for 1.5 h at room temperature, and then DMF was removed under reduced pressure and added water. The resulting mixture was extracted with diethyl ether, washed with brine, dried over anhydrous magnesium sulfate, and concentrated under reduced pressure. The residue was subjected to silica gel column chromatography to give 3.05 g of compound 16.

$^1$H-NMR(CDCl$_3$): 1.24(3H, t, J=7.0 Hz), 2.55(6H, s), 2.67(3H, s), 3.55(2H, q, J=7.0 Hz), 4.43(2H, s), 8.41(1H, s).

Step 2

To a suspension of compound 16 (3.05 g) and 2,2,2-trifluoroethylamine hydrochloride (6.09 g) in 30 ml of DMF was added triethylamine (4.55 g) and the mixture was stirred for 4days at 50° C. To the mixture was added water, and then mixture was extracted with diethyl ether, washed with brine, dried over anhydrous magnesium sulfate, and concentrated under reduced pressure. The residue was subjected to silica gel column chromatography to give 2.62 g of compound 17.

$^1$H-NMR(CDCl$_3$): 1.27(3H, t, J=7.3 Hz), 2.55(3H, s), 2.58(3H, s), 3.60(2H, q, J=7.3 Hz), 4.03(2H, dq, J=8.6 Hz, 6.3 Hz), 4.62(2H, s), 8.50(1H, s).

Step 3

A solution of compound 17 (2.62 g) and 40% methylamine in methanol (50 ml) in 15 ml of DMF was stirred for 2 days at 60° C. The reaction mixture was concentrated under reduced pressure and the residue was subjected to silica gel column chromatography to give 2.10 g of compound 18.

$^1$H-NMR(CDCl$_3$): 1.26(3H, t, J=7.1 Hz), 2.52(3H, s), 2.98(3H, d, J=5.1 Hz), 3.60(2H, q, J=7.1 Hz), 4.20(2H, dq, J=8.9 Hz, 6.4 Hz), 4.52(2H, s), 8.29(1H, s).

Step 4

A solution of compound 18 (2.10 g) in 20 ml of 25% hydrobromic acid in acetic acid was reacted for 7 h at 70° C. The solvent was removed under reduced pressure, and the residue was dissolved in 15 ml of DMF. The resulting mixture was added to a suspension of 2-(4-nitrophenyl)-5-mercapto-1,3,4-oxadiazole (1.69 g) and potassium carbonate (3.80 g) in 15 ml of DMF at ice-cooling. The reaction mixture was stirred for 1 h at room temperature and added water. The appeared precipitate was filtered, dried, and subjected to silica gel column chromatography and crystalized from methanol/dichloromethane/diethyl ether to give 3.24 g of compound C-1. The physical data was shown in Table 6.

Reference 2

Step 1

To a compound A-1 (4.00 g) were added DMF (200 ml) and propargylamine (7.66 g), and the mixture was stirred for 17 h at 65° C. DMF was removed under reduced pressure and water and brine were added. The mixture was extracted with ethyl acetate, and the organic layer was dried over anhydrous magnesium sulfate, and concentrated under reduced pressure. The residue was subjected to silica gel column chromatography and crystalized from methanol/dichloromethane/diethyl ether to give 0.74 g of compound C-2. The physical data were shown in Table 6.

TABLE 1

Structures:

5-(4-R$^{18}$-phenyl)-1,3,4-oxadiazol-2-yl-S-CHR$^X$-[pyrimidine with N=C(R$^{15}$)(R$^{16}$) and 2-methyl] — two regioisomers (R$^{15}$/R$^{16}$ swapped)

| Example No. | Compound No. | R$^{18}$ | R$^X$ | R$^{15}$ | R$^{16}$ | $^1$H-NMR(CDCl$_3$) (δ)ppm |
|---|---|---|---|---|---|---|
| 1 | A-1 | NO$_2$ | H | SMe | NHMe | 2.56(3H, s), 2.57(3H, s), 3.10(3H, d, J=5.3), 4.58(2H, s), 8.16(2H, d, J=9.1), 8.35(2H, d, J=9.1), 8.53(1H, s), 11.18(1H, br) |
| 2 | A-2 | NO$_2$ | H | SMe | NH$_2$ | 2.57(3H, s), 2.58(3H, s), 4.60(2H, s), 8.17(2H, d, J=9.1), 8.36(2H, d, J=9.1), 8.61(1H, s) |
| 3 | A-3 | NO$_2$ | H | SMe | NHEt | 1.35(3H, t, J=7.3), 2.55(3H, s), 2.57(3H, s), 3.45(2H, dq, J=7.3, 5.3), 4.58(2H, s), 8.16(2H, d, J=8.7), 8.36(2H, d, J=8.7), 8.53(1H, s), 11.31(1H, br) |
| 4 | A-4 | NO$_2$ | H | SMe | NHPr | 1.07(3H, t, J=7.3), 1.73(2H, sext, J=7.3), 2.55(3H, s), 2.57(3H, s), 3.38(2H, q, J=7.3), 4.58(2H, s), 8.16(2H, d, J=9.1), 8.35(2H, d, J=9.1), 8.53(1H, s), 11.44(1H, br) |
| 5 | A-5 | NO$_2$ | H | SEt | NHMe | 1.41(3H, t, J=7.3), 2.55(3H, s), 3.09(3H, d, J=5.1), 3.22(2H, q, J=7.3), 4.57(2H, s), 8.17(2H, d, J=9.1), 8.35(2H, d, J=9.1), 8.53(1H, s), 11.23(2H, br) |
| 6 | A-6 | NO$_2$ | H | SEt | NHEt | 1.34(3H, t, J=7.3), 1.41(3H, t, J=7.3), 2.51(3H, s), 3.21(2H, q, J=7.3), 3.44(2H, dq, J=7.3, 5.3), 4.57(2H, s), 8.17(2H, d, J=9.1), 8.35(2H, d, J=9.1), 8.53(1H, s), 11.39(1H, br) |
| 7 | A-7 | NO$_2$ | H | SPr | NHMe | 1.05(3H, t, J=7.3), 1.80(2H, sext, J=7.3), 2.55(3H, s), 3.10(3H, d, J=5.1), 3.19(2H, t, J=7.3), 4.56(2H, s), 8.17(2H, d, J=9.1), 8.35(2H, d, J=9.1), 8.53(1H, s), 11.26(1H, br) |
| 8 | A-8 | NO$_2$ | H | SPr | NHEt | 1.05(3H, t, J=7.3), 1.34(3H, t, J=7.3), 1.79(2H, sext, J=7.3), 2.54(3H, s), 3.18(2H, t, J=7.3), 3.45(2H, dq, J=7.3, 5.4), 4.56(2H, s), 8.17(2H, d, J=9.1), 8.35(2H, d, J=9.1), 8.53(1H, s), 11.38(1H, br) |
| 9 | A-9 | NH$_2$ | H | SMe | NH$_2$ | 2.56(3H, s), 2.58(3H, s), 4.03(2H, s), 4.53(2H, s), 6.71(2H, d, J=8.7), 7.76(2H, d, J=8.7), 8.58(1H, s) |

TABLE 2

| Example No. | Compound No. | R$^{18}$ | R$^X$ | R$^{15}$ | R$^{16}$ | $^1$H-NMR(CDCl$_3$) (δ) ppm |
|---|---|---|---|---|---|---|
| 10 | A-10 | NH$_2$ | H | SMe | NHMe | 2.55(3H, s), 2.56(3H, s), 3.08(3H, d, J = 5.3), 4.02(2H, br), 4.51(2H, s), 6.70(2H, d, J = 8.9), 7.76(2H, d, J = 8.9), 8.49(1H, s), 11.13(1H, br) |
| 11 | A-11 | NH$_2$ | H | SMe | NHEt | 1.34(3H, t, J = 7.3), 2.54(3H, s), 2.56(3H, s), 3.43(2H, dq, J = 7.3, 5.4), 3.50(2H, br), 4.01(2H, s), 6.71(2H, d, J = 8.7), 7.76(2H, d, J = 8.7), 8.49(1H, s), 11.30(1H, br) |
| 12 | A-12 | NH$_2$ | H | SMe | NHPr | 1.06(3H, t, J = 7.3), 1.72(2H, sext, J = 7.3), 2.54(3H, s), 2.56(3H, s), 3.36(2H, q, J = 7.3), 4.02(2H, br), 4.51(2H, s), 6.71(2H, d, J = 8.7), 7.76(2H, d, J = 8.7), 8.49(1H, s) |
| 13 | A-13 | NH$_2$ | H | SEt | NHMe | 1.41(3H, t, J = 7.3), 2.55(3H, s), 3.08(3H, d, J = 5.1), 3.21(2H, q, J = 7.3), 4.02(2H, br), 4.51(2H, s), 6.70(2H, d, J = 8.5), 7.76(2H, d, J = 8.5), 8.50(1H, s) |

TABLE 2-continued

| Example No. | Compound No. | R[18] | R[X] | R[15] | R[16] | $^1$H-NMR(CDCl$_3$) (δ) ppm |
|---|---|---|---|---|---|---|
| 14 | A-14 | NH$_2$ | H | SEt | NHEt | 1.33(3H, t, J = 7.3), 1.39(3H, t, J = 7.3), 2.54(3H, s), 3.20(2H, q, J = 7.3), 3.43(2H, dq, J = 7.3, 5.4), 4.02(2H, br), 4.50(2H, s), 6.71(2H, d, J = 8.9), 7.77(2H, d, J = 8.9), 8.49(1H, s), 11.33(1H, br) |
| 15 | A-15 | NH$_2$ | H | SPr | NHMe | 1.04(3H, t, J = 7.3), 1.78(2H, sext, J = 7.3), 2.54(3H, s), 3.08(3H, d, J = 5.3), 3.18(2H, t, J = 7.3), 4.03(2H, br), 4.49(2H, s), 6.70(2H, d, J = 8.9), 7.76(2H, d, J = 8.9), 8.49(1H, s), 11.20(1H, br) |
| 16 | A-16 | NH$_2$ | H | SPr | NHEt | 1.04(3H, t, J = 7.3), 1.33(3H, t, J = 7.3), 1.78(2H, sext, J = 7.3), 2.54(3H, s), 3.18(2H, t, J = 7.3), 3.44(2H, dq, J = 7.3, 5.4), 4.01(2H, br), 4.49(2H, s), 6.71(2H, d, J = 8.9), 7.76(2H, d, J = 8.9), 8.49(1H, s), 11.35(1H, br) |
| 17 | A-17 | Me | H | SMe | NHPr | 1.06(3H, t, J = 7.3), 1.72(2H, sext, J = 7.3), 2.41(3H, s), 2.54(3H, s), 2.56(3H, s), 3.37(2H, dt, J = 5.4, 7.3), 4.54(2H, s), 7.28(2H, d, J = 8.2), 7.86(2H, d, J = 8.2), 8.51(1H, s) |
| 18 | A-18 | NO$_2$ | H | NHNMe$_2$ | NHPr | 1.00(3H, t, J = 7.3), 1.67(2H, sext, J = 7.3), 2.51(3H, s), 2.64(6H, s), 3.44(2H, q, J = 7.3), 4.52(2H, s), 6.39(1H, br), 8.18(2H, d, J = 9.0), 8.34(1H, s), 8.36(2H, d, J = 9.0) |

TABLE 3

| Example No. | Compound No. | R[18] | R[X] | R[15] | R[16] | $^1$H-NMR(CDCl$_3$) (δ) ppm |
|---|---|---|---|---|---|---|
| 19 | A-19 | NO$_2$ | H | NHOMe | NHMe | 2.52(1.95H, s), 2.58(1.05H, s), 2.83(1.05H, d, J = 5.1), 3.05(1.95H, d, J = 5.1), 3.75(1.05H, s), 3.81(1.95H, s), 4.49(0.7H, s), 4.53(1.3H, s), 5.62(0.65H, br), 7.77(0.35H, br), 8.16(2H, d, J = 8.5), 8.35(2H, d, J = 8.5), 8.36(1H, s) |
| 20 | A-20 | NO$_2$ | H | S(CH$_2$)$_3$NH | | 2.13–2.25(2H, m), 2.53(3H, s), 3.08–3.13(2H, m), 3.55–3.65(2H, m), 4.50(2H, s), 8.16(2H, d, J = 8.9), 8.35(2H, d, J = 8.9), 8.49(1H, s), 11.85(1H, br) |
| 21 | A-21 | NO$_2$ | H | S(CH$_2$)$_2$NH | | 2.59(3H, s), 3.31(2H, t, J = 7.3), 3.92(2H, br), 4.53(2H, s), 8.16(2H, d, J = 8.9), 8.35(2H, d, J = 8.9), 8.55(1H, s) |
| 22 | A-22 | NO$_2$ | Me | SMe | NHEt | 1.34(3H, t, J = 7.2), 1.95(3H, d, J = 7.2), 2.56(3H, s), 2.57(3H, s), 3.44(2H, dq, J = 5.4, 7.2), 5.49(1H, q, J = 7.2), 8.16(2H, d, J = 8.8), 8.35(2H, d, J = 8.8), 8.46(1H, s), 11.36(1H, br) |
| 23 | A-23 | NO$_2$ | Me | NHEt | NHEt | 1.29(6H, t, J = 7.1), 1.95(3H, d, J = 7.1), 2.48(3H, s), 3.39(4H, br), 5.33(1H, q, J = 7.1), 8.17(2H, d, J = 9.0), 8.25(1H, s), 8.34(2H, d, J = 9.0) |
| 24 | A-24 | NO$_2$ | H | OMe | NHMe | 2.56(3H, s), 2.99(3H, d, J = 5.1), 3.98(3H, s), 4.55(2H, s), 8.16(2H, d, J = 9.2), 8.41(2H, d, J = 9.2), 8.47(1H, s), 9.96(1H, br) |
| 25 | A-25 | NO$_2$ | H | OEt | NHMe | 1.40(3H, t, J = 7.2), 2.55(3H, s), 2.98(3H, d, J = 4.9), 4.45(2H, q, J = 7.2), 4.53(2H, s), 8.16(2H, d, J = 9.0), 8.35(2H, d, J = 9.0), 8.45(1H, s), 10.01(1H, br) |
| 26 | A-26 | Me | H | OMe | NHPr | 1.02(3H, t, J = 7.3), 1.63(2H, tq, J = 6.8, 7.3), 2.41(3H, s), 2.54(3H, s), 3.31(2H, dt, J = 5.6, 6.8), 3.95(3H, s), 4.51(2H, s), 7.28(2H, d, J = 8.3), 7.86(2H, d, J = 8.3), 8.44(1H, s), 10.18(1H, br) |
| 27 | A-27 | Me | H | OEt | NHPr | 1.02(3H, t, J = 7.3), 1.37(3H, t, J = 7.1), 1.64(2H, sext, J = 7.3), 2.41(3H, s), 2.54(3H, s), 3.32(2H, dt, J = 5.5, 7.3), 4.44(2H, q, J = 7.1), 4.49(2H, s), 7.28(2H, d, J = 8.4), 7.86(2H, d, J = 8.4), 8.43(1H, s) |

TABLE 3-continued

| Example No. | Compound No. | $R^{18}$ | $R^X$ | $R^{15}$ | $R^{16}$ | $^1$H-NMR(CDCl$_3$) ($\delta$) ppm |
|---|---|---|---|---|---|---|
| 33 | A-28 | Cl | H | SEt | SEt | 1.37(6H, t, J = 7.4), 2.67(3H, s), 3.16(4H, q, J = 7.4), 4.44(2H, s), 7.47(2H, d, J = 8.9), 7.92(2 H, d, J = 8.9), 8.67(1H, s), |

TABLE 4

| Example No. | Compound No. | $R^{18}$ | $R^X$ | $R^{15}$ | $R^{16}$ | $^1$H-NMR(CDCl$_3$) ($\delta$) ppm |
|---|---|---|---|---|---|---|
| 34 | A-29 | NO$_2$ | H | SMe | NHCH$_2$CF$_3$ | 2.58(3H, s), 2.61(3H, s), 4.05(2H, dq, J = 6.4, 8.7), 4.60(2H, s), 8.16(2H, d, J = 8.9), 8.35(2H, d, J = 8.9), 8.63(1H, s), 12.03(1H, br). |
| 35 | A-30 | NH$_2$ | H | SMe | NHCH$_2$CF$_3$ | 2.57(3H, s), 2.60(3H, s), 4.02(2H, br), 4.03(2H, dq, J = 6.5, 8.7), 4.53(2H, s), 6.71(2H, d, J = 8.8), 7.76(2H, d, J = 8.8), 8.59(1H, s), 12.02(1H, br). |
| 36 | A-31 | NO$_2$ | H | SMe | NHPh | 2.54(3H, s), 2.59(3H, s), 4.64(2H, s), 7.34(1H, t, J = 7.6), 7.35(2H, d, J = 7.6), 7.44(2H, t, J = 7.6), 8.17(2H, d, J = 9.2), 8.36(2H, d, J = 9.2), 8.63(1H, s), 13.11(1H, br). |
| 37 | A-32 | NO$_2$ | H | OMe | NHEt | 1.26(3H, t, J = 7.3), 2.55(3H, s), 3.39(2H, dq, J = 5.6, 7.3), 3.97(3H, s), 4.55(2H, s), 8.16(2H, d, J = 9.0), 8.35(2H, d, J = 9.0), 8.46( 1H, s), 10.09(1H, t-like, J = 5.6). |
| 38 | A-33 | NO$_2$ | H | OEt | NHEt | 1.27(3H, t, J = 7.3), 1.39(3H, t, J = 7.1), 2.55(3H, s), 3.40(2H, dq, J = 5.6, 7.3), 4.45(2H, q, J = 7.1), 4.53(2H, s), 8.16(2H, d, J = 9.0), 8.35(2H, d, J = 9.0), 8.45(1H, s), 10.14(1H, t-like, J = 5.6). |
| 39 | A-34 | NO$_2$ | H | O$^i$Pr | NHMe | 1.38(6H, d, J = 6.1), 2.55(3H, s), 2.96(3H, d, J = 4.9), 4.52(2H, s), 5.40(1H, sept, J = 6.1), 8.17(2H, d, J = 8.9), 8.35(2H, d, J = 8.9), 8.44(1H, s), 10.06(1H, br). |
| 40 | A-35 | NO$_2$ | H | O$^i$Pr | NHEt | 1.26(3H, t, J = 7.3), 1.37(6H, d, J = 6.3), 2.54(3H, s), 3.38(2H, dq, J = 5.4, 7.3), 4.52(2H, s), 5.40(1H, sept, J = 6.3), 8.17(2H, d, J = 9.0), 8.35(2H, d, J = 9.0), 8.44(1H, s), 10.19(1H, br). |

TABLE 5

| Example No. | Compound No. | $R^{18}$ | $R^{20}$ | $R^{19}$ | X | $^1$H-NMR(CDCl$_3$) ($\delta$)ppm |
|---|---|---|---|---|---|---|
| 28 | B-1 | NO$_2$ | H | NHEt | O | 1.28(3H, t, J=7.3), 2.60(3H, s), 3.45(2H, dq, J=5.1, 7.3), 4.60(2H, s), 8.17(2H, d, J=8.8), 8.36(2H, d, J=8.8), 8.54(1H, s), 8.85(1H, br), 9.64(1H, t-like, J=5.1) |
| 29 | B-2 | Cl | H | NHEt | O | 1.27(3H, t, J=7.2), 2.59(3H, s), 3.44(2H, dq, J=5.2, 7.2), 4.57(2H, s), 7.46(2H, d, J=8.5), 7.90(2H, d, J=8.5), 8.52(1H, s), 8.97(1H, br), 9.66(1H, t-like, J=5.2) |
| 30 | B-3 | NH$_2$ | H | NHEt | O | 1.27(3H, t, J=7.3), 2.59(3H, s), 3.44(2H, dq, J=5.2, 7.3), 4.03(2H, br), 4.49(2H, |

TABLE 5-continued

[Structure: 5-(R18-phenyl)-1,3,4-oxadiazol-2-ylthiomethyl connected to 2-methylpyrimidin-4-yl bearing N(R20)C(=X)R19]

| Example No. | Compound No. | R18 | R20 | R19 | X | 1H-NMR(CDCl3) (δ)ppm |
|---|---|---|---|---|---|---|
| | | | | | | s), 6.69(2H, d, J=8.5), 7.75(2H, d, J=8.5), 8.47(1H, s), 8.67(1H, br), 9.59(1H, t-like, J=5.2) |
| 31 | B-4 | NO2 | H | NHPr | O | 1.03(3H, t, J=7.3), 1.67(2H, sext, J=7.3), 2.60(3H, s), 3.39(2H, dt, J=5.2, 7.3), 4.62(2H, s), 8.17(2H, d, J=8.8), 8.35(2H, d, J=8.8), 8.57(1H, s), 9.13(1H, br), 9.79(1H, t-like, J=5.2) |
| 32 | B-5 | Cl | H | NHEt | S | 1.29(3H, t, J=7.2), 2.64(3H, s), 3.80(2H, dq, J=5.2, 7.2), 4.43(2H, s), 7.50(2H, d, J=8.7), 7.98(2H, d, J=8.7), 8.14(1H, br), 8.28(1H, s) |
| 33 | B-6 | Cl | H | SEt | S | 1.35(3H, t, J=7.3), 2.62(3H, s), 3.38(2H, q, J=7.3), 4.65(2H, s), 7.49(2H, d, J=8.7), 8.01(2H, d, J=8.7), 8.27(1H, s) |
| 33 | B-7 | Cl | Et | SEt | S | 1.33(3H, t, J=7.4), 1.45(3H, t, J=7.2), 2.65(3H, s), 3.36(2H, q, J=7.4), 4.02(2H, q, J=7.2), 4.64(2H, s), 7.47(2H, d, J=8.8), 7.83(2H, d, J=8.8), 8.48(1H, s) |
| 41 | B-8 | NO2 | H | NH(CH2)3Cl | O | 2.11(2H, quint, J=6.3), 2.62(3H, s), 3.62(2H, q, J=6.3), 3.68(2H, t, J=6.3), 4.62(2H, s), 8.17(2H, d, J=8.8), 8.36(2H, d, J=8.8), 9.14(1H, br), 9.91(1H, t, J=6.1) |
| 42 | B-9 | NO2 | H | NHCH2CF3 | O | 2.62(3H, s), 4.10(2H, dq, J=8.9, 6.3), 4.63(2H, s), 8.18(2H, d, J=8.9), 8.36(2H, d, J=8.9), 8.64(1H, s), 9.48(1H, br), 10.52(1H, t, J=6.3) |

TABLE 6

[Two tautomeric structures: 5-(4-nitrophenyl)-1,3,4-oxadiazol-2-ylthiomethyl-2-methylpyrimidin-4-yl guanidine derivatives with NHMe/NHR21 or NHR21/NHMe arrangement]

| Reference No. | Compound No. | R21 | 1H-NMR (δ)ppm |
|---|---|---|---|
| 1 | C-1 | CH2CF3 | 2.41(3H, s), 2.91(3H, d, J=4.6), 4.24(2H, dq, J=9.5, 5.7), 4.46(2H, s), 7.37(1H, br), 8.22(2H, d, J=8.8), 8.28(1H, s), 8.41(2H, d, J=8.8), 10.20(1H, br)(in DMSOd6) |
| 2 | C-2 | CH2C≡CH | 2.33(1H, s), 2.51(3H, s), 3.00(3H, d, J=4.9), 4.24(2H, br), 4.54(2H, s), 8.16(2H, d, J=9.1), 8.35(2H, d, J=9.1), 8.38(1H, s)(in CDCl3) |

Compounds D-1 to D-1700 shown in Tablse 7 to Table 23 are able to synthesize in a manner similar to those described in Example 1 or Example 18, and were compounds E-1 to E-60 shown in Table 24 are able to synthesize in a manner similar to described in Example 20.

Table 7 to Table 24

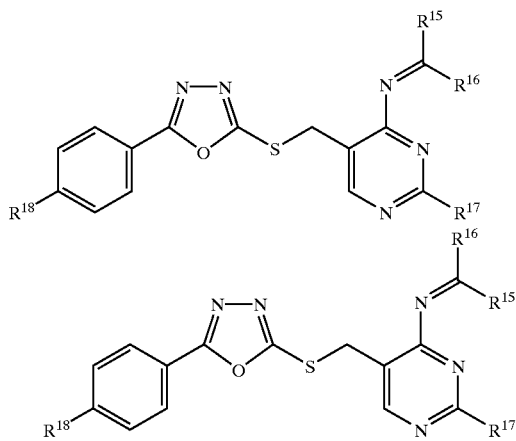

TABLE 7

| Compound No. | $R^{15}$ | $R^{16}$ | $R^{17}$ | $R^{18}$ |
|---|---|---|---|---|
| D-1 | $NH_2$ | SH | H | 4-$NH_2$ |
| D-2 | $NH_2$ | SMe | H | 4-$NH_2$ |
| D-3 | $NH_2$ | SEt | H | 4-$NH_2$ |
| D-4 | $NH_2$ | S-n-Pr | H | 4-$NH_2$ |
| D-5 | $NH_2$ | S-i-Pr | H | 4-$NH_2$ |
| D-6 | $NH_2$ | S-n-Bu | H | 4-$NH_2$ |
| D-7 | $NH_2$ | S-allyl | H | 4-$NH_2$ |
| D-8 | $NH_2$ | S-propargyl | H | 4-$NH_2$ |
| D-9 | $NH_2$ | $SCH_2CF_3$ | H | 4-$NH_2$ |
| D-10 | $NH_2$ | $SCH_2CH_2F$ | H | 4-$NH_2$ |
| D-11 | NHMe | SH | H | 4-$NH_2$ |
| D-12 | NHMe | SMe | H | 4-$NH_2$ |
| D-13 | NHMe | SEt | H | 4-$NH_2$ |
| D-14 | NHMe | S-n-Pr | H | 4-$NH_2$ |
| D-15 | NHMe | S-i-Pr | H | 4-$NH_2$ |
| D-16 | NHMe | S-n-Bu | H | 4-$NH_2$ |
| D-17 | NHMe | S-allyl | H | 4-$NH_2$ |
| D-18 | NHMe | S-propargyl | H | 4-$NH_2$ |
| D-19 | NHMe | $SCH_2CF_3$ | H | 4-$NH_2$ |
| D-20 | NHMe | $SCH_2CH_2F$ | H | 4-$NH_2$ |
| D-21 | NHEt | SH | H | 4-$NH_2$ |
| D-22 | NHEt | SMe | H | 4-$NH_2$ |
| D-23 | NHEt | SEt | H | 4-$NH_2$ |
| D-24 | NHEt | S-n-Pr | H | 4-$NH_2$ |
| D-25 | NHEt | S-i-Pr | H | 4-$NH_2$ |
| D-26 | NHEt | S-n-Bu | H | 4-$NH_2$ |
| D-27 | NHEt | S-allyl | H | 4-$NH_2$ |
| D-28 | NHEt | S-propargyl | H | 4-$NH_2$ |
| D-29 | NHEt | $SCH_2CF_3$ | H | 4-$NH_2$ |
| D-30 | NHEt | $SCH_2CH_2F$ | H | 4-$NH_2$ |
| D-31 | NHPr | SH | H | 4-$NH_2$ |
| D-32 | NHPr | SMe | H | 4-$NH_2$ |
| D-33 | NHPr | SEt | H | 4-$NH_2$ |
| D-34 | NHPr | S-n-Pr | H | 4-$NH_2$ |
| D-35 | NHPr | S-i-Pr | H | 4-$NH_2$ |
| D-36 | NHPr | S-n-Bu | H | 4-$NH_2$ |
| D-37 | NHPr | S-allyl | H | 4-$NH_2$ |
| D-38 | NHPr | S-propargyl | H | 4-$NH_2$ |
| D-39 | NHPr | $SCH_2CF_3$ | H | 4-$NH_2$ |
| D-40 | NHPr | $SCH_2CH_2F$ | H | 4-$NH_2$ |
| D-41 | NH-i-Pr | SH | H | 4-$NH_2$ |
| D-42 | NH-i-Pr | SMe | H | 4-$NH_2$ |
| D-43 | NH-i-Pr | SEt | H | 4-$NH_2$ |

TABLE 7-continued

| Compound No. | $R^{15}$ | $R^{16}$ | $R^{17}$ | $R^{18}$ |
|---|---|---|---|---|
| D-44 | NH-i-Pr | S-n-Pr | H | 4-$NH_2$ |
| D-45 | NH-i-Pr | S-i-Pr | H | 4-$NH_2$ |
| D-46 | NH-i-Pr | S-n-Bu | H | 4-$NH_2$ |
| D-47 | NH-i-Pr | S-allyl | H | 4-$NH_2$ |
| D-48 | NH-i-Pr | S-propargyl | H | 4-$NH_2$ |
| D-49 | NH-i-Pr | $SCH_2CF_3$ | H | 4-$NH_2$ |
| D-50 | NH-i-Pr | $SCH_2CH_2F$ | H | 4-$NH_2$ |
| D-51 | NH-allyl | SH | H | 4-$NH_2$ |
| D-52 | NH-allyl | SMe | H | 4-$NH_2$ |
| D-53 | NH-allyl | SEt | H | 4-$NH_2$ |
| D-54 | NH-allyl | S-n-Pr | H | 4-$NH_2$ |
| D-55 | NH-allyl | S-i-Pr | H | 4-$NH_2$ |
| D-56 | NH-allyl | S-n-Bu | H | 4-$NH_2$ |
| D-57 | NH-allyl | S-allyl | H | 4-$NH_2$ |
| D-58 | NH-allyl | S-propargyl | H | 4-$NH_2$ |
| D-59 | NH-allyl | $SCH_2CF_3$ | H | 4-$NH_2$ |
| D-60 | NH-allyl | $SCH_2CH_2F$ | H | 4-$NH_2$ |
| D-61 | NH-propargyl | SH | H | 4-$NH_2$ |
| D-62 | NH-propargyl | SMe | H | 4-$NH_2$ |
| D-63 | NH-propargyl | SEt | H | 4-$NH_2$ |
| D-64 | NH-propargyl | S-n-Pr | H | 4-$NH_2$ |
| D-65 | NH-propargyl | S-i-Pr | H | 4-$NH_2$ |
| D-66 | NH-propargyl | S-n-Bu | H | 4-$NH_2$ |
| D-67 | NH-propargyl | S-allyl | H | 4-$NH_2$ |
| D-68 | NH-propargyl | S-propargyl | H | 4-$NH_2$ |
| D-69 | NH-propargyl | $SCH_2CF_3$ | H | 4-$NH_2$ |
| D-70 | NH-propargyl | $SCH_2CH_2F$ | H | 4-$NH_2$ |
| D-71 | $NHCH_2CF_3$ | SH | H | 4-$NH_2$ |
| D-72 | $NHCH_2CF_3$ | SMe | H | 4-$NH_2$ |
| D-73 | $NHCH_2CF_3$ | SEt | H | 4-$NH_2$ |
| D-74 | $NHCH_2CF_3$ | S-n-Pr | H | 4-$NH_2$ |
| D-75 | $NHCH_2CF_3$ | S-i-Pr | H | 4-$NH_2$ |
| D-76 | $NHCH_2CF_3$ | S-n-Bu | H | 4-$NH_2$ |
| D-77 | $NHCH_2CF_3$ | S-allyl | H | 4-$NH_2$ |
| D-78 | $NHCH_2CF_3$ | S-propargyl | H | 4-$NH_2$ |
| D-79 | $NHCH_2CF_3$ | $SCH_2CF_3$ | H | 4-$NH_2$ |
| D-80 | $NHCH_2CF_3$ | $SCH_2CH_2F$ | H | 4-$NH_2$ |
| D-81 | $NHCH_2CH_2F$ | SH | H | 4-$NH_2$ |
| D-82 | $NHCH_2CH_2F$ | SMe | H | 4-$NH_2$ |
| D-83 | $NHCH_2CH_2F$ | SEt | H | 4-$NH_2$ |
| D-84 | $NHCH_2CH_2F$ | S-n-Pr | H | 4-$NH_2$ |
| D-85 | $NHCH_2CH_2F$ | S-i-Pr | H | 4-$NH_2$ |
| D-86 | $NHCH_2CH_2F$ | S-n-Bu | H | 4-$NH_2$ |
| D-87 | $NHCH_2CH_2F$ | S-allyl | H | 4-$NH_2$ |
| D-88 | $NHCH_2CH_2F$ | S-propargyl | H | 4-$NH_2$ |
| D-89 | $NHCH_2CH_2F$ | $SCH_2CF_3$ | H | 4-$NH_2$ |
| D-90 | $NHCH_2CH_2F$ | $SCH_2CH_2F$ | H | 4-$NH_2$ |
| D-91 | NH-n-Bu | SH | H | 4-$NH_2$ |
| D-92 | NH-n-Bu | SMe | H | 4-$NH_2$ |
| D-93 | NH-n-Bu | SEt | H | 4-$NH_2$ |
| D-94 | NH-n-Bu | S-n-Pr | H | 4-$NH_2$ |
| D-95 | NH-n-Bu | S-i-Pr | H | 4-$NH_2$ |
| D-96 | NH-n-Bu | S-n-Bu | H | 4-$NH_2$ |
| D-97 | NH-n-Bu | S-allyl | H | 4-$NH_2$ |
| D-98 | NH-n-Bu | S-propargyl | H | 4-$NH_2$ |
| D-99 | NH-n-Bu | $SCH_2CF_3$ | H | 4-$NH_2$ |
| D-100 | NH-n-Bu | $SCH_2CH_2F$ | H | 4-$NH_2$ |

TABLE 8

| Compound No. | $R^{15}$ | $R^{16}$ | $R^{17}$ | $R^{18}$ |
|---|---|---|---|---|
| D-101 | $NH_2$ | SH | H | 2-$NH_2$ |
| D-102 | $NH_2$ | SMe | H | 2-$NH_2$ |
| D-103 | $NH_2$ | SEt | H | 2-$NH_2$ |
| D-104 | $NH_2$ | S-n-Pr | H | 2-$NH_2$ |
| D-105 | $NH_2$ | S-i-Pr | H | 2-$NH_2$ |
| D-106 | $NH_2$ | S-n-Bu | H | 2-$NH_2$ |
| D-107 | $NH_2$ | S-allyl | H | 2-$NH_2$ |
| D-108 | $NH_2$ | S-propargyl | H | 2-$NH_2$ |

TABLE 8-continued

| Compound No. | R¹⁵ | R¹⁶ | R¹⁷ | R¹⁸ |
|---|---|---|---|---|
| D-109 | NH₂ | SCH₂CF₃ | H | 2-NH₂ |
| D-110 | NH₂ | SCH₂CH₂F | H | 2-NH₂ |
| D-111 | NHMe | SH | H | 2-NH₂ |
| D-112 | NHMe | SMe | H | 2-NH₂ |
| D-113 | NHMe | SEt | H | 2-NH₂ |
| D-114 | NHMe | S-n-Pr | H | 2-NH₂ |
| D-115 | NHMe | S-i-Pr | H | 2-NH₂ |
| D-116 | NHMe | S-n-Bu | H | 2-NH₂ |
| D-117 | NHMe | S-allyl | H | 2-NH₂ |
| D-118 | NHMe | S-propargyl | H | 2-NH₂ |
| D-119 | NHMe | SCH₂CF₃ | H | 2-NH₂ |
| D-120 | NHMe | SCH₂CH₂F | H | 2-NH₂ |
| D-121 | NHEt | SH | H | 2-NH₂ |
| D-122 | NHEt | SMe | H | 2-NH₂ |
| D-123 | NHEt | SEt | H | 2-NH₂ |
| D-124 | NHEt | S-n-Pr | H | 2-NH₂ |
| D-125 | NHEt | S-i-Pr | H | 2-NH₂ |
| D-126 | NHEt | S-n-Bu | H | 2-NH₂ |
| D-127 | NHEt | S-allyl | H | 2-NH₂ |
| D-128 | NHEt | S-propargyl | H | 2-NH₂ |
| D-129 | NHEt | SCH₂CF₃ | H | 2-NH₂ |
| D-130 | NHEt | SCH₂CH₂F | H | 2-NH₂ |
| D-131 | NHPr | SH | H | 2-NH₂ |
| D-132 | NHPr | SMe | H | 2-NH₂ |
| D-133 | NHPr | SEt | H | 2-NH₂ |
| D-134 | NHPr | S-n-Pr | H | 2-NH₂ |
| D-135 | NHPr | S-i-Pr | H | 2-NH₂ |
| D-136 | NHPr | S-n-Bu | H | 2-NH₂ |
| D-137 | NHPr | S-allyl | H | 2-NH₂ |
| D-138 | NHPr | S-propargyl | H | 2-NH₂ |
| D-139 | NHPr | SCH₂CF₃ | H | 2-NH₂ |
| D-140 | NHPr | SCH₂CH₂F | H | 2-NH₂ |
| D-141 | NH-i-Pr | SH | H | 2-NH₂ |
| D-142 | NH-i-Pr | SMe | H | 2-NH₂ |
| D-143 | NH-i-Pr | SEt | H | 2-NH₂ |
| D-144 | NH-i-Pr | S-n-Pr | H | 2-NH₂ |
| D-145 | NH-i-Pr | S-i-Pr | H | 2-NH₂ |
| D-146 | NH-i-Pr | S-n-Bu | H | 2-NH₂ |
| D-147 | NH-i-Pr | S-allyl | H | 2-NH₂ |
| D-148 | NH-i-Pr | S-propargyl | H | 2-NH₂ |
| D-149 | NH-i-Pr | SCH₂CF₃ | H | 2-NH₂ |
| D-150 | NH-i-Pr | SCH₂CH₂F | H | 2-NH₂ |
| D-151 | NH-allyl | SH | H | 2-NH₂ |
| D-152 | NH-allyl | SMe | H | 2-NH₂ |
| D-153 | NH-allyl | SEt | H | 2-NH₂ |
| D-154 | NH-allyl | S-n-Pr | H | 2-NH₂ |
| D-155 | NH-allyl | S-i-Pr | H | 2-NH₂ |
| D-156 | NH-allyl | S-n-Bu | H | 2-NH₂ |
| D-157 | NH-allyl | S-allyl | H | 2-NH₂ |
| D-158 | NH-allyl | S-propargyl | H | 2-NH₂ |
| D-159 | NH-allyl | SCH₂CF₃ | H | 2-NH₂ |
| D-160 | NH-allyl | SCH₂CH₂F | H | 2-NH₂ |
| D-161 | NH-propargyl | SH | H | 2-NH₂ |
| D-162 | NH-propargyl | SMe | H | 2-NH₂ |
| D-163 | NH-propargyl | SEt | H | 2-NH₂ |
| D-164 | NH-propargyl | S-n-Pr | H | 2-NH₂ |
| D-165 | NH-propargyl | S-i-Pr | H | 2-NH₂ |
| D-166 | NH-propargyl | S-n-Bu | H | 2-NH₂ |
| D-167 | NH-propargyl | S-allyl | H | 2-NH₂ |
| D-168 | NH-propargyl | S-propargyl | H | 2-NH₂ |
| D-169 | NH-propargyl | SCH₂CF₃ | H | 2-NH₂ |
| D-170 | NH-propargyl | SCH₂CH₂F | H | 2-NH₂ |
| D-171 | NHCH₂CF₃ | SH | H | 2-NH₂ |
| D-172 | NHCH₂CF₃ | SMe | H | 2-NH₂ |
| D-173 | NHCH₂CF₃ | SEt | H | 2-NH₂ |
| D-174 | NHCH₂CF₃ | S-n-Pr | H | 2-NH₂ |
| D-175 | NHCH₂CF₃ | S-i-Pr | H | 2-NH₂ |
| D-176 | NHCH₂CF₃ | S-n-Bu | H | 2-NH₂ |
| D-177 | NHCH₂CF₃ | S-allyl | H | 2-NH₂ |
| D-178 | NHCH₂CF₃ | S-propargyl | H | 2-NH₂ |
| D-179 | NHCH₂CF₃ | SCH₂CF₃ | H | 2-NH₂ |
| D-180 | NHCH₂CF₃ | SCH₂CH₂F | H | 2-NH₂ |
| D-181 | NHCH₂CH₂F | SH | H | 2-NH₂ |
| D-182 | NHCH₂CH₂F | SMe | H | 2-NH₂ |
| D-183 | NHCH₂CH₂F | SEt | H | 2-NH₂ |
| D-184 | NHCH₂CH₂F | S-n-Pr | H | 2-NH₂ |
| D-185 | NHCH₂CH₂F | S-i-Pr | H | 2-NH₂ |
| D-186 | NHCH₂CH₂F | S-n-Bu | H | 2-NH₂ |
| D-187 | NHCH₂CH₂F | S-allyl | H | 2-NH₂ |
| D-188 | NHCH₂CH₂F | S-propargyl | H | 2-NH₂ |
| D-189 | NHCH₂CH₂F | SCH₂CF₃ | H | 2-NH₂ |
| D-190 | NHCH₂CH₂F | SCH₂CH₂F | H | 2-NH₂ |
| D-191 | NH-n-Bu | SH | H | 2-NH₂ |
| D-192 | NH-n-Bu | SMe | H | 2-NH₂ |
| D-193 | NH-n-Bu | SEt | H | 2-NH₂ |
| D-194 | NH-n-Bu | S-n-Pr | H | 2-NH₂ |
| D-195 | NH-n-Bu | S-i-Pr | H | 2-NH₂ |
| D-196 | NH-n-Bu | S-n-Bu | H | 2-NH₂ |
| D-197 | NH-n-Bu | S-allyl | H | 2-NH₂ |
| D-198 | NH-n-Bu | S-propargyl | H | 2-NH₂ |
| D-199 | NH-n-Bu | SCH₂CF₃ | H | 2-NH₂ |
| D-200 | NH-n-Bu | SCH₂CH₂F | H | 2-NH₂ |

TABLE 9

| Compound No. | R¹⁵ | R¹⁶ | R¹⁷ | R¹⁸ |
|---|---|---|---|---|
| D-201 | NH₂ | SH | H | 4-Cl |
| D-202 | NH₂ | SMe | H | 4-Cl |
| D-203 | NH₂ | SEt | H | 4-Cl |
| D-204 | NH₂ | S-n-Pr | H | 4-Cl |
| D-205 | NH₂ | S-i-Pr | H | 4-Cl |
| D-206 | NH₂ | S-n-Bu | H | 4-Cl |
| D-207 | NH₂ | S-allyl | H | 4-Cl |
| D-208 | NH₂ | S-propargyl | H | 4-Cl |
| D-209 | NH₂ | SCH₂CF₃ | H | 4-Cl |
| D-210 | NH₂ | SCH₂CH₂F | H | 4-Cl |
| D-211 | NHMe | SH | H | 4-Cl |
| D-212 | NHMe | SMe | H | 4-Cl |
| D-213 | NHMe | SEt | H | 4-Cl |
| D-214 | NHMe | S-n-Pr | H | 4-Cl |
| D-215 | NHMe | S-i-Pr | H | 4-Cl |
| D-216 | NHMe | S-n-Bu | H | 4-Cl |
| D-217 | NHMe | S-allyl | H | 4-Cl |
| D-218 | NHMe | S-propargyl | H | 4-Cl |
| D-219 | NHMe | SCH₂CF₃ | H | 4-Cl |
| D-220 | NHMe | SCH₂CH₂F | H | 4-Cl |
| D-221 | NHEt | SH | H | 4-F |
| D-222 | NHEt | SMe | H | 4-Cl |
| D-223 | NHEt | SEt | H | 4-Cl |
| D-224 | NHEt | S-n-Pr | H | 4-Cl |
| D-225 | NHEt | S-i-Pr | H | 4-Cl |
| D-226 | NHEt | S-n-Bu | H | 4-Cl |
| D-227 | NHEt | S-allyl | H | 4-Cl |
| D-228 | NHEt | S-propargyl | H | 4-Cl |
| D-229 | NHEt | SCH₂CF₃ | H | 4-Cl |
| D-230 | NHEt | SCH₂CH₂F | H | 4-Cl |
| D-231 | NHPr | SH | H | 4-Cl |
| D-232 | NHPr | SMe | H | 4-Cl |
| D-233 | NHPr | SEt | H | 4-Cl |
| D-234 | NHPr | S-n-Pr | H | 4-Cl |
| D-235 | NHPr | S-i-Pr | H | 4-Cl |
| D-236 | NHPr | S-n-Bu | H | 4-Cl |
| D-237 | NHPr | S-allyl | H | 4-Cl |
| D-238 | NHPr | S-propargyl | H | 4-Cl |
| D-239 | NHPr | SCH₂CF₃ | H | 4-Cl |
| D-240 | NHPr | SCH₂CH₂F | H | 4-Cl |
| D-241 | NH-i-Pr | SH | H | 4-Cl |
| D-242 | NH-i-Pr | SMe | H | 4-Cl |
| D-243 | NH-i-Pr | SEt | H | 4-Cl |
| D-244 | NH-i-Pr | S-n-Pr | H | 4-Cl |
| D-245 | NH-i-Pr | S-i-Pr | H | 4-Cl |
| D-246 | NH-i-Pr | S-n-Bu | H | 4-Cl |
| D-247 | NH-i-Pr | S-allyl | H | 4-Cl |
| D-248 | NH-i-Pr | S-propargyl | H | 4-Cl |

TABLE 9-continued

| Compound No. | R$^{15}$ | R$^{16}$ | R$^{17}$ | R$^{18}$ |
|---|---|---|---|---|
| D-249 | NH-i-Pr | SCH$_2$CF$_3$ | H | 4-Cl |
| D-250 | NH-i-Pr | SCH$_2$CH$_2$F | H | 4-Cl |
| D-251 | NH-allyl | SH | H | 4-Cl |
| D-252 | NH-allyl | SMe | H | 4-Cl |
| D-253 | NH-allyl | SEt | H | 4-Cl |
| D-254 | NH-allyl | S-n-Pr | H | 4-Cl |
| D-255 | NH-allyl | S-i-Pr | H | 4-Cl |
| D-256 | NH-allyl | S-n-Bu | H | 4-Cl |
| D-257 | NH-allyl | S-allyl | H | 4-Cl |
| D-258 | NH-allyl | S-propargyl | H | 4-Cl |
| D-259 | NH-allyl | SCH$_2$CF$_3$ | H | 4-Cl |
| D-260 | NH-allyl | SCH$_2$CH$_2$F | H | 4-Cl |
| D-261 | NH-propargyl | SH | H | 4-Cl |
| D-262 | NH-propargyl | SMe | H | 4-Cl |
| D-263 | NH-propargyl | SEt | H | 4-Cl |
| D-264 | NH-propargyl | S-n-Pr | H | 4-Cl |
| D-265 | NH-propargyl | S-i-Pr | H | 4-Cl |
| D-266 | NH-propargyl | S-n-Bu | H | 4-Cl |
| D-267 | NH-propargyl | S-allyl | H | 4-Cl |
| D-268 | NH-propargyl | S-propargyl | H | 4-Cl |
| D-269 | NH-propargyl | SCH$_2$CF$_3$ | H | 4-Cl |
| D-270 | NH-propargyl | SCH$_2$CH$_2$F | H | 4-Cl |
| D-271 | NHCH$_2$CF$_3$ | SH | H | 4-Cl |
| D-272 | NHCH$_2$CF$_3$ | SMe | H | 4-Cl |
| D-273 | NHCH$_2$CF$_3$ | SEt | H | 4-Cl |
| D-274 | NHCH$_2$CF$_3$ | S-n-Pr | H | 4-Cl |
| D-275 | NHCH$_2$CF$_3$ | S-i-Pr | H | 4-Cl |
| D-276 | NHCH$_2$CF$_3$ | S-n-Bu | H | 4-Cl |
| D-277 | NHCH$_2$CF$_3$ | S-allyl | H | 4-Cl |
| D-278 | NHCH$_2$CF$_3$ | S-propargyl | H | 4-Cl |
| D-279 | NHCH$_2$CF$_3$ | SCH$_2$CF$_3$ | H | 4-Cl |
| D-280 | NHCH$_2$CF$_3$ | SCH$_2$CH$_2$F | H | 4-Cl |
| D-281 | NHCH$_2$CH$_2$F | SH | H | 4-Cl |
| D-282 | NHCH$_2$CH$_2$F | SMe | H | 4-Cl |
| D-283 | NHCH$_2$CH$_2$F | SEt | H | 4-Cl |
| D-284 | NHCH$_2$CH$_2$F | S-n-Pr | H | 4-Cl |
| D-285 | NHCH$_2$CH$_2$F | S-i-Pr | H | 4-Cl |
| D-286 | NHCH$_2$CH$_2$F | S-n-Bu | H | 4-Cl |
| D-287 | NHCH$_2$CH$_2$F | S-allyl | H | 4-Cl |
| D-288 | NHCH$_2$CH$_2$F | S-propargyl | H | 4-Cl |
| D-289 | NHCH$_2$CH$_2$F | SCH$_2$CF$_3$ | H | 4-Cl |
| D-290 | NHCH$_2$CH$_2$F | SCH$_2$CH$_2$F | H | 4-Cl |
| D-291 | NH-n-Bu | SH | H | 4-Cl |
| D-292 | NH-n-Bu | SMe | H | 4-Cl |
| D-293 | NH-n-Bu | SEt | H | 4-Cl |
| D-294 | NH-n-Bu | S-n-Pr | H | 4-Cl |
| D-295 | NH-n-Bu | S-i-Pr | H | 4-Cl |
| D-296 | NH-n-Bu | S-n-Bu | H | 4-Cl |
| D-297 | NH-n-Bu | S-allyl | H | 4-Cl |
| D-298 | NH-n-Bu | S-propargyl | H | 4-Cl |
| D-299 | NH-n-Bu | SCH$_2$CF$_3$ | H | 4-Cl |
| D-300 | NH-n-Bu | SCH$_2$CH$_2$F | H | 4-Cl |

TABLE 10

| Compound No. | R$^{15}$ | R$^{16}$ | R$^{17}$ | R$^{18}$ |
|---|---|---|---|---|
| D-301 | NH$_2$ | SH | H | 4-Me |
| D-302 | NH$_2$ | SMe | H | 4-Me |
| D-303 | NH$_2$ | SEt | H | 4-Me |
| D-304 | NH$_2$ | S-n-Pr | H | 4-Me |
| D-305 | NH$_2$ | S-i-Pr | H | 4-Me |
| D-306 | NH$_2$ | S-n-Bu | H | 4-Me |
| D-307 | NH$_2$ | S-allyl | H | 4-Me |
| D-308 | NH$_2$ | S-propargyl | H | 4-Me |
| D-309 | NH$_2$ | SCH$_2$CF$_3$ | H | 4-Me |
| D-310 | NH$_2$ | SCH$_2$CH$_2$F | H | 4-Me |
| D-311 | NHMe | SH | H | 4-Me |
| D-312 | NHMe | SMe | H | 4-Me |
| D-313 | NHMe | SEt | H | 4-Me |
| D-314 | NHMe | S-n-Pr | H | 4-Me |
| D-315 | NHMe | S-i-Pr | H | 4-Me |
| D-316 | NHMe | S-n-Bu | H | 4-Me |
| D-317 | NHMe | S-allyl | H | 4-Me |
| D-318 | NHMe | S-propargyl | H | 4-Me |
| D-319 | NHMe | SCH$_2$CF$_3$ | H | 4-Me |
| D-320 | NHMe | SCH$_2$CH$_2$F | H | 4-Me |
| D-321 | NHEt | SH | H | 4-Me |
| D-322 | NHEt | SMe | H | 4-Me |
| D-323 | NHEt | SEt | H | 4-Me |
| D-324 | NHEt | S-n-Pr | H | 4-Me |
| D-325 | NHEt | S-i-Pr | H | 4-Me |
| D-326 | NHEt | S-n-Bu | H | 4-Me |
| D-327 | NHEt | S-allyl | H | 4-Me |
| D-328 | NHEt | S-propargyl | H | 4-Me |
| D-329 | NHEt | SCH$_2$CF$_3$ | H | 4-Me |
| D-330 | NHEt | SCH$_2$CH$_2$F | H | 4-Me |
| D-331 | NHPr | SH | H | 4-Me |
| D-332 | NHPr | SMe | H | 4-Me |
| D-333 | NHPr | SEt | H | 4-Me |
| D-334 | NHPr | S-n-Pr | H | 4-Me |
| D-335 | NHPr | S-i-Pr | H | 4-Me |
| D-336 | NHPr | S-n-Bu | H | 4-Me |
| D-337 | NHPr | S-allyl | H | 4-Me |
| D-338 | NHPr | S-propargyl | H | 4-Me |
| D-339 | NHPr | SCH$_2$CF$_3$ | H | 4-Me |
| D-340 | NHPr | SCH$_2$CH$_2$F | H | 4-Me |
| D-341 | NH-i-Pr | SH | H | 4-Me |
| D-342 | NH-i-Pr | SMe | H | 4-Me |
| D-343 | NH-i-Pr | SEt | H | 4-Me |
| D-344 | NH-i-Pr | S-n-Pr | H | 4-Me |
| D-345 | NH-i-Pr | S-i-Pr | H | 4-Me |
| D-346 | NH-i-Pr | S-n-Bu | H | 4-Me |
| D-347 | NH-i-Pr | S-allyl | H | 4-Me |
| D-348 | NH-i-Pr | S-propargyl | H | 4-Me |
| D-349 | NH-i-Pr | SCH$_2$CF$_3$ | H | 4-Me |
| D-350 | NH-i-Pr | SCH$_2$CH$_2$F | H | 4-Me |
| D-351 | NH-allyl | SH | H | 4-Me |
| D-352 | NH-allyl | SMe | H | 4-Me |
| D-353 | NH-allyl | SEt | H | 4-Me |
| D-354 | NH-allyl | S-n-Pr | H | 4-Me |
| D-355 | NH-allyl | S-i-Pr | H | 4-Me |
| D-356 | NH-allyl | S-n-Bu | H | 4-Me |
| D-357 | NH-allyl | S-allyl | H | 4-Me |
| D-358 | NH-allyl | S-propargyl | H | 4-Me |
| D-359 | NH-allyl | SCH$_2$CF$_3$ | H | 4-Me |
| D-360 | NH-allyl | SCH$_2$CH$_2$F | H | 4-Me |
| D-361 | NH-propargyl | SH | H | 4-Me |
| D-362 | NH-propargyl | SMe | H | 4-Me |
| D-363 | NH-propargyl | SEt | H | 4-Me |
| D-364 | NH-propargyl | S-n-Pr | H | 4-Me |
| D-365 | NH-propargyl | S-i-Pr | H | 4-Me |
| D-366 | NH-propargyl | S-n-Bu | H | 4-Me |
| D-367 | NH-propargyl | S-allyl | H | 4-Me |
| D-368 | NH-propargyl | S-propargyl | H | 4-Me |
| D-369 | NH-propargyl | SCH$_2$CF$_3$ | H | 4-Me |
| D-370 | NH-propargyl | SCH$_2$CH$_2$F | H | 4-Me |
| D-371 | NHCH$_2$CF$_3$ | SH | H | 4-Me |
| D-372 | NHCH$_2$CF$_3$ | SMe | H | 4-Me |
| D-373 | NHCH$_2$CF$_3$ | SEt | H | 4-Me |
| D-374 | NHCH$_2$CF$_3$ | S-n-Pr | H | 4-Me |
| D-375 | NHCH$_2$CF$_3$ | S-i-Pr | H | 4-Me |
| D-376 | NHCH$_2$CF$_3$ | S-n-Bu | H | 4-Me |
| D-377 | NHCH$_2$CF$_3$ | S-allyl | H | 4-Me |
| D-378 | NHCH$_2$CF$_3$ | S-propargyl | H | 4-Me |
| D-379 | NHCH$_2$CF$_3$ | SCH$_2$CF$_3$ | H | 4-Me |
| D-380 | NHCH$_2$CF$_3$ | SCH$_2$CH$_2$F | H | 4-Me |
| D-381 | NHCH$_2$CH$_2$F | SH | H | 4-Me |
| D-382 | NHCH$_2$CH$_2$F | SMe | H | 4-Me |
| D-383 | NHCH$_2$CH$_2$F | SEt | H | 4-Me |
| D-384 | NHCH$_2$CH$_2$F | S-n-Pr | H | 4-Me |
| D-385 | NHCH$_2$CH$_2$F | S-i-Pr | H | 4-Me |
| D-386 | NHCH$_2$CH$_2$F | S-n-Bu | H | 4-Me |
| D-387 | NHCH$_2$CH$_2$F | S-allyl | H | 4-Me |
| D-388 | NHCH$_2$CH$_2$F | S-propargyl | H | 4-Me |

TABLE 10-continued

| Compound No. | R¹⁵ | R¹⁶ | R¹⁷ | R¹⁸ |
|---|---|---|---|---|
| D-389 | NHCH₂CH₂F | SCH₂CF₃ | H | 4-Me |
| D-390 | NHCH₂CH₂F | SCH₂CH₂F | H | 4-Me |
| D-391 | NH-n-Bu | SH | H | 4-Me |
| D-392 | NH-n-Bu | SMe | H | 4-Me |
| D-393 | NH-n-Bu | SEt | H | 4-Me |
| D-394 | NH-n-Bu | S-n-Pr | H | 4-Me |
| D-395 | NH-n-Bu | S-i-Pr | H | 4-Me |
| D-396 | NH-n-Bu | S-n-Bu | H | 4-Me |
| D-397 | NH-n-Bu | S-allyl | H | 4-Me |
| D-398 | NH-n-Bu | S-propargyl | H | 4-Me |
| D-399 | NH-n-Bu | SCH₂CF₃ | H | 4-Me |
| D-400 | NH-n-Bu | SCH₂CH₂F | H | 4-Me |

TABLE 11

| Compound No. | R¹⁵ | R¹⁶ | R¹⁷ | R¹⁸ |
|---|---|---|---|---|
| D-401 | NH₂ | SH | Me | 2-NH₂ |
| D-402 | NH₂ | SMe | Me | 2-NH₂ |
| D-403 | NH₂ | SEt | Me | 2-NH₂ |
| D-404 | NH₂ | S-n-Pr | Me | 2-NH₂ |
| D-405 | NH₂ | S-i-Pr | Me | 2-NH₂ |
| D-406 | NH₂ | S-n-Bu | Me | 2-NH₂ |
| D-407 | NH₂ | S-allyl | Me | 2-NH₂ |
| D-408 | NH₂ | S-propargyl | Me | 2-NH₂ |
| D-409 | NH₂ | SCH₂CF₃ | Me | 2-NH₂ |
| D-410 | NH₂ | SCH₂CH₂F | Me | 2-NH₂ |
| D-411 | NHMe | SH | Me | 2-NH₂ |
| D-412 | NHMe | SMe | Me | 2-NH₂ |
| D-413 | NHMe | SEt | Me | 2-NH₂ |
| D-414 | NHMe | S-n-Pr | Me | 2-NH₂ |
| D-415 | NHMe | S-i-Pr | Me | 2-NH₂ |
| D-416 | NHMe | S-n-Bu | Me | 2-NH₂ |
| D-417 | NHMe | S-allyl | Me | 2-NH₂ |
| D-418 | NHMe | S-propargyl | Me | 2-NH₂ |
| D-419 | NHMe | SCH₂CF₃ | Me | 2-NH₂ |
| D-420 | NHMe | SCH₂CH₂F | Me | 2-NH₂ |
| D-421 | NHEt | SH | Me | 2-NH₂ |
| D-422 | NHEt | SMe | Me | 2-NH₂ |
| D-423 | NHEt | SEt | Me | 2-NH₂ |
| D-424 | NHEt | S-n-Pr | Me | 2-NH₂ |
| D-425 | NHEt | S-i-Pr | Me | 2-NH₂ |
| D-426 | NHEt | S-n-Bu | Me | 2-NH₂ |
| D-427 | NHEt | S-allyl | Me | 2-NH₂ |
| D-428 | NHEt | S-propargyl | Me | 2-NH₂ |
| D-429 | NHEt | SCH₂CF₃ | Me | 2-NH₂ |
| D-430 | NHEt | SCH₂CH₂F | Me | 2-NH₂ |
| D-431 | NHPr | SH | Me | 2-NH₂ |
| D-432 | NHPr | SMe | Me | 2-NH₂ |
| D-433 | NHPr | SEt | Me | 2-NH₂ |
| D-434 | NHPr | S-n-Pr | Me | 2-NH₂ |
| D-435 | NHPr | S-i-Pr | Me | 2-NH₂ |
| D-436 | NHPr | S-n-Bu | Me | 2-NH₂ |
| D-437 | NHPr | S-allyl | Me | 2-NH₂ |
| D-438 | NHPr | S-propargyl | Me | 2-NH₂ |
| D-439 | NHPr | SCH₂CF₃ | Me | 2-NH₂ |
| D-440 | NHPr | SCH₂CH₂F | Me | 2-NH₂ |
| D-441 | NH-i-Pr | SH | Me | 2-NH₂ |
| D-442 | NH-i-Pr | SMe | Me | 2-NH₂ |
| D-443 | NH-i-Pr | SEt | Me | 2-NH₂ |
| D-444 | NH-i-Pr | S-n-Pr | Me | 2-NH₂ |
| D-445 | NH-i-Pr | S-i-Pr | Me | 2-NH₂ |
| D-446 | NH-i-Pr | S-n-Bu | Me | 2-NH₂ |
| D-447 | NH-i-Pr | S-allyl | Me | 2-NH₂ |
| D-448 | NH-i-Pr | S-propargyl | Me | 2-NH₂ |
| D-449 | NH-i-Pr | SCH₂CF₃ | Me | 2-NH₂ |
| D-450 | NH-i-Pr | SCH₂CH₂F | Me | 2-NH₂ |
| D-451 | NH-allyl | SH | Me | 2-NH₂ |
| D-452 | NH-allyl | SMe | Me | 2-NH₂ |
| D-453 | NH-allyl | SEt | Me | 2-NH₂ |

TABLE 11-continued

| Compound No. | R¹⁵ | R¹⁶ | R¹⁷ | R¹⁸ |
|---|---|---|---|---|
| D-454 | NH-allyl | S-n-Pr | Me | 2-NH₂ |
| D-455 | NH-allyl | S-i-Pr | Me | 2-NH₂ |
| D-456 | NH-allyl | S-n-Bu | Me | 2-NH₂ |
| D-457 | NH-allyl | S-allyl | Me | 2-NH₂ |
| D-458 | NH-allyl | S-propargyl | Me | 2-NH₂ |
| D-459 | NH-allyl | SCH₂CF₃ | Me | 2-NH₂ |
| D-460 | NH-allyl | SCH₂CH₂F | Me | 2-NH₂ |
| D-461 | NH-propargyl | SH | Me | 2-NH₂ |
| D-462 | NH-propargyl | SMe | Me | 2-NH₂ |
| D-463 | NH-propargyl | SEt | Me | 2-NH₂ |
| D-464 | NH-propargyl | S-n-Pr | Me | 2-NH₂ |
| D-465 | NH-propargyl | S-i-Pr | Me | 2-NH₂ |
| D-466 | NH-propargyl | S-n-Bu | Me | 2-NH₂ |
| D-467 | NH-propargyl | S-allyl | Me | 2-NH₂ |
| D-468 | NH-propargyl | S-propargyl | Me | 2-NH₂ |
| D-469 | NH-propargyl | SCH₂CF₃ | Me | 2-NH₂ |
| D-470 | NH-propargyl | SCH₂CH₂F | Me | 2-NH₂ |
| D-471 | NHCH₂CF₃ | SH | Me | 2-NH₂ |
| D-472 | NHCH₂CF₃ | SMe | Me | 2-NH₂ |
| D-473 | NHCH₂CF₃ | SEt | Me | 2-NH₂ |
| D-474 | NHCH₂CF₃ | S-n-Pr | Me | 2-NH₂ |
| D-475 | NHCH₂CF₃ | S-i-Pr | Me | 2-NH₂ |
| D-476 | NHCH₂CF₃ | S-n-Bu | Me | 2-NH₂ |
| D-477 | NHCH₂CF₃ | S-allyl | Me | 2-NH₂ |
| D-478 | NHCH₂CF₃ | S-propargyl | Me | 2-NH₂ |
| D-479 | NHCH₂CF₃ | SCH₂CF₃ | Me | 2-NH₂ |
| D-480 | NHCH₂CF₃ | SCH₂CH₂F | Me | 2-NH₂ |
| D-481 | NHCH₂CH₂F | SH | Me | 2-NH₂ |
| D-482 | NHCH₂CH₂F | SMe | Me | 2-NH₂ |
| D-483 | NHCH₂CH₂F | SEt | Me | 2-NH₂ |
| D-484 | NHCH₂CH₂F | S-n-Pr | Me | 2-NH₂ |
| D-485 | NHCH₂CH₂F | S-i-Pr | Me | 2-NH₂ |
| D-486 | NHCH₂CH₂F | S-n-Bu | Me | 2-NH₂ |
| D-487 | NHCH₂CH₂F | S-allyl | Me | 2-NH₂ |
| D-488 | NHCH₂CH₂F | S-propargyl | Me | 2-NH₂ |
| D-489 | NHCH₂CH₂F | SCH₂CF₃ | Me | 2-NH₂ |
| D-490 | NHCH₂CH₂F | SCH₂CH₂F | Me | 2-NH₂ |
| D-491 | NH-n-Bu | SH | Me | 2-NH₂ |
| D-492 | NH-n-Bu | SMe | Me | 2-NH₂ |
| D-493 | NH-n-Bu | SEt | Me | 2-NH₂ |
| D-494 | NH-n-Bu | S-n-Pr | Me | 2-NH₂ |
| D-495 | NH-n-Bu | S-i-Pr | Me | 2-NH₂ |
| D-496 | NH-n-Bu | S-n-Bu | Me | 2-NH₂ |
| D-497 | NH-n-Bu | S-allyl | Me | 2-NH₂ |
| D-498 | NH-n-Bu | S-propargyl | Me | 2-NH₂ |
| D-499 | NH-n-Bu | SCH₂CF₃ | Me | 2-NH₂ |
| D-500 | NH-n-Bu | SCH₂CH₂F | Me | 2-NH₂ |

TABLE 12

| Compound No. | R¹⁵ | R¹⁶ | R¹⁷ | R¹⁸ |
|---|---|---|---|---|
| D-501 | NH₂ | SH | Et | 4-NO₂ |
| D-502 | NH₂ | SMe | Et | 4-NO₂ |
| D-503 | NH₂ | SEt | Et | 4-NO₂ |
| D-504 | NH₂ | S-n-Pr | Et | 4-NO₂ |
| D-505 | NH₂ | S-i-Pr | Et | 4-NO₂ |
| D-506 | NH₂ | S-n-Bu | Et | 4-NO₂ |
| D-507 | NH₂ | S-allyl | Et | 4-NO₂ |
| D-508 | NH₂ | S-propargyl | Et | 4-NO₂ |
| D-509 | NH₂ | SCH₂CF₃ | Et | 4-NO₂ |
| D-510 | NH₂ | SCH₂CH₂F | Et | 4-NO₂ |
| D-511 | NHMe | SH | Et | 4-NO₂ |
| D-512 | NHMe | SMe | Et | 4-NO₂ |
| D-513 | NHMe | SEt | Et | 4-NO₂ |
| D-514 | NHMe | S-n-Pr | Et | 4-NO₂ |
| D-515 | NHMe | S-i-Pr | Et | 4-NO₂ |
| D-516 | NHMe | S-n-Bu | Et | 4-NO₂ |
| D-517 | NHMe | S-allyl | Et | 4-NO₂ |
| D-518 | NHMe | S-propargyl | Et | 4-NO₂ |

TABLE 12-continued

| Compound No. | $R^{15}$ | $R^{16}$ | $R^{17}$ | $R^{18}$ |
|---|---|---|---|---|
| D-519 | NHMe | $SCH_2CF_3$ | Et | $4-NO_2$ |
| D-520 | NHMe | $SCH_2CH_2F$ | Et | $4-NO_2$ |
| D-521 | NHEt | SH | Et | $4-NO_2$ |
| D-522 | NHEt | SMe | Et | $4-NO_2$ |
| D-523 | NHEt | SEt | Et | $4-NO_2$ |
| D-524 | NHEt | S-n-Pr | Et | $4-NO_2$ |
| D-525 | NHEt | S-i-Pr | Et | $4-NO_2$ |
| D-526 | NHEt | S-n-Bu | Et | $4-NO_2$ |
| D-527 | NHEt | S-allyl | Et | $4-NO_2$ |
| D-528 | NHEt | S-propargyl | Et | $4-NO_2$ |
| D-529 | NHEt | $SCH_2CF_3$ | Et | $4-NO_2$ |
| D-530 | NHEt | $SCH_2CH_2F$ | Et | $4-NO_2$ |
| D-531 | NHPr | SH | Et | $4-NO_2$ |
| D-532 | NHPr | SMe | Et | $4-NO_2$ |
| D-533 | NHPr | SEt | Et | $4-NO_2$ |
| D-534 | NHPr | S-n-Pr | Et | $4-NO_2$ |
| D-535 | NHPr | S-i-Pr | Et | $4-NO_2$ |
| D-536 | NHPr | S-n-Bu | Et | $4-NO_2$ |
| D-537 | NHPr | S-allyl | Et | $4-NO_2$ |
| D-538 | NHPr | S-propargyl | Et | $4-NO_2$ |
| D-539 | NHPr | $SCH_2CF_3$ | Et | $4-NO_2$ |
| D-540 | NHPr | $SCH_2CH_2F$ | Et | $4-NO_2$ |
| D-541 | NH-i-Pr | SH | Et | $4-NO_2$ |
| D-542 | NH-i-Pr | SMe | Et | $4-NO_2$ |
| D-543 | NH-i-Pr | SEt | Et | $4-NO_2$ |
| D-544 | NH-i-Pr | S-n-Pr | Et | $4-NO_2$ |
| D-545 | NH-i-Pr | S-i-Pr | Et | $4-NO_2$ |
| D-546 | NH-i-Pr | S-n-Bu | Et | $4-NO_2$ |
| D-547 | NH-i-Pr | S-allyl | Et | $4-NO_2$ |
| D-548 | NH-i-Pr | S-propargyl | Et | $4-NO_2$ |
| D-549 | NH-i-Pr | $SCH_2CF_3$ | Et | $4-NO_2$ |
| D-550 | NH-i-Pr | $SCH_2CH_2F$ | Et | $4-NO_2$ |
| D-551 | NH-allyl | SH | Et | $4-NO_2$ |
| D-552 | NH-allyl | SMe | Et | $4-NO_2$ |
| D-553 | NH-allyl | SEt | Et | $4-NO_2$ |
| D-554 | NH-allyl | S-n-Pr | Et | $4-NO_2$ |
| D-555 | NH-allyl | S-i-Pr | Et | $4-NO_2$ |
| D-556 | NH-allyl | S-n-Bu | Et | $4-NO_2$ |
| D-557 | NH-allyl | S-allyl | Et | $4-NO_2$ |
| D-558 | NH-allyl | S-propargyl | Et | $4-NO_2$ |
| D-559 | NH-allyl | $SCH_2CF_3$ | Et | $4-NO_2$ |
| D-560 | NH-allyl | $SCH_2CH_2F$ | Et | $4-NO_2$ |
| D-561 | NH-propargyl | SH | Et | $4-NO_2$ |
| D-562 | NH-propargyl | SMe | Et | $4-NO_2$ |
| D-563 | NH-propargyl | SEt | Et | $4-NO_2$ |
| D-564 | NH-propargyl | S-n-Pr | Et | $4-NO_2$ |
| D-565 | NH-propargyl | S-i-Pr | Et | $4-NO_2$ |
| D-566 | NH-propargyl | S-n-Bu | Et | $4-NO_2$ |
| D-567 | NH-propargyl | S-allyl | Et | $4-NO_2$ |
| D-568 | NH-propargyl | S-propargyl | Et | $4-NO_2$ |
| D-569 | NH-propargyl | $SCH_2CF_3$ | Et | $4-NO_2$ |
| D-570 | NH-propargyl | $SCH_2CH_2F$ | Et | $4-NO_2$ |
| D-571 | $NHCH_2CF_3$ | SH | Et | $4-NO_2$ |
| D-572 | $NHCH_2CF_3$ | SMe | Et | $4-NO_2$ |
| D-573 | $NHCH_2CF_3$ | SEt | Et | $4-NO_2$ |
| D-574 | $NHCH_2CF_3$ | S-n-Pr | Et | $4-NO_2$ |
| D-575 | $NHCH_2CF_3$ | S-i-Pr | Et | $4-NO_2$ |
| D-576 | $NHCH_2CF_3$ | S-n-Bu | Et | $4-NO_2$ |
| D-577 | $NHCH_2CF_3$ | S-allyl | Et | $4-NO_2$ |
| D-578 | $NHCH_2CF_3$ | S-propargyl | Et | $4-NO_2$ |
| D-579 | $NHCH_2CF_3$ | $SCH_2CF_3$ | Et | $4-NO_2$ |
| D-580 | $NHCH_2CF_3$ | $SCH_2CH_2F$ | Et | $4-NO_2$ |
| D-581 | $NHCH_2CH_2F$ | SH | Et | $4-NO_2$ |
| D-582 | $NHCH_2CH_2F$ | SMe | Et | $4-NO_2$ |
| D-583 | $NHCH_2CH_2F$ | SEt | Et | $4-NO_2$ |
| D-584 | $NHCH_2CH_2F$ | S-n-Pr | Et | $4-NO_2$ |
| D-585 | $NHCH_2CH_2F$ | S-i-Pr | Et | $4-NO_2$ |
| D-586 | $NHCH_2CH_2F$ | S-n-Bu | Et | $4-NO_2$ |
| D-587 | $NHCH_2CH_2F$ | S-allyl | Et | $4-NO_2$ |
| D-588 | $NHCH_2CH_2F$ | S-propargyl | Et | $4-NO_2$ |
| D-589 | $NHCH_2CH_2F$ | $SCH_2CF_3$ | Et | $4-NO_2$ |
| D-590 | $NHCH_2CH_2F$ | $SCH_2CH_2F$ | Et | $4-NO_2$ |
| D-591 | NH-n-Bu | SH | Et | $4-NO_2$ |
| D-592 | NH-n-Bu | SMe | Et | $4-NO_2$ |
| D-593 | NH-n-Bu | SEt | Et | $4-NO_2$ |
| D-594 | NH-n-Bu | S-n-Pr | Et | $4-NO_2$ |
| D-595 | NH-n-Bu | S-i-Pr | Et | $4-NO_2$ |
| D-596 | NH-n-Bu | S-n-Bu | Et | $4-NO_2$ |
| D-597 | NH-n-Bu | S-allyl | Et | $4-NO_2$ |
| D-598 | NH-n-Bu | S-propargyl | Et | $4-NO_2$ |
| D-599 | NH-n-Bu | $SCH_2CF_3$ | Et | $4-NO_2$ |
| D-600 | NH-n-Bu | $SCH_2CH_2F$ | Et | $4-NO_2$ |

TABLE 13

| Compound No. | $R^{15}$ | $R^{16}$ | $R^{17}$ | $R^{18}$ |
|---|---|---|---|---|
| D-601 | $NH_2$ | SH | Et | $4-NH_2$ |
| D-602 | $NH_2$ | SMe | Et | $4-NH_2$ |
| D-603 | $NH_2$ | SEt | Et | $4-NH_2$ |
| D-604 | $NH_2$ | S-n-Pr | Et | $4-NH_2$ |
| D-605 | $NH_2$ | S-i-Pr | Et | $4-NH_2$ |
| D-606 | $NH_2$ | S-n-Bu | Et | $4-NH_2$ |
| D-607 | $NH_2$ | S-allyl | Et | $4-NH_2$ |
| D-608 | $NH_2$ | S-propargyl | Et | $4-NH_2$ |
| D-609 | $NH_2$ | $SCH_2CF_3$ | Et | $4-NH_2$ |
| D-610 | $NH_2$ | $SCH_2CH_2F$ | Et | $4-NH_2$ |
| D-611 | NHMe | SH | Et | $4-NH_2$ |
| D-612 | NHMe | SMe | Et | $4-NH_2$ |
| D-613 | NHMe | SEt | Et | $4-NH_2$ |
| D-614 | NHMe | S-n-Pr | Et | $4-NH_2$ |
| D-615 | NHMe | S-i-Pr | Et | $4-NH_2$ |
| D-616 | NHMe | S-n-Bu | Et | $4-NH_2$ |
| D-617 | NHMe | S-allyl | Et | $4-NH_2$ |
| D-618 | NHMe | S-propargyl | Et | $4-NH_2$ |
| D-619 | NHMe | $SCH_2CF_3$ | Et | $4-NH_2$ |
| D-620 | NHMe | $SCH_2CH_2F$ | Et | $4-NH_2$ |
| D-621 | NHEt | SH | Et | $4-NH_2$ |
| D-622 | NHEt | SMe | Et | $4-NH_2$ |
| D-623 | NHEt | SEt | Et | $4-NH_2$ |
| D-624 | NHEt | S-n-Pr | Et | $4-NH_2$ |
| D-625 | NHEt | S-i-Pr | Et | $4-NH_2$ |
| D-626 | NHEt | S-n-Bu | Et | $4-NH_2$ |
| D-627 | NHEt | S-allyl | Et | $4-NH_2$ |
| D-628 | NHEt | S-propargyl | Et | $4-NH_2$ |
| D-629 | NHEt | $SCH_2CF_3$ | Et | $4-NH_2$ |
| D-630 | NHEt | $SCH_2CH_2F$ | Et | $4-NH_2$ |
| D-631 | NHPr | SH | Et | $4-NH_2$ |
| D-632 | NHPr | SMe | Et | $4-NH_2$ |
| D-633 | NHPr | SEt | Et | $4-NH_2$ |
| D-634 | NHPr | S-n-Pr | Et | $4-NH_2$ |
| D-635 | NHPr | S-i-Pr | Et | $4-NH_2$ |
| D-636 | NHPr | S-n-Bu | Et | $4-NH_2$ |
| D-637 | NHPr | S-allyl | Et | $4-NH_2$ |
| D-638 | NHPr | S-propargyl | Et | $4-NH_2$ |
| D-639 | NHPr | $SCH_2CF_3$ | Et | $4-NH_2$ |
| D-640 | NHPr | $SCH_2CH_2F$ | Et | $4-NH_2$ |
| D-641 | NH-i-Pr | SH | Et | $4-NH_2$ |
| D-642 | NH-i-Pr | SMe | Et | $4-NH_2$ |
| D-643 | NH-i-Pr | SEt | Et | $4-NH_2$ |
| D-644 | NH-i-Pr | S-n-Pr | Et | $4-NH_2$ |
| D-645 | NH-i-Pr | S-i-Pr | Et | $4-NH_2$ |
| D-646 | NH-i-Pr | S-n-Bu | Et | $4-NH_2$ |
| D-647 | NH-i-Pr | S-allyl | Et | $4-NH_2$ |
| D-648 | NH-i-Pr | S-propargyl | Et | $4-NH_2$ |
| D-649 | NH-i-Pr | $SCH_2CF_3$ | Et | $4-NH_2$ |
| D-650 | NH-i-Pr | $SCH_2CH_2F$ | Et | $4-NH_2$ |
| D-651 | NH-allyl | SH | Et | $4-NH_2$ |
| D-652 | NH-allyl | SMe | Et | $4-NH_2$ |
| D-653 | NH-allyl | SEt | Et | $4-NH_2$ |
| D-654 | NH-allyl | S-n-Pr | Et | $4-NH_2$ |
| D-655 | NH-allyl | S-i-Pr | Et | $4-NH_2$ |
| D-656 | NH-allyl | S-n-Bu | Et | $4-NH_2$ |
| D-657 | NH-allyl | S-allyl | Et | $4-NH_2$ |
| D-658 | NH-allyl | S-propargyl | Et | $4-NH_2$ |

TABLE 13-continued

| Compound No. | $R^{15}$ | $R^{16}$ | $R^{17}$ | $R^{18}$ |
|---|---|---|---|---|
| D-659 | NH-allyl | $SCH_2CF_3$ | Et | 4-$NH_2$ |
| D-660 | NH-allyl | $SCH_2CH_2F$ | Et | 4-$NH_2$ |
| D-661 | NH-propargyl | SH | Et | 4-$NH_2$ |
| D-662 | NH-propargyl | SMe | Et | 4-$NH_2$ |
| D-663 | NH-propargyl | SEt | Et | 4-$NH_2$ |
| D-664 | NH-propargyl | S-n-Pr | Et | 4-$NH_2$ |
| D-665 | NH-propargyl | S-i-Pr | Et | 4-$NH_2$ |
| D-666 | NH-propargyl | S-n-Bu | Et | 4-$NH_2$ |
| D-667 | NH-propargyl | S-allyl | Et | 4-$NH_2$ |
| D-668 | NH-propargyl | S-propargyl | Et | 4-$NH_2$ |
| D-669 | NH-propargyl | $SCH_2CF_3$ | Et | 4-$NH_2$ |
| D-670 | NH-propargyl | $SCH_2CH_2F$ | Et | 4-$NH_2$ |
| D-671 | $NHCH_2CF_3$ | SH | Et | 4-$NH_2$ |
| D-672 | $NHCH_2CF_3$ | SMe | Et | 4-$NH_2$ |
| D-673 | $NHCH_2CF_3$ | SEt | Et | 4-$NH_2$ |
| D-674 | $NHCH_2CF_3$ | S-n-Pr | Et | 4-$NH_2$ |
| D-675 | $NHCH_2CF_3$ | S-i-Pr | Et | 4-$NH_2$ |
| D-676 | $NHCH_2CF_3$ | S-n-Bu | Et | 4-$NH_2$ |
| D-677 | $NHCH_2CF_3$ | S-allyl | Et | 4-$NH_2$ |
| D-678 | $NHCH_2CF_3$ | S-propargyl | Et | 4-$NH_2$ |
| D-679 | $NHCH_2CF_3$ | $SCH_2CF_3$ | Et | 4-$NH_2$ |
| D-680 | $NHCH_2CF_3$ | $SCH_2CH_2F$ | Et | 4-$NH_2$ |
| D-681 | $NHCH_2CH_2F$ | SH | Et | 4-$NH_2$ |
| D-682 | $NHCH_2CH_2F$ | SMe | Et | 4-$NH_2$ |
| D-683 | $NHCH_2CH_2F$ | SEt | Et | 4-$NH_2$ |
| D-684 | $NHCH_2CH_2F$ | S-n-Pr | Et | 4-$NH_2$ |
| D-685 | $NHCH_2CH_2F$ | S-i-Pr | Et | 4-$NH_2$ |
| D-686 | $NHCH_2CH_2F$ | S-n-Bu | Et | 4-$NH_2$ |
| D-687 | $NHCH_2CH_2F$ | S-allyl | Et | 4-$NH_2$ |
| D-688 | $NHCH_2CH_2F$ | S-propargyl | Et | 4-$NH_2$ |
| D-689 | $NHCH_2CH_2F$ | $SCH_2CF_3$ | Et | 4-$NH_2$ |
| D-690 | $NHCH_2CH_2F$ | $SCH_2CH_2F$ | Et | 4-$NH_2$ |
| D-691 | NH-n-Bu | SH | Et | 4-$NH_2$ |
| D-692 | NH-n-Bu | SMe | Et | 4-$NH_2$ |
| D-693 | NH-n-Bu | SEt | Et | 4-$NH_2$ |
| D-694 | NH-n-Bu | S-n-Pr | Et | 4-$NH_2$ |
| D-695 | NH-n-Bu | S-i-Pr | Et | 4-$NH_2$ |
| D-696 | NH-n-Bu | S-n-Bu | Et | 4-$NH_2$ |
| D-697 | NH-n-Bu | S-allyl | Et | 4-$NH_2$ |
| D-698 | NH-n-Bu | S-propargyl | Et | 4-$NH_2$ |
| D-699 | NH-n-Bu | $SCH_2CF_3$ | Et | 4-$NH_2$ |
| D-700 | NH-n-Bu | $SCH_2CH_2F$ | Et | 4-$NH_2$ |

TABLE 14

| Compound No. | $R^{15}$ | $R^{16}$ | $R^{17}$ | $R^{18}$ |
|---|---|---|---|---|
| D-701 | $NH_2$ | SH | Me | 4-$NO_2$ |
| D-702 | $NH_2$ | SMe | Me | 4-OMe |
| D-703 | $NH_2$ | SEt | Me | 4-$NO_2$ |
| D-704 | $NH_2$ | S-n-Pr | Me | 4-$NO_2$ |
| D-705 | $NH_2$ | S-i-Pr | Me | 4-$NO_2$ |
| D-706 | $NH_2$ | S-n-Bu | Me | 4-$NO_2$ |
| D-707 | $NH_2$ | S-allyl | Me | 4-$NO_2$ |
| D-708 | $NH_2$ | S-propargyl | Me | 4-$NO_2$ |
| D-709 | $NH_2$ | $SCH_2CF_3$ | Me | 4-$NO_2$ |
| D-710 | $NH_2$ | $SCH_2CH_2F$ | Me | 4-$NO_2$ |
| D-711 | NHMe | SH | Me | 4-$NO_2$ |
| D-712 | NHMe | SMe | Me | 4-OMe |
| D-713 | NHMe | SEt | Me | 4-OMe |
| D-714 | NHMe | S-n-Pr | Me | 4-OMe |
| D-715 | NHMe | S-i-Pr | Me | 4-$NO_2$ |
| D-716 | NHMe | S-n-Bu | Me | 4-$NO_2$ |
| D-717 | NHMe | S-allyl | Me | 4-$NO_2$ |
| D-718 | NHMe | S-propargyl | Me | 4-$NO_2$ |
| D-719 | NHMe | $SCH_2CF_3$ | Me | 4-$NO_2$ |
| D-720 | NHMe | $SCH_2CH_2F$ | Me | 4-$NO_2$ |
| D-721 | NHEt | SH | Me | 4-$NO_2$ |
| D-722 | NHEt | SMe | Me | 4-OMe |
| D-723 | NHEt | SEt | Me | 4-OMe |

TABLE 14-continued

| Compound No. | $R^{15}$ | $R^{16}$ | $R^{17}$ | $R^{18}$ |
|---|---|---|---|---|
| D-724 | NHEt | S-n-Pr | Me | 4-OMe |
| D-725 | NHEt | S-i-Pr | Me | 4-$NO_2$ |
| D-726 | NHEt | S-n-Bu | Me | 4-$NO_2$ |
| D-727 | NHEt | S-allyl | Me | 4-$NO_2$ |
| D-728 | NHEt | S-propargyl | Me | 4-$NO_2$ |
| D-729 | NHEt | $SCH_2CF_3$ | Me | 4-$NO_2$ |
| D-730 | NHEt | $SCH_2CH_2F$ | Me | 4-$NO_2$ |
| D-731 | NHPr | SH | Me | 4-$NO_2$ |
| D-732 | NHPr | SMe | Me | 4-OMe |
| D-733 | NHPr | SEt | Me | 4-$NO_2$ |
| D-734 | NHPr | S-n-Pr | Me | 4-$NO_2$ |
| D-735 | NHPr | S-i-Pr | Me | 4-$NO_2$ |
| D-736 | NHPr | S-n-Bu | Me | 4-$NO_2$ |
| D-737 | NHPr | S-allyl | Me | 4-$NO_2$ |
| D-738 | NHPr | S-propargyl | Me | 4-$NO_2$ |
| D-739 | NHPr | $SCH_2CF_3$ | Me | 4-$NO_2$ |
| D-740 | NHPr | $SCH_2CH_2F$ | Me | 4-$NO_2$ |
| D-741 | NH-i-Pr | SH | Me | 4-$NO_2$ |
| D-742 | NH-i-Pr | SMe | Me | 4-$NO_2$ |
| D-743 | NH-i-Pr | SEt | Me | 4-$NO_2$ |
| D-744 | NH-i-Pr | S-n-Pr | Me | 4-$NO_2$ |
| D-745 | NH-i-Pr | S-i-Pr | Me | 4-$NO_2$ |
| D-746 | NH-i-Pr | S-n-Bu | Me | 4-$NO_2$ |
| D-747 | NH-i-Pr | S-allyl | Me | 4-$NO_2$ |
| D-748 | NH-i-Pr | S-propargyl | Me | 4-$NO_2$ |
| D-749 | NH-i-Pr | $SCH_2CF_3$ | Me | 4-$NO_2$ |
| D-750 | NH-i-Pr | $SCH_2CH_2F$ | Me | 4-$NO_2$ |
| D-751 | NH-allyl | SH | Me | 4-$NO_2$ |
| D-752 | NH-allyl | SMe | Me | 4-$NO_2$ |
| D-753 | NH-allyl | SEt | Me | 4-$NO_2$ |
| D-754 | NH-allyl | S-n-Pr | Me | 4-$NO_2$ |
| D-755 | NH-allyl | S-i-Pr | Me | 4-$NO_2$ |
| D-756 | NH-allyl | S-n-Bu | Me | 4-$NO_2$ |
| D-757 | NH-allyl | S-allyl | Me | 4-$NO_2$ |
| D-758 | NH-allyl | S-propargyl | Me | 4-$NO_2$ |
| D-759 | NH-allyl | $SCH_2CF_3$ | Me | 4-$NO_2$ |
| D-760 | NH-allyl | $SCH_2CH_2F$ | Me | 4-$NO_2$ |
| D-761 | NH-propargyl | SH | Me | 4-$NO_2$ |
| D-762 | NH-propargyl | SMe | Me | 4-$NO_2$ |
| D-763 | NH-propargyl | SEt | Me | 4-$NO_2$ |
| D-764 | NH-propargyl | S-n-Pr | Me | 4-$NO_2$ |
| D-765 | NH-propargyl | S-i-Pr | Me | 4-$NO_2$ |
| D-766 | NH-propargyl | S-n-Bu | Me | 4-$NO_2$ |
| D-767 | NH-propargyl | S-allyl | Me | 4-$NO_2$ |
| D-768 | NH-propargyl | S-propargyl | Me | 4-$NO_2$ |
| D-769 | NH-propargyl | $SCH_2CF_3$ | Me | 4-$NO_2$ |
| D-770 | NH-propargyl | $SCH_2CH_2F$ | Me | 4-$NO_2$ |
| D-771 | $NHCH_2CF_3$ | SH | Me | 4-$NO_2$ |
| D-772 | $NHCH_2CF_3$ | SMe | Me | 4-OMe |
| D-773 | $NHCH_2CF_3$ | SEt | Me | 4-$NO_2$ |
| D-774 | $NHCH_2CF_3$ | S-n-Pr | Me | 4-$NO_2$ |
| D-775 | $NHCH_2CF_3$ | S-i-Pr | Me | 4-$NO_2$ |
| D-776 | $NHCH_2CF_3$ | S-n-Bu | Me | 4-$NO_2$ |
| D-777 | $NHCH_2CF_3$ | S-allyl | Me | 4-$NO_2$ |
| D-778 | $NHCH_2CF_3$ | S-propargyl | Me | 4-$NO_2$ |
| D-779 | $NHCH_2CF_3$ | $SCH_2CF_3$ | Me | 4-$NO_2$ |
| D-780 | $NHCH_2CF_3$ | $SCH_2CH_2F$ | Me | 4-$NO_2$ |
| D-781 | $NHCH_2CH_2F$ | SH | Me | 4-$NO_2$ |
| D-782 | $NHCH_2CH_2F$ | SMe | Me | 4-$NO_2$ |
| D-783 | $NHCH_2CH_2F$ | SEt | Me | 4-$NO_2$ |
| D-784 | $NHCH_2CH_2F$ | S-n-Pr | Me | 4-$NO_2$ |
| D-785 | $NHCH_2CH_2F$ | S-i-Pr | Me | 4-$NO_2$ |
| D-786 | $NHCH_2CH_2F$ | S-n-Bu | Me | 4-$NO_2$ |
| D-787 | $NHCH_2CH_2F$ | S-allyl | Me | 4-$NO_2$ |
| D-788 | $NHCH_2CH_2F$ | S-propargyl | Me | 4-$NO_2$ |
| D-789 | $NHCH_2CH_2F$ | $SCH_2CF_3$ | Me | 4-$NO_2$ |
| D-790 | $NHCH_2CH_2F$ | $SCH_2CH_2F$ | Me | 4-$NO_2$ |
| D-791 | NH-n-Bu | SH | Me | 4-$NO_2$ |
| D-792 | NH-n-Bu | SMe | Me | 4-$NO_2$ |
| D-793 | NH-n-Bu | SEt | Me | 4-$NO_2$ |
| D-794 | NH-n-Bu | S-n-Pr | Me | 4-$NO_2$ |
| D-795 | NH-n-Bu | S-i-Pr | Me | 4-$NO_2$ |
| D-796 | NH-n-Bu | S-n-Bu | Me | 4-$NO_2$ |
| D-797 | NH-n-Bu | S-allyl | Me | 4-$NO_2$ |
| D-798 | NH-n-Bu | S-propargyl | Me | 4-$NO_2$ |

TABLE 14-continued

| Compound No. | R$^{15}$ | R$^{16}$ | R$^{17}$ | R$^{18}$ |
|---|---|---|---|---|
| D-799 | NH-n-Bu | SCH$_2$CF$_3$ | Me | 4-NO$_2$ |
| D-800 | NH-n-Bu | SCH$_2$CH$_2$F | Me | 4-NO$_2$ |

TABLE 15

| Compound No. | R$^{15}$ | R$^{16}$ | R$^{17}$ | R$^{18}$ |
|---|---|---|---|---|
| D-801 | NH$_2$ | SH | Me | 4-NH$_2$ |
| D-802 | NH$_2$ | SMe | Me | 4-OMe |
| D-803 | NH$_2$ | SEt | Me | 4-OMe |
| D-804 | NH$_2$ | S-n-Pr | Me | 4-NH$_2$ |
| D-805 | NH$_2$ | S-i-Pr | Me | 4-NH$_2$ |
| D-806 | NH$_2$ | S-n-Bu | Me | 4-NH$_2$ |
| D-807 | NH$_2$ | S-allyl | Me | 4-NH$_2$ |
| D-808 | NH$_2$ | S-propargyl | Me | 4-NH$_2$ |
| D-809 | NH$_2$ | SCH$_2$CF$_3$ | Me | 4-NH$_2$ |
| D-810 | NH$_2$ | SCH$_2$CH$_2$F | Me | 4-NH$_2$ |
| D-811 | NHMe | SH | Me | 4-NH$_2$ |
| D-812 | NHMe | SMe | Me | 4-OMe |
| D-813 | NHMe | SEt | Me | 4-OMe |
| D-814 | NHMe | S-n-Pr | Me | 4-OMe |
| D-815 | NHMe | S-i-Pr | Me | 4-NH$_2$ |
| D-816 | NHMe | S-n-Bu | Me | 4-NH$_2$ |
| D-817 | NHMe | S-allyl | Me | 4-NH$_2$ |
| D-818 | NHMe | S-propargyl | Me | 4-NH$_2$ |
| D-819 | NHMe | SCH$_2$CF$_3$ | Me | 4-NH$_2$ |
| D-820 | NHMe | SCH$_2$CH$_2$F | Me | 4-NH$_2$ |
| D-821 | NHEt | SH | Me | 4-NH$_2$ |
| D-822 | NHEt | SMe | Me | 4-OMe |
| D-823 | NHEt | SEt | Me | 4-OMe |
| D-824 | NHEt | S-n-Pr | Me | 4-OMe |
| D-825 | NHEt | S-i-Pr | Me | 4-NH$_2$ |
| D-826 | NHEt | S-n-Bu | Me | 4-NH$_2$ |
| D-827 | NHEt | S-allyl | Me | 4-NH$_2$ |
| D-828 | NHEt | S-propargyl | Me | 4-NH$_2$ |
| D-829 | NHEt | SCH$_2$CF$_3$ | Me | 4-NH$_2$ |
| D-830 | NHEt | SCH$_2$CH$_2$F | Me | 4-NH$_2$ |
| D-831 | NHPr | SH | Me | 4-NH$_2$ |
| D-832 | NHPr | SMe | Me | 4-OMe |
| D-833 | NHPr | SEt | Me | 4-NH$_2$ |
| D-834 | NHPr | S-n-Pr | Me | 4-NH$_2$ |
| D-835 | NHPr | S-i-Pr | Me | 4-NH$_2$ |
| D-836 | NHPr | S-n-Bu | Me | 4-NH$_2$ |
| D-837 | NHPr | S-allyl | Me | 4-NH$_2$ |
| D-838 | NHPr | S-propargyl | Me | 4-NH$_2$ |
| D-839 | NHPr | SCH$_2$CF$_3$ | Me | 4-NH$_2$ |
| D-840 | NHPr | SCH$_2$CH$_2$F | Me | 4-NH$_2$ |
| D-841 | NH-i-Pr | SH | Me | 4-NH$_2$ |
| D-842 | NH-i-Pr | SMe | Me | 4-NH$_2$ |
| D-843 | NH-i-Pr | SEt | Me | 4-NH$_2$ |
| D-844 | NH-i-Pr | S-n-Pr | Me | 4-NH$_2$ |
| D-845 | NH-i-Pr | S-i-Pr | Me | 4-NH$_2$ |
| D-846 | NH-i-Pr | S-n-Bu | Me | 4-NH$_2$ |
| D-847 | NH-i-Pr | S-allyl | Me | 4-NH$_2$ |
| D-848 | NH-i-Pr | S-propargyl | Me | 4-NH$_2$ |
| D-849 | NH-i-Pr | SCH$_2$CF$_3$ | Me | 4-NH$_2$ |
| D-850 | NH-i-Pr | SCH$_2$CH$_2$F | Me | 4-NH$_2$ |
| D-851 | NH-allyl | SH | Me | 4-NH$_2$ |
| D-852 | NH-allyl | SMe | Me | 4-NH$_2$ |
| D-853 | NH-allyl | SEt | Me | 4-NH$_2$ |
| D-854 | NH-allyl | S-n-Pr | Me | 4-NH$_2$ |
| D-855 | NH-allyl | S-i-Pr | Me | 4-NH$_2$ |
| D-856 | NH-allyl | S-n-Bu | Me | 4-NH$_2$ |
| D-857 | NH-allyl | S-allyl | Me | 4-NH$_2$ |
| D-858 | NH-allyl | S-propargyl | Me | 4-NH$_2$ |
| D-859 | NH-allyl | SCH$_2$CF$_3$ | Me | 4-NH$_2$ |
| D-860 | NH-allyl | SCH$_2$CH$_2$F | Me | 4-NH$_2$ |
| D-861 | NH-propargyl | SH | Me | 4-NH$_2$ |
| D-862 | NH-propargyl | SMe | Me | 4-NH$_2$ |
| D-863 | NH-propargyl | SEt | Me | 4-NH$_2$ |
| D-864 | NH-propargyl | S-n-Pr | Me | 4-NH$_2$ |
| D-865 | NH-propargyl | S-i-Pr | Me | 4-NH$_2$ |
| D-866 | NH-propargyl | S-n-Bu | Me | 4-NH$_2$ |
| D-867 | NH-propargyl | S-allyl | Me | 4-NH$_2$ |
| D-868 | NH-propargyl | S-propargyl | Me | 4-NH$_2$ |
| D-869 | NH-propargyl | SCH$_2$CF$_3$ | Me | 4-NH$_2$ |
| D-870 | NH-propargyl | SCH$_2$CH$_2$F | Me | 4-NH$_2$ |
| D-871 | NHCH$_2$CF$_3$ | SH | Me | 4-NH$_2$ |
| D-872 | NHCH$_2$CF$_3$ | SMe | Me | 4-OMe |
| D-873 | NHCH$_2$CF$_3$ | SEt | Me | 4-NH$_2$ |
| D-874 | NHCH$_2$CF$_3$ | S-n-Pr | Me | 4-NH$_2$ |
| D-875 | NHCH$_2$CF$_3$ | S-i-Pr | Me | 4-NH$_2$ |
| D-876 | NHCH$_2$CF$_3$ | S-n-Bu | Me | 4-NH$_2$ |
| D-877 | NHCH$_2$CF$_3$ | S-allyl | Me | 4-NH$_2$ |
| D-878 | NHCH$_2$CF$_3$ | S-propargyl | Me | 4-NH$_2$ |
| D-879 | NHCH$_2$CF$_3$ | SCH$_2$CF$_3$ | Me | 4-NH$_2$ |
| D-880 | NHCH$_2$CF$_3$ | SCH$_2$CH$_2$F | Me | 4-NH$_2$ |
| D-881 | NHCH$_2$CH$_2$F | SH | Me | 4-NH$_2$ |
| D-882 | NHCH$_2$CH$_2$F | SMe | Me | 4-NH$_2$ |
| D-883 | NHCH$_2$CH$_2$F | SEt | Me | 4-NH$_2$ |
| D-884 | NHCH$_2$CH$_2$F | S-n-Pr | Me | 4-NH$_2$ |
| D-885 | NHCH$_2$CH$_2$F | S-i-Pr | Me | 4-NH$_2$ |
| D-886 | NHCH$_2$CH$_2$F | S-n-Bu | Me | 4-NH$_2$ |
| D-887 | NHCH$_2$CH$_2$F | S-allyl | Me | 4-NH$_2$ |
| D-888 | NHCH$_2$CH$_2$F | S-propargyl | Me | 4-NH$_2$ |
| D-889 | NHCH$_2$CH$_2$F | SCH$_2$CF$_3$ | Me | 4-NH$_2$ |
| D-890 | NHCH$_2$CH$_2$F | SCH$_2$CH$_2$F | Me | 4-NH$_2$ |
| D-891 | NH-n-Bu | SH | Me | 4-NH$_2$ |
| D-892 | NH-n-Bu | SMe | Me | 4-NH$_2$ |
| D-893 | NH-n-Bu | SEt | Me | 4-NH$_2$ |
| D-894 | NH-n-Bu | S-n-Pr | Me | 4-NH$_2$ |
| D-895 | NH-n-Bu | S-i-Pr | Me | 4-NH$_2$ |
| D-896 | NH-n-Bu | S-n-Bu | Me | 4-NH$_2$ |
| D-897 | NH-n-Bu | S-allyl | Me | 4-NH$_2$ |
| D-898 | NH-n-Bu | S-propargyl | Me | 4-NH$_2$ |
| D-899 | NH-n-Bu | SCH$_2$CF$_3$ | Me | 4-NH$_2$ |
| D-900 | NH-n-Bu | SCH$_2$CH$_2$F | Me | 4-NH$_2$ |

TABLE 16

| Compound No. | R$^{15}$ | R$^{16}$ | R$^{17}$ | R$^{18}$ |
|---|---|---|---|---|
| D-901 | NH$_2$ | OH | H | 4-NH$_2$ |
| D-902 | NH$_2$ | OMe | H | 4-NH$_2$ |
| D-903 | NH$_2$ | OEt | H | 4-NH$_2$ |
| D-904 | NH$_2$ | O-n-Pr | H | 4-NH$_2$ |
| D-905 | NH$_2$ | O-i-Pr | H | 4-NH$_2$ |
| D-906 | NH$_2$ | O-n-Bu | H | 4-NH$_2$ |
| D-907 | NH$_2$ | O-allyl | H | 4-NH$_2$ |
| D-908 | NH$_2$ | O-propargyl | H | 4-NH$_2$ |
| D-909 | NH$_2$ | OCH$_2$CF$_3$ | H | 4-NH$_2$ |
| D-910 | NH$_2$ | OCH$_2$CH$_2$F | H | 4-NH$_2$ |
| D-911 | NHMe | OH | H | 4-NH$_2$ |
| D-912 | NHMe | OMe | H | 4-NH$_2$ |
| D-913 | NHMe | OEt | H | 4-NH$_2$ |
| D-914 | NHMe | O-n-Pr | H | 4-NH$_2$ |
| D-915 | NHMe | O-i-Pr | H | 4-NH$_2$ |
| D-916 | NHMe | O-n-Bu | H | 4-NH$_2$ |
| D-917 | NHMe | O-allyl | H | 4-NH$_2$ |
| D-918 | NHMe | O-propargyl | H | 4-NH$_2$ |
| D-919 | NHMe | OCH$_2$CF$_3$ | H | 4-NH$_2$ |
| D-920 | NHMe | OCH$_2$CH$_2$F | H | 4-NH$_2$ |
| D-921 | NHEt | OH | H | 4-NH$_2$ |
| D-922 | NHEt | OMe | H | 4-NH$_2$ |
| D-923 | NHEt | OEt | H | 4-NH$_2$ |
| D-924 | NHEt | O-n-Pr | H | 4-NH$_2$ |
| D-925 | NHEt | O-i-Pr | H | 4-NH$_2$ |
| D-926 | NHEt | O-n-Bu | H | 4-NH$_2$ |
| D-927 | NHEt | O-allyl | H | 4-NH$_2$ |
| D-928 | NHEt | O-propargyl | H | 4-NH$_2$ |

TABLE 16-continued

| Compound No. | R¹⁵ | R¹⁶ | R¹⁷ | R¹⁸ |
|---|---|---|---|---|
| D-929 | NHEt | OCH$_2$CF$_3$ | H | 4-NH$_2$ |
| D-930 | NHEt | OCH$_2$CH$_2$F | H | 4-NH$_2$ |
| D-931 | NHPr | OH | H | 4-NH$_2$ |
| D-932 | NHPr | OMe | H | 4-NH$_2$ |
| D-933 | NHPr | OEt | H | 4-NH$_2$ |
| D-934 | NHPr | O-n-Pr | H | 4-NH$_2$ |
| D-935 | NHPr | O-i-Pr | H | 4-NH$_2$ |
| D-936 | NHPr | O-n-Bu | H | 4-NH$_2$ |
| D-937 | NHPr | O-allyl | H | 4-NH$_2$ |
| D-938 | NHPr | O-propargyl | H | 4-NH$_2$ |
| D-939 | NHPr | OCH$_2$CF$_3$ | H | 4-NH$_2$ |
| D-940 | NHPr | OCH$_2$CH$_2$F | H | 4-NH$_2$ |
| D-941 | NH-i-Pr | OH | H | 4-NH$_2$ |
| D-942 | NH-i-Pr | OMe | H | 4-NH$_2$ |
| D-943 | NH-i-Pr | OEt | H | 4-NH$_2$ |
| D-944 | NH-i-Pr | O-n-Pr | H | 4-NH$_2$ |
| D-945 | NH-i-Pr | O-i-Pr | H | 4-NH$_2$ |
| D-946 | NH-i-Pr | O-n-Bu | H | 4-NH$_2$ |
| D-947 | NH-i-Pr | O-allyl | H | 4-NH$_2$ |
| D-948 | NH-i-Pr | O-propargyl | H | 4-NH$_2$ |
| D-949 | NH-i-Pr | OCH$_2$CF$_3$ | H | 4-NH$_2$ |
| D-950 | NH-i-Pr | OCH$_2$CH$_2$F | H | 4-NH$_2$ |
| D-951 | NH-allyl | OH | H | 4-NH$_2$ |
| D-952 | NH-allyl | OMe | H | 4-NH$_2$ |
| D-953 | NH-allyl | OEt | H | 4-NH$_2$ |
| D-954 | NH-allyl | O-n-Pr | H | 4-NH$_2$ |
| D-955 | NH-allyl | O-i-Pr | H | 4-NH$_2$ |
| D-956 | NH-allyl | O-n-Bu | H | 4-NH$_2$ |
| D-957 | NH-allyl | O-allyl | H | 4-NH$_2$ |
| D-958 | NH-allyl | O-propargyl | H | 4-NH$_2$ |
| D-959 | NH-allyl | OCH$_2$CF$_3$ | H | 4-NH$_2$ |
| D-960 | NH-allyl | OCH$_2$CH$_2$F | H | 4-NH$_2$ |
| D-961 | NH-propargyl | OH | H | 4-NH$_2$ |
| D-962 | NH-propargyl | OMe | H | 4-NH$_2$ |
| D-963 | NH-propargyl | OEt | H | 4-NH$_2$ |
| D-964 | NH-propargyl | O-n-Pr | H | 4-NH$_2$ |
| D-965 | NH-propargyl | O-i-Pr | H | 4-NH$_2$ |
| D-966 | NH-propargyl | O-n-Bu | H | 4-NH$_2$ |
| D-967 | NH-propargyl | O-allyl | H | 4-NH$_2$ |
| D-968 | NH-propargyl | O-propargyl | H | 4-NH$_2$ |
| D-969 | NH-propargyl | OCH$_2$CF$_3$ | H | 4-NH$_2$ |
| D-970 | NH-propargyl | OCH$_2$CH$_2$F | H | 4-NH$_2$ |
| D-971 | NHCH$_2$CF$_3$ | OH | H | 4-NH$_2$ |
| D-972 | NHCH$_2$CF$_3$ | OMe | H | 4-NH$_2$ |
| D-973 | NHCH$_2$CF$_3$ | OEt | H | 4-NH$_2$ |
| D-974 | NHCH$_2$CF$_3$ | O-n-Pr | H | 4-NH$_2$ |
| D-975 | NHCH$_2$CF$_3$ | O-i-Pr | H | 4-NH$_2$ |
| D-976 | NHCH$_2$CF$_3$ | O-n-Bu | H | 4-NH$_2$ |
| D-977 | NHCH$_2$CF$_3$ | O-allyl | H | 4-NH$_2$ |
| D-978 | NHCH$_2$CF$_3$ | O-propargyl | H | 4-NH$_2$ |
| D-979 | NHCH$_2$CF$_3$ | OCH$_2$CF$_3$ | H | 4-NH$_2$ |
| D-980 | NHCH$_2$CF$_3$ | OCH$_2$CH$_2$F | H | 4-NH$_2$ |
| D-981 | NHCH$_2$CH$_2$F | OH | H | 4-NH$_2$ |
| D-982 | NHCH$_2$CH$_2$F | OMe | H | 4-NH$_2$ |
| D-983 | NHCH$_2$CH$_2$F | OEt | H | 4-NH$_2$ |
| D-984 | NHCH$_2$CH$_2$F | O-n-Pr | H | 4-NH$_2$ |
| D-985 | NHCH$_2$CH$_2$F | O-i-Pr | H | 4-NH$_2$ |
| D-986 | NHCH$_2$CH$_2$F | O-n-Bu | H | 4-NH$_2$ |
| D-987 | NHCH$_2$CH$_2$F | O-allyl | H | 4-NH$_2$ |
| D-988 | NHCH$_2$CH$_2$F | O-propargyl | H | 4-NH$_2$ |
| D-989 | NHCH$_2$CH$_2$F | OCH$_2$CF$_3$ | H | 4-NH$_2$ |
| D-990 | NHCH$_2$CH$_2$F | OCH$_2$CH$_2$F | H | 4-NH$_2$ |
| D-991 | NH-n-Bu | OH | H | 4-NH$_2$ |
| D-992 | NH-n-Bu | OMe | H | 4-NH$_2$ |
| D-993 | NH-n-Bu | OEt | H | 4-NH$_2$ |
| D-994 | NH-n-Bu | O-n-Pr | H | 4-NH$_2$ |
| D-995 | NH-n-Bu | O-i-Pr | H | 4-NH$_2$ |
| D-996 | NH-n-Bu | O-n-Bu | H | 4-NH$_2$ |
| D-997 | NH-n-Bu | O-allyl | H | 4-NH$_2$ |
| D-998 | NH-n-Bu | O-propargyl | H | 4-NH$_2$ |
| D-999 | NH-n-Bu | OCH$_2$CF$_3$ | H | 4-NH$_2$ |
| D-1000 | NH-n-Bu | OCH$_2$CH$_2$F | H | 4-NH$_2$ |

TABLE 17

| Compound No. | R¹⁵ | R¹⁶ | R¹⁷ | R¹⁸ |
|---|---|---|---|---|
| D-1001 | NH$_2$ | OH | H | 4-NO$_2$ |
| D-1002 | NH$_2$ | OMe | H | 4-NO$_2$ |
| D-1003 | NH$_2$ | OEt | H | 4-NO$_2$ |
| D-1004 | NH$_2$ | O-n-Pr | H | 4-NO$_2$ |
| D-1005 | NH$_2$ | O-i-Pr | H | 4-NO$_2$ |
| D-1006 | NH$_2$ | O-n-Bu | H | 4-NO$_2$ |
| D-1007 | NH$_2$ | O-allyl | H | 4-NO$_2$ |
| D-1008 | NH$_2$ | O-propargyl | H | 4-NO$_2$ |
| D-1009 | NH$_2$ | OCH$_2$CF$_3$ | H | 4-NO$_2$ |
| D-1010 | NH$_2$ | OCH$_2$CH$_2$F | H | 4-NO$_2$ |
| D-1011 | NHMe | OH | H | 4-NO$_2$ |
| D-1012 | NHMe | OMe | H | 4-NO$_2$ |
| D-1013 | NHMe | OEt | H | 4-NO$_2$ |
| D-1014 | NHMe | O-n-Pr | H | 4-NO$_2$ |
| D-1015 | NHMe | O-i-Pr | H | 4-NO$_2$ |
| D-1016 | NHMe | O-n-Bu | H | 4-NO$_2$ |
| D-1017 | NHMe | O-allyl | H | 4-NO$_2$ |
| D-1018 | NHMe | O-propargyl | H | 4-NO$_2$ |
| D-1019 | NHMe | OCH$_2$CF$_3$ | H | 4-NO$_2$ |
| D-1020 | NHMe | OCH$_2$CH$_2$F | H | 4-NO$_2$ |
| D-1021 | NHEt | OH | H | 4-NO$_2$ |
| D-1022 | NHEt | OMe | H | 4-NO$_2$ |
| D-1023 | NHEt | OEt | H | 4-NO$_2$ |
| D-1024 | NHEt | O-n-Pr | H | 4-NO$_2$ |
| D-1025 | NHEt | O-i-Pr | H | 4-NO$_2$ |
| D-1026 | NHEt | O-n-Bu | H | 4-NO$_2$ |
| D-1027 | NHEt | O-allyl | H | 4-NO$_2$ |
| D-1028 | NHEt | O-propargyl | H | 4-NO$_2$ |
| D-1029 | NHEt | OCH$_2$CF$_3$ | H | 4-NO$_2$ |
| D-1030 | NHEt | OCH$_2$CH$_2$F | H | 4-NO$_2$ |
| D-1031 | NHPr | OH | H | 4-NO$_2$ |
| D-1032 | NHPr | OMe | H | 4-NO$_2$ |
| D-1033 | NHPr | OEt | H | 4-NO$_2$ |
| D-1034 | NHPr | O-n-Pr | H | 4-NO$_2$ |
| D-1035 | NHPr | O-i-Pr | H | 4-NO$_2$ |
| D-1036 | NHPr | O-n-Bu | H | 4-NO$_2$ |
| D-1037 | NHPr | O-allyl | H | 4-NO$_2$ |
| D-1038 | NHPr | O-propargyl | H | 4-NO$_2$ |
| D-1039 | NHPr | OCH$_2$CF$_3$ | H | 4-NO$_2$ |
| D-1040 | NHPr | OCH$_2$CH$_2$F | H | 4-NO$_2$ |
| D-1041 | NH-i-Pr | OH | H | 4-NO$_2$ |
| D-1042 | NH-i-Pr | OMe | H | 4-NO$_2$ |
| D-1043 | NH-i-Pr | OEt | H | 4-NO$_2$ |
| D-1044 | NH-i-Pr | O-n-Pr | H | 4-NO$_2$ |
| D-1045 | NH-i-Pr | O-i-Pr | H | 4-NO$_2$ |
| D-1046 | NH-i-Pr | O-n-Bu | H | 4-NO$_2$ |
| D-1047 | NH-i-Pr | O-allyl | H | 4-NO$_2$ |
| D-1048 | NH-i-Pr | O-propargyl | H | 4-NO$_2$ |
| D-1049 | NH-i-Pr | OCH$_2$CF$_3$ | H | 4-NO$_2$ |
| D-1050 | NH-i-Pr | OCH$_2$CH$_2$F | H | 4-NO$_2$ |
| D-1051 | NH-allyl | OH | H | 4-NO$_2$ |
| D-1052 | NH-allyl | OMe | H | 4-NO$_2$ |
| D-1053 | NH-allyl | OEt | H | 4-NO$_2$ |
| D-1054 | NH-allyl | O-n-Pr | H | 4-NO$_2$ |
| D-1055 | NH-allyl | O-i-Pr | H | 4-NO$_2$ |
| D-1056 | NH-allyl | O-n-Bu | H | 4-NO$_2$ |
| D-1057 | NH-allyl | O-allyl | H | 4-NO$_2$ |
| D-1058 | NH-allyl | O-propargyl | H | 4-NO$_2$ |
| D-1059 | NH-allyl | OCH$_2$CF$_3$ | H | 4-NO$_2$ |
| D-1060 | NH-allyl | OCH$_2$CH$_2$F | H | 4-NO$_2$ |
| D-1061 | NH-propargyl | OH | H | 4-NO$_2$ |
| D-1062 | NH-propargyl | OMe | H | 4-NO$_2$ |
| D-1063 | NH-propargyl | OEt | H | 4-NO$_2$ |
| D-1064 | NH-propargyl | O-n-Pr | H | 4-NO$_2$ |
| D-1065 | NH-propargyl | O-i-Pr | H | 4-NO$_2$ |
| D-1066 | NH-propargyl | O-n-Bu | H | 4-NO$_2$ |
| D-1067 | NH-propargyl | O-allyl | H | 4-NO$_2$ |
| D-1068 | NH-propargyl | O-propargyl | H | 4-NO$_2$ |
| D-1069 | NH-propargyl | OCH$_2$CF$_3$ | H | 4-NO$_2$ |
| D-1070 | NH-propargyl | OCH$_2$CH$_2$F | H | 4-NO$_2$ |
| D-1071 | NHCH$_2$CF$_3$ | OH | H | 4-NO$_2$ |
| D-1072 | NHCH$_2$CF$_3$ | OMe | H | 4-NO$_2$ |
| D-1073 | NHCH$_2$CF$_3$ | OEt | H | 4-NO$_2$ |
| D-1074 | NHCH$_2$CF$_3$ | O-n-Pr | H | 4-NO$_2$ |
| D-1075 | NHCH$_2$CF$_3$ | O-i-Pr | H | 4-NO$_2$ |

TABLE 17-continued

| Compound No. | $R^{15}$ | $R^{16}$ | $R^{17}$ | $R^{18}$ |
|---|---|---|---|---|
| D-1076 | NHCH$_2$CF$_3$ | O-n-Bu | H | 4-NO$_2$ |
| D-1077 | NHCH$_2$CF$_3$ | O-allyl | H | 4-NO$_2$ |
| D-1078 | NHCH$_2$CF$_3$ | O-propargyl | H | 4-NO$_2$ |
| D-1079 | NHCH$_2$CF$_3$ | OCH$_2$CF$_3$ | H | 4-NO$_2$ |
| D-1080 | NHCH$_2$CF$_3$ | OCH$_2$CH$_2$F | H | 4-NO$_2$ |
| D-1081 | NHCH$_2$CH$_2$F | OH | H | 4-NO$_2$ |
| D-1082 | NHCH$_2$CH$_2$F | OMe | H | 4-NO$_2$ |
| D-1083 | NHCH$_2$CH$_2$F | OEt | H | 4-NO$_2$ |
| D-1084 | NHCH$_2$CH$_2$F | O-n-Pr | H | 4-NO$_2$ |
| D-1085 | NHCH$_2$CH$_2$F | O-i-Pr | H | 4-NO$_2$ |
| D-1086 | NHCH$_2$CH$_2$F | O-n-Bu | H | 4-NO$_2$ |
| D-1087 | NHCH$_2$CH$_2$F | O-allyl | H | 4-NO$_2$ |
| D-1088 | NHCH$_2$CH$_2$F | O-propargyl | H | 4-NO$_2$ |
| D-1089 | NHCH$_2$CH$_2$F | OCH$_2$CF$_3$ | H | 4-NO$_2$ |
| D-1090 | NHCH$_2$CH$_2$F | OCH$_2$CH$_2$F | H | 4-NO$_2$ |
| D-1091 | NH-n-Bu | OH | H | 4-NO$_2$ |
| D-1092 | NH-n-Bu | OMe | H | 4-NO$_2$ |
| D-1093 | NH-n-Bu | OEt | H | 4-NO$_2$ |
| D-1094 | NH-n-Bu | O-n-Pr | H | 4-NO$_2$ |
| D-1095 | NH-n-Bu | O-i-Pr | H | 4-NO$_2$ |
| D-1096 | NH-n-Bu | O-n-Bu | H | 4-NO$_2$ |
| D-1097 | NH-n-Bu | O-allyl | H | 4-NO$_2$ |
| D-1098 | NH-n-Bu | O-propargyl | H | 4-NO$_2$ |
| D-1099 | NH-n-Bu | OCH$_2$CF$_3$ | H | 4-NO$_2$ |
| D-1100 | NH-n-Bu | OCH$_2$CH$_2$F | H | 4-NO$_2$ |

TABLE 18

| Compound No. | $R^{15}$ | $R^{16}$ | $R^{17}$ | $R^{18}$ |
|---|---|---|---|---|
| D-1101 | NH$_2$ | OH | Me | 4-NH$_2$ |
| D-1102 | NH$_2$ | OMe | Me | 4-NH$_2$ |
| D-1103 | NH$_2$ | OEt | Me | 4-NH$_2$ |
| D-1104 | NH$_2$ | O-n-Pr | Me | 4-NH$_2$ |
| D-1105 | NH$_2$ | O-i-Pr | Me | 4-NH$_2$ |
| D-1106 | NH$_2$ | O-n-Bu | Me | 4-NH$_2$ |
| D-1107 | NH$_2$ | O-allyl | Me | 4-NH$_2$ |
| D-1108 | NH$_2$ | O-propargyl | Me | 4-NH$_2$ |
| D-1109 | NH$_2$ | OCH$_2$CF$_3$ | Me | 4-NH$_2$ |
| D-1110 | NH$_2$ | OCH$_2$CH$_2$F | Me | 4-NH$_2$ |
| D-1111 | NHMe | OH | Me | 4-NH$_2$ |
| D-1112 | NHMe | OMe | Me | 4-NH$_2$ |
| D-1113 | NHMe | OEt | Me | 4-NH$_2$ |
| D-1114 | NHMe | O-n-Pr | Me | 4-NH$_2$ |
| D-1115 | NHMe | O-i-Pr | Me | 4-NH$_2$ |
| D-1116 | NHMe | O-n-Bu | Me | 4-NH$_2$ |
| D-1117 | NHMe | O-allyl | Me | 4-NH$_2$ |
| D-1118 | NHMe | O-propargyl | Me | 4-NH$_2$ |
| D-1119 | NHMe | OCH$_2$CF$_3$ | Me | 4-NH$_2$ |
| D-1120 | NHMe | OCH$_2$CH$_2$F | Me | 4-NH$_2$ |
| D-1121 | NHEt | OH | Me | 2-NH$_2$ |
| D-1122 | NHEt | OMe | Me | 4-NH$_2$ |
| D-1123 | NHEt | OEt | Me | 4-NH$_2$ |
| D-1124 | NHEt | O-n-Pr | Me | 4-NH$_2$ |
| D-1125 | NHEt | O-i-Pr | Me | 4-NH$_2$ |
| D-1126 | NHEt | O-n-Bu | Me | 4-NH$_2$ |
| D-1127 | NHEt | O-allyl | Me | 4-NH$_2$ |
| D-1128 | NHEt | O-propargyl | Me | 4-NH$_2$ |
| D-1129 | NHEt | OCH$_2$CF$_3$ | Me | 4-NH$_2$ |
| D-1130 | NHEt | OCH$_2$CH$_2$F | Me | 4-NH$_2$ |
| D-1131 | NHPr | OH | Me | 4-NH$_2$ |
| D-1132 | NHPr | OMe | Me | 4-NH$_2$ |
| D-1133 | NHPr | OEt | Me | 4-NH$_2$ |
| D-1134 | NHPr | O-n-Pr | Me | 4-NH$_2$ |
| D-1135 | NHPr | O-i-Pr | Me | 4-NH$_2$ |
| D-1136 | NHPr | O-n-Bu | Me | 4-NH$_2$ |
| D-1137 | NHPr | O-allyl | Me | 4-NH$_2$ |
| D-1138 | NHPr | O-propargyl | Me | 4-NH$_2$ |
| D-1139 | NHPr | OCH$_2$CF$_3$ | Me | 4-NH$_2$ |
| D-1140 | NHPr | OCH$_2$CH$_2$F | Me | 4-NH$_2$ |

TABLE 18-continued

| Compound No. | $R^{15}$ | $R^{16}$ | $R^{17}$ | $R^{18}$ |
|---|---|---|---|---|
| D-1141 | NH-i-Pr | OH | Me | 4-NH$_2$ |
| D-1142 | NH-i-Pr | OMe | Me | 4-NH$_2$ |
| D-1143 | NH-i-Pr | OEt | Me | 4-NH$_2$ |
| D-1144 | NH-i-Pr | O-n-Pr | Me | 4-NH$_2$ |
| D-1145 | NH-i-Pr | O-i-Pr | Me | 4-NH$_2$ |
| D-1146 | NH-i-Pr | O-n-Bu | Me | 4-NH$_2$ |
| D-1147 | NH-i-Pr | O-allyl | Me | 4-NH$_2$ |
| D-1148 | NH-i-Pr | O-propargyl | Me | 4-NH$_2$ |
| D-1149 | NH-i-Pr | OCH$_2$CF$_3$ | Me | 4-NH$_2$ |
| D-1150 | NH-i-Pr | OCH$_2$CH$_2$F | Me | 4-NH$_2$ |
| D-1151 | NH-allyl | OH | Me | 4-NH$_2$ |
| D-1152 | NH-allyl | OMe | Me | 4-NH$_2$ |
| D-1153 | NH-allyl | OEt | Me | 4-NH$_2$ |
| D-1154 | NH-allyl | O-n-Pr | Me | 4-NH$_2$ |
| D-1155 | NH-allyl | O-i-Pr | Me | 4-NH$_2$ |
| D-1156 | NH-allyl | O-n-Bu | Me | 4-NH$_2$ |
| D-1157 | NH-allyl | O-allyl | Me | 4-NH$_2$ |
| D-1158 | NH-allyl | O-propargyl | Me | 4-NH$_2$ |
| D-1159 | NH-allyl | OCH$_2$CF$_3$ | Me | 4-NH$_2$ |
| D-1160 | NH-allyl | OCH$_2$CH$_2$F | Me | 4-NH$_2$ |
| D-1161 | NH-propargyl | OH | Me | 4-NH$_2$ |
| D-1162 | NH-propargyl | OMe | Me | 4-NH$_2$ |
| D-1163 | NH-propargyl | OEt | Me | 4-NH$_2$ |
| D-1164 | NH-propargyl | O-n-Pr | Me | 4-NH$_2$ |
| D-1165 | NH-propargyl | O-i-Pr | Me | 4-NH$_2$ |
| D-1166 | NH-propargyl | O-n-Bu | Me | 4-NH$_2$ |
| D-1167 | NH-propargyl | O-allyl | Me | 4-NH$_2$ |
| D-1168 | NH-propargyl | O-propargyl | Me | 4-NH$_2$ |
| D-1169 | NH-propargyl | OCH$_2$CF$_3$ | Me | 4-NH$_2$ |
| D-1170 | NH-propargyl | OCH$_2$CH$_2$F | Me | 4-NH$_2$ |
| D-1171 | NHCH$_2$CF$_3$ | OH | Me | 4-NH$_2$ |
| D-1172 | NHCH$_2$CF$_3$ | OMe | Me | 4-NH$_2$ |
| D-1173 | NHCH$_2$CF$_3$ | OEt | Me | 4-NH$_2$ |
| D-1174 | NHCH$_2$CF$_3$ | O-n-Pr | Me | 4-NH$_2$ |
| D-1175 | NHCH$_2$CF$_3$ | O-i-Pr | Me | 4-NH$_2$ |
| D-1176 | NHCH$_2$CF$_3$ | O-n-Bu | Me | 4-NH$_2$ |
| D-1177 | NHCH$_2$CF$_3$ | O-allyl | Me | 4-NH$_2$ |
| D-1178 | NHCH$_2$CF$_3$ | O-propargyl | Me | 4-NH$_2$ |
| D-1179 | NHCH$_2$CF$_3$ | OCH$_2$CF$_3$ | Me | 4-NH$_2$ |
| D-1180 | NHCH$_2$CF$_3$ | OCH$_2$CH$_2$F | Me | 4-NH$_2$ |
| D-1181 | NHCH$_2$CH$_2$F | OH | Me | 4-NH$_2$ |
| D-1182 | NHCH$_2$CH$_2$F | OMe | Me | 4-NH$_2$ |
| D-1183 | NHCH$_2$CH$_2$F | OEt | Me | 4-NH$_2$ |
| D-1184 | NHCH$_2$CH$_2$F | O-n-Pr | Me | 4-NH$_2$ |
| D-1185 | NHCH$_2$CH$_2$F | O-i-Pr | Me | 4-NH$_2$ |
| D-1186 | NHCH$_2$CH$_2$F | O-n-Bu | Me | 4-NH$_2$ |
| D-1187 | NHCH$_2$CH$_2$F | O-allyl | Me | 4-NH$_2$ |
| D-1188 | NHCH$_2$CH$_2$F | O-propargyl | Me | 4-NH$_2$ |
| D-1189 | NHCH$_2$CH$_2$F | OCH$_2$CF$_3$ | Me | 4-NH$_2$ |
| D-1190 | NHCH$_2$CH$_2$F | OCH$_2$CH$_2$F | Me | 4-NH$_2$ |
| D-1191 | NH-n-Bu | OH | Me | 4-NH$_2$ |
| D-1192 | NH-n-Bu | OMe | Me | 4-NH$_2$ |
| D-1193 | NH-n-Bu | OEt | Me | 4-NH$_2$ |
| D-1194 | NH-n-Bu | O-n-Pr | Me | 4-NH$_2$ |
| D-1195 | NH-n-Bu | O-i-Pr | Me | 4-NH$_2$ |
| D-1196 | NH-n-Bu | O-n-Bu | Me | 4-NH$_2$ |
| D-1197 | NH-n-Bu | O-allyl | Me | 4-NH$_2$ |
| D-1198 | NH-n-Bu | O-propargyl | Me | 4-NH$_2$ |
| D-1199 | NH-n-Bu | OCH$_2$CF$_3$ | Me | 4-NH$_2$ |
| D-1200 | NH-n-Bu | OCH$_2$CH$_2$F | Me | 4-NH$_2$ |

TABLE 19

| Compound No. | $R^{15}$ | $R^{16}$ | $R^{17}$ | $R^{18}$ |
|---|---|---|---|---|
| D-1201 | NH$_2$ | OH | Me | 4-NO$_2$ |
| D-1202 | NH$_2$ | OMe | Me | 4-NO$_2$ |
| D-1203 | NH$_2$ | OEt | Me | 4-NO$_2$ |
| D-1204 | NH$_2$ | O-n-Pr | Me | 4-NO$_2$ |
| D-1205 | NH$_2$ | O-i-Pr | Me | 4-NO$_2$ |

TABLE 19-continued

| Compound No. | R15 | R16 | R17 | R18 |
|---|---|---|---|---|
| D-1206 | NH$_2$ | O-n-Bu | Me | 4-NO$_2$ |
| D-1207 | NH$_2$ | O-allyl | Me | 4-NO$_2$ |
| D-1208 | NH$_2$ | O-propargyl | Me | 4-NO$_2$ |
| D-1209 | NH$_2$ | OCH$_2$CF$_3$ | Me | 4-NO$_2$ |
| D-1210 | NH$_2$ | OCH$_2$CH$_2$F | Me | 4-NO$_2$ |
| D-1211 | NHMe | OH | Me | 4-NO$_2$ |
| D-1212 | NHMe | OMe | Me | 4-OMe |
| D-1213 | NHMe | OEt | Me | 4-Cl |
| D-1214 | NHMe | O-n-Pr | Me | 4-NO$_2$ |
| D-1215 | NHMe | O-i-Pr | Me | 4-OMe |
| D-1216 | NHMe | O-n-Bu | Me | 4-NO$_2$ |
| D-1217 | NHMe | O-allyl | Me | 4-NO$_2$ |
| D-1218 | NHMe | O-propargyl | Me | 4-NO$_2$ |
| D-1219 | NHMe | OCH$_2$CF$_3$ | Me | 4-NO$_2$ |
| D-1220 | NHMe | OCH$_2$CH$_2$F | Me | 4-NO$_2$ |
| D-1221 | NHEt | OH | Me | 4-Me |
| D-1222 | NHEt | OMe | Me | 4-OMe |
| D-1223 | NHEt | OEt | Me | 4-OMe |
| D-1224 | NHEt | O-n-Pr | Me | 4-NO$_2$ |
| D-1225 | NHEt | O-i-Pr | Me | 4-OMe |
| D-1226 | NHEt | O-n-Bu | Me | 4-NO$_2$ |
| D-1227 | NHEt | O-allyl | Me | 4-NO$_2$ |
| D-1228 | NHEt | O-propargyl | Me | 4-NO$_2$ |
| D-1229 | NHEt | OCH$_2$CF$_3$ | Me | 4-NO$_2$ |
| D-1230 | NHEt | OCH$_2$CH$_2$F | Me | 4-NO$_2$ |
| D-1231 | NHPr | OH | Me | 4-OMe |
| D-1232 | NHPr | OMe | Me | 4-NO$_2$ |
| D-1233 | NHPr | OEt | Me | 4-NO$_2$ |
| D-1234 | NHPr | O-n-Pr | Me | 4-NO$_2$ |
| D-1235 | NHPr | O-i-Pr | Me | 4-NO$_2$ |
| D-1236 | NHPr | O-n-Bu | Me | 4-NO$_2$ |
| D-1237 | NHPr | O-allyl | Me | 4-NO$_2$ |
| D-1238 | NHPr | O-propargyl | Me | 4-NO$_2$ |
| D-1239 | NHPr | OCH$_2$CF$_3$ | Me | 4-NO$_2$ |
| D-1240 | NHPr | OCH$_2$CH$_2$F | Me | 4-NO$_2$ |
| D-1241 | NH-i-Pr | OH | Me | 4-NO$_2$ |
| D-1242 | NH-i-Pr | OMe | Me | 4-NO$_2$ |
| D-1243 | NH-i-Pr | OEt | Me | 4-NO$_2$ |
| D-1244 | NH-i-Pr | O-n-Pr | Me | 4-NO$_2$ |
| D-1245 | NH-i-Pr | O-i-Pr | Me | 4-NO$_2$ |
| D-1246 | NH-i-Pr | O-n-Bu | Me | 4-NO$_2$ |
| D-1247 | NH-i-Pr | O-allyl | Me | 4-NO$_2$ |
| D-1248 | NH-i-Pr | O-propargyl | Me | 4-NO$_2$ |
| D-1249 | NH-i-Pr | OCH$_2$CF$_3$ | Me | 4-NO$_2$ |
| D-1250 | NH-i-Pr | OCH$_2$CH$_2$F | Me | 4-NO$_2$ |
| D-1251 | NH-allyl | OH | Me | 4-NO$_2$ |
| D-1252 | NH-allyl | OMe | Me | 4-NO$_2$ |
| D-1253 | NH-allyl | OEt | Me | 4-NO$_2$ |
| D-1254 | NH-allyl | O-n-Pr | Me | 4-NO$_2$ |
| D-1255 | NH-allyl | O-i-Pr | Me | 4-NO$_2$ |
| D-1256 | NH-allyl | O-n-Bu | Me | 4-NO$_2$ |
| D-1257 | NH-allyl | O-allyl | Me | 4-NO$_2$ |
| D-1258 | NH-allyl | O-propargyl | Me | 4-NO$_2$ |
| D-1259 | NH-allyl | OCH$_2$CF$_3$ | Me | 4-NO$_2$ |
| D-1260 | NH-allyl | OCH$_2$CH$_2$F | Me | 4-NO$_2$ |
| D-1261 | NH-propargyl | OH | Me | 4-NO$_2$ |
| D-1262 | NH-propargyl | OMe | Me | 4-NO$_2$ |
| D-1263 | NH-propargyl | OEt | Me | 4-NO$_2$ |
| D-1264 | NH-propargyl | O-n-Pr | Me | 4-NO$_2$ |
| D-1265 | NH-propargyl | O-i-Pr | Me | 4-NO$_2$ |
| D-1266 | NH-propargyl | O-n-Bu | Me | 4-NO$_2$ |
| D-1267 | NH-propargyl | O-allyl | Me | 4-NO$_2$ |
| D-1268 | NH-propargyl | O-propargyl | Me | 4-NO$_2$ |
| D-1269 | NH-propargyl | OCH$_2$CF$_3$ | Me | 4-NO$_2$ |
| D-1270 | NH-propargyl | OCH$_2$CH$_2$F | Me | 4-NO$_2$ |
| D-1271 | NHCH$_2$CF$_3$ | OH | Me | 4-NH$_2$ |
| D-1272 | NHCH$_2$CF$_3$ | OMe | Me | 4-NO$_2$ |
| D-1273 | NHCH$_2$CF$_3$ | OEt | Me | 4-NO$_2$ |
| D-1274 | NHCH$_2$CF$_3$ | O-n-Pr | Me | 4-NO$_2$ |
| D-1275 | NHCH$_2$CF$_3$ | O-i-Pr | Me | 4-NO$_2$ |
| D-1276 | NHCH$_2$CF$_3$ | O-n-Bu | Me | 4-NO$_2$ |
| D-1277 | NHCH$_2$CF$_3$ | O-allyl | Me | 4-NO$_2$ |
| D-1278 | NHCH$_2$CF$_3$ | O-propargyl | Me | 4-NO$_2$ |
| D-1279 | NHCH$_2$CF$_3$ | OCH$_2$CF$_3$ | Me | 4-NO$_2$ |
| D-1280 | NHCH$_2$CF$_3$ | OCH$_2$CH$_2$F | Me | 4-NO$_2$ |
| D-1281 | NHCH$_2$CH$_2$F | OH | Me | 4-NO$_2$ |
| D-1282 | NHCH$_2$CH$_2$F | OMe | Me | 4-NO$_2$ |
| D-1283 | NHCH$_2$CH$_2$F | OEt | Me | 4-NO$_2$ |
| D-1284 | NHCH2CH$_2$F | O-n-Pr | Me | 4-NO$_2$ |
| D-1285 | NHCH$_2$CH$_2$F | O-i-Pr | Me | 4-NO$_2$ |
| D-1286 | NHCH$_2$CH$_2$F | O-n-Bu | Me | 4-NO$_2$ |
| D-1287 | NHCH$_2$CH$_2$F | O-allyl | Me | 4-NO$_2$ |
| D-1288 | NHCH$_2$CH$_2$F | O-propargyl | Me | 4-NO$_2$ |
| D-1289 | NHCH$_2$CH$_2$F | OCH$_2$CF$_3$ | Me | 4-NO$_2$ |
| D-1290 | NHCH$_2$CH$_2$F | OCH$_2$CH$_2$F | Me | 4-NO$_2$ |
| D-1291 | NH-n-Bu | OH | Me | 4-NO$_2$ |
| D-1292 | NH-n-Bu | OMe | Me | 4-NO$_2$ |
| D-1293 | NH-n-Bu | OEt | Me | 4-NO$_2$ |
| D-1294 | NH-n-Bu | O-n-Pr | Me | 4-NO$_2$ |
| D-1295 | NH-n-Bu | O-i-Pr | Me | 4-NO$_2$ |
| D-1296 | NH-n-Bu | O-n-Bu | Me | 4-NO$_2$ |
| D-1297 | NH-n-Bu | O-allyl | Me | 4-NO$_2$ |
| D-1298 | NH-n-Bu | O-propargyl | Me | 4-NO$_2$ |
| D-1299 | NH-n-Bu | OCH$_2$CF$_3$ | Me | 4-NO$_2$ |
| D-1300 | NH-n-Bu | OCH$_2$CH$_2$F | Me | 4-NO$_2$ |

TABLE 20

| Compound No. | R15 | R16 | R17 | R18 |
|---|---|---|---|---|
| D-1301 | NH$_2$ | NHOH | Me | 4-NH$_2$ |
| D-1302 | NH$_2$ | NHOMe | Me | 4-NH$_2$ |
| D-1303 | NH$_2$ | NHOEt | Me | 4-NH$_2$ |
| D-1304 | NH$_2$ | NHNH$_2$ | Me | 4-NH$_2$ |
| D-1305 | NH$_2$ | NHNMe$_2$ | Me | 4-NH$_2$ |
| D-1306 | NH$_2$ | NHNHMe | Me | 4-NH$_2$ |
| D-1307 | NH$_2$ | NHNHEt | Me | 4-NH$_2$ |
| D-1308 | NH$_2$ | NMeNH$_2$ | Me | 4-NH$_2$ |
| D-1309 | NH$_2$ | NHCN | Me | 4-NH$_2$ |
| D-1310 | NH$_2$ | NHNO$_2$ | Me | 4-NH$_2$ |
| D-1311 | NHMe | NHOH | Me | 4-NH$_2$ |
| D-1312 | NHMe | NHOMe | Me | 4-NH$_2$ |
| D-1313 | NHMe | NHOEt | Me | 4-NH$_2$ |
| D-1314 | NHMe | NHNH$_2$ | Me | 4-NH$_2$ |
| D-1315 | NHMe | NHNMe$_2$ | Me | 4-NH$_2$ |
| D-1316 | NHMe | NHNHMe | Me | 4-NH$_2$ |
| D-1317 | NHMe | NHNHEt | Me | 4-NH$_2$ |
| D-1318 | NHMe | NMeNH$_2$ | Me | 4-NH$_2$ |
| D-1319 | NHMe | NHCN | Me | 4-NH$_2$ |
| D-1320 | NHMe | NHNO$_2$ | Me | 4-NH$_2$ |
| D-1321 | NHEt | NHOH | Me | 4-NH$_2$ |
| D-1322 | NHEt | NHOMe | Me | 4-NH$_2$ |
| D-1323 | NHEt | NHOEt | Me | 4-NH$_2$ |
| D-1324 | NHEt | NHNH$_2$ | Me | 4-NH$_2$ |
| D-1325 | NHEt | NHNMe$_2$ | Me | 4-NH$_2$ |
| D-1326 | NHEt | NHNHMe | Me | 4-NH$_2$ |
| D-1327 | NHEt | NHNHEt | Me | 4-NH$_2$ |
| D-1328 | NHEt | NMeNH$_2$ | Me | 4-NH$_2$ |
| D-1329 | NHEt | NHCN | Me | 4-NH$_2$ |
| D-1330 | NHEt | NHNO$_2$ | Me | 4-NH$_2$ |
| D-1331 | NH-i-Pr | NHOH | Me | 4-NH$_2$ |
| D-1332 | NH-i-Pr | NHOMe | Me | 4-NH$_2$ |
| D-1333 | NH-i-Pr | NHOEt | Me | 4-NH$_2$ |
| D-1334 | NH-i-Pr | NHNH$_2$ | Me | 4-NH$_2$ |
| D-1335 | NH-i-Pr | NHNMe$_2$ | Me | 4-NH$_2$ |
| D-1336 | NH-i-Pr | NHNHMe | Me | 4-NH$_2$ |
| D-1337 | NH-i-Pr | NHNHEt | Me | 4-NH$_2$ |
| D-1338 | NH-i-Pr | NMeNH$_2$ | Me | 4-NH$_2$ |
| D-1339 | NH-i-Pr | NHCN | Me | 4-NH$_2$ |
| D-1340 | NH-i-Pr | NHNO$_2$ | Me | 4-NH$_2$ |
| D-1341 | NH-allyl | NHOH | Me | 4-NH$_2$ |
| D-1342 | NH-allyl | NHOMe | Me | 4-NH$_2$ |
| D-1343 | NH-allyl | NHOEt | Me | 4-NH$_2$ |
| D-1344 | NH-allyl | NHNH$_2$ | Me | 4-NH$_2$ |
| D-1345 | NH-allyl | NHNMe$_2$ | Me | 4-NH$_2$ |

TABLE 20-continued

| Compound No. | $R^{15}$ | $R^{16}$ | $R^{17}$ | $R^{18}$ |
|---|---|---|---|---|
| D-1346 | NH-allyl | NHNHMe | Me | 4-NH$_2$ |
| D-1347 | NH-allyl | NHNHEt | Me | 4-NH$_2$ |
| D-1348 | NH-allyl | NMeNH$_2$ | Me | 4-NH$_2$ |
| D-1349 | NH-allyl | NHCN | Me | 4-NH$_2$ |
| D-1350 | NH-allyl | NHNO$_2$ | Me | 4-NH$_2$ |
| D-1351 | NH-propargyl | NHOH | Me | 4-NH$_2$ |
| D-1352 | NH-propargyl | NHOMe | Me | 4-NH$_2$ |
| D-1353 | NH-propargyl | NHOEt | Me | 4-NH$_2$ |
| D-1354 | NH-propargyl | NHNH$_2$ | Me | 4-NH$_2$ |
| D-1355 | NH-propargyl | NHNMe$_2$ | Me | 4-NH$_2$ |
| D-1356 | NH-propargyl | NHNHMe | Me | 4-NH$_2$ |
| D-1357 | NH-propargyl | NHNHEt | Me | 4-NH$_2$ |
| D-1358 | NH-propargyl | NMeNH$_2$ | Me | 4-NH$_2$ |
| D-1359 | NH-propargyl | NHCN | Me | 4-NH$_2$ |
| D-1360 | NH-propargyl | NHNO$_2$ | Me | 4-NH$_2$ |
| D-1361 | NHCH$_2$CH$_2$F | NHOH | Me | 4-NH$_2$ |
| D-1362 | NHCH$_2$CH$_2$F | NHOMe | Me | 4-NH$_2$ |
| D-1363 | NHCH$_2$CH$_2$F | NHOEt | Me | 4-NH$_2$ |
| D-1364 | NHCH$_2$CH$_2$F | NHNH$_2$ | Me | 4-NH$_2$ |
| D-1365 | NHCH$_2$CH$_2$F | NHNMe$_2$ | Me | 4-NH$_2$ |
| D-1366 | NHCH$_2$CH$_2$F | NHNHMe | Me | 4-NH$_2$ |
| D-1367 | NHCH$_2$CH$_2$F | NHNHEt | Me | 4-NH$_2$ |
| D-1368 | NHCH$_2$CH$_2$F | NMeNH$_2$ | Me | 4-NH$_2$ |
| D-1369 | NHCH$_2$CH$_2$F | NHCN | Me | 4-NH$_2$ |
| D-1370 | NHCH$_2$CH$_2$F | NHNO$_2$ | Me | 4-NH$_2$ |
| D-1371 | NHCH$_2$CF$_3$ | NHOH | Me | 4-NH$_2$ |
| D-1372 | NHCH$_2$CF$_3$ | NHOMe | Me | 4-NH$_2$ |
| D-1373 | NHCH$_2$CF$_3$ | NHOEt | Me | 4-NH$_2$ |
| D-1374 | NHCH$_2$CF$_3$ | NHNH$_2$ | Me | 4-NH$_2$ |
| D-1375 | NHCH$_2$CF$_3$ | NHNMe$_2$ | Me | 4-NH$_2$ |
| D-1376 | NHCH$_2$CF$_3$ | NHNHMe | Me | 4-NH$_2$ |
| D-1377 | NHCH$_2$CF$_3$ | NHNHEt | Me | 4-NH$_2$ |
| D-1378 | NHCH$_2$CF$_3$ | NMeNH$_2$ | Me | 4-NH$_2$ |
| D-1379 | NHCH$_2$CF$_3$ | NHCN | Me | 4-NH$_2$ |
| D-1380 | NHCH$_2$CF$_3$ | NHNO$_2$ | Me | 4-NH$_2$ |
| D-1381 | SMe | NHOH | Me | 4-NH$_2$ |
| D-1382 | SMe | NHOMe | Me | 4-NH$_2$ |
| D-1383 | SMe | NHOEt | Me | 4-NH$_2$ |
| D-1384 | SMe | NHNH$_2$ | Me | 4-NH$_2$ |
| D-1385 | SMe | NHNMe$_2$ | Me | 4-NH$_2$ |
| D-1386 | SMe | NHNHMe | Me | 4-NH$_2$ |
| D-1387 | SMe | NHNHEt | Me | 4-NH$_2$ |
| D-1388 | SMe | NMeNH$_2$ | Me | 4-NH$_2$ |
| D-1389 | SMe | NHCN | Me | 4-NH$_2$ |
| D-1390 | SMe | NHNO$_2$ | Me | 4-NH$_2$ |
| D-1391 | SEt | NHOH | Me | 4-NH$_2$ |
| D-1392 | SEt | NHOMe | Me | 4-NH$_2$ |
| D-1393 | SEt | NHOEt | Me | 4-NH$_2$ |
| D-1394 | SEt | NHNH$_2$ | Me | 4-NH$_2$ |
| D-1395 | SEt | NHNMe$_2$ | Me | 4-NH$_2$ |
| D-1396 | SEt | NHNHMe | Me | 4-NH$_2$ |
| D-1397 | SEt | NHNHEt | Me | 4-NH$_2$ |
| D-1398 | SEt | NMeNH$_2$ | Me | 4-NH$_2$ |
| D-1399 | SEt | NHCN | Me | 4-NH$_2$ |
| D-1400 | SEt | NHNO$_2$ | Me | 4-NH$_2$ |

TABLE 21

| Compound No. | $R^{15}$ | $R^{16}$ | $R^{17}$ | $R^{18}$ |
|---|---|---|---|---|
| D-1401 | NH$_2$ | NHOH | Me | 4-NO$_2$ |
| D-1402 | NH$_2$ | NHOMe | Me | 4-NO$_2$ |
| D-1403 | NH$_2$ | NHOEt | Me | 4-NO$_2$ |
| D-1404 | NH$_2$ | NHNH$_2$ | Me | 4-NO$_2$ |
| D-1405 | NH$_2$ | NHNMe$_2$ | Me | 4-NO$_2$ |
| D-1406 | NH$_2$ | NHNHMe | Me | 4-NO$_2$ |
| D-1407 | NH$_2$ | NHNHEt | Me | 4-NO$_2$ |
| D-1408 | NH$_2$ | NMeNH$_2$ | Me | 4-NO$_2$ |
| D-1409 | NH$_2$ | NHCN | Me | 4-NO$_2$ |
| D-1410 | NH$_2$ | NHNO$_2$ | Me | 4-NO$_2$ |

TABLE 21-continued

| Compound No. | $R^{15}$ | $R^{16}$ | $R^{17}$ | $R^{18}$ |
|---|---|---|---|---|
| D-1411 | NHMe | NHOH | Me | 4-NO$_2$ |
| D-1412 | NHMe | NHOMe | Me | 4-Cl |
| D-1413 | NHMe | NHOEt | Me | 4-NO$_2$ |
| D-1414 | NHMe | NHNH$_2$ | Me | 4-NO$_2$ |
| D-1415 | NHMe | NHNMe$_2$ | Me | 4-NO$_2$ |
| D-1416 | NHMe | NHNHMe | Me | 4-NO$_2$ |
| D-1417 | NHMe | NHNHEt | Me | 4-NO$_2$ |
| D-1418 | NHMe | NMeNH$_2$ | Me | 4-NO$_2$ |
| D-1419 | NHMe | NHCN | Me | 4-NO$_2$ |
| D-1420 | NHMe | NHNO$_2$ | Me | 4-NO$_2$ |
| D-1421 | NHEt | NHOH | Me | 4-NO$_2$ |
| D-1422 | NHEt | NHOMe | Me | 4-NO$_2$ |
| D-1423 | NHEt | NHOEt | Me | 4-NO$_2$ |
| D-1424 | NHEt | NHNH$_2$ | Me | 4-NO$_2$ |
| D-1425 | NHEt | NHNMe$_2$ | Me | 4-NO$_2$ |
| D-1426 | NHEt | NHNHMe | Me | 4-NO$_2$ |
| D-1427 | NHEt | NHNHEt | Me | 4-NO$_2$ |
| D-1428 | NHEt | NMeNH$_2$ | Me | 4-NO$_2$ |
| D-1429 | NHEt | NHCN | Me | 4-NO$_2$ |
| D-1430 | NHEt | NHNO$_2$ | Me | 4-NO$_2$ |
| D-1431 | NH-i-Pr | NHOH | Me | 4-NO$_2$ |
| D-1432 | NH-i-Pr | NHOMe | Me | 4-NO$_2$ |
| D-1433 | NH-i-Pr | NHOEt | Me | 4-NO$_2$ |
| D-1434 | NH-i-Pr | NHNH$_2$ | Me | 4-NO$_2$ |
| D-1435 | NH-i-Pr | NHNMe$_2$ | Me | 4-NO$_2$ |
| D-1436 | NH-i-Pr | NHNHMe | Me | 4-NO$_2$ |
| D-1437 | NH-i-Pr | NHNHEt | Me | 4-NO$_2$ |
| D-1438 | NH-i-Pr | NMeNH$_2$ | Me | 4-NO$_2$ |
| D-1439 | NH-i-Pr | NHCN | Me | 4-NO$_2$ |
| D-1440 | NH-i-Pr | NHNO$_2$ | Me | 4-NO$_2$ |
| D-1441 | NH-allyl | NHOH | Me | 4-NO$_2$ |
| D-1442 | NH-allyl | NHOMe | Me | 4-NO$_2$ |
| D-1443 | NH-allyl | NHOEt | Me | 4-NO$_2$ |
| D-1444 | NH-allyl | NHNH$_2$ | Me | 4-NO$_2$ |
| D-1445 | NH-allyl | NHNMe$_2$ | Me | 4-NO$_2$ |
| D-1446 | NH-allyl | NHNHMe | Me | 4-NO$_2$ |
| D-1447 | NH-allyl | NHNHEt | Me | 4-NO$_2$ |
| D-1448 | NH-allyl | NMeNH$_2$ | Me | 4-NO$_2$ |
| D-1449 | NH-allyl | NHCN | Me | 4-NO$_2$ |
| D-1450 | NH-allyl | NHNO$_2$ | Me | 4-NO$_2$ |
| D-1451 | NH-propargyl | NHOH | Me | 4-NO$_2$ |
| D-1452 | NH-propargyl | NHOMe | Me | 4-NO$_2$ |
| D-1453 | NH-propargyl | NHOEt | Me | 4-NO$_2$ |
| D-1454 | NH-propargyl | NHNH$_2$ | Me | 4-NO$_2$ |
| D-1455 | NH-propargyl | NHNMe$_2$ | Me | 4-NO$_2$ |
| D-1456 | NH-propargyl | NHNHMe | Me | 4-NO$_2$ |
| D-1457 | NH-propargyl | NHNHEt | Me | 4-NO$_2$ |
| D-1458 | NH-propargyl | NMeNH$_2$ | Me | 4-NO$_2$ |
| D-1459 | NH-propargyl | NHCN | Me | 4-NO$_2$ |
| D-1460 | NH-propargyl | NHNO$_2$ | Me | 4-NO$_2$ |
| D-1461 | NHCH$_2$CH$_2$F | NHOH | Me | 4-NO$_2$ |
| D-1462 | NHCH$_2$CH$_2$F | NHOMe | Me | 4-NO$_2$ |
| D-1463 | NHCH$_2$CH$_2$F | NHOEt | Me | 4-NO$_2$ |
| D-1464 | NHCH$_2$CH$_2$F | NHNH$_2$ | Me | 4-NO$_2$ |
| D-1465 | NHCH$_2$CH$_2$F | NHNMe$_2$ | Me | 4-NO$_2$ |
| D-1466 | NHCH$_2$CH$_2$F | NHNHMe | Me | 4-NO$_2$ |
| D-1467 | NHCH$_2$CH$_2$F | NHNHEt | Me | 4-NO$_2$ |
| D-1468 | NHCH$_2$CH$_2$F | NMeNH$_2$ | Me | 4-NO$_2$ |
| D-1469 | NHCH$_2$CH$_2$F | NHCN | Me | 4-NO$_2$ |
| D-1470 | NHCH$_2$CH$_2$F | NHNO$_2$ | Me | 4-NO$_2$ |
| D-1471 | NHCH$_2$CF$_3$ | NHOH | Me | 4-NO$_2$ |
| D-1472 | NHCH$_2$CF$_3$ | NHOMe | Me | 4-NO$_2$ |
| D-1473 | NHCH$_2$CF$_3$ | NHOEt | Me | 4-NO$_2$ |
| D-1474 | NHCH$_2$CF$_3$ | NHNH$_2$ | Me | 4-NO$_2$ |
| D-1475 | NHCH$_2$CF$_3$ | NHNMe$_2$ | Me | 4-NO$_2$ |
| D-1476 | NHCH$_2$CF$_3$ | NHNHMe | Me | 4-NO$_2$ |
| D-1477 | NHCH$_2$CF$_3$ | NHNHEt | Me | 4-NO$_2$ |
| D-1478 | NHCH$_2$CF$_3$ | NMeNH$_2$ | Me | 4-NO$_2$ |
| D-1479 | NHCH$_2$CF$_3$ | NHCN | Me | 4-NO$_2$ |
| D-1480 | NHCH$_2$CF$_3$ | NHNO$_2$ | Me | 4-NO$_2$ |
| D-1481 | SMe | NHOH | Me | 4-NO$_2$ |
| D-1482 | SMe | NHOMe | Me | 4-NO$_2$ |
| D-1483 | SMe | NHOEt | Me | 4-NO$_2$ |
| D-1484 | SMe | NHNH$_2$ | Me | 4-NO$_2$ |
| D-1485 | SMe | NHNMe$_2$ | Me | 4-NO$_2$ |

TABLE 21-continued

| Compound No. | $R^{15}$ | $R^{16}$ | $R^{17}$ | $R^{18}$ |
|---|---|---|---|---|
| D-1486 | SMe | NHNHMe | Me | 4-NO$_2$ |
| D-1487 | SMe | NHNHEt | Me | 4-NO$_2$ |
| D-1488 | SMe | NMeNH$_2$ | Me | 4-NO$_2$ |
| D-1489 | SMe | NHCN | Me | 4-NO$_2$ |
| D-1490 | SMe | NHNO$_2$ | Me | 4-NO$_2$ |
| D-1491 | SEt | NHOH | Me | 4-NO$_2$ |
| D-1492 | SEt | NHOMe | Me | 4-NO$_2$ |
| D-1493 | SEt | NHOEt | Me | 4-NO$_2$ |
| D-1494 | SEt | NHNH$_2$ | Me | 4-NO$_2$ |
| D-1495 | SEt | NHNMe$_2$ | Me | 4-NO$_2$ |
| D-1496 | SEt | NHNHMe | Me | 4-NO$_2$ |
| D-1497 | SEt | NHNHEt | Me | 4-NO$_2$ |
| D-1498 | SEt | NMeNH$_2$ | Me | 4-NO$_2$ |
| D-1499 | SEt | NHCN | Me | 4-NO$_2$ |
| D-1500 | SEt | NHNO$_2$ | Me | 4-NO$_2$ |

TABLE 22

| Compound No. | $R^{15}$ | $R^{16}$ | $R^{17}$ | $R^{18}$ |
|---|---|---|---|---|
| D-1501 | NH$_2$ | NHOH | H | 4-NH$_2$ |
| D-1502 | NH$_2$ | NHOMe | H | 4-NH$_2$ |
| D-1503 | NH$_2$ | NHOEt | H | 4-NH$_2$ |
| D-1504 | NH$_2$ | NHNH$_2$ | H | 4-NH$_2$ |
| D-1505 | NH$_2$ | NHNMe$_2$ | H | 4-NH$_2$ |
| D-1506 | NH$_2$ | NHNHMe | H | 4-NH$_2$ |
| D-1507 | NH$_2$ | NHNHEt | H | 4-NH$_2$ |
| D-1508 | NH$_2$ | NMeNH$_2$ | H | 4-NH$_2$ |
| D-1509 | NH$_2$ | NHCN | H | 4-NH$_2$ |
| D-1510 | NH$_2$ | NHNO$_2$ | H | 4-NH$_2$ |
| D-1511 | NHMe | NHOH | H | 4-NH$_2$ |
| D-1512 | NHMe | NHOMe | H | 4-NH$_2$ |
| D-1513 | NHMe | NHOEt | H | 4-NH$_2$ |
| D-1514 | NHMe | NHNH$_2$ | H | 4-NH$_2$ |
| D-1515 | NHMe | NHNMe$_2$ | H | 4-NH$_2$ |
| D-1516 | NHMe | NHNHMe | H | 4-NH$_2$ |
| D-1517 | NHMe | NHNHEt | H | 4-NH$_2$ |
| D-1518 | NHMe | NMeNH$_2$ | H | 4-NH$_2$ |
| D-1519 | NHMe | NHCN | H | 4-NH$_2$ |
| D-1520 | NHMe | NHNO$_2$ | H | 4-NH$_2$ |
| D-1521 | NHEt | NHOH | H | 4-NH$_2$ |
| D-1522 | NHEt | NHOMe | H | 4-NH$_2$ |
| D-1523 | NHEt | NHOEt | H | 4-NH$_2$ |
| D-1524 | NHEt | NHNH$_2$ | H | 4-NH$_2$ |
| D-1525 | NHEt | NHNMe$_2$ | H | 4-NH$_2$ |
| D-1526 | NHEt | NHNHMe | H | 4-NH$_2$ |
| D-1527 | NHEt | NHNHEt | H | 4-NH$_2$ |
| D-1528 | NHEt | NMeNH$_2$ | H | 4-NH$_2$ |
| D-1529 | NHEt | NHCN | H | 4-NH$_2$ |
| D-1530 | NHEt | NHNO$_2$ | H | 4-NH$_2$ |
| D-1531 | NH-i-Pr | NHOH | H | 4-NH$_2$ |
| D-1532 | NH-i-Pr | NHOMe | H | 4-NH$_2$ |
| D-1533 | NH-i-Pr | NHOEt | H | 4-NH$_2$ |
| D-1534 | NH-i-Pr | NHNH$_2$ | H | 4-NH$_2$ |
| D-1535 | NH-i-Pr | NHNMe$_2$ | H | 4-NH$_2$ |
| D-1536 | NH-i-Pr | NHNHMe | H | 4-NH$_2$ |
| D-1537 | NH-i-Pr | NHNHEt | H | 4-NH$_2$ |
| D-1538 | NH-i-Pr | NMeNH$_2$ | H | 4-NH$_2$ |
| D-1539 | NH-i-Pr | NHCN | H | 4-NH$_2$ |
| D-1540 | NH-i-Pr | NHNO$_2$ | H | 4-NH$_2$ |
| D-1541 | NH-allyl | NHOH | H | 4-NH$_2$ |
| D-1542 | NH-allyl | NHOMe | H | 4-NH$_2$ |
| D-1543 | NH-allyl | NHOEt | H | 4-NH$_2$ |
| D-1544 | NH-allyl | NHNH$_2$ | H | 4-NH$_2$ |
| D-1545 | NH-allyl | NHNMe$_2$ | H | 4-NH$_2$ |
| D-1546 | NH-allyl | NHNHMe | H | 4-NH$_2$ |
| D-1547 | NH-allyl | NHNHEt | H | 4-NH$_2$ |
| D-1548 | NH-allyl | NMeNH$_2$ | H | 4-NH$_2$ |
| D-1549 | NH-allyl | NHCN | H | 4-NH$_2$ |
| D-1550 | NH-allyl | NHNO$_2$ | H | 4-NH$_2$ |

TABLE 22-continued

| Compound No. | $R^{15}$ | $R^{16}$ | $R^{17}$ | $R^{18}$ |
|---|---|---|---|---|
| D-1551 | NH-propargyl | NHOH | H | 4-NH$_2$ |
| D-1552 | NH-propargyl | NHOMe | H | 4-NH$_2$ |
| D-1553 | NH-propargyl | NHOEt | H | 4-NH$_2$ |
| D-1554 | NH-propargyl | NHNH$_2$ | H | 4-NH$_2$ |
| D-1555 | NH-propargyl | NHNMe$_2$ | H | 4-NH$_2$ |
| D-1556 | NH-propargyl | NHNHMe | H | 4-NH$_2$ |
| D-1557 | NH-propargyl | NHNHEt | H | 4-NH$_2$ |
| D-1558 | NH-propargyl | NMeNH$_2$ | H | 4-NH$_2$ |
| D-1559 | NH-propargyl | NHCN | H | 4-NH$_2$ |
| D-1560 | NH-propargyl | NHNO$_2$ | H | 4-NH$_2$ |
| D-1561 | NHCH$_2$CH$_2$F | NHOH | H | 4-NH$_2$ |
| D-1562 | NHCH$_2$CH$_2$F | NHOMe | H | 4-NH$_2$ |
| D-1563 | NHCH$_2$CH$_2$F | NHOEt | H | 4-NH$_2$ |
| D-1564 | NHCH$_2$CH$_2$F | NHNH$_2$ | H | 4-NH$_2$ |
| D-1565 | NHCH$_2$CH$_2$F | NHNMe$_2$ | H | 4-NH$_2$ |
| D-1566 | NHCH$_2$CH$_2$F | NHNHMe | H | 4-NH$_2$ |
| D-1567 | NHCH$_2$CH$_2$F | NHNHEt | H | 4-NH$_2$ |
| D-1568 | NHCH$_2$CH$_2$F | NMeNH$_2$ | H | 4-NH$_2$ |
| D-1569 | NHCH$_2$CH$_2$F | NHCN | H | 4-NH$_2$ |
| D-1570 | NHCH$_2$CH$_2$F | NHNO$_2$ | H | 4-NH$_2$ |
| D-1571 | NHCH$_2$CF$_3$ | NHOH | H | 4-NH$_2$ |
| D-1572 | NHCH$_2$CF$_3$ | NHOMe | H | 4-NH$_2$ |
| D-1573 | NHCH$_2$CF$_3$ | NHOEt | H | 4-NH$_2$ |
| D-1574 | NHCH$_2$CF$_3$ | NHNH$_2$ | H | 4-NH$_2$ |
| D-1575 | NHCH$_2$CF$_3$ | NHNMe$_2$ | H | 4-NH$_2$ |
| D-1576 | NHCH$_2$CF$_3$ | NHNHMe | H | 4-NH$_2$ |
| D-1577 | NHCH$_2$CF$_3$ | NHNHEt | H | 4-NH$_2$ |
| D-1578 | NHCH$_2$CF$_3$ | NMeNH$_2$ | H | 4-NH$_2$ |
| D-1579 | NHCH$_2$CF$_3$ | NHCN | H | 4-NH$_2$ |
| D-1580 | NHCH$_2$CF$_3$ | NHNO$_2$ | H | 4-NH$_2$ |
| D-1581 | SMe | NHOH | H | 4-NH$_2$ |
| D-1582 | SMe | NHOMe | H | 4-NH$_2$ |
| D-1583 | SMe | NHOEt | H | 4-NH$_2$ |
| D-1584 | SMe | NHNH$_2$ | H | 4-NH$_2$ |
| D-1585 | SMe | NHNMe$_2$ | H | 4-NH$_2$ |
| D-1586 | SMe | NHNHMe | H | 4-NH$_2$ |
| D-1587 | SMe | NHNHEt | H | 4-NH$_2$ |
| D-1588 | SMe | NMeNH$_2$ | H | 4-NH$_2$ |
| D-1589 | SMe | NHCN | H | 4-NH$_2$ |
| D-1590 | SMe | NHNO$_2$ | H | 4-NH$_2$ |
| D-1591 | SEt | NHOH | H | 4-NH$_2$ |
| D-1592 | SEt | NHOMe | H | 4-NH$_2$ |
| D-1593 | SEt | NHOEt | H | 4-NH$_2$ |
| D-1594 | SEt | NHNH$_2$ | H | 4-NH$_2$ |
| D-1595 | SEt | NHNMe$_2$ | H | 4-NH$_2$ |
| D-1596 | SEt | NHNHMe | H | 4-NH$_2$ |
| D-1597 | SEt | NHNHEt | H | 4-NH$_2$ |
| D-1598 | SEt | NMeNH$_2$ | H | 4-NH$_2$ |
| D-1599 | SEt | NHCN | H | 4-NH$_2$ |
| D-1600 | SEt | NHNO$_2$ | H | 4-NH$_2$ |

TABLE 23

| Compound No. | $R^{15}$ | $R^{16}$ | $R^{17}$ | $R^{18}$ |
|---|---|---|---|---|
| D-1601 | NH$_2$ | NHOH | H | 4-NO$_2$ |
| D-1602 | NH$_2$ | NHOMe | H | 4-NO$_2$ |
| D-1603 | NH$_2$ | NHOEt | H | 4-NO$_2$ |
| D-1604 | NH$_2$ | NHNH$_2$ | H | 4-NO$_2$ |
| D-1605 | NH$_2$ | NHNMe$_2$ | H | 4-NO$_2$ |
| D-1606 | NH$_2$ | NHNHMe | H | 4-NO$_2$ |
| D-1607 | NH$_2$ | NHNHEt | H | 4-NO$_2$ |
| D-1608 | NH$_2$ | NMeNH$_2$ | H | 4-NO$_2$ |
| D-1609 | NH$_2$ | NHCN | H | 4-NO$_2$ |
| D-1610 | NH$_2$ | NHNO$_2$ | H | 4-NO$_2$ |
| D-1611 | NHMe | NHOH | H | 4-NO$_2$ |
| D-1612 | NHMe | NHOMe | H | 4-Cl |
| D-1613 | NHMe | NHOEt | H | 4-NO$_2$ |
| D-1614 | NHMe | NHNH$_2$ | H | 4-NO$_2$ |
| D-1615 | NHMe | NHNMe$_2$ | H | 4-NO$_2$ |

TABLE 23-continued

| Compound No. | R15 | R16 | R17 | R18 |
|---|---|---|---|---|
| D-1616 | NHMe | NHNHMe | H | 4-NO2 |
| D-1617 | NHMe | NHNHEt | H | 4-NO2 |
| D-1618 | NHMe | NMeNH2 | H | 4-NO2 |
| D-1619 | NHMe | NHCN | H | 4-NO2 |
| D-1620 | NHMe | NHNO2 | H | 4-NO2 |
| D-1621 | NHEt | NHOH | H | 4-NO2 |
| D-1622 | NHEt | NHOMe | H | 4-NO2 |
| D-1623 | NHEt | NHOEt | H | 4-NO2 |
| D-1624 | NHEt | NHNH2 | H | 4-NO2 |
| D-1625 | NHEt | NHNMe2 | H | 4-NO2 |
| D-1626 | NHEt | NHNHMe | H | 4-NO2 |
| D-1627 | NHEt | NHNHEt | H | 4-NO2 |
| D-1628 | NHEt | NMeNH2 | H | 4-NO2 |
| D-1629 | NHEt | NHCN | H | 4-NO2 |
| D-1630 | NHEt | NHNO2 | H | 4-NO2 |
| D-1631 | NH-i-Pr | NHOH | H | 4-NO2 |
| D-1632 | NH-i-Pr | NHOMe | H | 4-NO2 |
| D-1633 | NH-i-Pr | NHOEt | H | 4-NO2 |
| D-1634 | NH-i-Pr | NHNH2 | H | 4-NO2 |
| D-1635 | NH-i-Pr | NHNMe2 | H | 4-NO2 |
| D-1636 | NH-i-Pr | NHNHMe | H | 4-NO2 |
| D-1637 | NH-i-Pr | NHNHEt | H | 4-NO2 |
| D-1638 | NH-i-Pr | NMeNH2 | H | 4-NO2 |
| D-1639 | NH-i-Pr | NHCN | H | 4-NO2 |
| D-1640 | NH-i-Pr | NHNO2 | H | 4-NO2 |
| D-1641 | NH-allyl | NHOH | H | 4-NO2 |
| D-1642 | NH-allyl | NHOMe | H | 4-NO2 |
| D-1643 | NH-allyl | NHOEt | H | 4-NO2 |
| D-1644 | NH-allyl | NHNH2 | H | 4-NO2 |
| D-1645 | NH-allyl | NHNMe2 | H | 4-NO2 |
| D-1646 | NH-allyl | NHNHMe | H | 4-NO2 |
| D-1647 | NH-allyl | NHNHEt | H | 4-NO2 |
| D-1648 | NH-allyl | NMeNH2 | H | 4-NO2 |
| D-1649 | NH-allyl | NHCN | H | 4-NO2 |
| D-1650 | NH-allyl | NHNO2 | H | 4-NO2 |
| D-1651 | NH-propargyl | NHOH | H | 4-NO2 |
| D-1652 | NH-propargyl | NHOMe | H | 4-NO2 |
| D-1653 | NH-propargyl | NHOEt | H | 4-NO2 |
| D-1654 | NH-propargyl | NHNH2 | H | 4-NO2 |
| D-1655 | NH-propargyl | NHNMe2 | H | 4-NO2 |
| D-1656 | NH-propargyl | NHNHMe | H | 4-NO2 |
| D-1657 | NH-propargyl | NHNHEt | H | 4-NO2 |
| D-1658 | NH-propargyl | NMeNH2 | H | 4-NO2 |
| D-1659 | NH-propargyl | NHCN | H | 4-NO2 |
| D-1660 | NH-propargyl | NHNO2 | H | 4-NO2 |
| D-1661 | NHCH2CH2F | NHOH | H | 4-NO2 |
| D-1662 | NHCH2CH2F | NHOMe | H | 4-NO2 |
| D-1663 | NHCH2CH2F | NHOEt | H | 4-NO2 |
| D-1664 | NHCH2CH2F | NHNH2 | H | 4-NO2 |
| D-1665 | NHCH2CH2F | NHNMe2 | H | 4-NO2 |
| D-1666 | NHCH2CH2F | NHNHMe | H | 4-NO2 |
| D-1667 | NHCH2CH2F | NHNHEt | H | 4-NO2 |
| D-1668 | NHCH2CH2F | NMeNH2 | H | 4-NO2 |
| D-1669 | NHCH2CH2F | NHCN | H | 4-NO2 |
| D-1670 | NHCH2CH2F | NHNO2 | H | 4-NO2 |
| D-1671 | NHCH2CF3 | NHOH | H | 4-NO2 |
| D-1672 | NHCH2CF3 | NHOMe | H | 4-NO2 |
| D-1673 | NHCH2CF3 | NHOEt | H | 4-NO2 |
| D-1674 | NHCH2CF3 | NHNH2 | H | 4-NO2 |
| D-1675 | NHCH2CF3 | NHNMe2 | H | 4-NO2 |
| D-1676 | NHCH2CF3 | NHNHMe | H | 4-NO2 |
| D-1677 | NHCH2CF3 | NHNHEt | H | 4-NO2 |
| D-1678 | NHCH2CF3 | NMeNH2 | H | 4-NO2 |
| D-1679 | NHCH2CF3 | NHCN | H | 4-NO2 |
| D-1680 | NHCH2CF3 | NHNO2 | H | 4-NO2 |
| D-1681 | SMe | NHOH | H | 4-NO2 |
| D-1682 | SMe | NHOMe | H | 4-NO2 |
| D-1683 | SMe | NHOEt | H | 4-NO2 |
| D-1684 | SMe | NHNH2 | H | 4-NO2 |
| D-1685 | SMe | NHNMe2 | H | 4-NO2 |
| D-1686 | SMe | NHNHMe | H | 4-NO2 |
| D-1687 | SMe | NHNHEt | H | 4-NO2 |
| D-1688 | SMe | NMeNH2 | H | 4-NO2 |
| D-1689 | SMe | NHCN | H | 4-NO2 |
| D-1690 | SMe | NHNO2 | H | 4-NO2 |
| D-1691 | SEt | NHOH | H | 4-NO2 |
| D-1692 | SEt | NHOMe | H | 4-NO2 |
| D-1693 | SEt | NHOEt | H | 4-NO2 |
| D-1694 | SEt | NHNH2 | H | 4-NO2 |
| D-1695 | SEt | NHNMe2 | H | 4-NO2 |
| D-1696 | SEt | NHNHMe | H | 4-NO2 |
| D-1697 | SEt | NHNHEt | H | 4-NO2 |
| D-1698 | SEt | NMeNH2 | H | 4-NO2 |
| D-1699 | SEt | NHCN | H | 4-NO2 |
| D-1700 | SEt | NHNO2 | H | 4-NO2 |

TABLE 24

| Compound No. | R15 | R16 | R17 | R18 |
|---|---|---|---|---|
| E-1 | | —S(CH2)3NH— | H | 4-NO2 |
| E-2 | | —S(CH2)3NH— | H | 4-NH2 |
| E-3 | | —S(CH2)3NH— | H | 4-Cl |
| E-4 | | —S(CH2)3NH— | H | 4-OMe |
| E-5 | | —S(CH2)3NH— | H | 4-Me |
| E-6 | | —S(CH2)3NH— | Me | 2-NH2 |
| E-7 | | —S(CH2)3NH— | Me | 4-NH2 |
| E-8 | | —S(CH2)3NH— | Me | 4-Cl |
| E-9 | | —S(CH2)3NH— | Me | 4-OMe |
| E-10 | | —S(CH2)3NH— | Me | 4-Me |
| E-11 | | —S(CH2)3NH— | Et | 4-NO2 |
| E-12 | | —S(CH2)3NH— | Et | 4-NH2 |
| E-13 | | —S(CH2)3NH— | Et | 4-Cl |
| E-14 | | —S(CH2)3NH— | Et | 4-OMe |
| E-15 | | —S(CH2)3NH— | Et | 4-Me |
| E-16 | | —S(CH2)2NH— | H | 4-NO2 |
| E-17 | | —S(CH2)2NH— | H | 4-NH2 |
| E-18 | | —S(CH2)2NH— | H | 4-Cl |
| E-19 | | —S(CH2)2NH— | H | 4-OMe |
| E-20 | | —S(CH2)2NH— | H | 4-Me |
| E-21 | | —S(CH2)2NH— | Me | 2-NH2 |
| E-22 | | —S(CH2)2NH— | Me | 4-NH2 |
| E-23 | | —S(CH2)2NH— | Me | 4-Cl |
| E-24 | | —S(CH2)2NH— | Me | 4-OMe |
| E-25 | | —S(CH2)2NH— | Me | 4-Me |
| E-26 | | —S(CH2)2NH— | Et | 4-NO2 |
| E-27 | | —S(CH2)2NH— | Et | 4-NH2 |
| E-28 | | —S(CH2)2NH— | Et | 4-Cl |
| E-29 | | —S(CH2)2NH— | Et | 4-OMe |
| E-30 | | —S(CH2)2NH— | Et | 4-Me |
| E-31 | | —O(CH2)3NH— | H | 4-NO2 |
| E-32 | | —O(CH2)3NH— | H | 4-NH2 |
| E-33 | | —O(CH2)3NH— | H | 4-Cl |
| E-34 | | —O(CH2)3NH— | H | 4-OMe |
| E-35 | | —O(CH2)3NH— | H | 4-Me |
| E-36 | | —O(CH2)3NH— | Me | 4-NO2 |
| E-37 | | —O(CH2)3NH— | Me | 4-NH2 |
| E-38 | | —O(CH2)3NH— | Me | 4-Cl |
| E-39 | | —O(CH2)3NH— | Me | 4-OMe |
| E-40 | | —O(CH2)3NH— | Me | 4-Me |
| E-41 | | —O(CH2)3NH— | Et | 4-NO2 |
| E-42 | | —O(CH2)3NH— | Et | 4-NH2 |
| E-43 | | —O(CH2)3NH— | Et | 4-Cl |
| E-44 | | —O(CH2)3NH— | Et | 4-OMe |
| E-45 | | —O(CH2)3NH— | Et | 4-Me |
| E-46 | | —O(CH2)2NH— | H | 4-NO2 |
| E-47 | | —O(CH2)2NH— | H | 4-NH2 |
| E-48 | | —O(CH2)2NH— | H | 4-Cl |
| E-49 | | —O(CH2)2NH— | H | 4-OMe |
| E-50 | | —O(CH2)2NH— | H | 4-Me |
| E-51 | | —O(CH2)2NH— | Me | 4-NO2 |
| E-52 | | —O(CH2)2NH— | Me | 4-NH2 |
| E-53 | | —O(CH2)2NH— | Me | 4-Cl |
| E-54 | | —O(CH2)2NH— | Me | 4-OMe |
| E-55 | | —O(CH2)2NH— | Me | 4-Me |

TABLE 24-continued

| Compound No. | R15 | R16 | R17 | R18 |
|---|---|---|---|---|
| E-56 | —O(CH₂)₂NH— | | Et | 4-NO₂ |
| E-57 | —O(CH₂)₂NH— | | Et | 4-NH₂ |
| E-58 | —O(CH₂)₂NH— | | Et | 4-Cl |
| E-59 | —O(CH₂)₂NH— | | Et | 4-OMe |
| E-60 | —O(CH₂)₂NH— | | Et | 4-Me |

Compounds F-I to F-800 shown in Tablse 25 to Table 32 are able to synthesize in a manner similar to those described in Example 22 or Example 23. Table 25 to Table 32

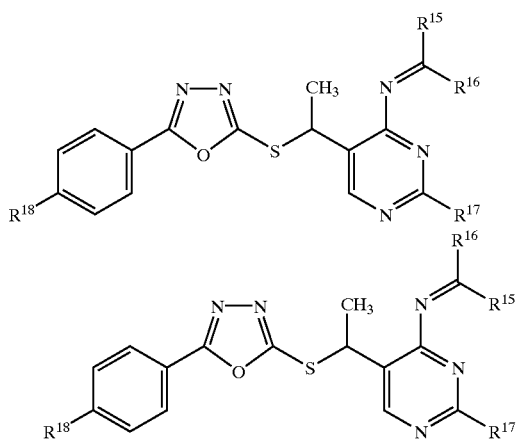

TABLE 25

| Compound No. | R15 | R16 | R17 | R18 |
|---|---|---|---|---|
| F-1 | NH₂ | SH | H | 4-NH₂ |
| F-2 | NH₂ | SMe | H | 4-NH₂ |
| F-3 | NH₂ | SEt | H | 4-NH₂ |
| F-4 | NH₂ | S-n-Pr | H | 4-NH₂ |
| F-5 | NH₂ | S-i-Pr | H | 4-NH₂ |
| F-6 | NH₂ | S-n-Bu | H | 4-NH₂ |
| F-7 | NH₂ | S-allyl | H | 4-NH₂ |
| F-8 | NH₂ | S-propargyl | H | 4-NH₂ |
| F-9 | NH₂ | SCH₂CF₃ | H | 4-NH₂ |
| F-10 | NH₂ | SCH₂CH₂F | H | 4-NH₂ |
| F-11 | NHMe | SH | H | 4-NH₂ |
| F-12 | NHMe | SMe | H | 4-NH₂ |
| F-13 | NHMe | SEt | H | 4-NH₂ |
| F-14 | NHMe | S-n-Pr | H | 4-NH₂ |
| F-15 | NHMe | S-i-Pr | H | 4-NH₂ |
| F-16 | NHMe | S-n-Bu | H | 4-NH₂ |
| F-17 | NHMe | S-allyl | H | 4-NH₂ |
| F-18 | NHMe | S-propargyl | H | 4-NH₂ |
| F-19 | NHMe | SCH₂CF₃ | H | 4-NH₂ |
| F-20 | NHMe | SCH₂CH₂F | H | 4-NH₂ |
| F-21 | NHEt | SH | H | 4-NH₂ |
| F-22 | NHEt | SMe | H | 4-NH₂ |
| F-23 | NHEt | SEt | H | 4-NH₂ |
| F-24 | NHEt | S-n-Pr | H | 4-NH₂ |
| F-25 | NHEt | S-i-Pr | H | 4-NH₂ |
| F-26 | NHEt | S-n-Bu | H | 4-NH₂ |
| F-27 | NHEt | S-allyl | H | 4-NH₂ |
| F-28 | NHEt | S-propargyl | H | 4-NH₂ |
| F-29 | NHEt | SCH₂CF₃ | H | 4-NH₂ |
| F-30 | NHEt | SCH₂CH₂F | H | 4-NH₂ |
| F-31 | NHPr | SH | H | 4-NH₂ |
| F-32 | NHPr | SMe | H | 4-NH₂ |
| F-33 | NHPr | SEt | H | 4-NH₂ |

TABLE 25-continued

| Compound No. | R15 | R16 | R17 | R18 |
|---|---|---|---|---|
| F-34 | NHPr | S-n-Pr | H | 4-NH₂ |
| F-35 | NHPr | S-i-Pr | H | 4-NH₂ |
| F-36 | NHPr | S-n-Bu | H | 4-NH₂ |
| F-37 | NHPr | S-allyl | H | 4-NH₂ |
| F-38 | NHPr | S-propargyl | H | 4-NH₂ |
| F-39 | NHPr | SCH₂CF₃ | H | 4-NH₂ |
| F-40 | NHPr | SCH₂CH₂F | H | 4-NH₂ |
| F-41 | NH-i-Pr | SH | H | 4-NH₂ |
| F-42 | NH-i-Pr | SMe | H | 4-NH₂ |
| F-43 | NH-i-Pr | SEt | H | 4-NH₂ |
| F-44 | NH-i-Pr | S-n-Pr | H | 4-NH₂ |
| F-45 | NH-i-Pr | S-i-Pr | H | 4-NH₂ |
| F-46 | NH-i-Pr | S-n-Bu | H | 4-NH₂ |
| F-47 | NH-i-Pr | S-allyl | H | 4-NH₂ |
| F-48 | NH-i-Pr | S-propargyl | H | 4-NH₂ |
| F-49 | NH-i-Pr | SCH₂CF₃ | H | 4-NH₂ |
| F-50 | NH-i-Pr | SCH₂CH₂F | H | 4-NH₂ |
| F-51 | NH-allyl | SH | H | 4-NH₂ |
| F-52 | NH-allyl | SMe | H | 4-NH₂ |
| F-53 | NH-allyl | SEt | H | 4-NH₂ |
| F-54 | NH-allyl | S-n-Pr | H | 4-NH₂ |
| F-55 | NH-allyl | S-i-Pr | H | 4-NH₂ |
| F-56 | NH-allyl | S-n-Bu | H | 4-NH₂ |
| F-57 | NH-allyl | S-allyl | H | 4-NH₂ |
| F-58 | NH-allyl | S-propargyl | H | 4-NH₂ |
| F-59 | NH-allyl | SCH₂CF₃ | H | 4-NH₂ |
| F-60 | NH-allyl | SCH₂CH₂F | H | 4-NH₂ |
| F-61 | NH-propargyl | SH | H | 4-NH₂ |
| F-62 | NH-propargyl | SMe | H | 4-NH₂ |
| F-63 | NH-propargyl | SEt | H | 4-NH₂ |
| F-64 | NH-propargyl | S-n-Pr | H | 4-NH₂ |
| F-65 | NH-propargyl | S-i-Pr | H | 4-NH₂ |
| F-66 | NH-propargyl | S-n-Bu | H | 4-NH₂ |
| F-67 | NH-propargyl | S-allyl | H | 4-NH₂ |
| F-68 | NH-propargyl | S-propargyl | H | 4-NH₂ |
| F-69 | NH-propargyl | SCH₂CF₃ | H | 4-NH₂ |
| F-70 | NH-propargyl | SCH₂CH₂F | H | 4-NH₂ |
| F-71 | NHCH₂CF₃ | SH | H | 4-NH₂ |
| F-72 | NHCH₂CF₃ | SMe | H | 4-NH₂ |
| F-73 | NHCH₂CF₃ | SEt | H | 4-NH₂ |
| F-74 | NHCH₂CF₃ | S-n-Pr | H | 4-NH₂ |
| F-75 | NHCH₂CF₃ | S-i-Pr | H | 4-NH₂ |
| F-76 | NHCH₂CF₃ | S-n-Bu | H | 4-NH₂ |
| F-77 | NHCH₂CF₃ | S-allyl | H | 4-NH₂ |
| F-78 | NHCH₂CF₃ | S-propargyl | H | 4-NH₂ |
| F-79 | NHCH₂CF₃ | SCH₂CF₃ | H | 4-NH₂ |
| F-80 | NHCH₂CF₃ | SCH₂CH₂F | H | 4-NH₂ |
| F-81 | NHCH₂CH₂F | SH | H | 4-NH₂ |
| F-82 | NHCH₂CH₂F | SMe | H | 4-NH₂ |
| F-83 | NHCH₂CH₂F | SEt | H | 4-NH₂ |
| F-84 | NHCH₂CH₂F | S-n-Pr | H | 4-NH₂ |
| F-85 | NHCH₂CH₂F | S-i-Pr | H | 4-NH₂ |
| F-86 | NHCH₂CH₂F | S-n-Bu | H | 4-NH₂ |
| F-87 | NHCH₂CH₂F | S-allyl | H | 4-NH₂ |
| F-88 | NHCH₂CH₂F | S-propargyl | H | 4-NH₂ |
| F-89 | NHCH₂CH₂F | SCH₂CF₃ | H | 4-NH₂ |
| F-90 | NHCH₂CH₂F | SCH₂CH₂F | H | 4-NH₂ |
| F-91 | NH-n-Bu | SH | H | 4-NH₂ |
| F-92 | NH-n-Bu | SMe | H | 4-NH₂ |
| F-93 | NH-n-Bu | SEt | H | 4-NH₂ |
| F-94 | NH-n-Bu | S-n-Pr | H | 4-NH₂ |
| F-95 | NH-n-Bu | S-i-Pr | H | 4-NH₂ |
| F-96 | NH-n-Bu | S-n-Bu | H | 4-NH₂ |
| F-97 | NH-n-Bu | S-allyl | H | 4-NH₂ |
| F-98 | NH-n-Bu | S-propargyl | H | 4-NH₂ |
| F-99 | NH-n-Bu | SCH₂CF₃ | H | 4-NH₂ |
| F-100 | NH-n-Bu | SCH₂CH₂F | H | 4-NH₂ |

TABLE 26

| Compound No. | $R^{15}$ | $R^{16}$ | $R^{17}$ | $R^{18}$ |
|---|---|---|---|---|
| F-101 | $NH_2$ | SH | H | 4-$NO_2$ |
| F-102 | $NH_2$ | SMe | H | 4-$NO_2$ |
| F-103 | $NH_2$ | SEt | H | 4-$NO_2$ |
| F-104 | $NH_2$ | S-n-Pr | H | 4-$NO_2$ |
| F-105 | $NH_2$ | S-i-Pr | H | 4-$NO_2$ |
| F-106 | $NH_2$ | S-n-Bu | H | 4-$NO_2$ |
| F-107 | $NH_2$ | S-allyl | H | 4-$NO_2$ |
| F-108 | $NH_2$ | S-propargyl | H | 4-$NO_2$ |
| F-109 | $NH_2$ | $SCH_2CF_3$ | H | 4-$NO_2$ |
| F-110 | $NH_2$ | $SCH_2CH_2F$ | H | 4-$NO_2$ |
| F-111 | NHMe | SH | H | 4-$NO_2$ |
| F-112 | NHMe | SMe | H | 4-$NO_2$ |
| F-113 | NHMe | SEt | H | 4-$NO_2$ |
| F-114 | NHMe | S-n-Pr | H | 4-$NO_2$ |
| F-115 | NHMe | S-i-Pr | H | 4-$NO_2$ |
| F-116 | NHMe | S-n-Bu | H | 4-$NO_2$ |
| F-117 | NHMe | S-allyl | H | 4-$NO_2$ |
| F-118 | NHMe | S-propargyl | H | 4-$NO_2$ |
| F-119 | NHMe | $SCH_2CF_3$ | H | 4-$NO_2$ |
| F-120 | NHMe | $SCH_2CH_2F$ | H | 4-$NO_2$ |
| F-121 | NHEt | SH | H | 4-$NO_2$ |
| F-122 | NHEt | SMe | H | 4-$NO_2$ |
| F-123 | NHEt | SEt | H | 4-$NO_2$ |
| F-124 | NHEt | S-n-Pr | H | 4-$NO_2$ |
| F-125 | NHEt | S-i-Pr | H | 4-$NO_2$ |
| F-126 | NHEt | S-n-Bu | H | 4-$NO_2$ |
| F-127 | NHEt | S-allyl | H | 4-$NO_2$ |
| F-128 | NHEt | S-propargyl | H | 4-$NO_2$ |
| F-129 | NHEt | $SCH_2CF_3$ | H | 4-$NO_2$ |
| F-130 | NHEt | $SCH_2CH_2F$ | H | 4-$NO_2$ |
| F-131 | NHPr | SH | H | 4-$NO_2$ |
| F-132 | NHPr | SMe | H | 4-$NO_2$ |
| F-133 | NHPr | SEt | H | 4-$NO_2$ |
| F-134 | NHPr | S-n-Pr | H | 4-$NO_2$ |
| F-135 | NHPr | S-i-Pr | H | 4-$NO_2$ |
| F-136 | NHPr | S-n-Bu | H | 4-$NO_2$ |
| F-137 | NHPr | S-allyl | H | 4-$NO_2$ |
| F-138 | NHPr | S-propargyl | H | 4-$NO_2$ |
| F-139 | NHPr | $SCH_2CF_3$ | H | 4-$NO_2$ |
| F-140 | NHPr | $SCH_2CH_2F$ | H | 4-$NO_2$ |
| F-141 | NH-i-Pr | SH | H | 4-$NO_2$ |
| F-142 | NH-i-Pr | SMe | H | 4-$NO_2$ |
| F-143 | NH-i-Pr | SEt | H | 4-$NO_2$ |
| F-144 | NH-i-Pr | S-n-Pr | H | 4-$NO_2$ |
| F-145 | NH-i-Pr | S-i-Pr | H | 4-$NO_2$ |
| F-146 | NH-i-Pr | S-n-Bu | H | 4-$NO_2$ |
| F-147 | NH-i-Pr | S-allyl | H | 4-$NO_2$ |
| F-148 | NH-i-Pr | S-propargyl | H | 4-$NO_2$ |
| F-149 | NH-i-Pr | $SCH_2CF_3$ | H | 4-$NO_2$ |
| F-150 | NH-i-Pr | $SCH_2CH_2F$ | H | 4-$NO_2$ |
| F-151 | NH-allyl | SH | H | 4-$NO_2$ |
| F-152 | NH-allyl | SMe | H | 4-$NO_2$ |
| F-153 | NH-allyl | SEt | H | 4-$NO_2$ |
| F-154 | NH-allyl | S-n-Pr | H | 4-$NO_2$ |
| F-155 | NH-allyl | S-i-Pr | H | 4-$NO_2$ |
| F-156 | NH-allyl | S-n-Bu | H | 4-$NO_2$ |
| F-157 | NH-allyl | S-allyl | H | 4-$NO_2$ |
| F-158 | NH-allyl | S-propargyl | H | 4-$NO_2$ |
| F-159 | NH-allyl | $SCH_2CF_3$ | H | 4-$NO_2$ |
| F-160 | NH-allyl | $SCH_2CH_2F$ | H | 4-$NO_2$ |
| F-161 | NH-propargyl | SH | H | 4-$NO_2$ |
| F-162 | NH-propargyl | SMe | H | 4-$NO_2$ |
| F-163 | NH-propargyl | SEt | H | 4-$NO_2$ |
| F-164 | NH-propargyl | S-n-Pr | H | 4-$NO_2$ |
| F-165 | NH-propargyl | S-i-Pr | H | 4-$NO_2$ |
| F-166 | NH-propargyl | S-n-Bu | H | 4-$NO_2$ |
| F-167 | NH-propargyl | S-allyl | H | 4-$NO_2$ |
| F-168 | NH-propargyl | S-propargyl | H | 4-$NO_2$ |
| F-169 | NH-propargyl | $SCH_2CF_3$ | H | 4-$NO_2$ |
| F-170 | NH-propargyl | $SCH_2CH_2F$ | H | 4-$NO_2$ |
| F-171 | $NHCH_2CF_3$ | SH | H | 4-$NO_2$ |
| F-172 | $NHCH_2CF_3$ | SMe | H | 4-$NO_2$ |
| F-173 | $NHCH_2CF_3$ | SEt | H | 4-$NO_2$ |
| F-174 | $NHCH_2CF_3$ | S-n-Pr | H | 4-$NO_2$ |
| F-175 | $NHCH_2CF_3$ | S-i-Pr | H | 4-$NO_2$ |
| F-176 | $NHCH_2CF_3$ | S-n-Bu | H | 4-$NO_2$ |
| F-177 | $NHCH_2CF_3$ | S-allyl | H | 4-$NO_2$ |
| F-178 | $NHCH_2CF_3$ | S-propargyl | H | 4-$NO_2$ |
| F-179 | $NHCH_2CF_3$ | $SCH_2CF_3$ | H | 4-$NO_2$ |
| F-180 | $NHCH_2CF_3$ | $SCH_2CH_2F$ | H | 4-$NO_2$ |
| F-181 | $NHCH_2CH_2F$ | SH | H | 4-$NO_2$ |
| F-182 | $NHCH_2CH_2F$ | SMe | H | 4-$NO_2$ |
| F-183 | $NHCH_2CH_2F$ | SEt | H | 4-$NO_2$ |
| F-184 | $NHCH_2CH_2F$ | S-n-Pr | H | 4-$NO_2$ |
| F-185 | $NHCH_2CH_2F$ | S-i-Pr | H | 4-$NO_2$ |
| F-186 | $NHCH_2CH_2F$ | S-n-Bu | H | 4-$NO_2$ |
| F-187 | $NHCH_2CH_2F$ | S-allyl | H | 4-$NO_2$ |
| F-188 | $NHCH_2CH_2F$ | S-propargyl | H | 4-$NO_2$ |
| F-189 | $NHCH_2CH_2F$ | $SCH_2CF_3$ | H | 4-$NO_2$ |
| F-190 | $NHCH_2CH_2F$ | $SCH_2CH_2F$ | H | 4-$NO_2$ |
| F-191 | NH-n-Bu | SH | H | 4-$NO_2$ |
| F-192 | NH-n-Bu | SMe | H | 4-$NO_2$ |
| F-193 | NH-n-Bu | SEt | H | 4-$NO_2$ |
| F-194 | NH-n-Bu | S-n-Pr | H | 4-$NO_2$ |
| F-195 | NH-n-Bu | S-i-Pr | H | 4-$NO_2$ |
| F-196 | NH-n-Bu | S-n-Bu | H | 4-$NO_2$ |
| F-197 | NH-n-Bu | S-allyl | H | 4-$NO_2$ |
| F-198 | NH-n-Bu | S-propargyl | H | 4-$NO_2$ |
| F-199 | NH-n-Bu | $SCH_2CF_3$ | H | 4-$NO_2$ |
| F-200 | NH-n-Bu | $SCH_2CH_2F$ | H | 4-$NO_2$ |

TABLE 27

| Compound No. | $R^{15}$ | $R^{16}$ | $R^{17}$ | $R^{18}$ |
|---|---|---|---|---|
| F-201 | $NH_2$ | SH | Me | 4-$NH_2$ |
| F-202 | $NH_2$ | SMe | Me | 4-$NH_2$ |
| F-203 | $NH_2$ | SEt | Me | 4-$NH_2$ |
| F-204 | $NH_2$ | S-n-Pr | Me | 4-$NH_2$ |
| F-205 | $NH_2$ | S-i-Pr | Me | 4-$NH_2$ |
| F-206 | $NH_2$ | S-n-Bu | Me | 4-$NH_2$ |
| F-207 | $NH_2$ | S-allyl | Me | 4-$NH_2$ |
| F-208 | $NH_2$ | S-propargyl | Me | 4-$NH_2$ |
| F-209 | $NH_2$ | $SCH_2CF_3$ | Me | 4-$NH_2$ |
| F-210 | $NH_2$ | $SCH_2CH_2F$ | Me | 4-$NH_2$ |
| F-211 | NHMe | SH | Me | 4-$NH_2$ |
| F-212 | NHMe | SMe | Me | 4-$NH_2$ |
| F-213 | NHMe | SEt | Me | 4-$NH_2$ |
| F-214 | NHMe | S-n-Pr | Me | 4-$NH_2$ |
| F-215 | NHMe | S-i-Pr | Me | 4-$NH_2$ |
| F-216 | NHMe | S-n-Bu | Me | 4-$NH_2$ |
| F-217 | NHMe | S-allyl | Me | 4-$NH_2$ |
| F-218 | NHMe | S-propargyl | Me | 4-$NH_2$ |
| F-219 | NHMe | $SCH_2CF_3$ | Me | 4-$NH_2$ |
| F-220 | NHMe | $SCH_2CH_2F$ | Me | 4-$NH_2$ |
| F-221 | NHEt | SH | Me | 4-$NH_2$ |
| F-222 | NHEt | SMe | Me | 4-$NH_2$ |
| F-223 | NHEt | SEt | Me | 4-$NH_2$ |
| F-224 | NHEt | S-n-Pr | Me | 4-$NH_2$ |
| F-225 | NHEt | S-i-Pr | Me | 4-$NH_2$ |
| F-226 | NHEt | S-n-Bu | Me | 4-$NH_2$ |
| F-227 | NHEt | S-allyl | Me | 4-$NH_2$ |
| F-228 | NHEt | S-propargyl | Me | 4-$NH_2$ |
| F-229 | NHEt | $SCH_2CF_3$ | Me | 4-$NH_2$ |
| F-230 | NHEt | $SCH_2CH_2F$ | Me | 4-$NH_2$ |
| F-231 | NHPr | SH | Me | 4-$NH_2$ |
| F-232 | NHPr | SMe | Me | 4-$NH_2$ |
| F-233 | NHPr | SEt | Me | 4-$NH_2$ |
| F-234 | NHPr | S-n-Pr | Me | 4-$NH_2$ |
| F-235 | NHPr | S-i-Pr | Me | 4-$NH_2$ |
| F-236 | NHPr | S-n-Bu | Me | 4-$NH_2$ |
| F-237 | NHPr | S-allyl | Me | 4-$NH_2$ |
| F-238 | NHPr | S-propargyl | Me | 4-$NH_2$ |
| F-239 | NHPr | $SCH_2CF_3$ | Me | 4-$NH_2$ |
| F-240 | NHPr | $SCH_2CH_2F$ | Me | 4-$NH_2$ |

TABLE 27-continued

| Compound No. | R15 | R16 | R17 | R18 |
|---|---|---|---|---|
| F-241 | NH-i-Pr | SH | Me | 4-NH2 |
| F-242 | NH-i-Pr | SMe | Me | 4-NH2 |
| F-243 | NH-i-Pr | SEt | Me | 4-NH2 |
| F-244 | NH-i-Pr | S-n-Pr | Me | 4-NH2 |
| F-245 | NH-i-Pr | S-i-Pr | Me | 4-NH2 |
| F-246 | NH-i-Pr | S-n-Bu | Me | 4-NH2 |
| F-247 | NH-i-Pr | S-allyl | Me | 4-NH2 |
| F-248 | NH-i-Pr | S-propargyl | Me | 4-NH2 |
| F-249 | NH-i-Pr | SCH2CF3 | Me | 4-NH2 |
| F-250 | NH-i-Pr | SCH2CH2F | Me | 4-NH2 |
| F-251 | NH-allyl | SH | Me | 4-NH2 |
| F-252 | NH-allyl | SMe | Me | 4-NH2 |
| F-253 | NH-allyl | SEt | Me | 4-NH2 |
| F-254 | NH-allyl | S-n-Pr | Me | 4-NH2 |
| F-255 | NH-allyl | S-i-Pr | Me | 4-NH2 |
| F-256 | NH-allyl | S-n-Bu | Me | 4-NH2 |
| F-257 | NH-allyl | S-allyl | Me | 4-NH2 |
| F-258 | NH-allyl | S-propargyl | Me | 4-NH2 |
| F-259 | NH-allyl | SCH2CF3 | Me | 4-NH2 |
| F-260 | NH-allyl | SCH2CH2F | Me | 4-NH2 |
| F-261 | NH-propargyl | SH | Me | 4-NH2 |
| F-262 | NH-propargyl | SMe | Me | 4-NH2 |
| F-263 | NH-propargyl | SEt | Me | 4-NH2 |
| F-264 | NH-propargyl | S-n-Pr | Me | 4-NH2 |
| F-265 | NH-propargyl | S-i-Pr | Me | 4-NH2 |
| F-266 | NH-propargyl | S-n-Bu | Me | 4-NH2 |
| F-267 | NH-propargyl | S-allyl | Me | 4-NH2 |
| F-268 | NH-propargyl | S-propargyl | Me | 4-NH2 |
| F-269 | NH-propargyl | SCH2CF3 | Me | 4-NH2 |
| F-270 | NH-propargyl | SCH2CH2F | Me | 4-NH2 |
| F-271 | NHCH2CF3 | SH | Me | 4-NH2 |
| F-272 | NHCH2CF3 | SMe | Me | 4-NH2 |
| F-273 | NHCH2CF3 | SEt | Me | 4-NH2 |
| F-274 | NHCH2CF3 | S-n-Pr | Me | 4-NH2 |
| F-275 | NHCH2CF3 | S-i-Pr | Me | 4-NH2 |
| F-276 | NHCH2CF3 | S-n-Bu | Me | 4-NH2 |
| F-277 | NHCH2CF3 | S-allyl | Me | 4-NH2 |
| F-278 | NHCH2CF3 | S-propargyl | Me | 4-NH2 |
| F-279 | NHCH2CF3 | SCH2CF3 | Me | 4-NH2 |
| F-280 | NHCH2CF3 | SCH2CH2F | Me | 4-NH2 |
| F-281 | NHCH2CH2F | SH | Me | 4-NH2 |
| F-282 | NHCH2CH2F | SMe | Me | 4-NH2 |
| F-283 | NHCH2CH2F | SEt | Me | 4-NH2 |
| F-284 | NHCH2CH2F | S-n-Pr | Me | 4-NH2 |
| F-285 | NHCH2CH2F | S-i-Pr | Me | 4-NH2 |
| F-286 | NHCH2CH2F | S-n-Bu | Me | 4-NH2 |
| F-287 | NHCH2CH2F | S-allyl | Me | 4-NH2 |
| F-288 | NHCH2CH2F | S-propargyl | Me | 4-NH2 |
| F-289 | NHCH2CH2F | SCH2CF3 | Me | 4-NH2 |
| F-290 | NHCH2CH2F | SCH2CH2F | Me | 4-NH2 |
| F-291 | NH-n-Bu | SH | Me | 4-NH2 |
| F-292 | NH-n-Bu | SMe | Me | 4-NH2 |
| F-293 | NH-n-Bu | SEt | Me | 4-NH2 |
| F-294 | NH-n-Bu | S-n-Pr | Me | 4-NH2 |
| F-295 | NH-n-Bu | S-i-Pr | Me | 4-NH2 |
| F-296 | NH-n-Bu | S-n-Bu | Me | 4-NH2 |
| F-297 | NH-n-Bu | S-allyl | Me | 4-NH2 |
| F-298 | NH-n-Bu | S-propargyl | Me | 4-NH2 |
| F-299 | NH-n-Bu | SCH2CF3 | Me | 4-NH2 |
| F-300 | NH-n-Bu | SCH2CH2F | Me | 4-NH2 |

TABLE 28

| Compound No. | R15 | R16 | R17 | R18 |
|---|---|---|---|---|
| F-301 | NH2 | SH | Me | 4-NO2 |
| F-302 | NH2 | SMe | Me | 4-NO2 |
| F-303 | NH2 | SEt | Me | 4-NO2 |
| F-304 | NH2 | S-n-Pr | Me | 4-NO2 |
| F-305 | NH2 | S-i-Pr | Me | 4-NO2 |
| F-306 | NH2 | S-n-Bu | Me | 4-NO2 |
| F-307 | NH2 | S-allyl | Me | 4-NO2 |
| F-308 | NH2 | S-propargyl | Me | 4-NO2 |
| F-309 | NH2 | SCH2CF3 | Me | 4-NO2 |
| F-310 | NH2 | SCH2CH2F | Me | 4-NO2 |
| F-311 | NHMe | SH | Me | 4-NO2 |
| F-312 | NHMe | SMe | Me | 4-NO2 |
| F-313 | NHMe | SEt | Me | 4-NO2 |
| F-314 | NHMe | S-n-Pr | Me | 4-NO2 |
| F-315 | NHMe | S-i-Pr | Me | 4-NO2 |
| F-316 | NHMe | S-n-Bu | Me | 4-NO2 |
| F-317 | NHMe | S-allyl | Me | 4-NO2 |
| F-318 | NHMe | S-propargyl | Me | 4-NO2 |
| F-319 | NHMe | SCH2CF3 | Me | 4-NO2 |
| F-320 | NHMe | SCH2CH2F | Me | 4-NO2 |
| F-321 | NHEt | SH | Me | 4-NO2 |
| F-322 | NHEt | SMe | Me | 4-OMe |
| F-323 | NHEt | SEt | Me | 4-Cl |
| F-324 | NHEt | S-n-Pr | Me | 4-NO2 |
| F-325 | NHEt | S-i-Pr | Me | 4-NO2 |
| F-326 | NHEt | S-n-Bu | Me | 4-NO2 |
| F-327 | NHEt | S-allyl | Me | 4-NO2 |
| F-328 | NHEt | S-propargyl | Me | 4-NO2 |
| F-329 | NHEt | SCH2CF3 | Me | 4-NO2 |
| F-330 | NHEt | SCH2CH2F | Me | 4-NO2 |
| F-331 | NHPr | SH | Me | 4-NO2 |
| F-332 | NHPr | SMe | Me | 4-NO2 |
| F-333 | NHPr | SEt | Me | 4-NO2 |
| F-334 | NHPr | S-n-Pr | Me | 4-NO2 |
| F-335 | NHPr | S-i-Pr | Me | 4-NO2 |
| F-336 | NHPr | S-n-Bu | Me | 4-NO2 |
| F-337 | NHPr | S-allyl | Me | 4-NO2 |
| F-338 | NHPr | S-propargyl | Me | 4-NO2 |
| F-339 | NHPr | SCH2CF3 | Me | 4-NO2 |
| F-340 | NHPr | SCH2CH2F | Me | 4-NO2 |
| F-341 | NH-i-Pr | SH | Me | 4-NO2 |
| F-342 | NH-i-Pr | SMe | Me | 4-NO2 |
| F-343 | NH-i-Pr | SEt | Me | 4-NO2 |
| F-344 | NH-i-Pr | S-n-Pr | Me | 4-NO2 |
| F-345 | NH-i-Pr | S-i-Pr | Me | 4-NO2 |
| F-346 | NH-i-Pr | S-n-Bu | Me | 4-NO2 |
| F-347 | NH-i-Pr | S-allyl | Me | 4-NO2 |
| F-348 | NH-i-Pr | S-propargyl | Me | 4-NO2 |
| F-349 | NH-i-Pr | SCH2CF3 | Me | 4-NO2 |
| F-350 | NH-i-Pr | SCH2CH2F | Me | 4-NO2 |
| F-351 | NH-allyl | SH | Me | 4-NO2 |
| F-352 | NH-allyl | SMe | Me | 4-NO2 |
| F-353 | NH-allyl | SEt | Me | 4-NO2 |
| F-354 | NH-allyl | S-n-Pr | Me | 4-NO2 |
| F-355 | NH-allyl | S-i-Pr | Me | 4-NO2 |
| F-356 | NH-allyl | S-n-Bu | Me | 4-NO2 |
| F-357 | NH-allyl | S-allyl | Me | 4-NO2 |
| F-358 | NH-allyl | S-propargyl | Me | 4-NO2 |
| F-359 | NH-allyl | SCH2CF3 | Me | 4-NO2 |
| F-360 | NH-allyl | SCH2CH2F | Me | 4-NO2 |
| F-361 | NH-propargyl | SH | Me | 4-NO2 |
| F-362 | NH-propargyl | SMe | Me | 4-NO2 |
| F-363 | NH-propargyl | SEt | Me | 4-NO2 |
| F-364 | NH-propargyl | S-n-Pr | Me | 4-NO2 |
| F-365 | NH-propargyl | S-i-Pr | Me | 4-NO2 |
| F-366 | NH-propargyl | S-n-Bu | Me | 4-NO2 |
| F-367 | NH-propargyl | S-allyl | Me | 4-NO2 |
| F-368 | NH-propargyl | S-propargyl | Me | 4-NO2 |
| F-369 | NH-propargyl | SCH2CF3 | Me | 4-NO2 |
| F-370 | NH-propargyl | SCH2CH2F | Me | 4-NO2 |
| F-371 | NHCH2CF3 | SH | Me | 4-NO2 |
| F-372 | NHCH2CF3 | SMe | Me | 4-NO2 |
| F-373 | NHCH2CF3 | SEt | Me | 4-NO2 |
| F-374 | NHCH2CF3 | S-n-Pr | Me | 4-NO2 |
| F-375 | NHCH2CF3 | S-i-Pr | Me | 4-NO2 |
| F-376 | NHCH2CF3 | S-n-Bu | Me | 4-NO2 |
| F-377 | NHCH2CF3 | S-allyl | Me | 4-NO2 |
| F-378 | NHCH2CF3 | S-propargyl | Me | 4-NO2 |
| F-379 | NHCH2CF3 | SCH2CF3 | Me | 4-NO2 |
| F-380 | NHCH2CF3 | SCH2CH2F | Me | 4-NO2 |

TABLE 28-continued

| Compound No. | $R^{15}$ | $R^{16}$ | $R^{17}$ | $R^{18}$ |
|---|---|---|---|---|
| F-381 | NHCH$_2$CH$_2$F | SH | Me | 4-NO$_2$ |
| F-382 | NHCH$_2$CH$_2$F | SMe | Me | 4-NO$_2$ |
| F-383 | NHCH$_2$CH$_2$F | SEt | Me | 4-NO$_2$ |
| F-384 | NHCH$_2$CH$_2$F | S-n-Pr | Me | 4-NO$_2$ |
| F-385 | NHCH$_2$CH$_2$F | S-i-Pr | Me | 4-NO$_2$ |
| F-386 | NHCH$_2$CH$_2$F | S-n-Bu | Me | 4-NO$_2$ |
| F-387 | NHCH$_2$CH$_2$F | S-allyl | Me | 4-NO$_2$ |
| F-388 | NHCH$_2$CH$_2$F | S-propargyl | Me | 4-NO$_2$ |
| F-389 | NHCH$_2$CH$_2$F | SCH$_2$CF$_3$ | Me | 4-NO$_2$ |
| F-390 | NHCH$_2$CH$_2$F | SCH$_2$CH$_2$F | Me | 4-NO$_2$ |
| F-391 | NH-n-Bu | SH | Me | 4-NO$_2$ |
| F-392 | NH-n-Bu | SMe | Me | 4-NO$_2$ |
| F-393 | NH-n-Bu | SEt | Me | 4-NO$_2$ |
| F-394 | NH-n-Bu | S-n-Pr | Me | 4-NO$_2$ |
| F-395 | NH-n-Bu | S-i-Pr | Me | 4-NO$_2$ |
| F-396 | NH-n-Bu | S-n-Bu | Me | 4-NO$_2$ |
| F-397 | NH-n-Bu | S-allyl | Me | 4-NO$_2$ |
| F-398 | NH-n-Bu | S-propargyl | Me | 4-NO$_2$ |
| F-399 | NH-n-Bu | SCH$_2$CF$_3$ | Me | 4-NO$_2$ |
| F-400 | NH-n-Bu | SCH$_2$CH$_2$F | Me | 4-NO$_2$ |

TABLE 29

| Compound No. | $R^{15}$ | $R^{16}$ | $R^{17}$ | $R^{18}$ |
|---|---|---|---|---|
| F-401 | NH$_2$ | NH$_2$ | Me | 4-NO$_2$ |
| F-402 | NH$_2$ | NHMe | Me | 4-NO$_2$ |
| F-403 | NH$_2$ | NHEt | Me | 4-NO$_2$ |
| F-404 | NH$_2$ | NHPr | Me | 4-NO$_2$ |
| F-405 | NH$_2$ | NH-i-Pr | Me | 4-NO$_2$ |
| F-406 | NH$_2$ | NH-n-Bu | Me | 4-NO$_2$ |
| F-407 | NH$_2$ | NH-allyl | Me | 4-NO$_2$ |
| F-408 | NH$_2$ | NH-propargyl | Me | 4-NO$_2$ |
| F-409 | NH$_2$ | NHCH$_2$CF$_3$ | Me | 4-NO$_2$ |
| F-410 | NH$_2$ | NHCH$_2$CH$_2$F | Me | 4-NO$_2$ |
| F-411 | NHMe | NHMe | Me | 4-NO$_2$ |
| F-412 | NHMe | NHEt | Me | 4-NO$_2$ |
| F-413 | NHMe | NHPr | Me | 4-NO$_2$ |
| F-414 | NHMe | NH-i-Pr | Me | 4-NO$_2$ |
| F-415 | NHMe | NH-n-Bu | Me | 4-NO$_2$ |
| F-416 | NHMe | NH-allyl | Me | 4-NO$_2$ |
| F-417 | NHMe | NH-propargyl | Me | 4-NO$_2$ |
| F-418 | NHMe | NHCH$_2$CF$_3$ | Me | 4-NO$_2$ |
| F-419 | NHMe | NHCH$_2$CH$_2$F | Me | 4-NO$_2$ |
| F-420 | NHEt | NHEt | Me | 4-Cl |
| F-421 | NHEt | NHPr | Me | 4-NO$_2$ |
| F-422 | NHEt | NH-i-Pr | Me | 4-NO$_2$ |
| F-423 | NHEt | NH-n-Bu | Me | 4-NO$_2$ |
| F-424 | NHEt | NH-allyl | Me | 4-NO$_2$ |
| F-425 | NHEt | NH-propargyl | Me | 4-NO$_2$ |
| F-426 | NHEt | NHCH$_2$CF$_3$ | Me | 4-NO$_2$ |
| F-427 | NHEt | NHCH$_2$CH$_2$F | Me | 4-NO$_2$ |
| F-428 | NHPr | NHPr | Me | 4-NO$_2$ |
| F-429 | NHPr | NH-i-Pr | Me | 4-NO$_2$ |
| F-430 | NHPr | NH-n-Bu | Me | 4-NO$_2$ |
| F-431 | NHPr | NH-allyl | Me | 4-NO$_2$ |
| F-432 | NHPr | NH-propargyl | Me | 4-NO$_2$ |
| F-433 | NHPr | NHCH$_2$CF$_3$ | Me | 4-NO$_2$ |
| F-434 | NHPr | NHCH$_2$CH$_2$F | Me | 4-NO$_2$ |
| F-435 | NH-i-Pr | NH-i-Pr | Me | 4-NO$_2$ |
| F-436 | NH-i-Pr | NH-n-Bu | Me | 4-NO$_2$ |
| F-437 | NH-i-Pr | NH-allyl | Me | 4-NO$_2$ |
| F-438 | NH-i-Pr | NH-propargyl | Me | 4-NO$_2$ |
| F-439 | NH-i-Pr | NHCH$_2$CF$_3$ | Me | 4-NO$_2$ |
| F-440 | NH-i-Pr | NHCH$_2$CH$_2$F | Me | 4-NO$_2$ |
| F-441 | NH-n-Bu | NH-n-Bu | Me | 4-NO$_2$ |
| F-442 | NH-n-Bu | NH-allyl | Me | 4-NO$_2$ |
| F-443 | NH-n-Bu | NH-propargyl | Me | 4-NO$_2$ |
| F-444 | NH-n-Bu | NHCH$_2$CF$_3$ | Me | 4-NO$_2$ |
| F-445 | NH-n-Bu | NHCH$_2$CH$_2$F | Me | 4-NO$_2$ |

TABLE 29-continued

| Compound No. | $R^{15}$ | $R^{16}$ | $R^{17}$ | $R^{18}$ |
|---|---|---|---|---|
| F-446 | NH-allyl | NH-allyl | Me | 4-NO$_2$ |
| F-447 | NH-allyl | NH-propargyl | Me | 4-NO$_2$ |
| F-448 | NH-allyl | NHCH$_2$CF$_3$ | Me | 4-NO$_2$ |
| F-449 | NH-allyl | NHCH$_2$CH$_2$F | Me | 4-NO$_2$ |
| F-450 | NH-propargyl | NH-propargyl | Me | 4-NO$_2$ |
| F-451 | NH-propargyl | NHCH$_2$CF$_3$ | Me | 4-NO$_2$ |
| F-452 | NH-propargyl | NHCH$_2$CH$_2$F | Me | 4-NO$_2$ |
| F-453 | NHCH$_2$CF$_3$ | NHCH$_2$CF$_3$ | Me | 4-NO$_2$ |
| F-454 | NHCH$_2$CF$_3$ | NHCH$_2$CH$_2$F | Me | 4-NO$_2$ |
| F-455 | NHCH$_2$CH$_2$F | NHCH$_2$CH$_2$F | Me | 4-NO$_2$ |
| F-456 | NHOMe | NH$_2$ | Me | 4-NO$_2$ |
| F-457 | NHOMe | NHMe | Me | 4-NO$_2$ |
| F-458 | NHOMe | NHEt | Me | 4-NO$_2$ |
| F-459 | NHOMe | NHPr | Me | 4-NO$_2$ |
| F-460 | NHOMe | NH-i-Pr | Me | 4-NO$_2$ |
| F-461 | NHOMe | NH-n-Bu | Me | 4-NO$_2$ |
| F-462 | NHOMe | NH-allyl | Me | 4-NO$_2$ |
| F-463 | NHOMe | NH-propargyl | Me | 4-NO$_2$ |
| F-464 | NHOMe | NHCH$_2$CF$_3$ | Me | 4-NO$_2$ |
| F-465 | NHOMe | NHCH$_2$CH$_2$F | Me | 4-NO$_2$ |
| F-466 | NHOEt | NH$_2$ | Me | 4-NO$_2$ |
| F-467 | NHOEt | NHMe | Me | 4-NO$_2$ |
| F-468 | NHOEt | NHEt | Me | 4-NO$_2$ |
| F-469 | NHOEt | NHPr | Me | 4-NO$_2$ |
| F-470 | NHOEt | NH-i-Pr | Me | 4-NO$_2$ |
| F-471 | NHOEt | NH-n-Bu | Me | 4-NO$_2$ |
| F-472 | NHOEt | NH-allyl | Me | 4-NO$_2$ |
| F-473 | NHOEt | NH-propargyl | Me | 4-NO$_2$ |
| F-474 | NHOEt | NHCH$_2$CF$_3$ | Me | 4-NO$_2$ |
| F-475 | NHOEt | NHCH$_2$CH$_2$F | Me | 4-NO$_2$ |
| F-476 | NHNMe$_2$ | NH$_2$ | Me | 4-NO$_2$ |
| F-477 | NHNMe$_2$ | NHMe | Me | 4-NO$_2$ |
| F-478 | NHNMe$_2$ | NHEt | Me | 4-NO$_2$ |
| F-479 | NHNMe$_2$ | NHPr | Me | 4-NO$_2$ |
| F-480 | NHNMe$_2$ | NH-i-Pr | Me | 4-NO$_2$ |
| F-481 | NHNMe$_2$ | NH-n-Bu | Me | 4-NO$_2$ |
| F-482 | NHNMe$_2$ | NH-allyl | Me | 4-NO$_2$ |
| F-483 | NHNMe$_2$ | NH-propargyl | Me | 4-NO$_2$ |
| F-484 | NHNMe$_2$ | NHCH$_2$CF$_3$ | Me | 4-NO$_2$ |
| F-485 | NHNMe$_2$ | NHCH$_2$CH$_2$F | Me | 4-NO$_2$ |
| F-486 | NHNH$_2$ | NH$_2$ | Me | 4-NO$_2$ |
| F-487 | NHNH$_2$ | NHMe | Me | 4-NO$_2$ |
| F-488 | NHNH$_2$ | NHEt | Me | 4-NO$_2$ |
| F-489 | NHNH$_2$ | NHPr | Me | 4-NO$_2$ |
| F-490 | NHNH$_2$ | NH-i-Pr | Me | 4-NO$_2$ |
| F-491 | NHNH$_2$ | NH-n-Bu | Me | 4-NO$_2$ |
| F-492 | NHNH$_2$ | NH-allyl | Me | 4-NO$_2$ |
| F-493 | NHNH$_2$ | NH-propargyl | Me | 4-NO$_2$ |
| F-494 | NHNH$_2$ | NHCH$_2$CF$_3$ | Me | 4-NO$_2$ |
| F-495 | NHNH$_2$ | NHCH$_2$CH$_2$F | Me | 4-NO$_2$ |
| F-496 | NHNHMe | NHMe | Me | 4-NO$_2$ |
| F-497 | NHNHMe | NHEt | Me | 4-NO$_2$ |
| F-498 | NHNHMe | NHPr | Me | 4-NO$_2$ |
| F-499 | NHNHMe | NH-i-Pr | Me | 4-NO$_2$ |
| F-500 | NHNHMe | NHCH$_2$CF$_3$ | Me | 4-NO$_2$ |

TABLE 30

| Compound No. | $R^{15}$ | $R^{16}$ | $R^{17}$ | $R^{18}$ |
|---|---|---|---|---|
| F-501 | NH$_2$ | NH$_2$ | H | 4-NO$_2$ |
| F-502 | NH$_2$ | NHMe | H | 4-NO$_2$ |
| F-503 | NH$_2$ | NHEt | H | 4-NO$_2$ |
| F-504 | NH$_2$ | NHPr | H | 4-NO$_2$ |
| F-505 | NH$_2$ | NH-i-Pr | H | 4-NO$_2$ |
| F-506 | NH$_2$ | NH-n-Bu | H | 4-NO$_2$ |
| F-507 | NH$_2$ | NH-allyl | H | 4-NO$_2$ |
| F-508 | NH$_2$ | NH-propargyl | H | 4-NO$_2$ |
| F-509 | NH$_2$ | NHCH$_2$CF$_3$ | H | 4-NO$_2$ |
| F-510 | NH$_2$ | NHCH$_2$CH$_2$F | H | 4-NO$_2$ |

TABLE 30-continued

| Compound No. | $R^{15}$ | $R^{16}$ | $R^{17}$ | $R^{18}$ |
|---|---|---|---|---|
| F-511 | NHMe | NHMe | H | 4-NO$_2$ |
| F-512 | NHMe | NHEt | H | 4-NO$_2$ |
| F-513 | NHMe | NHPr | H | 4-NO$_2$ |
| F-514 | NHMe | NH-i-Pr | H | 4-NO$_2$ |
| F-515 | NHMe | NH-n-Bu | H | 4-NO$_2$ |
| F-516 | NHMe | NH-allyl | H | 4-NO$_2$ |
| F-517 | NHMe | NH-propargyl | H | 4-NO$_2$ |
| F-518 | NHMe | NHCH$_2$CF$_3$ | H | 4-NO$_2$ |
| F-519 | NHMe | NHCH$_2$CH$_2$F | H | 4-NO$_2$ |
| F-520 | NHEt | NHEt | H | 4-NO$_2$ |
| F-521 | NHEt | NHPr | H | 4-NO$_2$ |
| F-522 | NHEt | NH-i-Pr | H | 4-NO$_2$ |
| F-523 | NHEt | NH-n-Bu | H | 4-NO$_2$ |
| F-524 | NHEt | NH-allyl | H | 4-NO$_2$ |
| F-525 | NHEt | NH-propargyl | H | 4-NO$_2$ |
| F-526 | NHEt | NHCH$_2$CF$_3$ | H | 4-NO$_2$ |
| F-527 | NHEt | NHCH$_2$CH$_2$F | H | 4-NO$_2$ |
| F-528 | NHPr | NHPr | H | 4-NO$_2$ |
| F-529 | NHPr | NH-i-Pr | H | 4-NO$_2$ |
| F-530 | NHPr | NH-n-Bu | H | 4-NO$_2$ |
| F-531 | NHPr | NH-allyl | H | 4-NO$_2$ |
| F-532 | NHPr | NH-propargyl | H | 4-NO$_2$ |
| F-533 | NHPr | NHCH$_2$CF$_3$ | H | 4-NO$_2$ |
| F-534 | NHPr | NHCH$_2$CH$_2$F | H | 4-NO$_2$ |
| F-535 | NH-i-Pr | NH-i-Pr | H | 4-NO$_2$ |
| F-536 | NH-i-Pr | NH-n-Bu | H | 4-NO$_2$ |
| F-537 | NH-i-Pr | NH-allyl | H | 4-NO$_2$ |
| F-538 | NH-i-Pr | NH-propargyl | H | 4-NO$_2$ |
| F-539 | NH-i-Pr | NHCH$_2$CF$_3$ | H | 4-NO$_2$ |
| F-540 | NH-i-Pr | NHCH$_2$CH$_2$F | H | 4-NO$_2$ |
| F-541 | NH-n-Bu | NH-n-Bu | H | 4-NO$_2$ |
| F-542 | NH-n-Bu | NH-allyl | H | 4-NO$_2$ |
| F-543 | NH-n-Bu | NH-propargyl | H | 4-NO$_2$ |
| F-544 | NH-n-Bu | NHCH$_2$CF$_3$ | H | 4-NO$_2$ |
| F-545 | NH-n-Bu | NHCH$_2$CH$_2$F | H | 4-NO$_2$ |
| F-546 | NH-allyl | NH-allyl | H | 4-NO$_2$ |
| F-547 | NH-allyl | NH-propargyl | H | 4-NO$_2$ |
| F-548 | NH-allyl | NHCH$_2$CF$_3$ | H | 4-NO$_2$ |
| F-549 | NH-allyl | NHCH$_2$CH$_2$F | H | 4-NO$_2$ |
| F-550 | NH-propargyl | NH-propargyl | H | 4-NO$_2$ |
| F-551 | NH-propargyl | NHCH$_2$CF$_3$ | H | 4-NO$_2$ |
| F-552 | NH-propargyl | NHCH$_2$CH$_2$F | H | 4-NO$_2$ |
| F-553 | NHCH$_2$CF$_3$ | NHCH$_2$CF$_3$ | H | 4-NO$_2$ |
| F-554 | NHCH$_2$CF$_3$ | NHCH$_2$CH$_2$F | H | 4-NO$_2$ |
| F-555 | NHCH$_2$CH$_2$F | NHCH$_2$CH$_2$F | H | 4-NO$_2$ |
| F-556 | NHOMe | NH$_2$ | H | 4-NO$_2$ |
| F-557 | NHOMe | NHMe | H | 4-NO$_2$ |
| F-558 | NHOMe | NHEt | H | 4-NO$_2$ |
| F-559 | NHOMe | NHPr | H | 4-NO$_2$ |
| F-560 | NHOMe | NH-i-Pr | H | 4-NO$_2$ |
| F-561 | NHOMe | NH-n-Bu | H | 4-NO$_2$ |
| F-562 | NHOMe | NH-allyl | H | 4-NO$_2$ |
| F-563 | NHOMe | NH-propargyl | H | 4-NO$_2$ |
| F-564 | NHOMe | NHCH$_2$CF$_3$ | H | 4-NO$_2$ |
| F-565 | NHOMe | NHCH$_2$CH$_2$F | H | 4-NO$_2$ |
| F-566 | NHOEt | NH$_2$ | H | 4-NO$_2$ |
| F-567 | NHOEt | NHMe | H | 4-NO$_2$ |
| F-568 | NHOEt | NHEt | H | 4-NO$_2$ |
| F-569 | NHOEt | NHPr | H | 4-NO$_2$ |
| F-570 | NHOEt | NH-i-Pr | H | 4-NO$_2$ |
| F-571 | NHOEt | NH-n-Bu | H | 4-NO$_2$ |
| F-572 | NHOEt | NH-allyl | H | 4-NO$_2$ |
| F-573 | NHOEt | NH-propargyl | H | 4-NO$_2$ |
| F-574 | NHOEt | NHCH$_2$CF$_3$ | H | 4-NO$_2$ |
| F-575 | NHOEt | NHCH$_2$CH$_2$F | H | 4-NO$_2$ |
| F-576 | NHNMe$_2$ | NH$_2$ | H | 4-NO$_2$ |
| F-577 | NHNMe$_2$ | NHMe | H | 4-NO$_2$ |
| F-578 | NHNMe$_2$ | NHEt | H | 4-NO$_2$ |
| F-579 | NHNMe$_2$ | NHPr | H | 4-NO$_2$ |
| F-580 | NHNMe$_2$ | NH-i-Pr | H | 4-NO$_2$ |
| F-581 | NHNMe$_2$ | NH-n-Bu | H | 4-NO$_2$ |
| F-582 | NHNMe$_2$ | NH-allyl | H | 4-NO$_2$ |
| F-583 | NHNMe$_2$ | NH-propargyl | H | 4-NO$_2$ |
| F-584 | NHNMe$_2$ | NHCH$_2$CF$_3$ | H | 4-NO$_2$ |
| F-585 | NHNMe$_2$ | NHCH$_2$CH$_2$F | H | 4-NO$_2$ |
| F-586 | NHNH$_2$ | NH$_2$ | H | 4-NO$_2$ |
| F-587 | NHNH$_2$ | NHMe | H | 4-NO$_2$ |
| F-588 | NHNH$_2$ | NHEt | H | 4-NO$_2$ |
| F-589 | NHNH$_2$ | NHPr | H | 4-NO$_2$ |
| F-590 | NHNH$_2$ | NH-i-Pr | H | 4-NO$_2$ |
| F-591 | NHNH$_2$ | NH-n-Bu | H | 4-NO$_2$ |
| F-592 | NHNH$_2$ | NH-allyl | H | 4-NO$_2$ |
| F-593 | NHNH$_2$ | NH-propargyl | H | 4-NO$_2$ |
| F-594 | NHNH$_2$ | NHCH$_2$CF$_3$ | H | 4-NO$_2$ |
| F-595 | NHNH$_2$ | NHCH$_2$CH$_2$F | H | 4-NO$_2$ |
| F-596 | NHNHMe | NHMe | H | 4-NO$_2$ |
| F-597 | NHNHMe | NHEt | H | 4-NO$_2$ |
| F-598 | NHNHMe | NHPr | H | 4-NO$_2$ |
| F-599 | NHNHMe | NH-i-Pr | H | 4-NO$_2$ |
| F-600 | NHNHMe | NHCH$_2$CF$_3$ | H | 4-NO$_2$ |

TABLE 31

| Compound No. | $R^{15}$ | $R^{16}$ | $R^{17}$ | $R^{18}$ |
|---|---|---|---|---|
| F-601 | NH$_2$ | NH$_2$ | Me | 4-NH$_2$ |
| F-602 | NH$_2$ | NHMe | Me | 4-NH$_2$ |
| F-603 | NH$_2$ | NHEt | Me | 4-NH$_2$ |
| F-604 | NH$_2$ | NHPr | Me | 4-NH$_2$ |
| F-605 | NH$_2$ | NH-i-Pr | Me | 4-NH$_2$ |
| F-606 | NH$_2$ | NH-n-Bu | Me | 4-NH$_2$ |
| F-607 | NH$_2$ | NH-allyl | Me | 4-NH$_2$ |
| F-608 | NH$_2$ | NH-propargyl | Me | 4-NH$_2$ |
| F-609 | NH$_2$ | NHCH$_2$CF$_3$ | Me | 4-NH$_2$ |
| F-610 | NH$_2$ | NHCH$_2$CH$_2$F | Me | 4-NH$_2$ |
| F-611 | NHMe | NHMe | Me | 4-NH$_2$ |
| F-612 | NHMe | NHEt | Me | 4-NH$_2$ |
| F-613 | NHMe | NHPr | Me | 4-NH$_2$ |
| F-614 | NHMe | NH-i-Pr | Me | 4-NH$_2$ |
| F-615 | NHMe | NH-n-Bu | Me | 4-NH$_2$ |
| F-616 | NHMe | NH-allyl | Me | 4-NH$_2$ |
| F-617 | NHMe | NH-propargyl | Me | 4-NH$_2$ |
| F-618 | NHMe | NHCH$_2$CF$_3$ | Me | 4-NH$_2$ |
| F-619 | NHMe | NHCH$_2$CH$_2$F | Me | 4-NH$_2$ |
| F-620 | NHEt | NHEt | Me | 4-NH$_2$ |
| F-621 | NHEt | NHPr | Me | 4-NH$_2$ |
| F-622 | NHEt | NH-i-Pr | Me | 4-NH$_2$ |
| F-623 | NHEt | NH-n-Bu | Me | 4-NH$_2$ |
| F-624 | NHEt | NH-allyl | Me | 4-NH$_2$ |
| F-625 | NHEt | NH-propargyl | Me | 4-NH$_2$ |
| F-626 | NHEt | NHCH$_2$CF$_3$ | Me | 4-NH$_2$ |
| F-627 | NHEt | NHCH$_2$CH$_2$F | Me | 4-NH$_2$ |
| F-628 | NHPr | NHPr | Me | 4-NH$_2$ |
| F-629 | NHPr | NH-i-Pr | Me | 4-NH$_2$ |
| F-630 | NHPr | NH-n-Bu | Me | 4-NH$_2$ |
| F-631 | NHPr | NH-allyl | Me | 4-NH$_2$ |
| F-632 | NHPr | NH-propargyl | Me | 4-NH$_2$ |
| F-633 | NHPr | NHCH$_2$CF$_3$ | Me | 4-NH$_2$ |
| F-634 | NHPr | NHCH$_2$CH$_2$F | Me | 4-NH$_2$ |
| F-635 | NH-i-Pr | NH-i-Pr | Me | 4-NH$_2$ |
| F-636 | NH-i-Pr | NH-n-Bu | Me | 4-NH$_2$ |
| F-637 | NH-i-Pr | NH-allyl | Me | 4-NH$_2$ |
| F-638 | NH-i-Pr | NH-propargyl | Me | 4-NH$_2$ |
| F-639 | NH-i-Pr | NHCH$_2$CF$_3$ | Me | 4-NH$_2$ |
| F-640 | NH-i-Pr | NHCH$_2$CH$_2$F | Me | 4-NH$_2$ |
| F-641 | NH-n-Bu | NH-n-Bu | Me | 4-NH$_2$ |
| F-642 | NH-n-Bu | NH-allyl | Me | 4-NH$_2$ |
| F-643 | NH-n-Bu | NH-propargyl | Me | 4-NH$_2$ |
| F-644 | NH-n-Bu | NHCH$_2$CF$_3$ | Me | 4-NH$_2$ |
| F-645 | NH-n-Bu | NHCH$_2$CH$_2$F | Me | 4-NH$_2$ |
| F-646 | NH-allyl | NH-allyl | Me | 4-NH$_2$ |
| F-647 | NH-allyl | NH-propargyl | Me | 4-NH$_2$ |
| F-648 | NH-allyl | NHCH$_2$CF$_3$ | Me | 4-NH$_2$ |
| F-649 | NH-allyl | NHCH$_2$CH$_2$F | Me | 4-NH$_2$ |
| F-650 | NH-propargyl | NH-propargyl | Me | 4-NH$_2$ |

TABLE 31-continued

| Compound No. | $R^{15}$ | $R^{16}$ | $R^{17}$ | $R^{18}$ |
|---|---|---|---|---|
| F-651 | NH-propargyl | NHCH$_2$CF$_3$ | Me | 4-NH$_2$ |
| F-652 | NH-propargyl | NHCH$_2$CH$_2$F | Me | 4-NH$_2$ |
| F-653 | NHCH$_2$CF$_3$ | NHCH$_2$CF$_3$ | Me | 4-NH$_2$ |
| F-654 | NHCH$_2$CF$_3$ | NHCH$_2$CH$_2$F | Me | 4-NH$_2$ |
| F-655 | NHCH$_2$CH$_2$F | NHCH$_2$CH$_2$F | Me | 4-NH$_2$ |
| F-656 | NHOMe | NH$_2$ | Me | 4-NH$_2$ |
| F-657 | NHOMe | NHMe | Me | 4-NH$_2$ |
| F-658 | NHOMe | NHEt | Me | 4-NH$_2$ |
| F-659 | NHOMe | NHPr | Me | 4-NH$_2$ |
| F-660 | NHOMe | NH-i-Pr | Me | 4-NH$_2$ |
| F-661 | NHOMe | NH-n-Bu | Me | 4-NH$_2$ |
| F-662 | NHOMe | NH-allyl | Me | 4-NH$_2$ |
| F-663 | NHOMe | NH-propargyl | Me | 4-NH$_2$ |
| F-664 | NHOMe | NHCH$_2$CF$_3$ | Me | 4-NH$_2$ |
| F-665 | NHOMe | NHCH$_2$CH$_2$F | Me | 4-NH$_2$ |
| F-666 | NHOEt | NH$_2$ | Me | 4-NH$_2$ |
| F-667 | NHOEt | NHMe | Me | 4-NH$_2$ |
| F-668 | NHOEt | NHEt | Me | 4-NH$_2$ |
| F-669 | NHOEt | NHPr | Me | 4-NH$_2$ |
| F-670 | NHOEt | NH-i-Pr | Me | 4-NH$_2$ |
| F-671 | NHOEt | NH-n-Bu | Me | 4-NH$_2$ |
| F-672 | NHOEt | NH-allyl | Me | 4-NH$_2$ |
| F-673 | NHOEt | NH-propargyl | Me | 4-NH$_2$ |
| F-674 | NHOEt | NHCH$_2$CF$_3$ | Me | 4-NH$_2$ |
| F-675 | NHOEt | NHCH$_2$CH$_2$F | Me | 4-NH$_2$ |
| F-676 | NHNMe$_2$ | NH$_2$ | Me | 4-NH$_2$ |
| F-677 | NHNMe$_2$ | NHMe | Me | 4-NH$_2$ |
| F-678 | NHNMe$_2$ | NHEt | Me | 4-NH$_2$ |
| F-679 | NHNMe$_2$ | NHPr | Me | 4-NH$_2$ |
| F-680 | NHNMe$_2$ | NH-i-Pr | Me | 4-NH$_2$ |
| F-681 | NHNMe$_2$ | NH-n-Bu | Me | 4-NH$_2$ |
| F-682 | NHNMe$_2$ | NH-allyl | Me | 4-NH$_2$ |
| F-683 | NHNMe$_2$ | NH-propargyl | Me | 4-NH$_2$ |
| F-684 | NHNMe$_2$ | NHCH$_2$CF$_3$ | Me | 4-NH$_2$ |
| F-685 | NHNMe$_2$ | NHCH$_2$CH$_2$F | Me | 4-NH$_2$ |
| F-686 | NHNH$_2$ | NH$_2$ | Me | 4-NH$_2$ |
| F-687 | NHNH$_2$ | NHMe | Me | 4-NH$_2$ |
| F-688 | NHNH$_2$ | NHEt | Me | 4-NH$_2$ |
| F-689 | NHNH$_2$ | NHPr | Me | 4-NH$_2$ |
| F-690 | NHNH$_2$ | NH-i-Pr | Me | 4-NH$_2$ |
| F-691 | NHNH$_2$ | NH-n-Bu | Me | 4-NH$_2$ |
| F-692 | NHNH$_2$ | NH-allyl | Me | 4-NH$_2$ |
| F-693 | NHNH$_2$ | NH-propargyl | Me | 4-NH$_2$ |
| F-694 | NHNH$_2$ | NHCH$_2$CF$_3$ | Me | 4-NH$_2$ |
| F-695 | NHNH$_2$ | NHCH$_2$CH$_2$F | Me | 4-NH$_2$ |
| F-696 | NHNHMe | NHMe | Me | 4-NH$_2$ |
| F-697 | NHNHMe | NHEt | Me | 4-NH$_2$ |
| F-698 | NHNHMe | NHPr | Me | 4-NH$_2$ |
| F-699 | NHNHMe | NH-i-Pr | Me | 4-NH$_2$ |
| F-700 | NHNHMe | NHCH$_2$CF$_3$ | Me | 4-NH$_2$ |

TABLE 32

| Compound No. | $R^{15}$ | $R^{16}$ | $R^{17}$ | $R^{18}$ |
|---|---|---|---|---|
| F-701 | NH$_2$ | NH$_2$ | H | 4-NH$_2$ |
| F-702 | NH$_2$ | NHMe | H | 4-NH$_2$ |
| F-703 | NH$_2$ | NHEt | H | 4-NH$_2$ |
| F-704 | NH$_2$ | NHPr | H | 4-NH$_2$ |
| F-705 | NH$_2$ | NH-i-Pr | H | 4-NH$_2$ |
| F-706 | NH$_2$ | NH-n-Bu | H | 4-NH$_2$ |
| F-707 | NH$_2$ | NH-allyl | H | 4-NH$_2$ |
| F-708 | NH$_2$ | NH-propargyl | H | 4-NH$_2$ |
| F-709 | NH$_2$ | NHCH$_2$CF$_3$ | H | 4-NH$_2$ |
| F-710 | NH$_2$ | NHCH$_2$CH$_2$F | H | 4-NH$_2$ |
| F-711 | NHMe | NHMe | H | 4-NH$_2$ |
| F-712 | NHMe | NHEt | H | 4-NH$_2$ |
| F-713 | NHMe | NHPr | H | 4-NH$_2$ |
| F-714 | NHMe | NH-i-Pr | H | 4-NH$_2$ |
| F-715 | NHMe | NH-n-Bu | H | 4-NH$_2$ |
| F-716 | NHMe | NH-allyl | H | 4-NH$_2$ |
| F-717 | NHMe | NH-propargyl | H | 4-NH$_2$ |
| F-718 | NHMe | NHCH$_2$CF$_3$ | H | 4-NH$_2$ |
| F-719 | NHMe | NHCH$_2$CH$_2$F | H | 4-NH$_2$ |
| F-720 | NHEt | NHEt | H | 4-NH$_2$ |
| F-721 | NHEt | NHPr | H | 4-NH$_2$ |
| F-722 | NHEt | NH-i-Pr | H | 4-NH$_2$ |
| F-723 | NHEt | NH-n-Bu | H | 4-NH$_2$ |
| F-724 | NHEt | NH-allyl | H | 4-NH$_2$ |
| F-725 | NHEt | NH-propargyl | H | 4-NH$_2$ |
| F-726 | NHEt | NHCH$_2$CF$_3$ | H | 4-NH$_2$ |
| F-727 | NHEt | NHCH$_2$CH$_2$F | H | 4-NH$_2$ |
| F-728 | NHPr | NHPr | H | 4-NH$_2$ |
| F-729 | NHPr | NH-i-Pr | H | 4-NH$_2$ |
| F-730 | NHPr | NH-n-Bu | H | 4-NH$_2$ |
| F-731 | NHPr | NH-allyl | H | 4-NH$_2$ |
| F-732 | NHPr | NH-propargyl | H | 4-NH$_2$ |
| F-733 | NHPr | NHCH$_2$CF$_3$ | H | 4-NH$_2$ |
| F-734 | NHPr | NHCH$_2$CH$_2$F | H | 4-NH$_2$ |
| F-735 | NH-i-Pr | NH-i-Pr | H | 4-NH$_2$ |
| F-736 | NH-i-Pr | NH-n-Bu | H | 4-NH$_2$ |
| F-737 | NH-i-Pr | NH-allyl | H | 4-NH$_2$ |
| F-738 | NH-i-Pr | NH-propargyl | H | 4-NH$_2$ |
| F-739 | NH-i-Pr | NHCH$_2$CF$_3$ | H | 4-NH$_2$ |
| F-740 | NH-i-Pr | NHCH$_2$CH$_2$F | H | 4-NH$_2$ |
| F-741 | NH-n-Bu | NH-n-Bu | H | 4-NH$_2$ |
| F-742 | NH-n-Bu | NH-allyl | H | 4-NH$_2$ |
| F-743 | NH-n-Bu | NH-propargyl | H | 4-NH$_2$ |
| F-744 | NH-n-Bu | NHCH$_2$CF$_3$ | H | 4-NH$_2$ |
| F-745 | NH-n-Bu | NHCH$_2$CH$_2$F | H | 4-NH$_2$ |
| F-746 | NH-allyl | NH-allyl | H | 4-NH$_2$ |
| F-747 | NH-allyl | NH-propargyl | H | 4-NH$_2$ |
| F-748 | NH-allyl | NHCH$_2$CF$_3$ | H | 4-NH$_2$ |
| F-749 | NH-allyl | NHCH$_2$CH$_2$F | H | 4-NH$_2$ |
| F-750 | NH-propargyl | NH-propargyl | H | 4-NH$_2$ |
| F-751 | NH-propargyl | NHCH$_2$CF$_3$ | H | 4-NH$_2$ |
| F-752 | NH-propargyl | NHCH$_2$CH$_2$F | H | 4-NH$_2$ |
| F-753 | NHCH$_2$CF$_3$ | NHCH$_2$CF$_3$ | H | 4-NH$_2$ |
| F-754 | NHCH$_2$CF$_3$ | NHCH$_2$CH$_2$F | H | 4-NH$_2$ |
| F-755 | NHCH$_2$CH$_2$F | NHCH$_2$CH$_2$F | H | 4-NH$_2$ |
| F-756 | NHOMe | NH$_2$ | H | 4-NH$_2$ |
| F-757 | NHOMe | NHMe | H | 4-NH$_2$ |
| F-758 | NHOMe | NHEt | H | 4-NH$_2$ |
| F-759 | NHOMe | NHPr | H | 4-NH$_2$ |
| F-760 | NHOMe | NH-i-Pr | H | 4-NH$_2$ |
| F-761 | NHOMe | NH-n-Bu | H | 4-NH$_2$ |
| F-762 | NHOMe | NH-allyl | H | 4-NH$_2$ |
| F-763 | NHOMe | NH-propargyl | H | 4-NH$_2$ |
| F-764 | NHOMe | NHCH$_2$CF$_3$ | H | 4-NH$_2$ |
| F-765 | NHOMe | NHCH$_2$CH$_2$F | H | 4-NH$_2$ |
| F-766 | NHOEt | NH$_2$ | H | 4-NH$_2$ |
| F-767 | NHOEt | NHMe | H | 4-NH$_2$ |
| F-768 | NHOEt | NHEt | H | 4-NH$_2$ |
| F-769 | NHOEt | NHPr | H | 4-NH$_2$ |
| F-770 | NHOEt | NH-i-Pr | H | 4-NH$_2$ |
| F-771 | NHOEt | NH-n-Bu | H | 4-NH$_2$ |
| F-772 | NHOEt | NH-allyl | H | 4-NH$_2$ |
| F-773 | NHOEt | NH-propargyl | H | 4-NH$_2$ |
| F-774 | NHOEt | NHCH$_2$CF$_3$ | H | 4-NH$_2$ |
| F-775 | NHOEt | NHCH$_2$CH$_2$F | H | 4-NH$_2$ |
| F-776 | NHNMe$_2$ | NH$_2$ | H | 4-NH$_2$ |
| F-777 | NHNMe$_2$ | NHMe | H | 4-NH$_2$ |
| F-778 | NHNMe$_2$ | NHEt | H | 4-NH$_2$ |
| F-779 | NHNMe$_2$ | NHPr | H | 4-NH$_2$ |
| F-780 | NHNMe$_2$ | NH-i-Pr | H | 4-NH$_2$ |
| F-781 | NHNMe$_2$ | NH-n-Bu | H | 4-NH$_2$ |
| F-782 | NHNMe$_2$ | NH-allyl | H | 4-NH$_2$ |
| F-783 | NHNMe$_2$ | NH-propargyl | H | 4-NH$_2$ |
| F-784 | NHNMe$_2$ | NHCH$_2$CF$_3$ | H | 4-NH$_2$ |
| F-785 | NHNMe$_2$ | NHCH$_2$CH$_2$F | H | 4-NH$_2$ |
| F-786 | NHNH$_2$ | NH$_2$ | H | 4-NH$_2$ |
| F-787 | NHNH$_2$ | NHMe | H | 4-NH$_2$ |
| F-788 | NHNH$_2$ | NHEt | H | 4-NH$_2$ |
| F-789 | NHNH$_2$ | NHPr | H | 4-NH$_2$ |
| F-790 | NHNH$_2$ | NH-i-Pr | H | 4-NH$_2$ |

TABLE 32-continued

| Compound No. | $R^{15}$ | $R^{16}$ | $R^{17}$ | $R^{18}$ |
|---|---|---|---|---|
| F-791 | NHNH$_2$ | NH-n-Bu | H | 4-NH$_2$ |
| F-792 | NHNH$_2$ | NH-allyl | H | 4-NH$_2$ |
| F-793 | NHNH$_2$ | NH-propargyl | H | 4-NH$_2$ |
| F-794 | NHNH$_2$ | NHCH$_2$CF$_3$ | H | 4-NH$_2$ |
| F-795 | NHNH$_2$ | NHCH$_2$CH$_2$F | H | 4-NH$_2$ |
| F-796 | NHNHMe | NHMe | H | 4-NH$_2$ |
| F-797 | NHNHMe | NHEt | H | 4-NH$_2$ |
| F-798 | NHNHMe | NHPr | H | 4-NH$_2$ |
| F-799 | NHNHMe | NH-i-Pr | H | 4-NH$_2$ |
| F-800 | NHNHMe | NHCH$_2$CF$_3$ | H | 4-NH$_2$ |

Test Example 1 Inhibitory effect against cellular signaling derived from Ras oncogene products 1) Establishment of Cell Lines Used in Assay Based on the reporter plasmid (pGV-P (Toyo Ink, Japan)), in which luciferase gene was ligated to SV40-derived minimal promoter, we constructed a plasmid designated pRRE3-luc by inserting 3 copies of chemically synthesized oligonucleotides (Sequence: CAGGATATGACTCT, derived from mouse NVL-3 (M. A. Reddy et al.(1992)Mol. Endocrinol., 6, 1051)) into upstream of the promoter. v-ki-ras-transformed NIH373 cells (DT cells, provided by Dr. Makoto Noda (Kyoto Univ., School of medicine)) were transfected with this plasmid by liposome-mediated transfection and transfected cell lines stably incorporated and maintained each plasmid were obtained. We named pGV-P and pRRE3-transfected cell line as DT-C and DT-R, respectively and used in the assay described below.

2) Preparation of Samples i) All the cell lines were cultured in Dulbecco's Modified Essential Medium (DMEM: 10% Fetal Calf Serum(FCS: Hyclone, USA)) including 60 mg/ml kanamycin (Meiji Seika, Japan) in humidified incubator under condition of 5% $CO_2$ at 37° C.

ii) DT-C and DT-R cells were seeded at 2500 cells/well into flat-bottom 96 well multiplate (Sumitomo bakelite) and incubated for 24 hours.

iii) Test compounds were prepared as 1 mg/ml DMSO solution.

iv) The solution of test compounds were added to the culture. Tested compounds are used at the concentration from 10 mg/ml to 0.51 ng/ml with 3-fold dilution.

v) After 24 hours, the culture supernatant was completely aspirated and 20 μl of cell-lysing solution (PGC-50 (Toyo Ink, Japan)) was added before cells were dried up. In order to lyse the cells completely, multiwell plates were left at room temperature for 10 to 30 min. The plates were wrapped up and stored at −20° C. till the day of measurement.

3) Measurement of Samples i) Melt the samples by putting 96 well multiplate at 37° C. and add 90 μl/well 25 mM Tris (pH 7.5).

ii) Transfer 50 μl of the sample (110 μl) to the 96 well microplate (Microlite 1 (Dynatech)) for measurement.

iii) Measure the samples by the luminometer, LUMINOUS CT9000D (Dia-Yatron, Japan). We used Pickagene luminescence kit PGL2000 or LT2.0 (Toyo Ink, Japan) as enzyme substrates for luminescence measurement (50 μl/well).

4) Judgment of the Results i) The luciferase activity of DT-C cells and DT-R cells were plotted in the graph where the relative activity and the compound concentration were expressed as Y-axis and X-axis, respectively. We judged by the degree of dissociation between the activities of DT-C cells and DT-R cells as an index.

ii) Concretely, efficacy of the compound was expressed by two values described below.

a) Among the points of concentration tested, the minimal concentration (Minimal Active Concentration: MAC), at which the activities of DT-C cells and DT-R cells dissociated, was shown as an index of efficacy of the compound.

b) Among the points of concentration tested, the concentration which is the nearest to 50% inhibition concentration at DT-C cells (IC50-C), was shown as an index of non-specific transcription-inhibitory effect or of cytotoxicity. In case of positive compounds, 50% inhibition concentration in DT-C cells which was higher than the active concentration was expressed as $IC_{50}$-C.

The results of the assay were shown in table 33.

TABLE 33

| Compound No. | MAC (μg/ml) | IC50 (μg/ml) |
|---|---|---|
| A-1 | 1.11 | >10 |
| A-2 | 1.11 | >10 |
| A-3 | 0.37 | >10 |
| A-4 | 0.37 | >10 |
| A-5 | 0.123 | 10 |
| A-6 | 0.0412 | 10 |
| A-7 | 0.123 | 3.33 |
| A-8 | 0.123 | >10 |
| A-10 | 1.11 | >10 |
| A-11 | 0.0412 | >10 |
| A-12 | 0.0137 | >10 |
| A-13 | 0.0137 | 10 |
| A-14 | 0.0412 | >10 |
| A-15 | 0.00152 | >10 |
| A-16 | <0.000508 | >10 |
| A-17 | 0.0412 | >10 |
| A-18 | 0.00457 | >10 |
| A-19 | 0.37 | >10 |
| A-21 | 0.37 | 10 |
| A-22 | 1.11 | >10 |
| A-23 | 3.33 | >10 |
| A-32 | 0.123 | >10 |
| A-33 | 0.0412 | >10 |
| A-34 | 0.0137 | >10 |
| A-35 | 0.0412 | >10 |
| C-1 | 0.0412 | 10 |
| C-2 | 0.0137 | >10 |

Test Example 2 In vitro cell growth inhibition test Cells and MTT assay

Human squamous lung cancer RERF-RC-AI, human squamous lung cancer Ma44, human lung adenocarcinoma A549, human colon cancer HT29 and human pancreas cancer PANC-1 were used. All cell lines were cultured with Eagle's Modified Essential Medium (EMEM, supplemented with 10% fetal calf serum (FCS: Hyclone, USA) and 60 μg/ml Kanamycin (Meiji-seika, Japan) at 37° C. in a humidified incubator (5% $CO_2$). The cells were plated in 96-well microcultureplate. Twenty-four hours later, compound were added at the concentration from 10 μg/ml to 0.1 ng/ml with 2-fold dilution. MT7 assay was performed 4 days later and $IC_{50}$ values were determined. The results were shown in Table 34 in terms of concentration at ng/ml.

TABLE 34

| Compound No. | A549 | HT-29 | Ma44 | PANC-1 | RERF-LC-AI | H460 |
|---|---|---|---|---|---|---|
| A-1 | 0.9 | 45 | 120 | 46 | | |
| A-2 | 34 | 140 | 370 | 160 | | |
| A-3 | 63 | 52 | 56 | 51 | 46 | |
| A-4 | 38 | 23 | 51 | 26 | 30 | |
| A-5 | 70 | 48.4 | 44.6 | 66.5 | 33 | 89 |
| A-6 | 25.6 | 24.4 | 18.2 | 14.8 | 15 | 25.6 |
| A-7 | 2.1 | 3.6 | 1.6 | 0.6 | 1.3 | 3.8 |
| A-8 | 9.3 | 41.4 | 34.1 | 37.1 | 27.8 | 6.8 |
| A-10 | | | 80 | | | |
| A-11 | 14 | 6.7 | 77 | 6.4 | | |
| A-12 | 8 | 6.3 | 9.5 | 9.1 | 5.7 | 11.5 |
| A-13 | 15 | 8.9 | 30 | 7.7 | | |
| A-14 | 12 | 11 | 32 | 9.8 | 12 | |
| A-15 | 11.1 | 10.3 | 12.7 | 12.4 | 6.5 | 15.3 |
| A-16 | 14.6 | 8.1 | 13.6 | 6.5 | 7.3 | 10.7 |
| A-17 | 17.4 | 15 | 24.1 | 10.7 | 13.2 | 15 |
| A-18 | 51.4 | 0.4 | 0.4 | 0.4 | 0.4 | 27.5 |
| A-19 | | | 83 | | | |
| A-21 | | | 22 | | | |
| A-22 | | | 42 | | | |
| A-32 | 64 | 31 | 42 | 34 | 31 | |
| A-33 | 23 | 6.6 | 9.1 | 8.6 | 9.3 | |
| A-34 | 21 | 4.6 | 9.1 | 7.5 | 13 | |
| A-35 | 11 | 3.3 | 6.9 | 5.4 | 6.7 | |
| C-1 | 16 | 6.6 | 11 | 6.4 | | |
| C-2 | 4.4 | 2 | 3.4 | 2 | | |

FORMULATION EXAMPLE

Formulation Example 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose were made pass through a 60 mesh sieve. Corn starch was made pass through a 120 mesh sieve. They were mixed by a twin shell blender. An aqueous solution of HPC-L (low mucosity hydroxypropylcellulose) was added to the mixture and the resulting mixture was kneaded, granulated (by the extrusion with pore size 0.5 to 1 mm mesh), and dried. The dried granules thus obtained were sieved by a swing sieve (12/60 mesh) to yield the granules.

Formulation 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose were made pass through a 60 mesh sieve. Corn starch was made pass through a 120 mesh sieve. These ingredients and magnesium stearate were mixed by a twin shell blender. 100 mg of the 10-fold trituration was filled into a No. 5 hard gelatin capsule.

Formulation 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose were made pass through a 60 mesh sieve. Corn starch was made pass through a 120 mesh sieve. After mixing them, an aqueous solution of HPC-L was added to the mixture and the resulting mixture was kneaded, granulated, and dried. After the dried granules were lubricated, 150 mg of that were filled into a No. 4 hard gelatin capsule.

Formulation 4

| Ingredients | |
|---|---|
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) were made pass through a 60 mesh sieve and then mixed. The resulting mixture was mixed with magnesium stearate to obtain the mixed powder for the tablet formulation. The mixed powder was compressed to yield tablets of 150 mg.

INDUSTRIAL APPLICABILITY

The pyrimidine derivatives of the present invention have an inhibitory activity against a signal derived from Ras oncogene products, whereby they are effective for solid cancer having, high frequency ras activation such as pancreatic cancer, colon cancer, and lung cancer.

What is claimed is:

1. A compound represented by the formula (I):

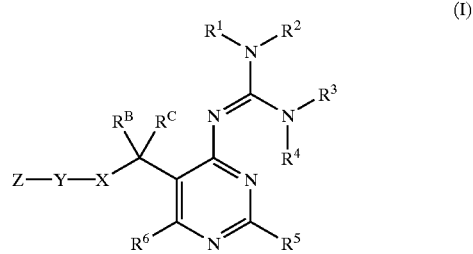

wherein R¹, R², R³, and R⁴ are each independently hydrogen atom, optionally substituted alkyl, optionally substituted alkenyl, optionally substituted alkynyl, optionally substituted aryl, optionally substituted heteroaryl, optionally substituted aralkyl, an optionally substituted non-aromatic heterocyclic group, acyl, optionally substituted amino, alkyloxy, hydroxy, cyano, or nitro; or R¹ and R², R³ and R⁴, and R² and R³ each taken together with the adjacent nitrogen atom form the same or different 3- to 7-membered ring optionally containing O, N, or S, provided that R¹ and R² and R³ and R⁴ do not form a ring when R² and R³ taken together form a ring;

R⁵ and R⁶ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen, hydroxy, mercapto, optionally substituted amino, carboxy, cyano, or nitro;

R^B and R^C are each independently hydrogen atom, alkyl, or alkyloxy; provided that in the case of both of R^B and R^C are hydrogen atom, R¹ is hydrogen atom or alkyl, R² is substituted amino, alkyloxy, hydroxy, cyano, or nitro;

X is —N(R⁷)—, —NH—NH—, —O—, or —S— wherein R⁷ is hydrogen atom or optionally substituted alkyl;

Y is optionally substituted 5-membered non-aromatic heterocycle-diyl or optionally substituted 5-membered heteroaryl-diyl;

Z is optionally substituted aryl or optionally substituted heteroaryl; or a pharmaceutically acceptable salt or enantiomer thereof.

2. A compound of claim 1, represented by the formula (II):

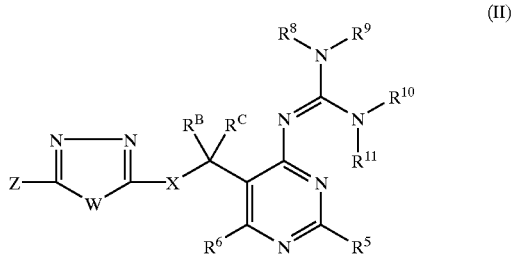

(II)

wherein R⁸, R⁹, R¹⁰, and R¹¹ are each independently hydrogen atom, optionally substituted alkyl, alkenyl, alkynyl, optionally substituted aryl, optionally substituted heteroaryl, optionally substituted aralkyl, a non-aromatic heterocyclic group, acyl, substituted amino, alkyloxy, hydroxy, cyano, or nitro;

R^B and R^C are each independently hydrogen atom, alkyl, or alkyloxy; provided that in the case of both of R^B and R^C are hydrogen atom, R⁸ is hydrogen atom or alkyl, R⁹ is substituted amino, alkyloxy, hydroxy, cyano, or nitro; and R¹⁰ and R¹¹ are each independently hydrogen atom, optionally substituted alkyl, alkenyl, alkynyl, optionally substituted aryl, optionally substituted heteroaryl, optionally substituted aralkyl, non-aromatic heterocyclic group, acyl, optionally substituted amino, alkyloxy, hydroxy, cyano, or nitro;

W is —O—, —S—, or —N(R^A)— wherein R^A is hydrogen atom or optionally substituted alkyl;

R⁵, R⁶, X, and Z are as defined in claim 1; or a pharmaceutically acceptable salt or enantiomer thereof.

3. A compound of claim 1, represented by the formula (III):

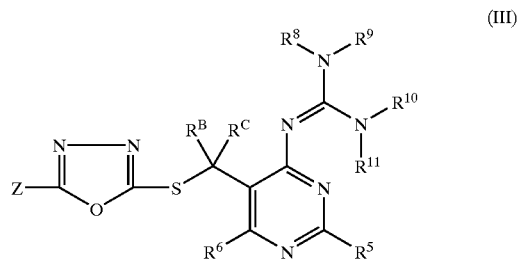

(III)

wherein R⁵, R⁶, and Z are as defined in claim 1, R⁸, R⁹, R¹⁰, R¹¹, R^B and R^C are as defined in claim 2, or a pharmaceutically acceptable salt or enantiomer thereof.

4. A compound of claim 1, represented by the formula (IV):

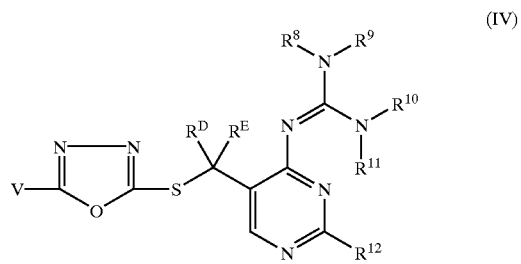

(IV)

wherein R⁸, R⁹, R¹⁰ and R¹¹ are as defined in claim 2;

R¹² is hydrogen atom or alkyl;

R^D and R^E are each independently hydrogen atom or alkyl; provided that in the case of both of R^D and R^E are hydrogen atom, R⁸ is hydrogen atom or alkyl, R⁹ is substituted amino, alkyloxy, hydroxy, cyano, or nitro; and R¹⁰ and R¹¹ are each independently hydrogen atom, optionally substituted alkyl, alkenyl, alkynyl, optionally substituted aryl, optionally substituted heteroaryl, optionally substituted aralkyl, non-aromatic heterocyclic group, acyl, optionally substituted amino, alkyloxy, hydroxy, cyano, or nitro;

V is optionally substituted aryl; or a pharmaceutically acceptable salt or enantiomer thereof.

5. A compound of claim 1 represented by the formula (V):

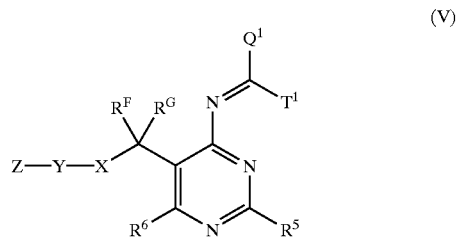

(V)

wherein R⁵ and R⁶ are each independently hydrogen atom, optionally substituted alkyl, optionally substituted alkenyl, optionally substituted alkynyl, optionally substituted alkyloxy, alkylthio, optionally substituted alkyloxycarbonyl, optionally substituted aryl, optionally substituted heteroaryl, halogen atoms, hydroxy, mercapto, optionally substituted amino, carboxy, cyano, or nitro;

$R^F$ and $R^G$ are each independently hydrogen atom, alkyl, or alkyloxy;

X is —N($R^7$)—, —NH—NH—, —O—, or —S— wherein $R^7$ is hydrogen atom or optionally substituted alkyl;

Y is optionally substituted 5-membered non-aromatic heterocycle-diyl or optionally substituted 5-membered heteroaryl-diyl;

Z is optionally substituted aryl or optionally substituted heteroaryl;

$Q^1$ is —$NR^1R^2$, —$OR^1$, or —$SR^1$, $T^1$ is —$OR^3$ or —$SR^3$ wherein $R^1$, $R^2$ and $R^3$ are each independently hydrogen atom, optionally substituted alkyl, optionally substituted alkenyl, optionally substituted alkynyl, optionally substituted aryl, optionally substituted heteroaryl, optionally substituted aralkyl, optionally substituted non-aromatic heterocyclic group, acyl, optionally substituted amino, alkyloxy, hydroxy, cyano, or nitro; or $R^1$ and $R^3$, and $R^2$ and $R^3$ each taken together with the adjacent heteroatom form 5- to 7-membered ring; or a pharmaceutically acceptable salt or enantiomer thereof.

6. A compound of claim 5, represented by the formula (VI):

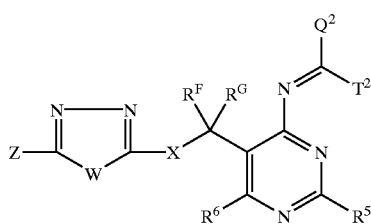

(VI)

wherein $Q^2$ is —$NR^8R^9$, —$OR^8$, or —$SR^8$, $T^2$ is —$OR^{10}$ or —$SR^{10}$ wherein $R^8$, $R^9$ and $R^{10}$ are each independently hydrogen atom, optionally substituted alkyl, alkenyl, alkynyl, optionally substituted aryl, optionally substituted heteroaryl, optionally substituted aralkyl, optionally substituted non-aromatic heterocyclic group, acyl, optionally substituted amino, alkyloxy, hydroxy, cyano, or nitro;

W is —O—, —S—, or —N($R^A$)— wherein $R^A$ is hydrogen atom or optionally substituted alkyl;

$R^5$, $R^6$, $R^F$, $R^G$, X, and Z are as defined in claim 5; or a pharmaceutically acceptable salt or enantiomer thereof.

7. A compound of claim 5, represented by the formula (VII):

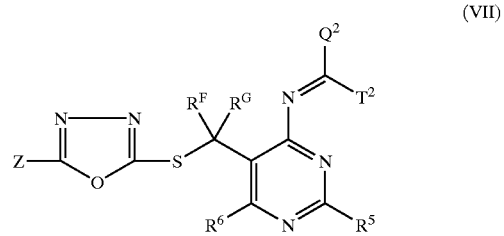

(VII)

wherein $R^5$, $R^6$, $R^F$, $R^G$, and Z are as defined in claim 5; $Q^2$ and $T^2$ are as defined in claim 6; or a pharmaceutically acceptable salt or enantiomer thereof.

8. A compound of claim 5, represented by the formula (VIII):

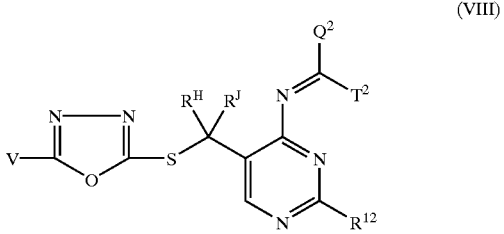

(VIII)

wherein $R^{12}$ is hydrogen or alkyl;

$R^H$ and $R^J$ are each independently hydrogen atom or alkyl;

the other symbols are as defined in claim 6; or a pharmaceutically acceptable salt or enantiomer thereof.

9. A compound, or a pharmaceutically acceptable salt or enantiomer thereof of claim 1 or 5, wherein $R^1$, $R^2$, $R^3$, and $R^4$ are each independently hydrogen atom, optionally substituted alkyl, alkenyl, alkynyl, or acyl.

10. A compound, or a pharmaceutically acceptable salt or enantiomer thereof of claim 2 or 6, wherein $R^8$, $R^9$, $R^{10}$, and $R^{11}$ are each independently hydrogen atom, optionally substituted alkyl, alkenyl, alkynyl, or acyl.

11. A pharmaceutical composition comprising as active ingredient the compound of claim 1 or 5, and a pharmaceutically acceptable carrier.

12. A method of treating cancer in a mammal, comprising the step of administering to the mammal a compound according to claim 1 or 5, wherein said cancer is selected from the group consisting of human squamous lung cancer, human lung adenocarcinoma, human colon cancer, and human pancreas cancer.

13. The method according to claim 12, wherein said mammal is a human.

* * * * *